US010604532B2

(12) United States Patent
Hitchcock et al.

(10) Patent No.: US 10,604,532 B2
(45) Date of Patent: Mar. 31, 2020

(54) SUBSTITUTED BENZYLINDAZOLES FOR USE AS BUB1 KINASE INHIBITORS IN THE TREATMENT OF HYPERPROLIFERATIVE DISEASES

(71) Applicants: Bayer Intellectual Property GmbH, Monheim (DE); Bayer Pharma Aktiengesellschaft, Berlin (DE)

(72) Inventors: Marion Hitchcock, Brookline, MA (US); Anne Mengel, Berlin (DE); Vera Pütter, Berlin (DE); Gerhard Siemeister, Berlin (DE); Antje Margret Wengner, Berlin (DE); Hans Briem, Berlin (DE); Knut Eis, Berlin (DE); Volker Schulze, Hohen Neuendorf (DE); Amaury Ernesto Fernandez-Montalvan, Berlin (DE); Stefan Prechtl, Berlin (DE); Simon Holton, Berlin (DE); Jörg Fanghänel, Berlin (DE); Philip Lienau, Berlin (DE); Cornelia Preusse, Berlin (DE); Mark Jean Gnoth, Mettmann (DE)

(73) Assignees: Bayer Intellectual Property GmbH, Monheim (DE); Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 16/360,811

(22) Filed: Mar. 21, 2019

(65) Prior Publication Data

US 2019/0284206 A1    Sep. 19, 2019

Related U.S. Application Data

(63) Continuation of application No. 15/438,254, filed on Feb. 21, 2017, now Pat. No. 10,266,548, which is a continuation of application No. 14/350,160, filed as application No. PCT/EP2012/069562 on Oct. 4, 2012, now abandoned.

(30) Foreign Application Priority Data

Oct. 6, 2011   (EP) ..................... 11184061

(51) Int. Cl.
| | |
|---|---|
| *C07D 401/14* | (2006.01) |
| *C07D 498/04* | (2006.01) |
| *C07D 405/14* | (2006.01) |
| *C07D 413/14* | (2006.01) |
| *A01H 6/36* | (2018.01) |
| *A61K 31/506* | (2006.01) |
| *A61K 31/5377* | (2006.01) |
| *A61K 31/5383* | (2006.01) |
| *A61K 45/06* | (2006.01) |
| *C07D 403/04* | (2006.01) |

(52) U.S. Cl.
CPC .......... *C07D 498/04* (2013.01); *A01H 6/368* (2018.05); *A61K 31/506* (2013.01); *A61K 31/5377* (2013.01); *A61K 31/5383* (2013.01); *A61K 45/06* (2013.01); *C07D 401/14* (2013.01); *C07D 403/04* (2013.01); *C07D 405/14* (2013.01); *C07D 413/14* (2013.01)

(58) Field of Classification Search
CPC ... C07D 401/14; C07D 405/14; A61K 31/506
USPC ...... 544/122, 298, 328; 514/235.8, 256, 269
See application file for complete search history.

(56) References Cited

U.S. PATENT DOCUMENTS

| | | |
|---|---|---|
| 5,470,862 A | 11/1995 | Lin |
| 6,462,068 B1 | 10/2002 | Straub et al. |
| 6,833,364 B1 | 12/2004 | Straub et al. |
| 7,427,617 B2 | 9/2008 | Feurer |
| 9,643,953 B2 | 5/2017 | Hitchcock |
| 9,682,974 B2 | 6/2017 | Mengel |
| 9,745,285 B2 | 8/2017 | Mengel |
| 9,765,058 B2 | 9/2017 | Hitchcock |
| 10,266,548 B2 * | 4/2019 | Hitchcock ............ C07D 401/14 |
| 2011/0130410 A1 | 6/2011 | Mais |
| 2014/0249133 A1 | 9/2014 | Hitchcock |
| 2015/0141372 A1 | 5/2015 | Hitchcock |
| 2016/0046604 A1 | 2/2016 | Hitchcock |
| 2016/0046610 A1 | 2/2016 | Hitchcock |
| 2016/0052912 A1 | 2/2016 | Hilger |
| 2016/0145238 A1 | 5/2016 | Mengel |
| 2016/0145239 A1 | 5/2016 | Hilger |
| 2016/0145267 A1 | 5/2016 | Hitchcock |
| 2016/0151370 A1 | 6/2016 | Hitchcock |
| 2016/0168130 A1 | 6/2016 | Hitchcock |
| 2016/0326159 A1 | 11/2016 | Mengel |
| 2017/0273980 A1 | 9/2017 | Mengel |
| 2017/0275267 A1 | 9/2017 | Hitchcock |

(Continued)

FOREIGN PATENT DOCUMENTS

| | | |
|---|---|---|
| CA | 2663297 A1 | 3/2008 |
| JP | 2010111624 | 5/2010 |

(Continued)

OTHER PUBLICATIONS

Bolanos-Garcia et al. (Mar. 2011). "BUB1 and BUBR1: multifaceted kinases of the cell cycle," Trends in Biochem. Sciences 36(3): 141-150.

(Continued)

*Primary Examiner* — Deepak R Rao
(74) *Attorney, Agent, or Firm* — Morrison & Foerster LLP

(57) ABSTRACT

Compounds of formula (I) which are inhibitors of Bub 1 kinase, processes for their production and their use as pharmaceuticals.

6 Claims, No Drawings

(56) References Cited

U.S. PATENT DOCUMENTS

| | | |
|---|---|---|
| 2017/0275268 A1 | 9/2017 | Hitchcock |
| 2017/0275269 A1 | 9/2017 | Mengel |
| 2017/0275270 A1 | 9/2017 | BÄrfacker et al. |
| 2017/0283396 A1 | 10/2017 | Hilger |
| 2017/0305882 A1 | 10/2017 | Mengel |

FOREIGN PATENT DOCUMENTS

| | | |
|---|---|---|
| WO | WO0021954 A1 | 4/2000 |
| WO | WO03051833 A3 | 10/2003 |
| WO | WO03082274 A1 | 10/2003 |
| WO | WO2004024159 A1 | 3/2004 |
| WO | WO2004031186 A1 | 4/2004 |
| WO | WO2005070900 A1 | 8/2005 |
| WO | WO2007038613 A2 | 4/2007 |
| WO | WO2007065010 A2 | 6/2007 |
| WO | WO2008141731 A2 | 11/2008 |
| WO | WO2010069966 A1 | 6/2010 |
| WO | WO2011049988 A2 | 4/2011 |
| WO | WO2011115804 A1 | 9/2011 |
| WO | WO2011126903 A2 | 10/2011 |
| WO | WO2012003405 A1 | 1/2012 |
| WO | WO2013050438 A1 | 4/2013 |
| WO | WO2013092512 A1 | 6/2013 |
| WO | WO2013101830 A1 | 7/2013 |
| WO | WO2013167698 A1 | 11/2013 |
| WO | WO2014047111 A1 | 3/2014 |
| WO | WO2014047325 A1 | 3/2014 |
| WO | WO2014047662 A2 | 3/2014 |
| WO | WO2014147144 A1 | 9/2014 |
| WO | WO2014147203 A1 | 9/2014 |
| WO | WO2014147204 A1 | 9/2014 |
| WO | WO2014202583 A1 | 12/2014 |
| WO | WO2014202584 A1 | 12/2014 |
| WO | WO2014202586 A1 | 12/2014 |
| WO | WO2014202588 A1 | 12/2014 |
| WO | WO2014202590 A1 | 12/2014 |
| WO | WO2015063003 A1 | 5/2015 |
| WO | WO2016041925 A1 | 3/2016 |
| WO | WO2016042080 A1 | 3/2016 |
| WO | WO2016042081 A1 | 3/2016 |
| WO | WO2016042084 A1 | 3/2016 |
| WO | WO2017148995 A1 | 9/2017 |
| WO | WO2017157991 A1 | 9/2017 |
| WO | WO2017157992 A1 | 9/2017 |
| WO | WO2018122168 A1 | 7/2018 |
| WO | WO2018158175 A1 | 9/2018 |
| WO | WO2018206547 A1 | 11/2018 |
| WO | WO2018215282 A1 | 11/2018 |

OTHER PUBLICATIONS

Elowe, S. (Aug. 2011 ). "Bub1 and BubR1: at the Interface between Chromosome Attachment and the Spindle Checkpoint," Molecular and Cellular Biolo_qy 31 (15): 3085-3093.

EPO Communication per Article 94(3) and Annex dated Sep. 11, 2018, for EP Application No. 157636192 filed on Sep. 17, 2015, 5 pages.

EPO Communication per Rule $^{161}/_{162}$ dated May 2, 2017, for EP Application No. 15763619.2 filed on Sep. 17, 2015, 2 pages.

Final Office Action dated Jun. 4, 2015 for U.S. Appl. No. 14/350,160, international filed Oct. 4, 2012, by Hitchcock et al., 14 pages.

Gura, T. (1997). "Systems for identifying new drugs are often faulty," Science 278(5340): 1041-1042.

Hanahan et al. (Jan. 7, 2000). "The Hallmarks of Cancer," Cell 100: 57-70.

Hanahan et al. (Mar. 4, 2011 ). "Hallmarks of Cancer: The Next Generation," Cell 144: 646-674.

International Search Report and Written Opinion dated Oct. 30, 2012 for PCT Application No. PCT/ EP2012/069562, filed Oct. 4, 2012, 11 pages.

Johnson, J. et al.(2001). "Relationships between drug activity in NCI preclinical in vitro and in vivo models and early clinical trials," British Journal of Cancer 84(10): 1424-1431.

Kang, J. et al. (Nov. 7, 2008). "Structure and Substrate Recruitment of the Human Spindle Checkpoint Kinase Bub1 ," Molecular Cell 32: 394-405.

Kawashima et al. (Jan. 8, 2010). "Phosphorylation of H2A by Bub1 Prevents Chromosomal Instability Through Localizing Shugoshin," Science 3.

King, R. W. (Acta 1786). "When 2+2=5: The origins and fates of aneuploidy and tetraploid cells," Biochimica et Biophys 2008: 4-14.

Kops, G.J.P.L. et al. (Oct. 2005). "On the Road to Cancer: Aneuploidy and The Mitotic Checkpoint," Nature Reviews 5: 773-785.

Krenn, V. et al. (Feb. 13, 2012). "Structural analysis reveals features of the spindle checkpoint kinase Bub1-kinetochore subunit Knl1 interaction," J Cell Biol. 196(4): 451-467.

Musacchio et al. (May 2007). "The spindle-assembly checkpoint in space and time," Nature Reviews/Molecular Cell Biology 8:379-393.

Non-final Office Action dated Apr. 21, 2016 for U.S. Appl. No. 14/350,160, international filing date Oct. 4, 2012, by Hitchcock et al., 15 pages.

Non-final Office Action dated Sep. 18, 2014 for U.S. Appl. No. 14/350,160, international filing date Oct. 4, 2012, by Hitchcock et al., 15 pages.

Nyati, S. et al. (2015). "The kinase activity of the Ser/Thr kinase BUB1 promotes TGF-l3 sianalina," Science Sianalina 8(356): 1-12.

Pearce, H. et al.(2008). "Failure modes in anticancer drug discovery and development," Cancer Drug Design and Discovery, ed. Stephen Neidle, Chapter 18, 424-435.

Response to EPO Communication per Rule $^{161}/_{162}$ dated Nov. 2, 2017, for EP Application No. 15763619.2 filed on Sep. 17, 2015, 41 pages.

Ricke, R.M. et al. (Dec. 3, 2012). "Bub1 kinase activity drives error correction and mitotic checkpoint control but not tumor suppression," J. Cell Bio/.199(6): 931-949.

Rieder et al. (Nov. 2004). "Stuck in Division or Passing through: Review What Happens When Cells Cannot Satisfy the Spindle Assembly Checkpoint," Developmental Cell 7:637-651.

Roberts et al. (Dec. 1994). "The *Saccharomyces cerevisiae* Checkpoint gene BUB1 Encodes a Novel Protein Kinase," Molecular and Cellular Biolo_qy 14(12): 8282-8291.

Schmidt et al. (2007). "Mitotic drug targets and the development of novel anti-mitotic anticancer druas," Drua Resistance Updates 10: 162-181.

Schmidt et al. (Jan. 16, 2006). "Exploiting the Compromised Spindle Assembly Checkpoint Function of Tumor Cells" Cell Cycle 5(2): 159-163.

Simone, J. (1996). "Oncology: Introduction," Cecil Textbook of Medicine, 20th Edition, vol. 1, 1004-1010.

Suijkerbuijk et al. (Acta 1786). "Preventing aneuploidy: The contribution of mitotic checkpoint proteins," Biochimica et Biophvsica 2008: 24-31.

U.S. Appl. No. 15/512,494, filed Mar. 17, 2017, for Mengel et al. (Also published as US-20170273980, cited herewith) (U.S. Patent Application is not submitted herewith pursuant to the waiver of 37 C.F.R. § 1.98 (a)(2)(iii) issued by the Office dated Sep. 21, 2004.).

U.S. Appl. No. 16/433,916, filed Jun. 6, 2019, for Mengel et al. (Not Yet Published) (U.S. Patent Application is not submitted herewith pursuant to the waiver of 37 C.F.R. § 1.98(a)(2)(iii) issued by the Office dated Sep. 21, 2004.).

Watanabe, Y., "Temporal and Spatial Regulation of Targeting Aurora B to the Inner Centromere," Cold Springs Harbor Symp. On Quantitative Biol. 75, 2010 Pub. Cold Spg. Harbor Lab Press, 419-423.

Weaver, B.A.A. et al. (Nov. 1, 2007). "Aneuploidy: Instigator and inhibitor of Tumorigenesis," Cancer Res. 67 (21): 10103-10105.

Written Opinion dated Nov. 10, 2015 for PCT Application No. PCT/EP2015/071340, filed Sep. 17, 2015, 9 pages.

Yuan et al. (Jan. 15, 2006). "Increased Expression of Mitotic Checkpoint Genes in Breast Cancer Cells with Chromosomal Instability," Clin. Cancer Res. 12(2): 405-410.

\* cited by examiner

SUBSTITUTED BENZYLINDAZOLES FOR USE AS BUB1 KINASE INHIBITORS IN THE TREATMENT OF HYPERPROLIFERATIVE DISEASES

CROSS REFERENCE TO RELATED APPLICATIONS

This application is a continuation application of U.S. patent application Ser. No. 15/438,254, file Feb. 21, 2017, which is a continuation application of U.S. patent application Ser. No. 14/350,160, which adopts the international filing date of Oct. 4, 2012, which is the National Phase application under 35 U.S.C. § 371 of International Application No. PCT/EP2012/069562, filed Oct. 4, 2012, which claims priority benefit to European Application No. 11184061.7, filed Oct. 6, 2011.

FIELD OF APPLICATION OF THE INVENTION

The Invention relates to substituted benzylindazole compounds, a process for their production and the use thereof.

BACKGROUND OF THE INVENTION

One of the most fundamental characteristics of cancer cells is their ability to sustain chronic proliferation whereas in normal tissues the entry into and progression through the cell division cycle is tightly controlled to ensure a homeostasis of cell number and maintenance of normal tissue function. Loss of proliferation control was emphasized as one of the six hallmarks of cancer [Hanahan D and Weinberg R A, Cell 100, 57, 2000; Hanahan D and Weinberg R A, Cell 144, 646, 2011].

The eukaryotic cell division cycle (or cell cycle) ensures the duplication of the genome and its distribution to the daughter cells by passing through a coordinated and regulated sequence of events. The cell cycle is divided into four successive phases:
1. The G1 phase represents the time before the DNA replication, in which the cell grows and is sensitive to external stimuli.
2. In the S phase the cell replicates its DNA, and
3. in the G2 phase preparations are made for entry into mitosis.
4. In mitosis (M phase), the duplicated chromosomes get separated supported by a spindle device built from microtubules, and cell division into two daughter cells is completed.

To ensure the extraordinary high fidelity required for an accurate distribution of the chromosomes to the daughter cells, the passage through the cell cycle is strictly regulated and controlled. The enzymes that are necessary for the progression through the cycle must be activated at the correct time and are also turned off again as soon as the corresponding phase is passed. Corresponding control points ("checkpoints") stop or delay the progression through the cell cycle if DNA damage is detected, or the DNA replication or the creation of the spindle device is not yet completed. The mitotic checkpoint (also known as spindle checkpoint or a spindle assembly checkpoint) controls the accurate attachment of mircrotubules of the spindle device to the kinetochors (the attachment site for microtubules) of the duplicated chromosomes. The mitotic checkpoint is active as long as unattached kinetochores are present and generates a wait-signal to give the dividing cell the time to ensure that each kinetochore is attached to a spindle pole, and to correct attachment errors. Thus the mitotic checkpoint prevents a mitotic cell from completing cell division with unattached or erroneously attached chromosomes [Suijkerbuijk S J and Kops G J, Biochem. Biophys. Acta 1786, 24, 2008; Musacchio A and Salmon E D, Nat. Rev. Mol. Cell. Biol. 8, 379, 2007]. Once all kinetochores are attached with the mitotic spindle poles in a correct bipolar (amphitelic) fashion, the checkpoint is satisfied and the cell enters anaphase and proceeds through mitosis.

The mitotic checkpoint is established by a complex network of a number of essential proteins, including members of the MAD (mitotic arrest deficient, MAD 1-3) and Bub (Budding uninhibited by benzimidazole, Bub 1-3) families, Mps1 kinase, cdc20, as well as other components [reviewed in Bolanos-Garcia V M and Blundell T L, Trends Biochem. Sd. 36, 141, 2010], many of these being over-expressed in proliferating cells (e.g. cancer cells) and tissues [Yuan B et al., Clin. Cancer Res. 12, 405, 2006]. The major function of an unsatisfied mitotic checkpoint is to keep the anaphase-promoting complex/cyclosome (APC/C) in an inactive state. As soon as the checkpoint gets satisfied the APC/C ubiquitin-ligase targets cyclin B and securin for proteolytic degradation leading to separation of the paired chromosomes and exit from mitosis.

Inactive mutations of the Ser/Thr kinase Bub1 prevented the delay in progression through mitosis upon treatment of cells of the yeast *S. cerevisiae* with microtubule-destabilizing drugs, which led to the identification of Bub1 as a mitotic checkpoint protein [Roberts B T et al., Mol. Cell Biol., 14, 8282, 1994]. A number of recent publications provide evidence that Bub1 plays multiple roles during mitosis which, have been reviewed by Elowe [Elowe S, Mol. Cell. Biol. 31, 3085, 2011. In particular, Bub1 is one of the first mitotic checkpoint proteins that binds to the kinetochores of duplicated chromosomes and probably acts as a scaffolding protein to constitute the mitotic checkpoint complex. Furthermore, via phosphorylation of hiss tone H2A, Bub1 localizes the protein shugoshin to the centromeric region of the chromosomes to prevent premature segregation of the paired chromosomes [Kawashima et al. Science 327, 172, 2010]. In addition, together with a Thr-3 phosphorylated Histone H3 the shugoshin protein functions as a binding site for the chromosomal passenger complex which includes the proteins survivin, borealin, INCENP and Aurora B. The chromosomal passenger complex is seen as a tension sensor within the mitotic checkpoint mechanism, which dissolves erroneously formed microtubule-kinetochor attachments such as syntelic (both sister kinetochors are attached to one spindle pole) or merotelic (one kinetochor is attached to two spindle poles) attachments [Watanabe Y, Cold Spring Herb. Symp. Quant. Biol. 75, 419, 2010].

Incomplete mitotic checkpoint function has been linked with aneuploidy and tumourigenesis [Weaver B A and Cleveland D W, Cancer Res. 67, 10103, 2007; King R W, Biochim Biophys Acta 1786, 4, 2008]. In contrast, complete inhibition of the mitotic checkpoint has been recognised to result in severe chromosome missegregation and induction of apoptosis in tumour cells [Kops G J et al., Nature Rev. Cancer 5, 773, 2005; Schmidt M and Medema R H, Cell Cycle 5, 159, 2006; Schmidt M and Bastians H, Drug Res. Updates 10, 162, 2007]. Thus, mitotic checkpoint abrogation through pharmacological inhibition of components of the mitotic checkpoint, such as Bub1 kinase, represents a new approach for the treatment of proliferative disorders, including solid tumours such as carcinomas, sarcomas, leukaemias and lymphoid malignancies or other disorders, associated with uncontrolled cellular proliferation.

The present invention relates to chemical compounds that inhibit Bub1 kinase.

Established anti-mitotic drugs such as *vinca* alkaloids, taxanes or epothilones activate the mitotic checkpoint, inducing a mitotic arrest either by stabilising or destabilising microtubule dynamics. This arrest prevents separation of the duplicated chromosomes to form the two daughter cells. Prolonged arrest in mitosis forces a cell either into mitotic exit without cytokinesis (mitotic slippage or adaption) or into mitotic catastrophe leading to cell death [Rieder C L and Malato H, Dev. Cell 7, a 637, 2004]. In contrast, inhibitors of Bub1 prevent the establishment and/or functionality of the mitotic checkpoint, which finally results in severe chromosomal missegregation, induction of apoptosis and cell death.

These findings suggest that Bub1 Inhibitors should be of therapeutic value for the treatment of proliferative disorders associated with enhanced uncontrolled proliferative cellular processes such as, for example, cancer, inflammation, arthritis, viral diseases, cardiovascular diseases, or fungal diseases in a warm-blooded animal such as man.

Due to the fact that especially cancer disease as being expressed by uncontrolled proliferative cellular processes in tissues of different organs of the human- or animal body still is not considered to be a controlled disease in that sufficient drug therapies already exist, there is a strong need to provide further new therapeutically useful drugs, preferably inhibiting new targets and providing new therapeutic options.

DESCRIPTION OF THE INVENTION

Therefore, inhibitors of Bub1 represent valuable compounds that should complement therapeutic options either as single agents or in combination with other drugs.

In accordance with a first aspect, the invention relates to compounds of formula (I)

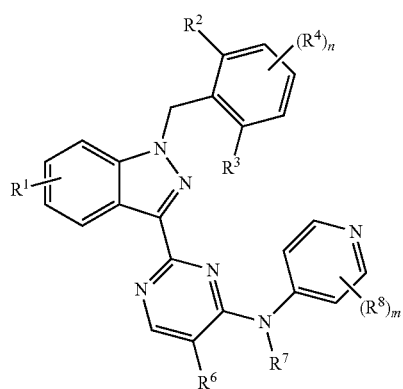

(I)

in which
$R^1$ is hydrogen, halogen, 1-3C-alkyl,
$R^2/R^3$ are independently from each other hydrogen, halogen, cyano, hydroxy 1-6C-haloalkyl, 1-6C-haloalkoxy, 1-6C-alkoxy,
$R^4$ is independently hydrogen, hydroxy, halogen, cyano, $NO_2$, 1-6C-alkyl, 2-6C-alkenyl, 2-6C-alkynyl, 1-6C-haloalkyl, 1-6C-hydroxyalkyl, 1-6C-alkoxy, —O-(2-6Calkylen)-O—C(O)-(1-6C-alkyl), 1-6C-haloalkoxy, —C(O)OR$^9$, -(1-6C-alkylen)-C(O)OR$^9$, —C(O)-(1-6C-alkyl), —C(O)NR$^{10}$R$^{11}$, 3-7C-cycloalkyl, —S-(1-6C-haloalkyl), SF$_5$, —SO$_2$NH-(3-7C-cycloalkyl), —SO$_2$NR$^{10}$R$^{11}$, NR$^{10}$R$^{11}$, heteroaryl which optionally is substituted independently one or more times with cyano, 1-4C-alkyl, 1-6C-haloalkyl, 1-6C-haloalkoxy, C(O)OR$^9$, C(O)NR$^{10}$R$^{11}$,
whereby two of $R^2$, $R^3(R^4)_n$, when positioned ortho to each other, may form together with the two carbon atoms to which they are attached, a heterocyclic 5-, 6- or 7-membered ring containing 1 or 2 heteroatoms selected from O or N, and optionally containing an additional double bond and/or optionally substituted by an oxo (=O) group and/or an 1-4C-alkyl group, n 0-3
$R^6$ is (a) hydrogen;
(b) hydroxy;
(c) cyano;
(d) 1-6C-alkoxy optionally substituted independently one or more times with
  (d1) OH,
  (d2) —O-(1-6C-alkyl)
  (d3) C(O)OR$^9$,
  (d4) C(O)NR$^{10}$R$^{11}$,
  (d5) NR$^{10}$R$^{11}$,
  (d6) —S-(1-6C-alkyl),
  (d7) —S(O)-(1-6C-alkyl),
  (d8) —SO$_2$-(1-6C-alkyl)
  (d9) SO$_2$NR$^{10}$R$^{11}$,
  (d10) heterocyclyl, which is optionally substituted with C(O)OR$^9$, or oxo (=O),
  (d11) heteroaryl, which is optionally substituted independently one or more times with cyano, 1-4C-alkyl, 1-6C-haloalkyl, 1-6C-haloalkoxy, C(O)OR$^9$, C(O)NR$^{10}$R$^{11}$, (1-6C-alkylen)-O-(1-6C-alkyl),
(e) SO$_2$NR$^{10}$R$^{11}$,
(f) 3-7C-cycloalkoxy,
(g) 1-6C-haloalkoxy,
(h) COOR$^9$,
(i) —C(O)NR$^{10}$R$^{11}$,
(j) —O-heteroaryl opt. subst. with CN

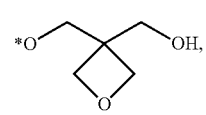

(k)

hereby the * is the point of attachment,
(l) —O-(2-6C-alkylen)-O-(1-6C-alkyl) which is optionally substituted with hydroxy, NH(CO)OR$^9$,
$R^7$ is
(a) hydrogen,
(b) 1-6C-alkyl, which is optionally substituted with heteroaryl
(c) 1-6C-haloalkyl,
(d) 1-6C-hydroxyalkyl,

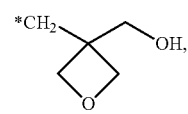

(e)

whereby the * is the point of attachment,
(f) —C(O)-(1-6C-alkyl)
(g) —C(O)-(1-6C-alkylen)O-(1-6C-alkyl)

(h) —C(O)-(1-6C-alkylen)-O-(2-6C-alkylen)-O-(1-6C-alkyl)
(i) —C(O)-heterocyclyl,
(j) benzyl whereby the phenyl ring Is opt. subst with 1-5 substituents independently selected from the group consisting of hydrogen, halogen, 1-4C-alkyl, 1-4C-haloalkyl, 1-4C-alkoxy, 1-4C-haloalkoxy, cyano, C(O)OR$^9$,
(k) heteroaryl
or
optionally, R$^6$ and R$^7$ together with the nitrogen atom to which R$^7$ is attached form a 6-membered ring which may contain one further heteroatom selected from the group consisting of O, S, N,
and which is optionally substituted by (1-6C-alkyl)-OH, (1-6C-alkyl)-NR$^{10}$R$^{11}$,
R$^8$ is hydrogen, halogen, hydroxy, cyano, 1-6C-alkyl, 1-6C-hydroxyalkyl, 1-6C-haloalkyl, 1-6C-haloalkoxy, C(O)OR$^9$, C(O)NR$^{10}$R$^{11}$,
m is 0-4
R$^9$ is (a) hydrogen,
(b) 1-6C-alkyl which optionally is substituted with hydroxy,
R$^{10}$, R$^{11}$ are independently from each other hydrogen, 1-4C-alkyl, 1-4C-hydroxyalkyl, 1-4C-alkoxy, —(CO)-(1-6C-alkyl), CHO, COOR$^9$, or together with the nitrogen atom to which they are attached form a 4-6-membered heterocyclic ring optionally containing one further heteroatom selected from the group consisting of O, S or N, and which is optionally substituted with 1-2 fluorine atoms or COOR$^9$,
or an N-oxide, a salt, a tautomer or a stereoisomer of said compound, or a salt of said N-oxide, tautomer or stereoisomer.

According to a further aspect of the invention, the invention relates to compounds of formula (I)
wherein
R$^1$ is hydrogen, halogen, 1-3C-alkyl,
R$^2$/R$^3$ are independently from each other hydrogen, halogen, cyano, 1-6C-haloalkyl, 1-6C-haloalkoxy,
R$^4$ is independently hydrogen, halogen, cyano, 1-6C-alkyl, 2-6C-alkenyl, 1-6C-haloalkyl, 1-6C-hydroxyalkyl, 1-6C-alkoxy, 1-6C-haloalkoxy, —C(O)OR$^9$, -(1-6C-alkylen)-C(O)OR$^9$, —C(O)-(1-6C-alkyl), —C(O)NR$^{11}$R$^{11}$, 3-7C-cycloalkyl, —S-(1-6C-haloalkyl), SF$_5$, —SO$_2$NH-(3-7-cycloalkyl), —SO$_2$NR$^{10}$R$^{11}$, heteroaryl which optionally is substituted independently one or more times with cyano, 1-4C-alkyl, 1-6C-haloalkyl, 1-6C-haloalkoxy, C(O)OR$^9$, C(O)NR$^{10}$R$^{11}$,
whereby two of R$^2$, R$^3$(R$^4$)$_n$, when positioned ortho to each other, may form together with the two carbon atoms to which they are attached, a heterocyclic 5-, 6- or 7-membered ring containing 1 or 2 heteroatoms selected from O or N, and optionally an additional double bond and/or a carbonyl group and/or an 1-4C-alkyl group,
n 0-3
R$^6$ is (a) hydrogen;
(b) hydroxy;
(c) cyano;
(d) 1-6C-alkoxy opt. subst. with
(d1) 1-2 OH,
(d2) NR$^{10}$R$^{11}$,
(d3) SO$_2$NR$^{10}$R$^{11}$,
(d4) heterocyclyl,
(d5) heteroaryl, which is optionally substituted independently one or more times with cyano, 1-4Calkyl, 1-6C-haloalkyl, 1-6C-haloalkoxy, C(O)OR$^9$, C(O)NR$^{10}$R$^{11}$,
(e) SO$_2$NR$^{10}$R$^{11}$,
(f) 3-7C-cycloalkoxy,
(g) 1-6C-haloalkoxy,
(h) —C(O)NR$^{10}$R$^{11}$,
(i) —O-heteroaryl opt. subst. with CN

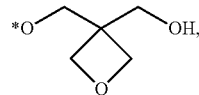

(j)

whereby the * is the point of attachment,
R$^7$ is
(a) hydrogen,
(b) 1-6C-alkyl, which is optionally substituted with heteroaryl
(c) 1-6C-haloalkyl,
(d) 1-6C-hydroxyalkyl,

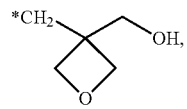

(e)

whereby the * is the point of attachment,
(f) —C(O)-(1-6C-alkyl)
(g) —C(O)-(1-6C-alkylen)-O-(1-6C-alkyl)
(h) —C(O)-(1-6C-alkylen)-O-(1-6C-alkylen)-O-(1-6C-alkyl)
(i) —C(O)-heterocyclyl,
(j) benzyl whereby the phenyl ring is opt. subst with 1-5 substituents independently selected from the group consisting of
hydrogen, halogen, 1-4Calkyl, 1-4C-haloalkyl, 1-4C-alkoxy, 1-4C-haloalkoxy, cyano,
C(O)OR$^9$,
(k) heteroaryl
or
optionally R$^6$ and R$^7$ together with the nitrogen atom to which they are attached form a 6-membered ring which may contain one further heteroatom selected from the group consisting of O, S, N,
and which is optionally substituted by hydroxy-(1-6alkyl),
R$^8$ is hydrogen, halogen, cyano, 1-6C-haloalkyl, 1-6C-haloalkoxy, C(O)OR$^9$, C(O)NR$^{10}$R$^{11}$,
m is 0-4
R$^9$ is (a) hydrogen,
(b) 1-6C-alkyl which optionally may be substituted with hydroxy,
R$^{10}$, R$^{11}$ are independently from each other hydrogen, 1-4C-alkyl, 1-4C-hydroxyalkyl, 1-4C-alkoxy, or
together with the nitrogen atom to which they are attached form a 5-6-membered heterocyclic ring optionally containing one further heteroatom selected from the group consisting of O, S or N,
or an N-oxide, a salt, a tautomer or a stereoisomer of said compound, or a salt of said N-oxide, tautomer or stereoisomer.

Another aspect of the invention are compounds of formula (I) according to claim 1, wherein
$R^1$ is hydrogen, halogen, 1-3C-alkyl,
$R^2/R^3$ are independently from each other hydrogen, halogen, cyano, hydroxy, 1-3C-haloalkyl, 1-3C-haloalkoxy, 1-3C-alkoxy,
$R^4$ is independently hydrogen, hydroxy, halogen, cyano, $NO_2$, 1-3C-alkyl, 2-3C-alkenyl, 2-3C-alkynyl, 1-3C-haloalkyl, 1-3C-hydroxyalkyl, 1-3C-alkoxy, —O-(2-3C-alkylen)-O—C(O)-(1-3C-alkyl), 1-3C-haloalkoxy, —C(O)OR$^9$, -(1-3C-alkylen)-C(O)OR$^9$, —C(O)-(1-3C-alkyl), —C(O)NR$^{10}$R$^{11}$, 3-7C-cycloalkyl, —S-(1-3C-haloalkyl), SF$_5$, —SO$_2$NH-(3-7C-cycloalkyl), —SO$_2$NR$^{10}$R$^{11}$, NR$^{10}$R$^{11}$, heteroaryl which optionally is substituted independently one or more times so with cyano, 1-3C-alkyl, 1-3C-haloalkyl, 1-3C-haloalkoxy, C(O)OR$^9$, C(O)NR$^{10}$R$^{11}$,
whereby two of R$^2$, R$^3$(R$^4$)$_n$, when positioned ortho to each other, may form together with the two carbon atoms to which they are attached, a heterocyclic 5-, 6- or 7-membered ring containing 1 or 2 heteroatoms selected from O or N, and optionally containing an additional double bond and/or optionally substituted by an oxo (═O) group and/or an 1-3C-alkyl group,
n 0-3
$R^6$ is (a) hydrogen;
(b) hydroxy;
(c) cyano;
(d) 1-6C-alkoxy optionally substituted independently one or more times with
(d1) OH,
(d2) —O-(1-3C-alkyl)
(d3) C(O)OR$^9$,
(d4) C(O)NR$^{10}$R$^{11}$,
(d5) NR$^{10}$R$^{11}$,
(d6) —S-(1-3C-alkyl),
(d7) —S(O)-1-3C-alkyl),
(d8) —SO$_2$-(1-3C-alkyl)
(d9) SO$_2$NR$^{10}$R$^{11}$,
(d10) heterocyclyl, which is optionally substituted with C(O)OR$^9$, or oxo (═O),
(d11) heteroaryl, which is optionally substituted independently one or more times with cyano, 1-3C-alkyl, 1-3C-haloalkyl, 1-3C-haloalkoxy, C(O)OR$^9$, C(O)NR$^{11}$R$^{11}$, (1-3C-alkylen)-O-(1-3C-alkyl),
(e) SO$_2$NR$^{10}$R$^{11}$,
(f) 3-7C-cycloalkoxy,
(g) 1-6C-haloalkoxy,
(h) COOR$^9$,
(i) —C(O)NR$^{10}$R$^{11}$,
(j) —O-heteroaryl opt. subst. with CN

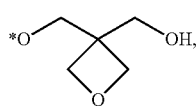

(k)

whereby the * is the point of attachment,
(l) —O-(2-3C-alkylen)-O-(1-3C-alkyl) which is optionally substituted with hydroxy, NH(CO)OR$^9$,
$R^7$ is
(a) hydrogen,
(b) 1-3C-alkyl, which is optionally substituted with heteroaryl (c) 1-3C-haloalkyl,
(d) 1-3C-hydroxyalkyl,

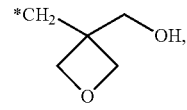

(e)

whereby the * is the point of attachment,
(f) —C(O)-(1-3C-alkyl)
(g) —C(O)-(1-3C-alkylen)-O-(1-3C-alkyl)
(h) —C(O)-(1-3C-alkylen)-O-(2-3C-alkylen)-O-(1-3C-alkyl)
(i) —C(O)-heterocyclyl,
(j) benzyl whereby the phenyl ring is opt. subst with 1-5 substituents independently selected from the group consisting of
hydrogen, halogen, 1-4C-alkyl, 1-4C-alkoxy, 1-4C-haloalkoxy, cyano, C(O)OR$^9$,
(k) heteroaryl
or
optionally, R$^6$ and R$^7$ together with the nitrogen atom to which R$^7$ is attached form a 6-membered ring which may contain one further heteroatom selected from the group consisting of O, S, N,
and which is optionally substituted by (1-3C-alkyl)-OH, (1-3C-alkyl)-NR$^{10}$R$^{11}$,
$R^8$ is hydrogen, halogen, hydroxy, cyano, 1-3C-alkyl, 1-3C-hydroxyalkyl, 1-3C-haloalkyl, 1-3C-haloalkoxy, C(O)OR$^9$, C(O)NR$^{10}$R$^{11}$,
m is 0-4
$R^9$ is (a) hydrogen,
(b) 1-3C-alkyl which optionally is substituted with hydroxy,
R$^{10}$, R$^{11}$ are independently from each other hydrogen, 1-3C-alkyl, 1-3C-hydroxyalkyl, 1-3C-alkoxy, —(CO)-(1-3C-alkyl), CHO, COOR$^9$ or together with the nitrogen atom to which they are attached form a 4-6-membered heterocyclic ring optionally containing one further heteroatom selected from the group consisting of 0, S or N, which is optionally substituted with 1-2 fluorine atoms or COOR$^9$, or an N-oxide, a salt, a tautomer or a stereoisomer of said compound, or a salt of said N-oxide, tautomer or stereoisomer.

A further aspect of the invention are compounds of formula (I) according to claim 1, wherein
$R^1$ is hydrogen, halogen, 1-4C-alkyl,
$R^2/R^3$ are independently from each other hydrogen, halogen, cyano, 1-4C-haloalkyl,
1-4C-haloalkoxy,
$R^4$ is independently hydrogen, halogen, cyano, 1-4C-alkyl, 2-4C-alkenyl, 1-4C-haloalkyl, 1-4C-hydroxyalkyl, 1-4C-alkoxy, 1-4C-haloalkoxy, —C(O)OR$^9$, -(1-4C-alkylen)-C(O)OR$^9$, —C(O)-(1-4C-alkyl), —C(O)NR$^{10}$R$^{11}$, 3-6C-cycloalkyl, —S-(1-6C-haloalkyl), SF$_5$, —SO$_2$NH-(3-6-cycloalkyl), —SO$_2$NR$^{10}$R$^{11}$, heteroaryl which optionally is substituted independently one or more times with cyano, 1-4C-alkyl, 1-6C-haloalkyl, 1-6C-haloalkoxy, C(O)OR$^9$, C(O)NR$^{10}$R$^{11}$,
whereby two of R$^2$, R$^3$(R$^4$)$_n$, when positioned ortho to each other, may form together with the two carbon atoms to which they are attached, a heterocyclic 5-, 6- or 7-membered ring containing 1 or 2 heteroatoms selected from O or N, and optionally an additional double bond and/or a carbonyl group and/or an 1-4C-alkyl group, n 0-3

$R^6$ is (a) hydrogen;
(b) hydroxy;
(c) cyano;
(d) 1-4C-alkoxy opt. subst. with
  (d1) 1-2 OH,
  (d2) $NR^{10}R^{11}$,
  (d3) $SO_2NR^{10}R^{11}$,
  (d4) heterocyclyl,
  (d5) heteroaryl, which is optionally independently one or more times substituted with cyano, 1-4C-alkyl, 1-6C-haloalkyl, 1-6C-haloalkoxy, $C(O)OR^9$, $C(O)NR^{10}R^{11}$,
(e) $SO2NR^{10}R^{11}$;
(f) 3-6C-cycloalkoxy,
(g) 1-4C-haloalkoxy,
(h) —$C(O)NR^{10}R^{11}$,
(i) O-heteroaryl opt. subst. with CN

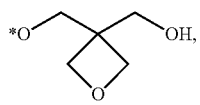 (j)

whereby the * is the point of attachment, $R^7$ is
(a) hydrogen,
(b) 1-4C-alkyl, which is optionally substituted with heteroaryl
(c) 1-4C-haloalkyl,
(d) 1-4C-hydroxyalkyl,

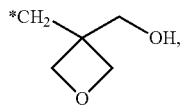 (e)

whereby the * is the point of attachment,
(f) —C(O)-(1-4C-alkyl)
(g) —C(O)-(1-4C-alkylen)-O-(1-4C-alkyl)
(h) —C(O)-(1-4C-alkylen)-O-(1-4C-alkylen)-O-(1-4C-alkyl)
(i) —C(O)-heterocyclyl,
(j) benzyl whereby the phenyl ring is opt. subst with 1-5 substituents independently selected from the group consisting of
  hydrogen, halogen, 1-4C-alkyl, 1-4C-haloalkyl, 1-4C-alkoxy, 1-4C-haloalkoxy, cyano,
  C(O)OR9,
(k) heteroaryl
or
optionally $R^6$ and $R^7$ together with the nitrogen atom to which they are attached form a 6-membered ring which may contain one further heteroatom selected from the group consisting of O, S, N,
  and which is optionally substituted by hydroxy-(1-4-alkyl), $R^8$ is hydrogen, halogen, $C(O)NR^{10}R^{11}$, $C(O)OR^9$, 1-4C-haloalkyl, 1-4C-haloalkoxy, cyano, m is 0-4

$R^9$ is (a) hydrogen,
(b) 1-4C-alkyl which optionally may be substituted with hydroxy, $R^{10}$, $R^{11}$ are independently from each other hydrogen, 1-4C-alkyl, 1-4C-hydroxyalkyl, 1-4C-alkoxy, or
together with the nitrogen atom to which they are attached form a 5-6-membered heterocyclic ring optionally containing one further heteroatom selected from the group consisting of O, S or N, or an N-oxide, a salt, a tautomer or a stereoisomer of said compound, or a salt of said N-oxide, tautomer or stereoisomer.

Another aspect of the invention are compounds of formula (I) according to claim 1, wherein $R^1$ is hydrogen, 1-3C-alkyl, $R^2/R^3$ are independently from each other hydrogen, halogen, cyano, hydroxy, 1-4C-haloalkyl, 1-4C-alkoxy, $R^4$ is independently hydrogen, hydroxy, halogen, cyano, 1-4C-alkyl, 2-4C-alkenyl, 2-4C-alkynyl, 1-4C-haloalkyl, 1-4C-hydroxyalkyl, 1-4C-alkoxy, —O-(2-4C-alkylen)-O—C(O)-(1-4C-alkyl), 1-4C-haloalkoxy, —$C(O)OR^9$, -(1-4C-alkylen)-$C(O)OR^9$, —C(O)-(1-4C-alkyl), —$C(O)NR^{10}R^{11}$, 3-7C-cycloalkyl, —S-(1-4C-haloalkyl), $SF_5$, —$SO_2NH$-(3-7C-cycloalkyl), —$SO_2NR^{10}R^{11}$, $NR^{10}R^{11}$, heteroaryl which optionally is substituted independently one or more times with cyano, 1-4C-alkyl, 1-4C-haloalkyl, 1-4C-haloalkoxy, $C(O)OR^9$, $C(O)NR^{10}R^{11}$,
  whereby two of $R^2$, $R^3(R^4)_n$, when positioned ortho to each other, may form together with the two carbon atoms to which they are attached, a heterocyclic 5-, 6- or 7-membered ring containing 1 or 2 heteroatoms selected from O or N, and optionally containing an additional double bond and/or optionally substituted by an oxo (=O) group and/or an 1-4C-alkyl group, n 0-3

$R^6$ is (a) hydrogen;
(b) hydroxy;
(d) 1-4C-alkoxy optionally substituted independently one or more times with
  (d1) OH,
  (d2) —O-(1-4C-alkyl)
  (d3) $C(O)OR^9$,
  (d4) $C(O)NR^{10}R^{11}$,
  (d5) $NR^{10}R^{11}$,
  (d6) —S-(1-4C-alkyl),
  (d7) —S(O)-(1-4C-alkyl),
  (d8) —$SO_2$-(1-4C-alkyl)
  (d9) $SO_2NR^{10}R^{11}$,
  (d10) heterocyclyl, which is optionally substituted with $C(O)OR^9$, or oxo (=O),
  (d11) heteroaryl, which is optionally substituted independently one or more times with cyano, 1-4C-alkyl, 1-4C-haloalkyl, 1-4C-haloalkoxy, $C(O)OR^9$, $C(O)NR^{10}R^{11}$, (1-4C-alkylen)-O-(1-4C-alkyl),
(e) $SO_2NR^{10}R^{11}$,
(f) 3-7C-cycloalkoxy,
(g) 1-6C-haloalkoxy,
(h) $COOR^9$,
(i) —$C(O)NR^{10}R^{11}$,
(j) —O-heteroaryl opt. subst. with CN

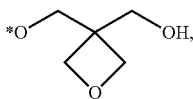

whereby the * is the point of attachment,
(l) —O-(2-4C-alkylen)-O-(1-4C-alkyl) which is optionally substituted with hydroxy, NH(CO)OR$^9$,
R$^7$ is
(a) hydrogen,
(b) (1-4C-alkyl)-heteroaryl
(c) 1-4C-haloalkyl,
(d) 1-4C-hydroxyalkyl,

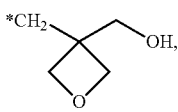

whereby * is the point of attachment,
(f) —C(O)-(1-4C-alkyl)
(g) —C(O)-(1-4C-alkylen)-O-(1-4C-alkyl)
(h) —C(O)-(1-4C-alkylen)-O-(2-4C-alkylen)-O-(1-4C-alkyl)
(i) —C(O)-heterocyclyl,
(j) benzyl whereby the phenyl ring is opt. subst with 1-5 substituents independently selected from the group consisting of
hydrogen, halogen, 1-4C-alkyl, 1-4C-alkoxy, 1-4C-haloalkoxy, cyano, C(O)OR$^9$,
(k) heteroaryl
or
optionally, R$^6$ and R$^7$ together with the nitrogen atom to which R$^7$ is attached form a 6-membered ring which may contain one further heteroatom selected from the group consisting of O, S, N,
and which is optionally substituted by (1-4C-alkyl)-OH, (1-4C-alkyl)-NR$^{10}$R$^{11}$,
R$^8$ is hydrogen, halogen, hydroxy, cyano, C(O)NR$^{10}$R$^{11}$, 1-4C-alkyl, 1-4C-hydroxyalkyl, 1-4C-haloalkyl, 1-4C-haloalkoxy,
m is 0-2,
R$^9$ is hydrogen, 1-4C-alkyl which optionally is substituted with hydroxy,
R$^{10}$, R$^{11}$ are independently from each other hydrogen, 1-4C-alkyl, 1-4C-hydroxyalkyl, 1-4C-alkoxy, —C(O)-(1-4C-alkyl), or COOR$^9$ or together with the nitrogen atom to which they are attached form a 4-6-membered heterocyclic ring optionally containing one further heteroatom selected from the group consisting of 0, S or N, which is optionally substituted with 1-2 fluorine atoms or COOR$^9$, or an N-oxide, a salt, a tautomer or a stereoisomer of said compound, or a salt of said N-oxide, tautomer or stereoisomer.

A further aspect of the invention are compounds of formula (I) according to claim 1, wherein
R$^1$ is hydrogen, halogen,
R$^2$/R$^3$ are independently from each other hydrogen, halogen, cyano, 1-4C-haloalkyl,
R$^4$ is independently hydrogen, halogen, cyano, 1-4C-alkyl, 2-4C-alkenyl, 1-4C-haloalkyl, 1-4C-hydroxyalkyl, 1-4C-alkoxy, 1-4C-haloalkoxy, —C(O)OR$^9$, -(1-4C-alkylen)-C(O)OR$^9$, —C(O)-(1-4C-alkyl), —C(O)NR10R11, 3-7C-cycloalkyl, —S-(1-4C-haloalkyl), SF$_5$, —SO$_2$NH-(3-7C-cycloalkyl), —SO$_2$NR$^{10}$R$^{11}$, heteroaryl which optionally is substituted independently one or more times with cyano, 1-4C-alkyl, 1-6C-haloalkyl, 1-6C-haloalkoxy, C(O)OR$^9$, C(O)NR$^{10}$R$^{11}$,
whereby two of R$^2$, R$^3$(R$^4$)$_m$, when positioned ortho to each other, may form together with the two carbon atoms to which they are attached, a heterocyclic 5-, 6- or 7-membered ring containing 1 or 2 heteroatoms selected from O or N, and optionally an additional double bond and/or a carbonyl group and/or an 1-4C.alkyl group,
n 0-3
R$^6$ is (a) hydrogen;
(b) hydroxy;
(d) 1-6C-alkoxy opt. subst. with
(d1) 1-2 OH,
(d2) NR$^{10}$R$^{11}$,
(d3) SO$_2$NR$^{10}$R$^{11}$,
(g) 1-6C-haloalkoxy,

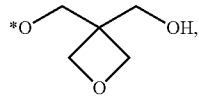

whereby * is the point of attachment,
R$^7$ is
(a) hydrogen,
(c) 1-6C-haloalkyl,
(d) 1-4C-hydroxyalkyl,

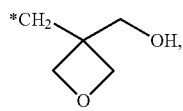

whereby * is the point of attachment,
(f) —C(O)-(1-4C-alkyl)
(g) —C(O)-(1-4C-alkylen)-O-(1-4C-alkyl)
(h) —C(O)-(1-4C-alkylen)-O-(1-4C-alkylen)-O-(1-4C-alkyl)
(i) —C(O)-heterocyclyl,
(j) benzyl whereby the phenyl ring is opt. subst with 1-5 substituents independently selected from the group consisting of
hydrogen, halogen, 1-4C-alkyl, 1-4C-haloalkyl, 1-4C-alkoxy, 1-4C-haloalkoxy, cyano, C(O)OR$^9$,
or
optionally R$^6$ and R$^7$ together with the nitrogen atom to which they are attached form a 6-membered ring which may contain one further heteroatom selected from the group consisting of O, S, N,
and which is optionally substituted by hydroxy-(1-4alkyl),
R$^8$ is hydrogen, halogen, C(O)NR$^{10}$R$^{11}$, 1-4C-haloalkyl, 1-4C-haloalkoxy, cyano,
m is 0-2,
R$^9$ is 1-4C-alkyl which optionally may be substituted with hydroxy, $R^{10}$, $R^{11}$ are independently from each other hydrogen, 1-4C-alkyl, 1-4C-hydroxyalkyl, 1-4C-alkoxy, or
together with the nitrogen atom to which they are attached form a 5-6-membered heterocyclic ring optionally containing one further heteroatom selected from the group consisting of O, S or N,
or an N-oxide, a salt, a tautomer or a stereoisomer of said compound, or a salt of said N-oxide, tautomer or stereoisomer.

A further aspect of the invention are compounds of formula (I) according to claim 1, wherein
$R^1$ is hydrogen,
$R^2/R^3$ are independently from each other hydrogen, halogen,
$R^4$ is independently hydrogen, 1-3C-alkyl, 2-3C-alkenyl, 1-3C-haloalkyl, 1-3C-hydroxyalkyl, 1-3C-alkoxy, 1-3C-haloalkoxy, —C(O)OR$^9$, —C(O)-(1-3C-alkyl), —C(O)NR$^{10}$R$^{11}$, 3-4C-cycloalkyl, —SO$_2$NR$^{10}$R$^{11}$,
n 0-3
$R^6$ is (a) hydrogen;
  (b) hydroxy;
  (d) 1-3C-alkoxy opt. subst. with
    (d1) 1-2 OH,
    (d2) NR$^{10}$R$^{11}$,
  (g) 1-3C-haloalkoxy,

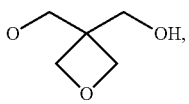
(k)

$R^7$ is hydrogen,
$R^8$ is hydrogen, C(O)NR$^{10}$R$^{11}$, 1-3C-haloalkyl,
m is 0-2,
$R^9$ is 1-3C-alkyl which optionally may be substituted with hydroxy,
$R^{10}$, $R^{11}$ are independently from each other hydrogen, 1-3C-alkyl, 1-3C-hydroxyalkyl, 1-3C-alkoxy, or
together with the nitrogen atom to which they are attached form a 5-6-membered heterocyclic ring optionally containing one further heteroatom selected from the group consisting of O, S or N,
or an N-oxide, a salt, a tautomer or a stereoisomer of said compound, or a salt of said N-oxide, tautomer or stereoisomer.

A further aspect of the invention are compounds of formula (I) according to claim 1, compounds of formula (I) according to claim 1,
wherein,
$R^1$ is hydrogen, $R^2/R^3$ is independently halogen, cyano, hydroxy, 1-3C-haloalkyl, 1-4C-alkoxy or 1-3C-haloalkoxy,
$R^4$ is independently of each other hydrogen, halogen, cyano, NO$_2$, hydroxy, -1-4C-alkyl, 2-3C-alkenyl, 2-3C-alkynyl, 1-3C-haloalkyl, (1-4C-alkyl)-OH, 1-3C-alkoxy, 1-3C-haloalkoxy, —O-(2-3C-alkylen)-O—C(O)-(1-3C-alkyl), —C(O)(1-3C-alkyl), —COOH, —C(O)O(1-4C-alkyl), (1-3C-alkyl)-COOH, -(1-4C-alkyl)C(O)O(1-3C-alkyl), —C(O)NR$^{10}$R$^{11}$, —SO$_2$—NH-(3-6C-cycloalkyl), —SO$_2$—NR$^{10}$R$^{11}$, NR$^{10}$R$^{11}$, heteroaryl, —S—CF$_3$, SF$_5$,
whereby two of R$^2$, R$^3$(R$^4$)$_n$, when positioned ortho to each other may form together
—O—CH$_2$—CH$_2$—CH$_2$—O—, —O—CH$_2$—CH$_2$—, —(CH$_3$)C═CH—(C═O)—O—,
—CH$_2$—(C═O)—O—, —(CH$_2$)$_2$—(C═O)—NH—,
which in addition together with the two carbon atoms to which they are attached form a 5-7-membered ring,
n is 0, 1, 2, 3,
$R^6$ is hydrogen, hydroxy, cyano, —O-cyclopropyl, 1-3C-alkyoxy, 1-3C-haloalkoxy, —O-(2-3C-alkyl)-OH, —O-(2-3C-alkyl)-NH$_2$, —O-(2-3C-alkyl)-O-(1-3C-alkyl), —O-(2-3C-alkyl)-O-(2-3C-alkyl)-OH, —O—CH$_2$—CH(OH)—CH$_2$OH, —O-(1-3C-alkyl)-COOH, —O-(1-3C-alkyl)C(O)—O-(1-3C-alkyl), —O-(2-3C-alkyl)-O-(2-3C-alkyl)-NH—C(O)—O-(1-4C-alkyl), C(O)—NH$_2$, —O—CH$_2$—C(O)-(3-fluoro-N-azetidine), —O—CH$_2$—C(O)-(3,3-difluoro-N-azetidine), —O(1-3C-alkyl)-NR$^{10}$R$^{11}$, —O—CH$_2$—CH(OH)—CH$_2$—N-piperidinyl, —O-(2-3C-alkyl)-S-(2-3C-alkyl), —O-(2-3C-alkyl)-SO$_2$NH$_2$, —O-(2-3C-alkyl)SO$_2$-(1-3C-alkyl), —O-(2-3C-alkyl)-S-(2-3C-alkyl),

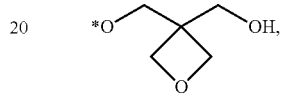

whereby * is the point of attachment,
—O-(1-3C-alkyl)heteroaryl,
—O-heteroaryl which is optionally substituted one or more times with cyano,
—O-(1-3C-alkyl)-(heterocyclyl, having 1-2 heteroatoms selected from the group consisting of N, O and which is optionally substituted with oxo (═O)),
—O-(1-3C-alkyl)-(heteroaryl)-(1-3C-alkyl)-O-(1-3C-alkyl),
—O-(1-3C-alkyl)-heterocyclyl which is optionally substituted with —C(O)—O-(1-4C-alkyl), C(O)NH$_2$, or
$R^6$ together with $R^7$ is a 6-membered ring including the nitrogen atom of the
$R^7$ bearing amino group which may contain one further heteroatom selected from O, S or N and which in addition may be substituted with oxo (═O), —CH$_2$—NH—CHO or (1-3C-alkyl)-OH,
$R^7$ is hydrogen, 1-3C-alkyl, 1-3C-haloalkyl, 1-3C-hydroxyalkyl

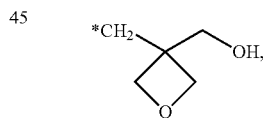

whereby * is the point of attachment,
-(1-3C-alkyl)heteroaryl, heteroaryl, —C(O)-heterocyclyl, —C(O)-(1-3C-alkyl)-O-(1-3C-alkyl), —C(O)-(1-3C-alkyl), —C(O)(1-3C-alkyl)-O-(2-3C-alkyl)-O-(1-3C-alkyl), or benzyl which is optionally substituted one or more times with halogen, cyano, methyl, difluoromethyl, 1-3C-alkoxy, 1-3C-haloalkoxy, —C(O)O(1-3C-alkyl),
$R^8$ is hydrogen, fluorine, cyano, CF$_3$, C(O)NH$_2$, C(O)NHCH$_3$, C(O)OH, C(O)O(1-3Calkyl), C(O)(1-3C-alkyl)-OH,
m is 0, 1 or 2
$R^{10}$/$R^{11}$ hydrogen, 1-3C-alkyl, (1-3C-alkyl)-OH, C(O)(1-3Calkyl),
or an N-oxide, a salt, a tautomer or a stereoisomer of said compound, or a salt of said N-oxide, tautomer or stereoisomer.

A further aspect of the invention are compounds of formula (I) according to claim 1, wherein
$R^1$ is hydrogen,
$R^2/R^3$ is independently fluorine, chlorine, bromine, cyano, $CF_3$, or —O—CH2-CF3,
$R^4$ is independently of each other hydrogen, fluorine, chlorine, bromine or iodine, cyano, —CH3, —C3H9, cyclopropyl, 1-propenyl, —CF3, —CH2-OH, —CH2-CH2-OH, —C(CH3)2-OH, —CH2-C(CH3)2-OH, —C(CH3)2-CH2-OH, —OCH3, —OCF3, —OCF2H, —OCH2CF3, —C(O)CH3, —COOH, —C(O)OCH3, —C(O)OC2H5, —C(O)OC(CH3)3, —CH2-COOC2H5, —CH2-COOH, —C(CH3)2-COOC2H5, —C(O)NH2, —C(O)NH(CH3), —C(O)N(CH3)2, —C(O)NH—(CH2)2-OH, —C(O)—(N-morpholino), —SO2-NH-cyclopropyl, —SO2-(N-morpholino), 5-methyl-oxa-diazol-3-yl, —S—CF3, SF5,
whereby two of $R^2$, $R^3(R^4)_n$, when positioned ortho to each other, form together with the two carbon atoms to which they are attached,
—O—CH2—CH2—CH2—O—, —O—CH2—CH2—, —(CH3)C=CH—(C=O)—O—,
—CH2—(C=O)—O—, —(CH2)2-(C=O)—NH—,
n is 0, 1, 2, 3,
$R^6$ is hydrogen, hydroxy, cyano, —O-cyclopropyl, —OCH3, —OCF3, —OCF2H, —OCH2CF3, —O—(CH2)2-OH, —O(CH2)2-N(CH3)2, —O-CH2-SO2NH2,

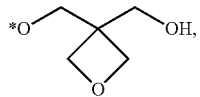

whereby * is the point of attachment,
—O—(CH2)2-tetrazolyl, —O-CH2-tetrazolyl, —O-pyridine-4-yl, —O-(3-cyanopyridine-4-yl), —C(O)NH2, or
$R^6$ together with $R^7$ is a 6-membered ring including the nitrogen atom of the
$R^7$ bearing amino group which may contain one further heteroatom selected from O, S or N and which in addition may be substituted with a carbonyl group or —CH2-OH,
$R^7$ is hydrogen, methyl, difluoromethyl, hydroxyethyl,

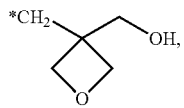

whereby * is the point of attachment,
—(CH2)2-tetrazolyl, pyridine-4-yl, —C(O)-tetrahydropyran-4-yl, —C(O)—CH2-O—CH3, —C(O)—CH3, —C(O)CH2-O—(CH2)2-O—CH3 or benzyl which is optionally substituted one or more times with fluorine, chlorine, cyano, methyl, difluoromethyl, methoxy, ethoxy, difluormethoxy, trifluoromethoxy, —O-CH2-CF3, —C(O)OCH3,
$R^8$ is hydrogen, fluorine, cyano, CF3, C(O)NH2, C(O)OH, C(O)OC2H5, C(O)(CH2)2-OH,
m is 0, 1 or 2
$R^9$ is hydrogen, methyl, ethyl, tert.-butyl, hydroxyethyl,
$R^{10}/R^{11}$ is independently from each other hydrogen, methyl, hydroxyethyl, or an N-oxide, a salt, a tautomer or a stereoisomer of said compound, or a salt of said N-oxide, tautomer or stereoisomer.

A further aspect of the invention are compounds of formula (I) according to claim 1, wherein
$R^1$ is hydrogen,
$R^2/R^3$ is independently fluorine, chlorine, bromine, cyano, $CF_3$, or —O—$CH_2$—$CF_3$,
$R^4$ is independently of each other hydrogen, fluorine, chlorine, bromine or iodine, cyano, —$CH_3$, —$C_3H_9$, cyclopropyl, 1-propenyl, —$CF_3$, —$CH_2$—OH, —$CH_2$—$CH_2$—OH, —$C(CH_3)_2$—OH, —$CH_2$—$C(CH_3)_2$—OH, —$C(CH_3)_2$—$CH_2$—OH, —$OCH_3$, —$OCF_3$, —$OCF_2H$, —$OCH_2CF_3$, —$C(O)CH_3$, —COOH, —$C(O)OCH_3$, —$C(O)OC_2H$, —$C(O)OC(CH_3)_3$, —$CH_2$—$COOC_2H_5$, —$CH_2$—COOH, —$C(CH_3)_2$—$COOC_2H_5$, —$C(O)NH_2$, —$C(O)NH(CH_3)$, —$C(O)N(CH_3)_2$, —$C(O)NH$—$(CH_2)_2$—OH, —C(O)—(N-morpholino), —$SO_2$—NH-cyclopropyl, —$SO_2$—(N-morpholino), 5-methyl-oxa-diazol-3-yl,
whereby two of $R^2$, $R^3(R^4)_n$, when positioned ortho to each other, form together with the two carbon atoms to which they are attached,
—O—$CH_2$—$CH_2$—$CH_2$—O—, —O—$CH_2$—$CH_2$—, —$(CH_3)C=CH$—$(C=O)$—O—, —$CH_2$—$(C=O)$—O—, —$(CH_2)2$-$(C=O)$—NH—,
n 0, 1, 2, or 3,
$R^6$ is hydrogen, hydroxy, —$OCH_3$, —$OCF_3$, —$OCF_2H$, —$OCH_2CF_3$, —O—$(CH_2)_2$—OH, —$O(CH_2)_2$—$N(CH_3)_2$, —O—$CH_2$—$SO_2NH_2$,

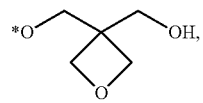

whereby * is the point of attachment,
$R^7$ is hydrogen, methyl, difluoromethyl, hydroxyethyl,

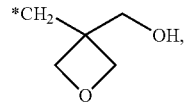

whereby * is the point of attachment,
—C(O)-tetrahydropyran-4-yl, —C(O)—$CH_2$—O—$CH_3$, —C(O)—$CH_3$, —$C(O)CH_2$—O—$(CH_2)_2$—O—$CH_3$ or benzyl which is optionally substituted one or more times with fluorine, chlorine, cyano, methyl, difluoromethyl, methoxy, ethoxy, difluormethoxy, trifluoromethoxy, —O—$CH_2$—$CF_3$, —$C(O)OCH_3$,
$R^8$ is hydrogen, fluorine, cyano, $C(O)NH_2$,
m is 0, 1 or 2
$R^9$ is hydrogen, methyl, ethyl, tert.-butyl, hydroxyethyl,
$R^{10}/R^{11}$ is independently from each other hydrogen, methyl, hydroxyethyl, or an N-oxide, a salt, a tautomer or a stereoisomer of said compound, or a salt of said N-oxide, tautomer or stereoisomer.

A further aspect of the invention are compounds of formula (I) according to claim 1,
wherein,
$R^1$ is hydrogen,
$R^2/R^3$ is independently hydrogen, fluorine, chlorine, bromine, cyano, hydroxy, $CF_3$, —O—$CH_3$ or —O—$CH_2$—$CF_3$,
$R^4$ is independently of each other hydrogen, fluorine, chlorine, bromine or iodine, cyano, $NO_2$, hydroxy, —$CH_3$, —C$_3$H$_7$, cyclopropyl, 1-propenyl, —C≡CH, —CF$_3$, —CH$_2$—OH, —CH$_2$—CH$_2$—OH, —C(CH$_3$)$_2$—OH, —CH$_2$—C(CH$_3$)$_2$—OH, —C(CH$_3$)$_2$—CH$_2$—OH, —OCH$_3$, —O—CH$_2$—CH$_3$, —OCF$_3$, —OCF$_2$H, —OCH$_2$CF$_3$, —O—(CH$_2$)—O—C(O)—CH$_3$, —C(O) CH$_3$, —COOH, —C(O)OCH$_3$, —C(O)OC$_2$H$_5$, —C(O) OC(CH$_3$)$_3$, —CH$_2$—COOH, —CH$_2$—COOC$_2$H, —C(CH$_3$)$_2$—COOC$_2$H$_5$, —C(O)NH$_2$, —C(O)NH(CH$_3$), —C(O)N(CH$_3$)$_2$, —C(O)NH—(CH$_2$)$_2$—OH, —C(O)—(N-morpholinyl), —SO$_2$—NH-cyclopropyl, —SO$_2$—(N-morpholinyl), NH$_2$, NH—C(O)(CH$_3$), 5-methyloxa-diazol-3-yl, N-pyrrolyl, N-pyrazolyl, —S—CF$_3$, SF$_5$, whereby two of R$^2$, R$^3$(R$^4$)$_n$, when positioned ortho to each other, form together —O—CH$_2$—CH$_2$—CH$_2$—O—, —O—CH$_2$—CH$_2$—, —(CH$_3$)C═CH—(C═O)—O—, —CH$_2$—(C═O)—O—, —(CH$_2$)$_2$—(C═O)—NH—, which together with the two carbon atoms to which they are attached form a 5-, 6- or 7-membered ring, n is 0, 1, 2, 3, R$^6$ is hydrogen, hydroxy, cyano, —O-cyclopropyl, —OCH$_3$, —OCF$_3$, —OCF$_2$H, —OCH$_2$CF$_3$, —O—(CH$_2$)$_2$—OH, —O—(CH$_2$)$_2$—NH$_2$, —O(CH$_2$)$_2$—N(CH$_3$)$_2$, —O—(CH$_2$)$_2$—OCH$_3$, —O—(CH$_2$)$_2$—O—(CH$_2$)$_2$—OH, —O—CH$_2$—CH(OH)—CH$_2$OH, —O—CH$_2$—CH(OH) CH$_2$—NH—C(O)OC(CH$_3$)$_3$, —O—CH$_2$—COOH, —O—CH$_2$—COOC$_2$H$_5$, C(O)NH$_2$, —O—CH$_2$—C(O)-(3-fluoro-N-azetidine), —O—CH$_2$—C(O)-(3,3-difluoro-N-azetidine), —O—CH$_2$—CH(OH)—CH$_2$—N-piperidi-nyl, —O—(CH$_2$)$_2$(morpholine-4-yl), —O—CH$_2$-(morpholine-2-yl), —O—CH$_2$-(morpholine-2-yl-4-tert.-butoxycarboxylate), —O—CH$_2$-(pyrrolidin-2-one-5-yl), —O—(CH$_2$)$_2$—S—CH$_3$, —O—(CH$_2$)$_2$—SO—CH$_3$, —O—(CH$_2$)$_2$—SO$_2$—CH$_2$, —O—CH$_2$—SO$_2$NH$_2$, —SO$_2$—CH(CH$_3$)$_2$,

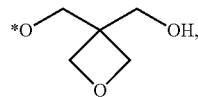

whereby
* is the point of attachment,
—O—(CH$_2$)$_2$-tetrazolyl, —O—CH$_2$-tetrazolyl, —O-pyridine-4-yl, —O-(3-cyanopyridine-4-yl), or —O—CH$_2$-(oxadiazole)-CH$_2$—O—CH$_3$, R$^7$ is hydrogen, methyl, difluoromethyl, hydroxyethyl,

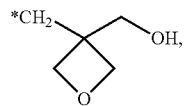

whereby * is the point of attachment,
—(CH$_2$)$_2$-tetrazolyl, pyridine-4-yl, —C(O)-tetrahydropy-ran-4-yl, —C(O)—CH$_2$—O—CH$_3$, —C(O)—CH$_3$, —C(O)CH$_2$—O—(CH$_2$)$_2$—O—CH$_3$, or benzyl which is optionally substituted one or more times with fluo-rine, chlorine, bromine, cyano, methyl, difluoromethyl, methoxy, ethoxy, difluormethoxy, trifluoromethoxy, —O—CH$_2$—CF$_3$, —C(O)OCH$_3$, or optionally, when R$^6$ is in position 5 of the pyrimidine ring system, R$^6$ and R$^7$ together with the nitrogen atom to which R$^7$ is attached form a 6-membered ring which may contain one further heteroatom selected from O, S or N and which in addition is optionally substituted by —CH$_2$—OH or —CH$_2$—NH—CHO R$^8$ is hydrogen, fluorine, hydroxy, cyano, CH$_3$, CF$_3$, CH$_2$—OH, OCH$_3$, C(O)OH, C(O)OCH$_3$, C(O)OC$_2$H, C(O)O(CH$_2$)$_2$—OH, C(O)NH$_2$, C(O)NHCH$_3$, m is 0, 1 or 2 or an N-oxide, a salt, a tautomer or a stereoisomer of said compound, or a salt of said N-oxide, tautomer or stereoiso-mer.

A further aspect of the invention are compounds of formula (I) according to claim 1, wherein wherein
R$^1$ is hydrogen or methyl,
R$^2$/R$^3$ is independently hydrogen, fluorine, chlorine, methyl,
R$^4$ is hydrogen, cyclopropyl, CH$_2$—OH, —C(CH$_3$)$_2$—OH, —O—CHF$_2$, —O—CH$_2$—CH$_3$, —CH═CH—CH$_3$,
R$^6$ is hydrogen, OCH$_3$, OCHF$_2$, O—CH$_2$—CF$_3$, —O—(CH$_2$)$_2$—OH, —O—(CH$_2$)$_2$—NH$_2$, —O—CH$_2$—CH(OH)CH$_2$—OH,

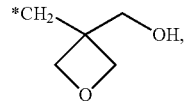

—O—(CH$_2$)$_2$—SO—CH$_3$, —O—(CH$_2$)$_2$—SO$_2$—CH$_3$, —O—CH$_2$—SO$_2$NH$_2$, —O—CH$_2$-(pyrrolidin-2-on-5-yl), —O—CH$_2$—CH(OH)—CH$_2$-(piperidin-4-yl), —O—CH$_2$-(morpholin-2-yl), R$^7$ is hydrogen
R$^8$ is hydrogen, CH$_2$—OH, C(O)NH$_2$, C(O)NHCH$_3$, A further aspect of the invention are compounds of formula (I) according to claim 1, wherein
R$^1$ is hydrogen or methyl
R$^2$/R$^3$ is hydrogen, fluorine, chlorine, hydroxy, methyl, methoxy,
R$^4$ is cyano, hydroxy, nitro, methyl, tert.-butoxy, CF$_3$, methoxy, ethoxy, propoxy,
NH$_2$, NH—C(O)—CH$_3$, —O—(CH$_2$)$_2$—OC(O)CH$_3$, C(O) NH$_2$,
n is 1
R$^6$ is OCH$_3$, —O—CH$_2$—C(O)OH, —O—(CH$_2$)$_2$—S—CH$_3$, O—(CH$_2$)$_2$—SO—CH$_3$, —O—(CH$_2$)$_2$—SO$_2$—CH$_2$, —O—(CH$_2$)$_2$—NH$_2$, —O—(CH$_2$)$_2$—O—CH$_3$, —O—(CH$_2$)$_2$—O—(CH$_2$)$_2$—OH, —O—(CH$_2$)$_2$—O(CH$_2$)$_2$—NH—C(O)OC(CH$_3$)$_3$, —O—CH$_2$-[morpholin-2-yl-(4-C(O)OC(CH$_3$)$_3$)], —O—(CHy)$_2$-morpholin-4-yl, —O—CH$_2$-(3-methoxymethyl-oxadiazol-5-yl), —O—CH$_2$—C(O)OC$_2$H$_2$, —O—CH$_2$—C(O)-(3,3-dif-luoroazetidin), —O—CH$_2$—C(O)-(3-fluoroazetidin), —O—CH$_2$-(pyrrolidinon-5-yl), —O—CH$_2$—CH(OH)—CH$_2$-(1-piperidin), SO$_2$—CH(CH$_2$)$_2$, C(O)OC$_2$H,
R$^7$ is NH—C(O)OC(CH$_3$)$_3$,
R$^8$ is fluorine, cyano, hydroxy, methyl, C(O)NH$_2$, C(O) OC$_2$H$_5$, CH$_2$—OH, and
m is 1, 2
or an N-oxide, a salt, a tautomer or a stereoisomer of said compound, or a salt of said N-oxide, tautomer or stereoiso-mer.

Yet another aspect of the invention are compounds of formula (I) according to claim 1, wherein R¹ is hydrogen,
R²/R³ is independently from each other hydrogen, fluorine, chlorine,
R⁴ is —O-(1-4C-alkyl), (2-4C-alkyl)-OH, 3-5C-cycloalkyl, 2-3C-alkenyl,
R⁶ is

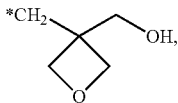

whereby * is the point of attachment,
—O-(2-3C-alkyl)-NH₂, —O—(CH₂)heterocyclyl (which optionally is substituted with oxo (=O) or C(O)OR⁹),
—O-(1-3C-alkyl), —O-(2-3C-alkyl)-OH, —O-(2-3C-alkyl)-SO-(2-3C-alkyl), —O-(2-3C-alkyl)-SO₂-(2-3C-alkyl), —O-(2-3Calkyl)-SO₂NH₂, —O—(CH₂)—CH(OH)—(CH₂)heterocyclyl, —O—(CH₂)—CH(OH)—(CH₂)—OH, —O—(CH₂)—C(O)NR¹⁰R¹¹,
R⁷ is hydrogen
R⁸ is hydrogen, C(O)NR¹⁰R¹¹,
R⁹ is hydrogen, 1-4C-alkyl which optionally is substituted with hydroxy,
R¹⁰, R¹¹ are independently from each other hydrogen, 1-4C-alkyl, 1-4C-hydroxyalkyl, 1-4C-alkoxy, —C(O)-(1-4C-alkyl), or COOR⁹ or
together with the nitrogen atom to which they are attached form a 4-6-membered heterocyclic ring optionally containing one further heteroatom selected from the group consisting of O, S or N, which is optionally substituted with 1-2 fluorine atoms or COOR⁹,
or a salt thereof.

A further aspect of the invention are compounds of formula (I) according to claim 1, wherein
R¹ is hydrogen,
R²/R³ is independently from each other hydrogen, fluorine, chlorine,
R⁴ is —O—CH₂—CH₃, CH₂—OH, C(CH₃)₃—OH, cyclopropyl, propenyl, —O—C(CH₃)₃,
R⁶ is

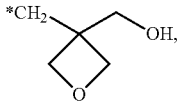

whereby * is the point of attachment, —O(CH₂)₂—NH₂, —O(CH₂)heterocyclyl (which optionally is substituted with oxo (=O)), —O—CH₃, —O(CH₂)₂—OH, —O—(CH₂)₂—SO—CH₃, —O—(CH₂)₂—SO₂—CH₃, —O—(CH₂)₂—SO₂NH₂, —O—(CH₂)CH(OH)—(CH₂)-heterocyclyl, —O—(CH₂)—CH(OH)—(CH₂)—OH, —O—(CH₂)—C(O)NR¹⁰R¹¹,
R⁷ is hydrogen
R⁸ is hydrogen, C(O)NR¹⁰R¹¹,
R⁹ is hydrogen, 1-4C-alkyl which optionally is substituted with hydroxy,
R¹⁰, R¹¹ are independently from each other hydrogen, 1-4C-alkyl, 1-4C-hydroxyalkyl, 1-4C-alkoxy, —C(O)-(1-4C-alkyl), or COOR⁹ or
together with the nitrogen atom to which they are attached form a 4-6-membered heterocyclic ring optionally containing one further heteroatom selected from the group consisting of O, S or N, which is optionally substituted with 1-2 fluorine atoms or COOR⁹,
or a salt thereof.

In one aspect of the invention compounds of formula (I) as described above are selected from the group consisting of:
2-[1-(6-chloro-2-fluoro-3-methylbenzyl)-1H-indazol-3-yl]-5-methoxy-N-(pyridin-4-yl)pyrimidin-4-amine,
2-[1-(6-chloro-2-fluoro-3-methoxybenzyl)-1H-indazol-3-yl]-5-methoxy-N-(pyridin-4-yl)pyrimidin-4-amine,
5-methoxy-2-{1-[3-(5-methyl-1,2,4-oxadiazol-3-yl)benzyl]-1H-indazol-3-yl}-N-(pyridin-4-yl)pyrimidin-4-amine,
2-[1-(2-chloro-4,5-dimethylbenzyl)-1H-indazol-3-yl]-5-methoxy-N-(pyridin-4-yl)pyrimidin-4-amine,
5-methoxy-2-{1-[4-(pentafluoro-λ¹-sulfanyl)benzyl]-1H-indazol-3-yl}-N-(pyridin-4-yl)pyrimidin-4-amine,
2-[1-(2,6-difluoro-3-methoxybenzyl)-1H-indazol-3-yl]-5-methoxy-N-(pyridin-4-yl)pyrimidin-4-amine,
N-(2,6-difluoro-3-methoxybenzyl)-2-[1-(2,6-difluoro-3-methoxybenzyl)-1H-indazol-3-yl]-5-methoxy-N-(pyridin-4-yl)pyrimidin-4-amine,
2-{1-[(6-bromo-1,3-benzodioxol-5-yl)methyl]-1H-indazol-3-yl}-5-methoxy-N-(pyridin-4-yl)pyrimidin-4-amine,
2-[1-(4-ethoxy-2,6-difluorobenzyl)-1H-indazol-3-yl]-5-methoxy-N-(pyridin-4-yl)pyrimidin-4-amine,
N-(4-ethoxy-2,6-difluorobenzyl)-2-[1-(4-ethoxy-2,6-difluorobenzyl)-1H-indazol-3-yl]-5-methoxy-N-(pyridin-4-yl)pyrimidin-4-amine,
2-({3-[5-methoxy-4-(pyridin-4-ylamino)pyrimidin-2-yl]-1H-indazol-1-yl}methyl)benzonitrile,
2-[1-(2-chloro-4-methoxybenzyl)-1H-indazol-3-yl]-5-methoxy-N-(pyridin-4-yl)pyrimidin-4-amine,
2-[1-(3,4-dihydro-2H-1,5-benzodioxepin-6-ylmethyl)-1H-indazol-3-yl]-5-methoxy-N-(pyridin-4-yl)pyrimidin-4-amine,
2-[1-(2,6-difluorobenzyl)-1H-indazol-3-yl]-5-methoxy-N-(pyridin-4-yl)pyrimidin-4-amine,
N-(2,6-difluorobenzyl)-2-[1-(2,6-difluorobenzyl)-1H-indazol-3-yl]-5-methoxy-N-(pyridin-4-yl)pyrimidin-4-amine,
5-methoxy-N-(pyridin-4-yl)-2-(1-{3-[(trifluoromethyl)sulfanyl]benzyl}-1H-indazol-3-yl)pyrimidin-4-amine,
2-[1-(2,3-difluoro-4-methylbenzyl)-1H-indazol-3-yl]-5-methoxy-N-(pyridin-4-yl)pyrimidin-4-amine,
N-(2,3-difluoro-4-methylbenzyl)-2-[1-(2,3-difluoro-4-methylbenzyl)-1H-indazol-3-yl]-5-methoxy-N-(pyridin-4-yl)pyrimidin-4-amine,
5-methoxy-2-{1-[4-(1H-pyrazol-1-yl)benzyl]-1H-indazol-3-yl}-N-(pyridin-4-yl)pyrimidin-4-amine,
2-[1-(2,6-dichlorobenzyl)-1H-indazol-3-yl]-5-methoxy-N-(pyridin-4-yl)pyrimidin-4-amine,
N-(2,6-dichlorobenzyl)-2-[1-(2,6-dichlorobenzyl)-1H-indazol-3-yl]-5-methoxy-N-(pyridin-4-yl)pyrimidin-4-amine,
5-methoxy-N-(pyridin-4-yl)-2-(1-{4-[(trifluoromethyl)sulfanyl]benzyl}-1H-indazol-3-yl)pyrimidin-4-amine,
2-[1-(2-chlorobenzyl)-1H-indazol-3-yl]-5-methoxy-N-(pyridin-4-yl)pyrimidin-4-amine,
N-(2-chlorobenzyl)-2-[1-(2-chlorobenzyl)-1H-indazol-3-yl]-5-methoxy-N-(pyridin-4-yl)pyrimidin-4-amine,
methyl 3-chloro-4-({3-[5-methoxy-4-(pyridin-4-ylamino)pyrimidin-2-yl]-1H-indazol-1-yl}methyl)benzoate,
methyl 3-chloro-4-{[(2-{1-[2-chloro-4-(methoxycarbonyl)benzyl]-1H-indazol-3-yl}-5-methoxypyrimidin-4-yl)(pyridin-4-yl)amino]methyl}benzoate,
2-[1-(4-bromo-2,6-difluorobenzyl)-1H-indazol-3-yl]-5-methoxy-N-(pyridin-4-yl)pyrimidin-4-amine,
2-[1-(2-chloro-4-fluoro-3-methoxybenzyl)-1H-indazol-3-yl]-5-methoxy-N-(pyridin-4-yl)pyrimidin-4-amine,
2-[1-(4-ethoxy-2,3-difluorobenzyl)-1H-indazol-3-yl]-5-methoxy-N-(pyridin-4-yl)pyrimidin-4-amine, N-(4-ethoxy-2,3-difluorobenzyl)-2-[1-(4-ethoxy-2,3-difluorobenzyl)-1H-indazol-3-yl]-5-methoxy-N-(pyridin-4-yl)pyrimidin-4-amine, 5-methoxy-N-(pyridin-4-yl)-2-{1-[2,3,5,6-tetrafluoro-4-(2,2,2-trifluoroethoxy)benzyl]-1H-indazol-3-yl}pyrimidin-4-amine, 5-methoxy-N-(pyridin-4-yl)-N-[2,3,5,6-tetrafluoro-4-(2,2,2-trifluoroethoxy)benzyl]-2-{1-[2,3,5,6-tetrafluoro-4-(2,2,2-trifluoroethoxy)benzyl]-1H-indazol-3-yl}pyrimidin-4-amine, methyl 2,4-dichloro-3-({3-[5-methoxy-4-(pyridin-4-ylamino)pyrimidin-2-yl]-1H-indazol-1-yl}methyl)benzoate, 5-methoxy-N-(pyridin-4-yl)-2-[1-(2,4,6-trifluorobenzyl)-1H-indazol-3-yl]pyrimidin-4-amine, 5-methoxy-N-(pyridin-4-yl)-N-(2,4,6-trifluorobenzyl)-2-[1-(2,4,6-trifluorobenzyl)-1H-indazol-3-yl]pyrimidin-4-amine, 2-[1-(2-fluorobenzyl)-1H-indazol-3-yl]-5-methoxy-N-(pyridin-4-yl)pyrimidin-4-amine, 2-[1-(2,4-dichlorobenzyl)-1H-indazol-3-yl]-5-methoxy-N-(pyridin-4-yl)pyrimidin-4-amine, 2-[1-(2-fluoro-4-iodobenzyl)-1H-indazol-3-yl]-5-methoxy-N-(pyridin-4-yl)pyrimidin-4-amine, 2-[1-(2-bromobenzyl)-1H-indazol-3-yl]-5-methoxy-N-(pyridin-4-yl)pyrimidin-4-amine, N-(2-bromobenzyl)-2-[1-(2-bromobenzyl)-1H-indazol-3-yl]-5-methoxy-N-(pyridin-4-yl)pyrimidin-4-amine,

[3-fluoro-4-({3-[5-methoxy-4-(pyridin-4-ylamino)pyrimidin-2-yl]-1H-indazol-1-yl}methyl)phenyl]acetic acid, 5-methoxy-N-(pyridin-4-yl)-2-[1-(2,3,5,6-tetrafluoro-4-methoxybenzyl)-1H-indazol-3-yl]pyrimidin-4-amine 5-methoxy-2-[1-(4-propylbenzyl)-1H-indazol-3-yl]-N-(pyridin-4-yl)pyrimidin-4-amine, 2-{1-[2,6-dichloro-4-(trifluoromethoxy)benzyl]-1H-indazol-3-yl}-5-methoxy-N-(pyridin-4-yl)pyrimidin-4-amine, N-[2,6-dichloro-4-(trifluoromethoxy)benzyl]-2-{1-[2,6-dichloro-4-(trifluoromethoxy)benzyl]-1H-indazol-3-yl}-5-methoxy-N-(pyridin-4-yl)pyrimidin-4-amine, 7-({3-[5-methoxy-4-(pyridin-4-ylamino)pyrimidin-2-yl]-1H-indazol-1-yl}methyl)-3,4-dihydroquinolin-2(1H)-one, 2-[1-(2-chloro-4-iodobenzyl)-1H-indazol-3-yl]-5-methoxy-N-(pyridin-4-yl)pyrimidin-4-amine, 2-[1-(3,5-dimethoxybenzyl)-1H-indazol-3-yl]-5-methoxy-N-(pyridin-4-yl)pyrimidin-4-amine, 2-{1-[2-chloro-6-(trifluoromethyl)benzyl]-1H-indazol-3-yl}-5-methoxy-N-(pyridine-4-yl)pyrimidin-4-amine, 2-[1-(2-chloro-5-fluorobenzyl)-1H-indazol-3-yl]-5-methoxy-N-(pyridin-4-yl)pyrimidin-4-amine, 7-({3-[5-methoxy-4-(pyridin-4-ylamino)pyrimidin-2-yl]-1H-indazol-1-yl}methyl)-4-methyl-2H-chromen-2-one, 3-fluoro-4-({3-[5-methoxy-4-(pyridin-4-ylamino)pyrimidin-2-yl]-1H-indazol-1-yl}methyl)benzonitrile, 4-{[{2-[1-(4-cyano-2-fluorobenzyl)-1H-indazol-3-yl]-5-methoxypyrimidin-4-yl}(pyridin-4-yl)amino]methyl}-3-fluorobenzonitrile, 2-{1-[2,6-dichloro-3-(trifluoromethyl)benzyl]-1H-indazol-3-yl}-5-methoxy-N-(pyridin-4-yl)pyrimidin-4-amine, ethyl [3-({3-[5-methoxy-4-(pyridin-4-ylamino)pyrimidin-2-yl]-1H-indazol-1-yl}methyl)phenyl]acetate, 2-[1-(4-fluorobenzyl)-1H-indazol-3-yl]-5-methoxy-N-(pyridin-4-yl)pyrimidin-4-amine, N-cyclopropyl-4-({3-[5-methoxy-4-(pyridin-4-ylamino)pyrimidin-2-yl]-1H-indazol-1-yl}methyl)benzenesulfonamide, 6-({3-[5-methoxy-4-(pyridin-4-ylamino)pyrimidin-2-yl]-1H-indazol-1-yl}methyl)-1-benzofuran-2(3H)-one, 2-{1-[4-(difluoromethoxy)-2,6-difluorobenzyl]-1H-indazol-3-yl}-5-methoxy-N-(pyridin-4-yl)pyrimidin-4-amine, tert-butyl 3-chloro-4-({3-[5-methoxy-4-(pyridin-4-ylamino)pyrimidin-2-yl]-1H-indazol-1-yl}methyl)benzoate, ethyl 2-[3-({3-[5-methoxy-4-(pyridin-4-ylamino)pyrimidin-2-yl]-1H-indazol-1-yl}methyl)phenyl]-2-methylpropanoate, 4-({3-[5-methoxy-4-(pyridin-4-ylamino)pyrimidin-2-yl]-1H-indazol-1-yl}methyl)benzonitrile, 5-methoxy-2-{1-[4-(morpholin-4-ylsulfonyl)benzyl]-1H-indazol-3-yl}-N-(pyridin-4-yl)pyrimidin-4-amine, 2-[1-(2,6-dichloro-3-nitrobenzyl)-1H-indazol-3-yl]-5-methoxy-N-(pyridin-4-yl)pyrimidin-4-amine, 3-({3-[5-methoxy-4-(pyridin-4-ylamino)pyrimidin-2-yl]-1H-indazol-1-yl}methyl)benzonitrile, N-[4-(difluoromethoxy)-2,6-difluorobenzyl]-2-{1-[4-(difluoromethoxy)-2,6-difluorobenzyl]-1H-indazol-3-yl}-5-methoxy-N-(pyridin-4-yl)pyrimidin-4-amine, 5-methoxy-N-(pyridin-4-yl)-2-{1-[3-(1H-pyrrol-1-yl)benzyl]-1H-indazol-3-yl}pyrimidin-4-amine, 3,5-difluoro-4-({3-[5-methoxy-4-(pyridin-4-ylamino)pyrimidin-2-yl]-1H-indazol-1-yl}methyl)benzonitrile, 5-methoxy-2-{1-[2-methoxy-4-(trifluoromethyl)benzyl]-1H-indazol-3-yl}-N-(pyridin-4-yl)pyrimidin-4-amine, 2-[1-(2,6-difluoro-3-methylbenzyl)-1H-indazol-3-yl]-5-methoxy-N-(pyridin-4-yl)pyrimidin-4-amine, 2-[1-(2-fluoro-6-methoxybenzyl)-1H-indazol-3-yl]-5-methoxy-N-(pyridin-4-yl)pyrimidin-4-amine, 3,5-difluoro-4-({3-[5-methoxy-4-(pyridin-4-ylamino)pyrimidin-2-yl]-1H-indazol-1-yl}methyl)benzamide, 2-[3,5-difluoro-4-({3-[5-methoxy-4-(pyridin-4-ylamino)pyrimidin-2-yl]-1H-indazol-1-yl}methyl)phenoxy]ethyl acetate, 2-[1-(2,6-difluoro-4-propoxybenzyl)-1H-indazol-3-yl]-5-methoxy-N-(pyridin-4-yl)pyrimidin-4-amine, 2-[1-(4-ethoxy-2-fluoro-6-methoxybenzyl)-1H-indazol-3-yl]-5-methoxy-N-(pyridin-4-yl)pyrimidin-4-amine, 2-[1-(4-ethoxy-2,6-difluorobenzyl)-1H-indazol-3-yl]-4-(pyridin-4-ylamino)pyrimidin-5-ol, 2-[1-(4-methoxybenzyl)-1H-indazol-3-yl]-4-(pyridin-4-ylamino)pyrimidin-5-ol, 2-[1-(2-fluorobenzyl)-1H-indazol-3-yl]-4-(pyridin-4-ylamino)pyrimidin-5-ol, 2-[1-(4-fluorobenzyl)-1H-indazol-3-yl]-4-(pyridin-4-ylamino)pyrimidin-5-ol, {3-[({2-[1-(4-ethoxy-2,6-difluorobenzyl)-1H-indazol-3-yl]-4-(pyridin-4-ylamino)pyrimidin-5-yl}oxy)methyl]oxetan-3-yl}methanol, {3-[({2-[1-(2-fluorobenzyl)-1H-indazol-3-yl]-4-(pyridin-4-ylamino)pyrimidin-5-yl}oxy)methyl]oxetan-3-yl}methanol, (3-{[({2-[1-(2-fluorobenzyl)-1H-indazol-3-yl]-5-{[3-(hydroxymethyl)oxetan-3-yl]methoxy}pyrimidin-4-yl)(pyridin-4-yl)amino]methyl}oxetan-3-yl)methanol, 1-({2-[1-(2-fluorobenzyl)-1H-indazol-3-yl]-4-(pyridin-4-ylamino)pyrimidin-5-yl}oxy)methanesulfonamide, 5-[2-(dimethylamino)ethoxy]-2-[1-(2-fluorobenzyl)-1H-indazol-3-yl]-N-(pyridin-4-yl)pyrimidin-4-amine, 2-[1-(2-fluorobenzyl)-1H-indazol-3-yl]-N-(pyridin-4-yl)-5-[2-(1H-tetrazol-5-yl)ethoxy]pyrimidin-4-amine, 2-[1-(2-fluorobenzyl)-1H-indazol-3-yl]-N-(pyridin-4-yl)-5-[2-(1H-tetrazol-5-yl)ethoxy]-N-[2-(1H-tetrazol-5-yl)ethyl]pyrimidin-4-amine, 5-[2-(dimethylamino)ethoxy]-2-[1-(4-fluorobenzyl)-1H-indazol-3-yl]-N-(pyridin-4-yl)pyrimidin-4-amine, 2-[1-(2-fluorobenzyl)-1H-indazol-3-yl]-N-(pyridin-4-yl)-5-(1H-tetrazol-5-ylmethoxy)pyrimidin-4-amine, 5-[2-(dimethylamino)ethoxy]-2-[1-(4-ethoxy-2,6-difluorobenzyl)-1H-indazol-3-yl]-N-(pyridin-4-yl)pyrimidin-4-amine 1-({2-[1-(4-ethoxy-2,6-difluorobenzyl)-1H-indazol-3-yl]-4-(pyridin-4-ylamino)pyrimidin-5-yl}oxy)-3-(piperidin-1-yl)propan-2-ol, 2-[1-(4-ethoxy-2,6-difluorobenzyl)-1H-indazol-3-yl]-5-(2-methoxyethoxy)-N-(pyridin-4-yl)pyrimidin-4-amine, tert-butyl 2-[({2-[1-(4-ethoxy-2,6-difluorobenzyl)-1H-indazol-3-yl]-4-(pyridin-4-ylamino)pyrimidin-5-yl}oxy)methyl]morpholine-4-carboxylate, 2-[1-(4-ethoxy-2,6-difluorobenzyl)-1H-indazol-3-yl]-5-[2-(morpholin-4-yl)ethoxy]-N-(pyridin-4-yl)pyrimidin-4-amine, 2-[1-(2-fluorobenzyl)-1H-indazol-3-yl]-5-{[3-(methoxymethyl)-1,2,4-oxadiazol-5-yl]methoxy}-N-(pyridin-4-yl)pyrimidin-4-amine, ethyl ({2-[1-(4-ethoxy-2,6-difluorobenzyl)-1H-indazol-3-yl]-4-(pyridin-4-ylamino)pyrimidin-5-yl}oxy)acetate, 1-(3,3-difluoroazetidin-1-yl)-2-({2-[1-(4-ethoxy-2,6-difluorobenzyl)-1H-indazol-3-yl]-4-(pyridin-4-ylamino)pyrimidin-5-yl}oxy)ethanone, 2-[1-(4-ethoxy-2,6-difluorobenzyl)-1H-indazol-3-yl]-5-[2-(methylsulfanyl)ethoxy]-N-(pyridin-4-yl)pyrimidin-4-amine, 2-[2-({2-[1-(4-ethoxy-2,6-difluorobenzyl)-1H-indazol-3-yl]-4-(pyridin-4-ylamino)pyrimidin-5-yl}oxy)ethoxy]ethanol, formic acid-(5S)-5-[({2-[1-(4-ethoxy-2,6-difluorobenzyl)-1H-indazol-3-yl]-4-(pyridin-4-ylamino)pyrimidin-5-yl}oxy)methyl]pyrrolidin-2-one (1:1), (5R)-5-[({2-[1-(4-ethoxy-2,6-difluorobenzyl)-1H-indazol-3-yl]-4-(pyridin-4-ylamino)pyrimidin-5-yl}oxy)methyl]pyrrolidine-2-one, tert-butyl {2-[2-({2-[1-(2-fluorobenzyl)-1H-indazol-3-yl]-4-(pyridin-4-ylamino)pyrimidin-5-yl}oxy)ethoxy]ethyl}carbamate, 2-({2-[1-(4-ethoxy-2,6-difluorobenzyl)-1H-indazol-3-yl]-4-(pyridin-4-ylamino)pyrimidin-5-yl}oxy)-1-(3-fluoroazetidin-1-yl)ethanone, (5S)-5-[({2-[1-(4-ethoxy-2,6-difluorobenzyl)-1H-indazol-3-yl]-4-(pyridin-4-ylamino)pyrimidin-5-yl}oxy)methyl]pyrrolidin-2-one, tert-butyl [2-({2-[1-(4-ethoxy-2,6-difluorobenzyl)-1H-indazol-3-yl]-4-(pyridin-4-ylamino)pyrimidin-5-yl}oxy)ethyl]carbamate, N-({2-[1-(4-ethoxy-2,6-difluorobenzyl)-1H-indazol-3-yl]-8-(pyridin-4-yl)-7,8-dihydro-6H-pyrimido[5,4-b][1,4]oxazin-7-yl}methyl)formamide, 2-[1-(4-ethoxy-2,6-difluorobenzyl)-1H-indazol-3-yl]-N-(pyridin-4-yl)pyrimidin-4-amine, 2-[1-(4-methoxybenzyl)-1H-indazol-3-yl]-N-(pyridin-4-yl)pyrimidin-4-amine, 2-[1-(2-fluorobenzyl)-1H-indazol-3-yl]-N-(pyridin-4-yl)pyrimidin-4-amine, 2-[1-(4-cyclopropyl-2,6-difluorobenzyl)-1H-indazol-3-yl]-5-methoxy-N-(pyridin-4-yl)pyrimidin-4-amine, 2-(1-{2,6-difluoro-4-[(1E)-prop-1-en-1-yl]benzyl}-1H-indazol-3-yl)-5-methoxy-N-(pyridin-4-yl)pyrimidin-4-amine, 1-[3,5-difluoro-4-({3-[5-methoxy-4-(pyridin-4-ylamino)pyrimidin-2-yl]-1H-indazol-1-yl}methyl)phenyl]ethanone,

[2,4-dichloro-3-({3-[5-methoxy-4-(pyridin-4-ylamino)pyrimidin-2-yl]-1H-indazol-1-yl}methyl)phenyl]methanol, 2-[3-({3-[5-methoxy-4-(pyridin-4-ylamino)pyrimidin-2-yl]-1H-indazol-1-yl}methyl)phenyl]ethanol, 2-[3-({3-[5-methoxy-4-(pyridin-4-ylamino)pyrimidin-2-yl]-1H-indazol-1-yl}methyl)phenyl]-2-methylpropan-1-ol,

[4-({2-[1-(4-ethoxy-2,6-difluorobenzyl)-1H-indazol-3-yl]-5-methoxypyrimidin-4-yl}amino)pyridin-3-yl]methanol, 2-[3-chloro-4-({3-[5-methoxy-4-(pyridin-4-ylamino)pyrimidin-2-yl]-1H-indazol-1-yl}methyl)phenyl]propan-2-ol, 1-[3-({3-[5-methoxy-4-(pyridin-4-ylamino)pyrimidin-2-yl]-1H-indazol-1-yl}methyl)phenyl]-2-methylpropan-2-ol, 2-[2,4-dichloro-3-({3-[5-methoxy-4-(pyridin-4-ylamino)pyrimidin-2-yl]-1H-indazol-1-yl}methyl)phenyl]propan-2-ol 5-(difluoromethoxy)-2-[1-(4-ethoxy-2,6-difluorobenzyl)-1H-indazol-3-yl]-N-(pyridin-4-yl)pyrimidin-4-amine, 5-(difluoromethoxy)-N-(difluoromethyl)-2-[1-(4-ethoxy-2,6-difluorobenzyl)-1H-indazol-3-yl]-N-(pyridin-4-yl)pyrimidin-4-amine, 4-[(difluoromethyl)(pyridin-4-yl)amino]-2-[1-(4-ethoxy-2,6-difluorobenzyl)-1H-indazol-3-yl]pyrimidin-5-ol, 2-[1-(4-methoxybenzyl)-1H-indazol-3-yl]-N-(pyridin-4-yl)-5-(2,2,2-trifluoroethoxy)pyrimidin-4-amine, 2-[1-(4-ethoxy-2,6-difluorobenzyl)-1H-indazol-3-yl]-N-(pyridin-4-yl)-5-(2,2,2-trifluoroethoxy)pyrimidin-4-amine, 3-({2-[1-(2-fluorobenzyl)-1H-indazol-3-yl]-4-(pyridin-4-ylamino)pyrimidin-5-yl}oxy)propane-1,2-diol, (2S)-3-({2-[1-(2-fluorobenzyl)-1H-indazol-3-yl]-4-(pyridin-4-ylamino)pyrimidin-5-yl}oxy)propane-1,2-diol, (2R)-3-({2-[1-(2-fluorobenzyl)-1H-indazol-3-yl]-4-(pyridin-4-ylamino)pyrimidin-5-yl}oxy)propane-1,2-diol, 2-({2-[1-(4-ethoxy-2,6-difluorobenzyl)-1H-indazol-3-yl]-4-(pyridin-4-ylamino)pyrimidin-5-yl}oxy)ethanol, 2-({2-[1-(2-fluorobenzyl)-1H-indazol-3-yl]-4-(pyridin-4-ylamino)pyrimidin-5-yl}oxy)ethanol, ethyl 4-({2-[1-(2-fluorobenzyl)-1H-indazol-3-yl]-5-(2-hydroxyethoxy)pyrimidin-4-yl}amino)pyridine-3-carboxylate, 4-({2-[1-(2-fluorobenzyl)-1H-indazol-3-yl]-5-(2-hydroxyethoxy)pyrimidin-4-yl}amino)-N-methyl pyridine-3-carboxamide, 4-({2-[1-(2-fluorobenzyl)-1H-indazol-3-yl]-5-(2-hydroxyethoxy)pyrimidin-4-yl}amino)pyridine-3-carboxamide, 2-hydroxyethyl 4-({2-[1-(2-fluorobenzyl)-1H-indazol-3-yl]-5-(2-hydroxyethoxy)pyrimidin-4-yl}amino)pyridine-3-carboxylate, 5-(cyclopropyloxy)-2-[1-(4-methoxybenzyl)-1H-indazol-3-yl]-N-(pyridin-4-yl)pyrimidin-4-amine, 2-[1-(4-ethoxy-2,6-difluorobenzyl)-1H-indazol-3-yl]-5-methoxy-N-(pyridin-4-yl)pyrimidin-4-amine hydrochloride (1:1), (2S)-3-({2-[1-(2-fluorobenzyl)-1H-indazol-3-yl]-4-(pyridin-4-ylamino)pyrimidin-5-yl}oxy)propane-1,2-diol hydrochloride (1:1), 2-({2-[1-(4-ethoxy-2,6-difluorobenzyl)-1H-indazol-3-yl]-4-(pyridin-4-ylamino)pyrimidin-5-yl}oxy)ethanol hydrochloride (1:1), 2-[1-(2,6-dichlorobenzyl)-1H-indazol-3-yl]-5-methoxy-N-(pyridin-4-yl)pyrimidin-4-amine hydrochloride (1:1),

[2,4-dichloro-3-({3-[5-methoxy-4-(pyridin-4-ylamino)pyrimidin-2-yl]-1H-indazol-1-yl}methyl)phenyl]methanol hydrochloride (1:1), (2R)-3-({2-[1-(2-fluorobenzyl)-1H-indazol-3-yl]-4-(pyridin-4-ylamino)pyrimidin-5-yl}oxy)propane-1,2-diol hydrochloride (1:1),
N-{2-[1-(4-ethoxy-2,6-difluorobenzyl)-1H-indazol-3-yl]pyrimidin-4-yl}-N-(pyridin-4-yl)acetamide,
N-{2-[1-(4-ethoxy-2,6-difluorobenzyl)-1H-indazol-3-yl]pyrimidin-4-yl}-2-methoxy-N-(pyridin-4-yl)acetamide,
N-{2-[1-(4-ethoxy-2,6-difluorobenzyl)-1H-indazol-3-yl]pyrimidin-4-yl}-N-(pyridin-4-yl)tetrahydro-2H-pyran-4-carboxamide,
N-{2-[1-(4-ethoxy-2,6-difluorobenzyl)-1H-indazol-3-yl]pyrimidin-4-yl}-2-(2-methoxyethoxy)-N-(pyridin-4-yl)acetamide,
2-[{2-[1-(4-ethoxy-2,6-difluorobenzyl)-1H-indazol-3-yl]pyrimidin-4-yl}(pyridin-4-yl)amino]ethanol,
(3-{[{2-[1-(4-ethoxy-2,6-difluorobenzyl)-1H-indazol-3-yl]pyrimidin-4-yl}(pyridin-4-yl)amino]methyl}oxetan-3-yl)methanol,
2-{1-[4-bromo-2-fluoro-6-(2,2,2-trifluoroethoxy)benzyl]-1H-indazol-3-yl}-5-methoxy-N-(pyridin-4-yl)pyrimidin-4-amine,
2-{1-[4-bromo-2,6-bis(2,2,2-trifluoroethoxy)benzyl]-1H-indazol-3-yl}-5-methoxy-N-(pyridin-4-yl)pyrimidin-4-amine,
2,4-dichloro-3-({3-[5-methoxy-4-(pyridin-4-ylamino)pyrimidin-2-yl]-1H-indazol-1-yl}methyl)benzoic acid,
({2-[1-(4-ethoxy-2,6-difluorobenzyl)-1H-indazol-3-yl]-4-(pyridin-4-ylamino)pyrimidin-5-yl}oxy)acetic acid,
2,4-dichloro-3-({3-[5-methoxy-4-(pyridin-4-ylamino)pyrimidin-2-yl]-1H-indazol-1-yl}methyl)-N-methylbenzamide,
2,4-dichloro-3-({3-[5-methoxy-4-(pyridin-4-ylamino)pyrimidin-2-yl]-1H-indazol-1-yl}methyl)benzamide,
2,4-dichloro-3-({3-[5-methoxy-4-(pyridin-4-ylamino)pyrimidin-2-yl]-1H-indazol-1-yl}methyl)-N,N-dimethylbenzamide,
2,4-dichloro-N-(2-hydroxyethyl)-3-({3-[5-methoxy-4-(pyridin-4-ylamino)pyrimidin-2-yl]-1H-indazol-1-yl}methyl)benzamide,
[2,4-dichloro-3-({3-[5-methoxy-4-(pyridin-4-ylamino)pyrimidin-2-yl]-1H-indazol-1-yl}methyl)phenyl](morpholin-4-yl)methanone,
3,5-difluoro-4-({3-[5-methoxy-4-(pyridin-4-ylamino)pyrimidin-2-yl]-1H-indazol-1-yl}methyl)-N-methylbenzamide,
2-[1-(4-ethynyl-2-fluorobenzyl)-1H-indazol-3-yl]-5-methoxy-N-(pyridin-4-yl)pyrimidin-4-amine,
{2-[1-(2-fluorobenzyl)-1H-indazol-3-yl]-8-(pyridin-4-yl)-7,8-dihydro-6H-pyrimido[5,4-b][1,4]oxazin-7-yl}methanol,
2-[1-(2-fluorobenzyl)-1H-indazol-3-yl]-5-methoxy-N-methyl-N-(pyridine-4-yl)pyrimidin-4-amine,
4-({2-[1-(2-fluorobenzyl)-1H-indazol-3-yl]-5-methoxypyrimidin-4-yl}amino)pyridine-3-carbonitrile,
2-[1-(2-fluorobenzyl)-1H-indazol-3-yl]-5-methoxy-N,N-di(pyridin-4-yl)pyrimidin-4-amine,
methyl 4-({2-[1-(2-fluorobenzyl)-1H-indazol-3-yl]-5-methoxypyrimidin-4-yl}amino)pyridine-3-carboxylate,
2-[1-(2-fluorobenzyl)-1H-indazol-3-yl]-5-methoxy-N-(pyridin-4-yl)pyrimidin-4-amine,
4-({2-[1-(4-ethoxy-2,6-difluorobenzyl)-1H-indazol-3-yl]-5-methoxypyrimidin-4-yl}amino)pyridine-3-carbonitrile,
2-[(3-{4-[(2,6-dimethylpyridin-4-yl)amino]-5-methoxypyrimidin-2-yl}-1H-indazol-1-yl)methyl]-5-ethoxy-3-fluorophenol,
4-({5-methoxy-2-[1-(4-methoxybenzyl)-1H-indazol-3-yl]pyrimidin-4-yl}amino)pyridin-2(1H)-one,
4-({2-[1-(4-ethoxy-2,6-difluorobenzyl)-1H-indazol-3-yl]-5-methoxypyrimidin-4-yl}amino)pyridin-2(1H)-one,
4-({5-methoxy-2-[1-(4-propyl benzyl)-1H-indazol-3-yl]pyrimidin-4-yl}amino)nicotinonitrile,
4-({2-[1-(2-fluorobenzyl)-1H-indazol-3-yl]-5-methoxypyrimidin-4-yl}amino)pyridine-3-carboxamide,
4-({5-methoxy-2-[1-(4-propyl benzyl)-1H-indazol-3-yl]pyrimidin-4-yl}amino)pyridine-3-carboxamide,
4-({2-[1-(4-ethoxy-2,6-difluorobenzyl)-1H-indazol-3-yl]-5-methoxypyrimidin-4-yl}amino)pyridine-3-carboxamide,
4-({2-[1-(2,6-difluoro-4-hydroxybenzyl)-1H-indazol-3-yl]-5-methoxypyrimidin-4-yl}amino)pyridine-3-carboxamide,
4-({2-[1-(2-fluorobenzyl)-1H-indazol-3-yl]-5-hydroxypyrimidin-4-yl}amino)pyridine-3-carbonitrile,
4-({4-[(3-cyanopyridin-4-yl)amino]-2-[1-(2-fluorobenzyl)-1H-indazol-3-yl]pyrimidin-5-yl}oxy)pyridine-3-carbonitrile,
5-methoxy-2-[1-(4-methoxybenzyl)-1H-indazol-3-yl]-N-[3-(trifluoromethyl)pyridin-4-yl]pyrimidin-4-amine,
3-chloro-4-({3-[5-methoxy-4-(pyridin-4-ylamino)pyrimidin-2-yl]-1H-indazol-1-yl}methyl)benzoic acid,
formic acid-3-chloro-4-({3-[5-methoxy-4-(pyridin-4-ylamino)pyrimidin-2-yl]-1H-indazol-1-yl}methyl)-N-methylbenzamide (1:1),
3-chloro-4-({3-[5-methoxy-4-(pyridin-4-ylamino)pyrimidin-2-yl]-1H-indazol-yl}methyl)-N-methylbenzamide,
4-({2-[1-(2-fluorobenzyl)-1H-indazol-3-yl]-5-hydroxypyrimidin-4-yl}amino)pyridine-3-carboxamide,
4-({2-[1-(2-fluorobenzyl)-1H-indazol-3-yl]-5-hydroxypyrimidin-4-yl}amino)pyridine-3-carboxylic acid,
ethyl 4-({2-[1-(2-fluorobenzyl)-1H-indazol-3-yl]-5-hydroxypyrimidin-4-yl}amino)pyridine-3-carboxylate,
2-[1-(2-fluorobenzyl)-1H-indazol-3-yl]-4-(pyridin-4-ylamino)pyrimidine-5-carbonitrile,
2-[1-(2-fluorobenzyl)-1H-indazol-3-yl]-4-(pyridin-4-ylamino)pyrimidine-5-carboxamide,
4-({2-[1-(2-fluorobenzyl)-1H-indazol-3-yl]-5-(2-hydroxyethoxy)pyridin-4-yl}amino)pyridine-3-carboxylic acid hydrochloride (1:1),
N-(2-fluoropyridin-4-yl)-5-methoxy-2-[1-(4-methoxybenzyl)-1H-indazol-3-yl]pyrimidin-4-amine,
N-(2,6-difluoropyridin-4-yl)-5-methoxy-2-[1-(4-methoxybenzyl)-1H-indazol-3-yl]pyrimidin-4-amine,
N-(3-fluoropyridin-4-yl)-5-methoxy-2-[1-(4-methoxybenzyl)-1H-indazol-3-yl]pyrimidin-4-amine,
5-methoxy-2-[1-(4-methoxybenzyl)-1H-indazol-3-yl]-N-(2-methylpyridin-4-yl)pyrimidin-4-amine,
N-(difluoromethyl)-2-[1-(4-ethoxy-2,6-difluorobenzyl)-1H-indazol-3-yl]-N-(pyridin-4-yl)pyrimidin-4-amine,
2-[1-(4-ethoxy-2,6-difluorobenzyl)-1H-indazol-3-yl]-5-[2-(methylsulfinyl)ethoxy]-N-(pyridin-4-yl)pyrimidin-4-amine,
2-[1-(4-ethoxy-2,6-difluorobenzyl)-1H-indazol-3-yl]-5-[2-(methylsulfinyl)ethoxy]-N-(pyridin-4-yl)pyrimidin-4-amine (Enantiomer 1),
2-[1-(4-ethoxy-2,6-difluorobenzyl)-1H-indazol-3-yl]-5-[2-(methylsulfinyl)ethoxy]-N-(pyridin-4-yl)pyrimidin-4-amine (Enantiomer 2),
2-[1-(4-ethoxy-2,6-difluorobenzyl)-1H-indazol-3-yl]-5-[2-(methylsulfonyl)ethoxy]-N-(pyridin-4-yl)pyrimidin-4-amine,
5-(2-aminoethoxy)-2-[1-(4-ethoxy-2,6-difluorobenzyl)-1H-indazol-3-yl]-N-(pyridine-4-yl)pyrimidin-4-amine,
2-[1-(4-ethoxy-2,6-difluorobenzyl)-1H-indazol-3-yl]-5-(morpholin-2-ylmethoxy)-N-(pyridin-4-yl)pyrimidin-4-amine, Preparation of ethyl 4-({2-[1-(4-ethoxy-2,6-difluorobenzyl)-1H-indazol-3-yl]-5-methoxypyrimidin-4-yl}amino)pyridine-3-carboxylate,
N-(3,5-difluoropyridin-4-yl)-2-[1-(4-ethoxy-2,6-difluorobenzyl)-1H-indazol-3-yl]-5-methoxypyrimidin-4-amine,
2-[1-(3-amino-2,6-dichlorobenzyl)-1H-indazol-3-yl]-5-methoxy-N-(pyridin-4-yl)pyrimidin-4-amine,
N-[2,4-dichloro-3-({3-[5-methoxy-4-(pyridin-4-ylamino)pyrimidin-2-yl]-1H-indazol-1-yl}methyl)phenyl]acetamide,
2-[1-(4-ethoxy-2,6-difluorobenzyl)-4-methyl-1H-indazol-3-yl]-5-methoxy-N-(pyridin-4-yl)pyrimidin-4-amine,
or an N-oxide, a salt, a tautomer or a stereoisomer of said compound, or a salt of said N-oxide, tautomer or stereoisomer.

One aspect of the invention are all compounds being named in the list below.

2-[1-(2,6-dichloro-3-nitrobenzyl)-1H-indazol-3-yl]-5-methoxy-N-(pyridin-4-yl)pyrimidin-4-amine,
3-({3-[5-methoxy-4-(pyridin-4-ylamino)pyrimidin-2-yl]-1H-indazol-1-yl}methyl)benzonitrile,
3,5-difluoro-4-({3-[5-methoxy-4-(pyridin-4-ylamino)pyrimidin-2-yl]-1H-indazol-1-yl}methyl)benzonitrile,
5-methoxy-2-{1-[2-methoxy-4-(trifluoromethyl)benzyl]-1H-indazol-3-yl}-N-(pyridin-4-yl)pyrimidin-4-amine,
2-[1-(2,6-difluoro-3-methylbenzyl)-1H-indazol-3-yl]-5-methoxy-N-(pyridin-4-yl)pyrimidin-4-amine,
2-[1-(2-fluoro-6-methoxybenzyl)-1H-indazol-3-yl]-5-methoxy-N-(pyridin-4-yl)pyrimidin-4-amine,
3,5-difluoro-4-({3-[5-methoxy-4-(pyridin-4-ylamino)pyrimidin-2-yl]-1H-indazol-1-yl}methyl)benzamide,
2-[3,5-difluoro-4-({3-[5-methoxy-4-(pyridin-4-ylamino)pyrimidin-2-yl]-1H-indazol-1-yl}methyl)phenoxy]ethyl acetate,
2-[1-(2,6-difluoro-4-propoxybenzyl)-1H-indazol-3-yl]-5-methoxy-N-(pyridin-4-yl)pyrimidin-4-amine,
2-[1-(4-ethoxy-2-fluoro-6-methoxybenzyl)-1H-indazol-3-yl]-5-methoxy-N-(pyridin-4-yl)pyrimidin-4-amine,
1-({2-[1-(4-ethoxy-2,6-difluorobenzyl)-1H-indazol-3-yl]-4-(pyridin-4-ylamino)pyrimidin-5-yl}oxy)-3-(piperidin-1-yl)propan-2-ol,
2-[1-(4-ethoxy-2,6-difluorobenzyl)-1H-indazol-3-yl]-5-(2-methoxyethoxy)-N-(pyridin-4-yl)pyrimidin-4-amine,
tert-butyl 2-[({2-[1-(4-ethoxy-2,6-difluorobenzyl)-1H-indazol-3-yl]-4-(pyridin-4-ylamino)pyrimidin-5-yl}oxy)methyl]morpholine-4-carboxylate,
2-[1-(4-ethoxy-2,6-difluorobenzyl)-1H-indazol-3-yl]-5-[2-(morpholin-4-yl)ethoxy]-N-(pyridin-4-yl)pyrimidin-4-amine,
2-[1-(2-fluorobenzyl)-1H-indazol-3-yl]-5-{[3-(methoxymethyl)-1,2,4-oxadiazol-5-yl]methoxy}-N-(pyridin-4-yl)pyrimidin-4-amine,
ethyl ({2-[1-(4-ethoxy-2,6-difluorobenzyl)-1H-indazol-3-yl]-4-(pyridin-4-ylamino)pyrimidin-5-yl}oxy)acetate,
1-(3,3-difluoroazetidin-1-yl)-2-({2-[1-(4-ethoxy-2,6-difluorobenzyl)-1H-indazol-3-yl]-4-(pyridin-4-ylamino)pyrimidin-5-yl}oxy)ethanone,
2-[1-(4-ethoxy-2,6-difluorobenzyl)-1H-indazol-3-yl]-5-[2-(methylsulfanyl)ethoxy]-N-(pyridin-4-yl)pyrimidin-4-amine,
2-[2-({2-[1-(4-ethoxy-2,6-difluorobenzyl)-1H-indazol-3-yl]-4-(pyridin-4-ylamino)pyrimidin-5-yl}oxy)ethoxy]ethanol,
formic acid-(5S)-5-[({2-[1-(4-ethoxy-2,6-difluorobenzyl)-1H-indazol-3-yl]-4-(pyridin-4-ylamino)pyrimidin-5-yl}oxy)methyl]pyrrolidin-2-one (1:1),
(5R)-5-[({2-[1-(4-ethoxy-2,6-difluorobenzyl)-1H-indazol-3-yl]-4-(pyridin-4-ylamino)pyrimidin-5-yl}oxy)methyl]pyrrolidin-2-one,
tert-butyl {2-[2-({2-[1-(2-fluorobenzyl)-1H-indazol-3-yl]-4-(pyridin-4-ylamino)pyrimidin-5-yl}oxy)ethoxy]ethyl}carbamate,
2-({2-[1-(4-ethoxy-2,6-difluorobenzyl)-1H-indazol-3-yl]-4-(pyridin-4-ylamino)pyrimidin-5-yl}oxy)-1-(3-fluoroazetidin-1-yl)ethanone,
(S)-5-[({2-[1-(4-ethoxy-2,6-difluorobenzyl)-1H-indazol-3-yl]-4-(pyridin-4-ylamino)pyrimidin-5-yl}oxy)methyl]pyrrolidin-2-one,
N-({2-[1-(4-ethoxy-2,6-difluorobenzyl)-1H-indazol-3-yl]-8-(pyridin-4-yl)-7,8-dihydro-6H-pyrimido[5,4-b][1,4]oxazin-7-yl}methyl)formamide,
[4-({2-[1-(4-ethoxy-2,6-difluorobenzyl)-1H-indazol-3-yl]-5-methoxypyrimidin-4-yl}amino)pyridin-3-yl]methanol,
({2-[1-(4-ethoxy-2,6-difluorobenzyl)-1H-indazol-3-yl]-4-(pyridin-4-ylamino)pyrimidin-5-yl}oxy)acetic acid,
2-[1-(2-fluorobenzyl)-1H-indazol-3-yl]-5-methoxy-N-(pyridin-4-yl)pyrimidin-4-amine,
4-({2-[1-(4-ethoxy-2,6-difluorobenzyl)-1H-indazol-3-yl]-5-methoxypyrimidin-4-yl}amino)pyridine-3-carbonitrile,
2-[(3-{4-[(2,6-dimethylpyridin-4-yl)amino]-5-methoxypyrimidin-2-yl}-1H-indazol-1-yl)methyl]-5-ethoxy-3-fluorophenol,
4-({5-methoxy-2-[1-(4-methoxybenzyl)-1H-indazol-3-yl]pyrimidin-4-yl}amino)pyridin-2(1H)-one,
4-({2-[1-(4-ethoxy-2,6-difluorobenzyl)-1H-indazol-3-yl]-5-methoxypyrimidin-4-yl}amino)pyridin-2(1H)-one,
4-({5-methoxy-2-[1-(4-propyl benzyl)-1H-indazol-3-yl]pyrimidin-4-yl}amino)nicotinonitrile,
4-({2-[1-(4-ethoxy-2,6-difluorobenzyl)-1H-indazol-3-yl]-5-methoxypyrimidin-4-yl}amino)pyridine-3-carboxamide,
4-({2-[1-(2,6-difluoro-4-hydroxybenzyl)-1H-indazol-3-yl]-5-methoxypyrimidin-4-yl}amino)pyridine-3-carboxamide,
5-methoxy-2-[1-(4-methoxybenzyl)-1H-indazol-3-yl]-N-(2-methylpyridin-4-yl)pyrimidin-4-amine,
2-[1-(4-ethoxy-2,6-difluorobenzyl)-1H-indazol-3-yl]-5-[2-(methylsulfinyl)ethoxy]-N-(pyridin-4-yl)pyrimidin-4-amine,
2-[1-(4-ethoxy-2,6-difluorobenzyl)-1H-indazol-3-yl]-5-[2-(methylsulfinyl)ethoxy]-N-(pyridin-4-yl)pyrimidin-4-amine (Enantiomer 1),
2-[1-(4-ethoxy-2,6-difluorobenzyl)-1H-indazol-3-yl]-5-[2-(methylsulfinyl)ethoxy]-N-(pyridin-4-yl)pyrimidin-4-amine (Enantiomer 2),
2-[1-(4-ethoxy-2,6-difluorobenzyl)-1H-indazol-3-yl]-5-[2-(methylsulfonyl)ethoxy]-N-(pyridin-4-yl)pyrimidin-4-amine,
5-(2-aminoethoxy)-2-[1-(4-ethoxy-2,6-difluorobenzyl)-1H-indazol-3-yl]-N-(pyridin-4-yl)pyrimidin-4-amine,
2-[1-(4-ethoxy-2,6-difluorobenzyl)-1H-indazol-3-yl]-5-(morpholin-2-ylmethoxy)-N-(pyridin-4-yl)pyrimidin-4-amine,
Preparation of ethyl 4-({2-[1-(4-ethoxy-2,6-difluorobenzyl)-1H-indazol-3-yl]-5-methoxypyrimidin-4-yl}amino)pyridine-3-carboxylate,
N-(3,5-difluoropyridin-4-yl)-2-[1-(4-ethoxy-2,6-difluorobenzyl)-1H-indazol-3-yl]-5-methoxypyrimidin-4-amine,
2-[1-(3-amino-2,6-dichlorobenzyl)-1H-indazol-3-yl]-5-methoxy-N-(pyridin-4-yl)pyrimidin-4-amine,
N-[2,4-dichloro-3-({3-[5-methoxy-4-(pyridin-4-ylamino)pyrimidin-2-yl]-1H-indazol-1-yl}methyl)phenyl]acetamide, 2-[1-(4-ethoxy-2,6-difluorobenzyl)-4-methyl-1H-indazol-3-yl]-5-methoxy-N-(pyridin-4-yl)pyrimidin-4-amine
or an N-oxide, a salt, a tautomer or a stereoisomer of said compound, or a salt of said N-oxide, tautomer or stereoisomer.

In one aspect of the invention compounds of formula (I) as described above are selected from the group consisting of:
2-[1-(6-chloro-2-fluoro-3-methylbenzyl)-1H-indazol-3-yl]-5-methoxy-N-(pyridin-4-yl)pyrimidin-4-amine,
2-[1-(6-chloro-2-fluoro-3-methoxybenzyl)-1H-indazol-3-yl]-5-methoxy-N-(pyridin-4-yl)pyrimidin-4-amine,
5-methoxy-2-{1-[3-(5-methyl-1,2,4-oxadiazol-3-yl)benzyl]-1H-indazol-3-yl}-N-(pyridin-4-yl)pyrimidin-4-amine,
2-[1-(2-chloro-4,5-dimethylbenzyl)-1H-indazol-3-yl]-5-methoxy-N-(pyridin-4-yl)pyrimidin-4-amine,
5-methoxy-2-{1-[4-(pentafluoro-lambda<sup>6</sup>←sulfanyl)benzyl]-1H-indazol-3-yl}-N-(pyridin-4-yl)pyrimidin-4-amine,
2-[1-(2,6-difluoro-3-methoxybenzyl)-1H-indazol-3-yl]-5-methoxy-N-(pyridin-4-yl)pyrimidin-4-amine,
N-(2,6-difluoro-3-methoxybenzyl)-2-[1-(2,6-difluoro-3-methoxybenzyl)-1H-Indazol-3-yl]-5-methoxy-N-(pyridin-4-yl)pyrimidin-4-amine,
2-{1-[(6-bromo-1,3-benzodioxol-5-yl)methyl]-1H-indazol-3-yl}-5-methoxy-N-(pyridin-4-yl)pyrimidin-4-amine,
2-[1-(4-ethoxy-2,6-difluorobenzyl)-1H-indazol-3-yl]-5-methoxy-N-(pyridin-4-yl)pyrimidin-4-amine,
N-(4-ethoxy-2,6-difluorobenzyl)-2-[1-(4-ethoxy-2,6-difluorobenzyl)-1H-indazol-3-yl]-5-methoxy-N-(pyridin-4-yl)pyrimidin-4-amine,
2-({3-[5-methoxy-4-(pyridin-4-ylamino)pyrimidin-2-yl]-1H-indazol-1-yl}methyl)benzonitrile,
2-[1-(2-chloro-4-methoxybenzyl)-1H-indazol-3-yl]-5-methoxy-N-(pyridin-4-yl)pyrimidin-4-amine,
2-[1-(3,4-dihydro-2H-1,5-benzodioxepin-6-yl methyl)-1H-indazol-3-yl]-5-methoxy-N-(pyridin-4-yl)pyrimidin-4-amine,
2-[1-(2,6-difluorobenzyl)-1H-indazol-3-yl]-5-methoxy-N-(pyridin-4-yl)pyrimidin-4-amine,
N-(2,6-difluorobenzyl)-2-[1-(2,6-difluorobenzyl)-1H-indazol-3-yl]-5-methoxy-N-(pyridin-4-yl)pyrimidin-4-amine,
5-methoxy-N-(pyridin-4-yl)-2-(1-{3-[(trifluoromethyl)sulfanyl]benzyl}-1H-indazol-3-yl)pyrimidin-4-amine,
2-[1-(2,3-difluoro-4-methylbenzyl)-1H-indazol-3-yl]-5-methoxy-N-(pyridin-4-yl)pyrimidin-4-amine,
N-(2,3-difluoro-4-methylbenzyl)-2-[1-(2,3-difluoro-4-methylbenzyl)-1H-indazol-3-yl]-5-methoxy-N-(pyridin-4-yl)pyrimidin-4-amine,
5-methoxy-2-{1-[4-(1H-pyrazol-1-yl)benzyl]-1H-indazol-3-yl}-N-(pyridin-4-yl)pyrimidin-4-amine,
2-[1-(2,6-dichlorobenzyl)-1H-indazol-3-yl]-5-methoxy-N-(pyridin-4-yl)pyrimidin-4-amine,
N-(2,6-dichlorobenzyl)-2-[1-(2,6-dichlorobenzyl)-1H-indazol-3-yl]-5-methoxy-N-(pyridin-4-yl)pyrimidin-4-amine,
5-methoxy-N-(pyridin-4-yl)-2-(1-{4-[(trifluoromethyl)sulfanyl]benzyl}-1H-indazol-3-yl)pyrimidin-4-amine,
2-[1-(2-chlorobenzyl)-1H-indazol-3-yl]-5-methoxy-N-(pyridin-4-yl)pyrimidin-4-amine,
N-(2-chlorobenzyl)-2-[1-(2-chlorobenzyl)-1H-indazol-3-yl]-5-methoxy-N-(pyridin-4-yl)pyrimidin-4-amine,
methyl 3-chloro-4-({3-[5-methoxy-4-(pyridin-4-ylamino)pyrimidin-2-yl]-1H-indazol-1-yl}methyl)benzoate,
methyl 3-chloro-4-{[(2-{1-[2-chloro-4-(methoxycarbonyl)benzyl]-1H-indazol-3-yl}-5-methoxypyridine-4-yl)(pyridin-4-yl)amino]methyl}benzoate,
2-[1-(4-bromo-2,6-difluorobenzyl)-1H-indazol-3-yl]-5-methoxy-N-(pyridin-4-yl)pyrimidin-4-amine,
2-[1-(2-chloro-4-fluoro-3-methoxybenzyl)-1H-indazol-3-yl]-5-methoxy-N-(pyridin-4-yl)pyrimidin-4-amine,
2-[1-(4-ethoxy-2,3-difluorobenzyl)-1H-indazol-3-yl]-5-methoxy-N-(pyridin-4-yl)pyrimidin-4-amine,
N-(4-ethoxy-2,3-difluorobenzyl)-2-[1-(4-ethoxy-2,3-difluorobenzyl)-1H-indazol-3-yl]-5-methoxy-N-(pyridin-4-yl)pyrimidin-4-amine,
5-methoxy-N-(pyridin-4-yl)-2-{1-[2,3,5,6-tetrafluoro-4-(2,2,2-trifluoroethoxy)benzyl]-1H-indazol-3-yl}pyrimidin-4-amine,
5-methoxy-N-(pyridin-4-yl)-N-[2,3,5,6-tetrafluoro-4-(2,2,2-trifluoroethoxy)benzyl]-2-{1-[2,3,5,6-tetrafluoro-4-(2,2,2-trifluoroethoxy)benzyl]-1H-indazol-3-yl}pyrimidin-4-amine,
methyl 2,4-dichloro-3-({3-[5-methoxy-4-(pyridin-4-ylamino)pyrimidin-2-yl]-1H-indazol-1-yl}methyl)benzoate,
5-methoxy-N-(pyridin-4-yl)-2-[1-(2,4,6-trifluorobenzyl)-1H-indazol-3-yl]pyrimidin-4-amine,
5-methoxy-N-(pyridin-4-yl)-N-(2,4,6-trifluorobenzyl)-2-[1-(2,4,6-trifluorobenzyl)-1H-indazol-3-yl]pyrimidin-4-amine,
2-[1-(2-fluorobenzyl)-1H-indazol-3-yl]-5-methoxy-N-(pyridin-4-yl)pyrimidin-4-amine,
2-[1-(2,4-dichloro benzyl)-1H-indazol-3-yl]-5-methoxy-N-(pyridin-4-yl)pyrimidino-4-amine,
2-[1-(2-fluoro-4-iodobenzyl)-1H-indazol-3-yl]-5-methoxy-N-(pyridin-4-yl)pyrimidin-4-amine,
2-[1-(2-bromobenzyl)-1H-indazol-3-yl]-5-methoxy-N-(pyridin-4-yl)pyrimidin-4-amine,
N-(2-bromobenzyl)-2-[1-(2-bromobenzyl)-1H-indazol-3-yl]-5-methoxy-N-(pyridin-4-yl)pyrimidin-4-amine,
[3-fluoro-4-({3-[5-methoxy-4-(pyridin-4-ylamino)pyrimidin-2-yl]-1H-indazol-1-yl}methyl)phenyl]acetic acid,
5-methoxy-N-(pyridin-4-yl)-2-[1-(2,3,5,6-tetrafluoro-4-methoxybenzyl)-1H-indazol-3-yl]pyrimidin-4-amine,
5-methoxy-2-[1-(4-propylbenzyl)-1H-indazol-3-yl]-N-(pyridin-4-yl)pyrimidin-4-amine,
2-{1-[2,6-dichloro-4-(trifluoromethoxy)benzyl]-1H-indazol-3-yl}-5-methoxy-N-(pyridin-4-yl)pyrimidin-4-amine,
N-[2,6-dichloro-4-(trifluoromethoxy)benzyl]-2-{1-[2,6-dichloro-4-(trifluoromethoxy)benzyl]-1H-indazol-3-yl}-5-methoxy-N-(pyridin-4-yl)pyrimidin-4-amine,
7-({3-[5-methoxy-4-(pyridin-4-ylamino)pyrimidin-2-yl]-1H-indazol-1 yl}methyl)-3,4-dihydroquinolin-2(1H)-one,
2-[1-(2-chloro-4-iodobenzyl)-1H-indazol-3-yl]-5-methoxy-N-(pyridin-4-yl)pyrimidin-4-amine,
2-[1-(3,5-dimethoxybenzyl)-1H-indazol-3-yl]-5-methoxy-N-(pyridin-4-yl)pyrimidin-4-amine,
2-{1-[2-chloro-6-(trifluoromethyl)benzyl]-1H-indazol-3-yl}-5-methoxy-N-(pyridin-4-yl)pyrimidin-4-amine,
2-[1-(2-chloro-5-fluorobenzyl)-1H-indazol-3-yl]-5-methoxy-N-(pyridin-4-yl)pyrimidin-4-amine,
7-({3-[5-methoxy-4-(pyridin-4-ylamino)pyrimidin-2-yl]-1H-indazol-1-yl}methyl)-4-methyl-2H-chromen-2-one,
3-fluoro-4-({3-[5-methoxy-4-(pyridin-4-ylamino)pyrimidin-2-yl]-1H-indazol-1-yl}methyl)benzonitrile,
4-{[{2-[1-(4-cyano-2-fluorobenzyl)-1H-indazol-3-yl]-5-methoxypyrimidin-4-yl}(pyridin-4-yl)amino]methyl}-3-fluorobenzonitrile,
2-{1-[2,6-dichloro-3-(trifluoromethyl)benzyl]-1H-indazol-3-yl}-5-methoxy-N-(pyrimidin-4-yl)pyrimidin-4-amine,
ethyl [3-({3-[5-methoxy-4-(pyridin-4-ylamino)pyrimidin-2-yl]-1H-indazol-1-yl}methyl)phenyl]acetate, 2-[1-(4-fluorobenzyl)-1H-indazol-3-yl]-5-methoxy-N-(pyridin-4-yl)pyrimidin-4-amine,
N-cyclopropyl-4-({3-[5-methoxy-4-(pyridin-4-ylamino)pyrimidin-2-yl]-1H-indazol-1-yl}methyl)benzenesulfonamide,
6-({3-[5-methoxy-4-(pyridin-4-ylamino)pyrimidin-2-yl]-1H-indazol-1-yl}methyl)-1-benzofuran-2(3H)-one,
2-{1-[4-(difluoromethoxy)-2,6-difluorobenzyl]-1H-indazol-3-yl}-5-methoxy-N-(pyridin-4-yl)pyrimidin-4-amine,
tert-butyl 3-chloro-4-({3-[5-methoxy-4-(pyridin-4-ylamino)pyrimidin-2-yl]-1H-indazol-1-yl}methyl)benzoate,
ethyl 2-[3-({3-[5-methoxy-4-(pyridin-4-ylamino)pyrimidin-2-yl]-1H-indazol-1-yl}methyl)phenyl]-2-methylpropanoate,
4-({3-[5-methoxy-4-(pyridin-4-ylamino)pyrimidin-2-yl]-1H-indazol-1-yl}methyl)benzonitrile
5-methoxy-2-{1-[4-(morpholin-4-ylsulfonyl)benzyl]-1H-indazol-3-yl}-N-(pyridin-4-yl)pyrimidin-4-amine,
N-[4-(difluoromethoxy)-2,6-difluorobenzyl]-2-{1-[4-(difluoromethoxy)-2,6-difluorobenzyl]-1H-indazol-3-yl}-5-methoxy-N-(pyridin-4-yl)pyrimidin-4-amine,
5-methoxy-N-(pyridin-4-yl)-2-{1-[3-(1H-pyrrol-1-yl)benzyl]-1H-indazol-3-yl}pyrimidin-4-amine,
2-[1-(4-ethoxy-2,6-difluorobenzyl)-1H-indazol-3-yl]-4-(pyridin-4-ylamino)pyrimidin-5-ol,
2-[1-(4-methoxybenzyl)-1H-indazol-3-yl]-4-(pyridin-4-ylamino)pyrimidin-5-ol,
2-[1-(2-fluorobenzyl)-1H-indazol-3-yl]-4-(pyridin-4-ylamino)pyrimidin-5-ol,
2-[1-(4-fluorobenzyl)-1H-indazol-3-yl]-4-(pyridin-4-ylamino)pyrimidin-5-ol,
{3-[({2-[1-(4-ethoxy-2,6-difluorobenzyl)-1H-indazol-3-yl]-4-(pyridin-4-ylamino)pyrimidin-5-yl}oxy)methyl]oxetan-3-yl}methanol,
{3-[({2-[1-(2-fluorobenzyl)-1H-indazol-3-yl]-4-(pyridin-4-ylamino)pyrimidin-5-yl}oxy)methyl]oxetan-3-yl}methanol,
(3-{[(2-[1-(2-fluorobenzyl)-1H-indazol-3-yl]-5-{[3-(hydroxymethyl)oxetan-3-yl]methoxy}pyrimidin-4-yl)(pyridin-4-yl)amino]methyl}oxetan-3-yl)methanol,
1-({2-[1-(2-fluorobenzyl)-1H-indazol-3-yl]-4-(pyridin-4-ylamino)pyrimidin-5-yl}oxy)methanesulfonamide,
5-[2-(dimethylamino)ethoxy]-2-[1-(2-fluorobenzyl)-1H-indazol-3-yl]-N-(pyridin-4-yl)pyrimidin-4-amine,
2-[1-(2-fluorobenzyl)-1H-indazol-3-yl]-N-(pyridin-4-yl)-5-[2-(1H-tetrazol-5-yl)ethoxy]pyrimidin-4-amine,
2-[1-(2-fluorobenzyl)-1H-indazol-3-yl]-N-(pyridin-4-yl)-5-[2-(1H-tetrazol-5-yl)ethoxy]-N-[2-(1H-tetrazol-5-yl)ethyl]pyrimidin-4-amine,
5-[2-(dimethylamino)ethoxy]-2-[1-(4-fluorobenzyl)-1H-indazol-3-yl]-N-(pyridin-4-yl)pyrimidin-4-amine,
2-[1-(2-fluorobenzyl)-1H-indazol-3-yl]-N-(pyridin-4-yl)-5-(1H-tetrazol-5-ylmethoxy)pyrimidin-4-amine,
5-[2-(dimethylamino)ethoxy]-2-[1-(4-ethoxy-2,6-difluorobenzyl)-1H-indazol-3-yl]-N-(pyridin-4-yl)pyrimidin-4-amine,
2-[1-(4-ethoxy-2,6-difluorobenzyl)-1H-indazol-3-yl]-N-(pyridin-4-yl)pyrimidine-4-amine,
2-[1-(4-methoxybenzyl)-1H-indazol-3-yl]-N-(pyridin-4-yl)pyrimidin-4-amine,
2-[1-(2-fluorobenzyl)-1H-indazol-3-yl]-N-(pyridin-4-yl)pyrimidin-4-amine,
2-[1-(4-cyclopropyl-2,6-difluorobenzyl)-1H-indazol-3-yl]-5-methoxy-N-(pyridin-4-yl)pyrimidin-4-amine,
2-(1-{2,6-difluoro-4-[(1E)-prop-1-en-1-yl]benzyl}-1H-indazol-3-yl)-5-methoxy-N-(pyridin-4-yl)pyrimidin-4-amine,
1-[3,5-difluoro-4-({3-[5-methoxy-4-(pyridin-4-ylamino)pyrimidin-2-yl]-1H-indazol-1-yl}methyl)phenyl]ethanone,
[2,4-dichloro-3-({3-[5-methoxy-4-(pyridin-4-ylamino)pyrimidin-2-yl]-1H-indazol-1-yl}methyl)phenyl]methanol,
2-[3-({3-[5-methoxy-4-(pyridin-4-ylamino)pyrimidin-2-yl]-1H-indazol-1 yl}methyl)phenyl]ethanol,
2-[3-({3-[5-methoxy-4-(pyridin-4-ylamino)pyrimidin-2-yl]-1H-indazol-1-yl}methyl)phenyl]-2-methylpropan-1-ol,
2-[3-chloro-4-({3-[5-methoxy-4-(pyridin-4-ylamino)pyrimidin-2-yl]-1H-indazol-1-yl}methyl)phenyl]propan-2-ol,
1-[3-({3-[5-methoxy-4-(pyridin-4-ylamino)pyrimidin-2-yl]-1H-indazol-1 yl}methyl)phenyl]-2-methylpropan-2-ol,
2-[2,4-dichloro-3-({3-[5-methoxy-4-(pyridin-4-ylamino)pyrimidin-2-yl]-1H-indazol-1-yl}methyl)phenyl]propan-2-ol,
5-(difluoromethoxy)-2-[1-(4-ethoxy-2,6-difluorobenzyl)-1H-indazol-3-yl]-N-(pyridin-4-yl)pyrimidin-4-amine,
5-(difluoromethoxy)-N-(difluoromethyl)-2-[1-(4-ethoxy-2,6-difluorobenzyl)-1H-indazol-3-yl]-N-(pyridin-4-yl)pyrimidin-4-amine,
4-[(difluoromethyl)(pyridin-4-yl)amino]-2-[1-(4-ethoxy-2,6-difluorobenzyl)-1H-indazol-3-yl]pyrimidin-5-ol,
2-[1-(4-methoxybenzyl)-1H-indazol-3-yl]-N-(pyridin-4-yl)-5-(2,2,2-trifluoroethoxy)pyrimidin-4-amine,
2-[1-(4-ethoxy-2,6-difluorobenzyl)-1H-indazol-3-yl]-N-(pyridin-4-yl)-5-(2,2,2-trifluoroethoxy)pyrimidin-4-amine,
3-({2-[1-(2-fluorobenzyl)-1H-indazol-3-yl]-4-(pyridin-4-ylamino)pyrimidin-5-yl}oxy)propane-1,2-diol,
(2S)-3-({2-[1-(2-fluorobenzyl)-1H-indazol-3-yl]-4-(pyridin-4-ylamino)pyrimidin-5-yl}oxy)propane-1,2-diol,
(2R)-3-({2-[1-(2-fluorobenzyl)-1H-indazol-3-yl]-4-(pyridin-4-ylamino)pyrimidin-5-yl}oxy)propane-1,2-diol,
2-({2-[1-(4-ethoxy-2,6-difluorobenzyl)-1H-indazol-3-yl]-4-(pyridin-4-ylamino)pyrimidin-5-yl}oxy)ethanol,
2-({2-[1-(2-fluorobenzyl)-1H-indazol-3-yl]-4-(pyridin-4-ylamino)pyrimidin-5-yl}oxy)ethanol,
ethyl 4-({2-[1-(2-fluorobenzyl)-1H-indazol-3-yl]-5-(2-hydroxyethoxy)pyrimidin-4-yl}amino)pyridine-3-carboxylate,
4-({2-[1-(2-fluorobenzyl)-1H-indazol-3-yl]-5-(2-hydroxyethoxy)pyrimidin-4-yl}amino)-N-methyl pyridine-3-carboxamide,
4-({2-[1-(2-fluorobenzyl)-1H-indazol-3-yl]-5-(2-hydroxyethoxy)pyrimidin-4-yl}amino)pyridine-3-carboxamide,
2-hydroxyethyl 4-({2-[1-(2-fluorobenzyl)-1H-indazol-3-yl]-5-(2-hydroxyethoxy)pyrimidin-4-yl}amino)pyridine-3-carboxylate,
5-(cyclopropyloxy)-2-[1-(4-methoxybenzyl)-1H-indazol-3-yl]-N-(pyridin-4-yl)pyrimidin-4-amine,
2-[1-(4-ethoxy-2,6-difluorobenzyl)-1H-indazol-3-yl]-5-methoxy-N-(pyridin-4-yl)pyrimidin-4-amine hydrochloride (1:1),
(2S)-3-({2-[1-(2-fluorobenzyl)-1H-indazol-3-yl]-4-(pyridin-4-ylamino)pyrimidin-5-yl}oxy)propane-1,2-diol hydrochloride (1:1),
2-({2-[1-(4-ethoxy-2,6-difluorobenzyl)-1H-indazol-3-yl]-4-(pyridin-4-ylamino)pyrimidin-5-yl}oxy)ethanol hydrochloride (1:1),
2-[1-(2,6-dichloro benzyl)-1H-indazol-3-yl]-5-methoxy-N-(pyridin-4-yl)pyrimidin-4-amine hydrochloride (1:1),
[2,4-dichloro-3-({3-[5-methoxy-4-(pyridin-4-ylamino)pyrimidin-2-yl]-1H-indazol-1-yl}methyl)phenyl]methanol hydrochloride (1:1), (2R)-3-({2-[1-(2-fluorobenzyl)-1H-indazol-3-yl]-4-(pyridin-4-ylamino)pyrimidin-5-yl}oxy)propane-1,2-diol hydrochloride (1:1),
N-{2-[1-(4-ethoxy-2,6-difluorobenzyl)-1H-indazol-3-yl]pyrimidin-4-yl}-N-(pyridin-4-yl)acetamide,
N-{2-[1-(4-ethoxy-2,6-difluorobenzyl)-1H-indazol-3-yl]pyrimidin-4-yl}-2-methoxy-N-(pyridin-4-yl)acetamide,
N-{2-[1-(4-ethoxy-2,6-difluorobenzyl)-1H-indazol-3-yl]pyrimidin-4-yl}-N-(pyridin-4-yl)tetrahydro-2H-pyran-4-carboxamide,
N-{2-[1-(4-ethoxy-2,6-difluorobenzyl)-1H-indazol-3-yl]pyrimidin-4-yl}-2-(2-methoxyethoxy)-N-(pyridin-4-yl)acetamide,
2-[{2-[1-(4-ethoxy-2,6-difluorobenzyl)-1H-indazol-3-yl]pyrimidin-4-yl}(pyridin-4-yl)amino]ethanol,
(3-{[{2-[1-(4-ethoxy-2,6-difluorobenzyl)-1H-indazol-3-yl]pyrimidin-4-yl}(pyridin-4-yl)amino]methyl}oxetan-3-yl)methanol,
2-{1-[4-bromo-2-fluoro-6-(2,2,2-trifluoroethoxy)benzyl]-1H-indazol-3-yl}-5-methoxy-N-(pyridin-4-yl)pyrimidin-4-amine,
2-{1-[4-bromo-2,6-bis(2,2,2-trifluoroethoxy)benzyl]-1H-indazol-3-yl}-5-methoxy-N-(pyridin-4-yl)pyrimidin-4-amine,
2,4-dichloro-3-({3-[5-methoxy-4-(pyridin-4-ylamino)pyrimidin-2-yl]-1H-indazol-1-yl}methyl)benzoic acid,
2,4-dichloro-3-({3-[5-methoxy-4-(pyridin-4-ylamino)pyrimidin-2-yl]-1H-indazol-1-yl}methyl)-N-methylbenzamide,
2,4-dichloro-3-({3-[5-methoxy-4-(pyridin-4-ylamino)pyrimidin-2-yl]-1H-indazol-1-yl}methyl)benzamide,
2,4-dichloro-3-({3-[5-methoxy-4-(pyridin-4-ylamino)pyrimidin-2-yl]-1H-indazol-1-yl}methyl)-N,N-dimethylbenzamide,
2,4-dichloro-N-(2-hydroxyethyl)-3-({3-[5-methoxy-4-(pyridin-4-ylamino)pyrimidin-2-yl]-1H-indazol-1-yl}methyl)benzamide,
[2,4-dichloro-3-({3-[5-methoxy-4-(pyridin-4-ylamino)pyrimidin-2-yl]-1H-indazol-1-yl}methyl)phenyl](morpholin-4-yl)methanone,
3,5-difluoro-4-({3-[5-methoxy-4-(pyridin-4-ylamino)pyrimidin-2-yl]-1H-indazol-1-yl}methyl)-N-methylbenzamide,
2-[1-(4-ethynyl-2-fluorobenzyl)-1H-indazol-3-yl]-5-methoxy-N-(pyridin-4-yl)pyrimidin-4-amine,
{2-[1-(2-fluorobenzyl)-1H-indazol-3-yl]-8-(pyridin-4-yl)-7,8-dihydro-6H-pyrimido[5,4-b][1,4]oxazin-7-yl}methanol,
2-[1-(2-fluorobenzyl)-1H-indazol-3-yl]-5-methoxy-N-methyl-N-(pyridin-4-yl)pyrimidin-4-amine,
4-({2-[1-(2-fluorobenzyl)-1H-indazol-3-yl]-5-methoxypyrimidin-4-yl}amino)pyridine-3-carbonitrile,
2-[1-(2-fluorobenzyl)-1H-indazol-3-yl]-5-methoxy-N,N-di(pyridin-4-yl)pyrimidin-4-amine,
methyl 4-({2-[1-(2-fluorobenzyl)-1H-indazol-3-yl]-5-methoxypyrimidin-4-yl}amino)pyridine-3-carboxylate,
4-({2-[1-(2-fluorobenzyl)-1H-indazol-3-yl]-5-methoxypyrimidin-4-yl}amino)pyridine-3-carboxamide,
4-({5-methoxy-2-[1-(4-propyl benzyl)-1H-indazol-3-yl]pyrimidin-4-yl}amino)pyridine-3-carboxamide,
4-({2-[1-(2-fluorobenzyl)-1H-indazol-3-yl]-5-hydroxypyrimidin-4-yl}amino)pyridine-3-carbonitrile,
4-({4-[(3-cyanopyridin-4-yl)amino]-2-[1-(2-fluorobenzyl)-1H-indazol-3-yl]pyrimidin-5-yl}oxy)pyridine-3-carbonitrile,
5-methoxy-2-[1-(4-methoxybenzyl)-1H-indazol-3-yl]-N-[3-(trifluoromethyl)pyridin-4-yl]pyrimidin-4-amine,
3-chloro-4-({3-[5-methoxy-4-(pyridin-4-ylamino)pyrimidin-2-yl]-1H-indazol-1-yl}methyl)benzoic acid,
formic acid-3-chloro-4-({3-[5-methoxy-4-(pyridin-4-ylamino)pyrimidin-2-yl]-1H-indazol-1-yl}methyl)-N-methylbenzamide (1:1),
3-chloro-4-({3-[5-methoxy-4-(pyridin-4-ylamino)pyrimidin-2-yl]-1H-indazol-1-yl}methyl)-N-methylbenzamide,
4-({2-[1-(2-fluorobenzyl)-1H-indazol-3-yl]-5-hydroxypyrimidin-4-yl}amino)pyridine-3-carboxamide,
4-({2-[1-(2-fluorobenzyl)-1H-indazol-3-yl]-5-hydroxypyrimidin-4-yl}amino)pyridine-3-carboxylic acid,
ethyl 4-({2-[1-(2-fluorobenzyl)-1H-indazol-3-yl]-5-hydroxypyrimidin-4-yl}amino)pyridine-3-carboxylate,
2-[1-(2-fluorobenzyl)-1H-indazol-3-yl]-4-(pyridin-4-ylamino)pyrimidine-5-carbonitrile,
2-[1-(2-fluorobenzyl)-1H-indazol-3-yl]-4-(pyridin-4-ylamino)pyrimidine-5-carboxamide,
4-({2-[1-(2-fluorobenzyl)-1H-indazol-3-yl]-5-(2-hydroxyethoxy)pyrimidin-4-yl}amino)pyridine-3-carboxylic acid hydrochloride (1:1),
N-(2-fluoropyrid in-4-yl)-5-methoxy-2-[1-(4-methoxybenzyl)-1H-indazol-3-yl]pyrimidin-4-amine,
N-(2,6-difluoropyridin-4-yl)-5-methoxy-2-[1-(4-methoxybenzyl)-1H-indazol-3-yl]pyrimidin-4-amine,
N-(3-fluoropyrid in-4-yl)-5-methoxy-2-[1-(4-methoxybenzyl)-1H-indazol-3-yl]pyrimidin-4-amine,
N-(difluoromethyl)-2-[1-(4-ethoxy-2,6-difluorobenzyl)-1H-indazol-3-yl]-N-(pyridin-4-yl)pyrimidin-4-amine
or an N-oxide, a salt, a tautomer or a stereoisomer of said compound, or a salt of said N-oxide, tautomer or stereoisomer.

One aspect of the invention are compounds of formula (I) as described in the examples as characterized by their names in the title as claimed in claim 5 and their structures as well as the subcombinations of all residues specifically disclosed in the compounds of the examples.

Another aspect of the present invention are the intermediates as used for their synthesis.

One special aspect of the invention is intermediate (1-5) wherein,

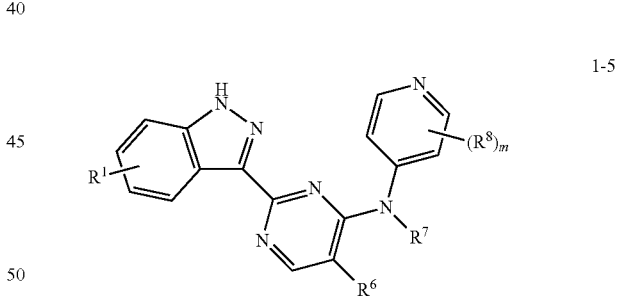

1-5 whereby $R^1$, $R^6$, $R^7 R^8$ and m have the meaning according to claim 1.

If embodiments of the invention as disclosed herein relate to compounds of formula (I), it is understood that those embodiments refer to the compounds of formula (I) as disclosed in the claims and the examples.

Another aspect of the invention are compounds of formula (I), wherein
$R^1$ is hydrogen, halogen, 1-3C-alkyl,
Another aspect of the invention are compounds of formula (I), wherein
$R^1$ is halogen.
Another aspect of the invention are compounds of formula (I), wherein
$R^1$ is 1-3C-alkyl.

A further aspect of the invention are compounds of formula (I), wherein
$R^1$ is hydrogen, 1-3C-alkyl.

Yet another aspect of the invention are compounds of formula (I) according to claims 1, 2, 3, 4, 5 or 6, wherein $R^1$ is hydrogen.

A further aspect of the invention are compounds of formula (I), wherein
$R^2/R^3$ are independently from each other hydrogen, halogen, cyano, hydroxy 1-6C-haloalkyl, 1-6C-haloalkoxy, 1-6C-alkoxy, A further aspect of the invention are compounds of formula (I) according to claim 1, wherein $R^2$ and/or $R^3$ are independently from each other hydrogen, halogen, cyano, 1-6C-haloalkyl, 1-6C-haloalkoxy.

Another aspect of the invention are compounds of formula (I), wherein
$R^2$ and/or $R^3$ is halogen, especially fluorine, chlorine or bromine, preferably fluorine or chlorine.

Another aspect of the invention are compounds of formula (I), wherein
$R^2$ and/or $R^3$ is 1-3C-haloalkyl, especially $CF_3$.

Another aspect of the invention are compounds of formula (I), wherein
$R^2$ and/or $R^3$ is 1-3C-haloalkoxy, especially —O—$CH_2$—$CF_3$.

Another aspect of the invention are compounds of formula (I), wherein
$R^2$ and/or $R^3$ is fluorine, chlorine, bromine, $CF_3$, or —O—$CH_2$—$CF_3$.

Another aspect of the invention are compounds of formula (I), wherein
$R^2$ and/or $R^3$ is fluorine, chlorine, bromine, hydroxy, methoxy, $CF_3$, or —O—$CH_2$—$CF_3$.

Yet another aspect of the invention are compounds of formula (I), wherein
$R^2$ and $R^3$ are halogen or 1-3C-haloalkoxy, especially fluorine, chlorine, or —O—$CH_2$—$CF_3$.

Another aspect of the invention are compounds of formula (I), wherein $R^2$ and/or $R^3$ are hydroxy, (1-6C-alkoxy).

A further aspect of the invention are compounds of formula (I), wherein
$R^2$ and $R^3$ are different.

Another aspect of the invention are compounds of formula (I), wherein one position of $R^2$ and $R^3$ is hydrogen and the other is halogen, 1-3C-haloalkyl, 1-3C-haloalkoxy or especially fluorine, chlorine, bromine, $CF_3$, or —O—$CH_2$—$CF_3$.

Another aspect of the invention are compounds of formula (I), wherein
$R^4$ is independently hydrogen, hydroxy, halogen, cyano, $NO_2$, 1-6C-alkyl, 2-6C-alkenyl, 2-6C-alkynyl, 1-6C-haloalkyl, 1-6C-hydroxyalkyl, 1-6C-alkoxy, —O—(2-6C-alkylen)-O—C(O)-(1-6C-alkyl), 1-6C-haloalkoxy, —C(O)$OR^9$, -1-6C-alkylen)-C(O)$OR^9$, —C(O)-(1-6C-alkyl), —C(O)$NR^{10}R^{11}$, 3-7C-cycloalkyl, —S-(1-6C-haloalkyl), $SF_5$, —$SO_2$NH-(3-7C-cycloalkyl), —$SO_2NR^{10}R^{11}$, $NR^{10}R^{11}$, heteroaryl which optionally is substituted independently one or more times with cyano, 1-4C-alkyl, 1-6C-haloalkyl, 1-6C-haloalkoxy, C(O)$OR^{11}$, C(O)$NR^{10}R^{11}$, whereby two of $R^2$, $R^3(R^4)_n$, when positioned ortho to each other, may form together with the two carbon atoms to which they are attached, a heterocyclic 5-, 6- or 7-membered ring containing 1 or 2 heteroatoms selected from O or N, and optionally containing an additional double bond and/or optionally substituted by an oxo (=O) group and/or an 1-4C-alkyl group, Another aspect of the invention are compounds of formula (I), wherein
$R^4$ is hydrogen.

Another aspect of the invention are compounds of formula (I), wherein
$R^4$ is hydrogen or halogen, especially hydrogen or fluorine.

Another aspect of the invention are compounds of formula (I), wherein
$R^4$ is selected from the group consisting of hydroxy, $NO_2$ or $NR^{10}R^{11}$.

Another aspect of the invention are compounds of formula (I), wherein
$R^4$ is selected from the group consisting of is independently hydrogen, halogen, cyano, 1-6C-alkyl, 2-6C-alkenyl, 1-6C-haloalkyl, 1-6C-hydroxyalkyl, 1-6C-alkoxy, 1-6C-haloalkoxy, —C(O)$OR^9$, -(1-6C-alkylen)-C(O)$OR^9$, —C(O)-(1-6C-alkyl), —C(O)$NR^{10}R^{11}$, 3-7C-cycloalkyl, —S-(1-6C-haloalkyl), $SF_5$, —$SO_2$NH-(3-7C-cycloalkyl), —$SO_2NR^{10}R^{11}$, heteroaryl which optionally is substituted independently one or more times with cyano, 1-4C-alkyl, 1-6C-haloalkyl, 1-6C-haloalkoxy, C(O)$OR^9$, C(O)$NR^{10}R^{11}$, whereby two of $R^2$, $R^3(R^4)_n$, when positioned ortho to each other, may form together with the two carbon atoms to which they are attached, a heterocyclic 5-, 6- or 7-membered ring containing 1 or 2 heteroatoms selected from O or N, and optionally an additional double bond and/or a carbonyl group and/or an 1-4C-alkyl group.

Another aspect of the invention are compounds of formula (I), wherein
$R^4$ is selected from the group consisting of hydrogen, halogen, cyano, 1-3C-alkyl, 3-6C-cycloalkyl, 2-3C-alkenyl, 1-3C-haloalkyl, 1-3C-hydroxyalkyl, 1-3C-alkoxy, 1-3C-haloalkoxy, —C(O)-(1-3C-alkyl), COOH, (1-3C-alkylen)-COOH, -(1-3C-alkylen)COO-(1-3C-alkyl), —COO-(1-4C-alkyl), —C(O)$NH_2$, —C(O)NH(1-3C-alkyl), —C(O)N(1-3C-alkyl)$_2$, —C(O)NH-(1-3C-alkyl)-OH, —C(O)—(N-heterocyclyl), —$SO_2$—NH(3-6C-cycloalkyl), —$SO_2$—(N-heterocyclyl), Yet another aspect of the invention are compounds of formula (I), wherein
$R^4$ is selected from the group consisting of hydrogen, hydroxy, fluorine, chlorine, bromine or iodine, cyano, nitro, —$CH_3$, —$C_3H_9$, cyclopropyl, 1-propenyl, —$CF_3$, —$CH_2$—OH, —$CH_2$—$CH_2$—OH, —C($CH_3$)$_2$—OH, —$CH_2$—C($CH_3$)$_2$—OH, —C($CH_3$)$_2$—$CH_2$—OH, —$OCH_3$, —$OCF_3$, —$OCF_2$H, —$OCH_2CF_3$, —C(O)$CH_3$, —COOH, —C(O)$OCH_3$, —C(O)$OC_2H_5$, —C(O)OC($CH_3$)$_3$, —$CH_2$—$COOC_2H_5$, —$CH_2$—COOH, —C($CH_3$)$_2$—$COOC_2H_5$, —C(O)$NH_2$, —C(O)NH($CH_3$), —C(O)N($CH_3$)$_2$, —C(O)NH—($CH_2$)$_2$—OH, —C(O)—(N-morpholino), —$SO_2$—NH-cyclopropyl, —$SO_2$—(N-morpholino), $NH_2$.

Yet another aspect of the invention are compounds of formula (I), wherein
$R^4$ is selected from the group consisting of hydrogen, fluorine, chlorine, bromine or iodine, cyano, —$CH_3$, —$C_3H_9$, cyclopropyl, 1-propenyl, —$CF_3$, —$CH_2$—OH, —$CH_2$—$CH_2$—OH, —C($CH_3$)$_2$—OH, —$CH_2$—C($CH_3$)$_2$—OH, —C($CH_3$)$_2$—$CH_2$—OH, —$OCH_3$, —$OCF_3$, —$OCF_2$H, —$OCH_2CF_3$, —C(O)$CH_3$, —COOH, —C(O)$OCH_3$, —C(O)$OC_2H_5$, —C(O)OC($CH_3$)$_3$, —$CH_2$—$COOC_2H_5$, —$CH_2$—COOH, —C($CH_3$)$_2$—$COOC_2H_5$, —C(O)$NH_2$, —C(O)NH($CH_3$), —C(O)N($CH_3$)$_2$, —C(O)

NH—(CH$_2$)$_2$—OH, —C(O)—(N-morpholino), —SO$_2$—NH-cyclopropyl, —SO$_2$—(N-morpholino).

A further aspect of the invention are compounds of formula (I), wherein whereby two of R$^2$, R$^3$(R$^4$)$_n$, when positioned ortho to each other, may form together with the two carbon atoms to which they are attached, a heterocyclic 5-, 6- or 7-membered ring containing 1 or 2 heteroatoms selected from O or N, and optionally an additional double bond and/or a carbonyl group and/or an 1-4C-alkyl group, especially whereby two of R$^2$, R$^3$(R$^4$)$_n$, when positioned ortho to each other, form together with the two carbon atoms to which they are attached, —O—CH$_2$—CH$_2$—CH$_2$—O—, —O—CH$_2$—CH$_2$—, —(CH$_3$)C=CH—(C=O)—O—, —CH$_2$—(C=O)—O—, —(CH$_2$)$_2$—(C=O)—NH—.

In another embodiment of the above-mentioned aspects, the invention relates to compounds of formula (I), wherein n is 0, 1 or 2.

Another aspect of the invention are compounds of formula (I), wherein
n is at least 1.

Another aspect of the invention are compounds of formula (I), wherein
n is 1.

Another aspect of the invention are compounds of formula (I), wherein
R$^6$ is (a) hydrogen;
(b) hydroxy;
(c) cyano;
(d) 1-6C-alkoxy optionally substituted independently one or more times with
(d1) OH,
(d2) —O-(1-6C-alkyl)
(d3) C(O)OR$^9$,
(d4) C(O)NR$^{10}$R$^{11}$,
(d5) NR$^{10}$R$^{11}$,
(d6) —S-(1-6C-alkyl),
(d7) —S(O)-(1-6C-alkyl),
(d8) —SO$_2$-(1-6C-alkyl)
(d9) SO$_2$NR$^{10}$R$^{11}$,
(d10) heterocyclyl, which is optionally substituted with C(O)OR$^9$, or oxo (=O),
(d11) heteroaryl, which is optionally substituted independently one or more times with cyano, 1-4C-alkyl, 1-6C-haloalkyl, 1-6C-haloalkoxy, C(O)OR$^9$, C(O)NR$^{10}$R$^{11}$, (1-6C-alkylen)-O-(1-6C-alkyl),
(e) SO$_2$NR$^{10}$R$^{11}$,
(f) 3-7C-cycloalkoxy,
(g) 1-6C-haloalkoxy,
(h) COOR$^9$,
(i) —C(O)NR$^{10}$R$^{11}$,
(j) —O-heteroaryl opt. subst. with CN

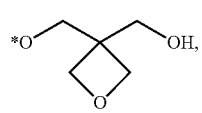
(k)

whereby the * is the point of attachment,
(l) —O-(2-6C-alkylen)-O-(1-6C-alkyl) which is optionally substituted with hydroxy, NH(CO)OR$^9$, A further aspect of the invention are compounds of formula (I), wherein
R$^6$ is 1-6C-alkoxy which is optionally substituted independently one or more times.

A further aspect of the invention are compounds of formula (I), wherein
R$^6$ is heteroaryl, which is optionally substituted independently one or more times with cyano, 1-4C-alkyl, 1-6C-haloalkyl, 1-6C-haloalkoxy,
C(O)OR$^9$, C(O)NR$^{10}$R$^{11}$, (1-6C-alkyl)-O-(1-6C-alkyl).
Another aspect of the invention are compounds of formula (I), wherein
R$^6$ is —O-(2-6Calkyl)-O-(1-6C-alkyl) which is optionally substituted with hydroxy or NH—C(O)OR$^9$.
Another aspect of the invention are compounds of formula (I), wherein
R$^6$ is 1-6C-alkoxy which is optionally substituted independently one or more times with
(d1) OH,
(d2) —O-(1-6C-alkyl)
(d3) C(O)OR$^9$,
(d4) C(O)NR$^{10}$R$^{11}$,
(d5) NR$^{10}$R$^{11}$,
(d6) —S-(1-6C-alkyl),
(d7) —S(O)-(1-6C-alkyl),
(d8) —SO$_2$-(1-6C-alkyl)
(d9) SO$_2$NR$^{10}$R$^{11}$,
(d10) heterocyclyl, which is optionally substituted with C(O)OR$^9$, or oxo (=O),
(d11) heteroaryl, which is optionally substituted independently one or more times with cyano, 1-4C-alkyl, 1-6C-haloalkyl, 1-6C-haloalkoxy, C(O)OR$^9$, C(O)NR$^{10}$R$^{11}$, (2-6C-alkylen)-O-(1-6C-alkyl), Another aspect of the invention are compounds of formula (I), wherein
R$^6$ is 1-6C-alkoxy which is optionally substituted independently one or more times with
(d2) C(O)OR$^9$,
(d3) C(O)NR$^{10}$R$^{11}$,
(d4) —S-(1-6C-alkyl),
(d6) —S(O)-(1-6C-alkyl),
(d7) —SO$_2$-(1-6C-alkyl),
(d9) heterocyclyl, which is optionally substituted with C(O)OR$^9$, oxo (=O).
Another aspect of the invention are compounds of formula (I), wherein
R$^6$ is (a) hydrogen;
(b) hydroxy;
(c) cyano;
(d) 1-6C-alkoxy opt. subst. with
(d1) 1-2 OH,
(d2) NR$^{10}$R$^{11}$,
(d3) SO$_2$NR$^{10}$R$^{11}$,
(d4) heterocyclyl,
(d5) heteroaryl, which is optionally substituted independently one or more times with cyano, 1-4Calkyl, 1-6C-haloalkyl, 1-6C-haloalkoxy, C(O)OR$^9$, C(O)NR$^{10}$R$^{11}$,
(e) SO$_2$NR$^{10}$R$^{11}$;
(f) 3-7C-cycloalkoxy,
(g) 1-6C-haloalkoxy,
(h) —C(O)NR$^1$OR$^{11}$,
(i) —O-heteroaryl opt. subst. with CN

(j)

whereby the * Is the point of attachment,

Another aspect of the invention are compounds of formula (I), wherein $R^6$ is hydrogen, hydroxy, cyano, —O-(3-6C-cycloalkyl), 1-3C-alkoxy, 1-3C-haloalkoxy, —O-(1-3C-alkylen)-OH, —O-(1-3C-alkylen)-NH2, —O-(1-3C-alkylen)-NH(1-3C-alkyl), —O-(1-3C-alkylen)-N(1-3C-alkyl)2, —O-(1-3C-alkylen)-SO2NH2, —O-(1-3C-alkylen)-SO2N(1-3C-alkyl)2, —O-(1-3C-alkylen)-(optionally substituted heteroaryl), —C(O)NH2, —C(O)N(1-3C-alkyl)2.

Another aspect of the invention are compounds of formula (I), wherein.

$R^6$ is hydrogen, hydroxy, cyano, —O-cyclopropyl, —OCH$_3$, —OCF$_3$, —OCF$_2$H, —OCH$_2$CF$_3$, —O—(CH$_2$)$_2$—OH, —O—(CH$_2$)$_2$—NH$_2$, —O(CH$_2$)$_2$—N(CH$_3$)$_2$, —O—(CH$_2$)$_2$—O—CH$_3$, —O—(CH$_2$)$_2$—(CH$_2$)$_2$—OH, —O—CH$_2$—CH(OH)—CH$_2$OH, —O—CH$_2$—CH(OH)—CH$_2$—NH—C(O)OC(CH$_3$)$_3$, —O—CH$_2$—COOH, —O—CH$_2$—COOC$_2$H$_5$, C(O)NH$_2$, —O—CH$_2$—C(O)-(3-fluoro-N-azetidine), —O—CH$_2$—C(O)-(3,3-difluoro-N-azetidine), —O—CH$_2$—CH(OH)—CH$_2$—N-piperidinyl, —O—(CH$_2$)$_2$(morpholine-4-yl), —O—CH$_2$-(morpholine-2-yl), —O—CH$_2$-(morpholine-2-yl-4-tert.-butoxycarboxylate), —O—CH$_2$-(pyrrolidin-2-one-5-yl), —O(CH$_2$)$_2$—S—CH$_3$, —O—(CH$_2$)$_2$—SO—CH$_3$, —O—(CH$_2$)$_2$—SO$_2$—CH$_2$, —O—CH$_2$—SO$_2$NH$_2$, —SO$_2$—CH(CH$_3$)$_2$,

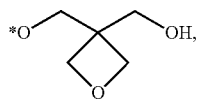

whereby * is the point of attachment, —O—(CH$_2$)$_2$-tetrazolyl, —O—CH$_2$-tetrazolyl, —O-pyridine-4-yl, —O-(3-cyano-pyridine-4-yl), or —O—CH$_2$-(oxadiazole)-CH$_2$—O—CH$_3$, Another aspect of the invention are compounds of formula (I), wherein $R^6$ is hydrogen, hydroxy, cyano, —O-cyclopropyl, —OCH$_3$, —OCF$_3$, —OCF$_2$H, —OCH$_2$CF$_3$, —O—(CH$_2$)$_2$—OH, —O(CH$_2$)$_2$—N(CH$_3$)$_2$, —O—CH$_2$—SO$_2$NH$_2$,

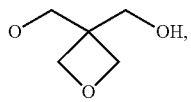

—O—(CH2)2-tetrazolyl, —O—CH$_2$-tetrazolyl, —O-pyridine-4-yl, —O-(3-cyano-pyridine-4-yl), —C(O)NH$_2$.

Another aspect of the invention are compounds of formula (I), wherein $R^6$ is hydrogen, hydroxy, cyano, —O-cyclopropyl, —OCH$_3$, —OCF$_3$, —OCF$_2$H, —OCH$_2$CF$_3$, —O—(CH$_2$)$_2$—OH, —O(CH$_2$)$_2$—N(CH$_3$)$_2$, —O—CH$_2$—SO$_2$NH$_2$,

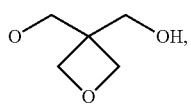

—O—(CH$_2$)$_2$-tetrazolyl, —O—CH$_2$-tetrazolyl, —O-pyridine-4-yl, —O-(3-cyano-pyridine-4-yl), —C(O)NH$_2$.

Another aspect of the invention are compounds of formula (I), wherein if $R^6$ is in the 5-position of the pyrimidine ring directly neighbouring the $R^7$ bearing amino substituent, $R^6$ together with $R^7$ is a 5 or 6-membered ring including the nitrogen atom of the amino substituent which may contain one further heteroatom selected from O, S or N and which in addition may be substituted with a carbonyl group or —CH$_2$—OH.

Another aspect of the invention are compounds of formula (I), wherein if $R^6$ is in the 5-position of the pyrimidine ring directly neighbouring the $R^7$ bearing amino substituent, $R^6$ together with $R^7$ is a 5 or 6-membered ring including the nitrogen atom of the amino substituent which may contain one further heteroatom selected from O, S or N and which in addition may be substituted with a carbonyl group or —CH$_2$—OH or —NH—CHO.

Another preferred aspect of the invention are compounds of formula (I), wherein $R^6$ is -O-(3-6C-cycloalkyl), 1-3C-alkoxy, 1-3C-haloalkoxy, —O-(1-3C-alkylen)OH, —O-(1-3C-alkylen)-NH2, —O-(1-3C-alkylen)-NH(1-3C-alkyl), —O-(1-3C-alkylen)-N(1-3C-alkyl)2, —O-(1-3C-alkylen)-SO2N H2, —O-(1-3C-alkylen)-SO2N(1-3C-alkyl)2, —O-(1-3C-alkylen)-(optionally substituted heteroaryl), especially —O-cyclopropyl, —OCH3, —OCF3, —OCF2H, —OCH2CF3, —O—(CH2)2-OH, —O(CH2)2-N(CH3)2, —O-CH2-SO2NH2,

—O—(CH2)2-tetrazolyl, —O—CH$_2$-tetrazolyl, —O-pyridine-4-yl, —O-(3-cyano-pyridine-4-yl).

Another preferred aspect of the invention are compounds of formula (I), wherein $R^6$ is hydrogen, hydroxy, cyano, —O-cyclopropyl, —O(1-3C-alkyl), —O-(1-3C-haloalkyl), —O-(1-3C-alkylen optionally substituted by a hydroxy group)-OH, —O(1-3C-alkylen optionally substituted by a hydroxy group)-NR$^{10}$R$^{11}$, —O-(1-3-alkylen)-O(1-3C-alkyl), —O-(1-3C-alkylen)-O-(1-3C-alkyl)-OH, —O-(1-3C-alkylen)-COOR$^9$, C(O)NR$^{10}$R$^{11}$, —O-(1-3C-alkylen)-C(O)-(heterocycyl optionally substituted 1 or two times by fluorine), —O-(1-3-alkylen)-(heterocyclyl optionally substituted by an oxo (=O) group and/or COOR$^9$ or a hydroxy group), —O-(1-3C-alkylen)-S—CH$_3$, —O-(1-3C-alkylen)-SO—CH$_3$, —O-(1-3C-alkylen)$_2$-SO$_2$—CH$_3$, —O-(1-3C-alkylen)-SO$_2$NH$_2$, SO$_2$-(1-3C-alkyl)

whereby * is the point of attachment, —O-(1-3-alkylen)-[heteroaryl optionally substituted by CN or (1-3C-alkylen)-O-(1-3C-alkyl)], Another preferred aspect of the invention are compounds of formula (I), wherein $R^6$ is -O-(3-6C-cycloalkyl), 1-3C-alkoxy, 1-3C-haloalkoxy, —O-(1-3C-alkylen)OH, —O-(1-3C-alkylen)-NH2, —O-(1-3C-alkylen)-NH(1-3C-alkyl), —O-(1-3C- alkylen)-N(1-3C-alkyl)$_2$, —O-(1-3C-alkylen)-SO$_2$NH$_2$, —O-(1-3C-alkylen)-SO$_2$N(1-3C-alkyl)$_2$, —O-(1-3C-alkylen)-(optionally substituted heteroaryl), especially —O-cyclopropyl, —OCH$_3$, —OCF$_3$, —OCF$_2$H, —OCH$_2$CF$_3$, —O—(CH$_2$)$_2$—OH, —O(CH$_2$)$_2$—N(CH$_3$)$_2$, —O—CH$_2$—SO$_2$NH$_2$,

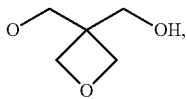

—O—(CH$_2$)$_2$-tetrazolyl, —O—CH$_2$-tetrazolyl, —O-pyridine-4-yl, —O-(3-cyano-pyridine-4-yl).

A further aspect of the invention are compounds of formula (I), wherein
R$^6$ is 1-6C-alkoxy which is substituted by —S-(1-6C-alkyl), —SO-(1-6C-alkyl) or —SO$_2$-(1-6C-alkyl).

A further aspect of the invention are compounds of formula (I), wherein
R$^6$ is SO$_2$NR$^{10}$R$^{11}$.

Another aspect of the invention are compounds of formula (I), wherein
R$^6$ is —C(O)NH$_2$, —C(O)N(1-3C-alkyl)$_2$ or cyano especially —C(O)NH$_2$.

Another aspect of the invention are compounds of formula (I), wherein
R$^7$ is
(a) hydrogen,
(b) 1-6C-alkyl, which is optionally substituted with heteroaryl
(c) 1-6C-haloalkyl,
(d) 1-6C-hydroxyalkyl,

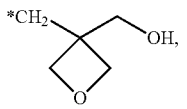

whereby the * is the point of attachment,
(f) —C(O)-(1-6C-alkyl)
(g) —C(O)-(1-6C-alkylen)-O-(1-6C-alkyl)
(h) —C(O)-(1-6C-alkylen)-O-(2-6C-alkylen)-O-(1-6C-alkyl)
(i) —C(O)-heterocyclyl,
(j) benzyl whereby the phenyl ring is opt. subst with 1-5 substituents independently selected from the group consisting of hydrogen, halogen, 1-4C-alkyl, 1-4C-haloalkyl, 1-4C-alkoxy, 1-4C-haloalkoxy, cyano, C(O)OR$^9$,
(k) heteroaryl
or
optionally, R$^6$ and R$^7$ together with the nitrogen atom to which R$^7$ is attached form a 6-membered ring which may contain one further heteroatom selected from the group consisting of O, S, N,
and which is optionally substituted by (1-6C-alkyl)-OH, (1-6C-alkyl)-NR$^{10}$R$^{11}$, Another aspect of the invention are compounds of formula (I), wherein
R$^7$ is
(a) hydrogen,
(b) 1-6C-alkyl, which is optionally substituted with heteroaryl
(c) 1-6C-haloalkyl,
(d) 1-6C-hydroxyalkyl,

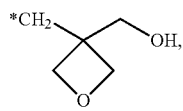

whereby the * is the point of attachment,
(f) —C(O)-(1-6C-alkyl)
(g) —C(O)-(1-6C-alkylen)-O-(1-6C-alkyl)
(h) —C(O)-(1-6C-alkylen)-O-(2-6C-alkylen)-O-(1-6C-alkyl)
(i) —C(O)-heterocyclyl,
(j) benzyl whereby the phenyl ring is opt. subst with 1-5 substituents independently selected from the group consisting of hydrogen, halogen, 1-4C-alkyl, 1-4C-alkoxy, 1-4C-haloalkoxy, cyano, C(O)OR$^9$,
(k) heteroaryl
or
optionally, R$^6$ and R$^7$ together with the nitrogen atom to which R$^7$ is attached form a 6-membered ring which may contain one further heteroatom selected from the group consisting of O, S, N,
and which is optionally substituted by (1-6C-alkyl)-OH, (1-6C-alkyl)-NR$^{10}$R$^{11}$, Another aspect of the invention are compounds of formula (I), wherein
R$^7$ is
(a) hydrogen,
(b) 1-3C-alkyl, which is optionally substituted with heteroaryl
(c) 1-3C-haloalkyl,
(d) 1-3C-hydroxyalkyl,

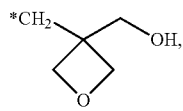

whereby the * is the point of attachment,
(f) —C(O)-(1-3C-alkyl)
(g) —C(O)-(1-3C-alkylen)-O-(1-3C-alkyl)
(h) —C(O)-(1-3C-alkylen)-O-(2-3C-alkylen)-O-(1-3C-alkyl)
(i) —C(O)-heterocyclyl,
(j) benzyl whereby the phenyl ring is opt. subst with 1-5 substituents independently selected from the group consisting of hydrogen, halogen, 1-3C-alkyl, 1-3C-alkoxy, 1-3C-haloalkoxy, cyano, C(O)OR$^9$,
(k) heteroaryl
or
optionally, R$^6$ and R$^7$ together with the nitrogen atom to which R$^7$ is attached form a 6-membered ring which may contain one further heteroatom selected from the group consisting of O, S, N,
and which is optionally substituted by (1-3C-alkyl)-OH, (1-3C-alkyl)-NR$^{10}$R$^{11}$.

Another aspect of the invention are compounds of formula (I), wherein $R^7$ is
(a) hydrogen,
(b) 1-6C-alkyl, which is optionally substituted with heteroaryl
(c) 1-6C-haloalkyl,
(d) 1-6C-hydroxyalkyl,

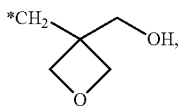
(e)

whereby the * is the point of attachment,
(f) —C(O)-(1-6C-alkyl)
(g) —C(O)-(1-6C-alkylen)-O-(1-6C-alkyl)
(h) —C(O)-(1-6C-alkylen)-O-(1-6C-alkylen)-O-(1-6C-alkyl)
(i) —C(O)-heterocyclyl,
(j) benzyl whereby the phenyl ring is opt. subst with 1-5 substituents independently selected from the group consisting of
  hydrogen, halogen, 1-4Calkyl, 1-4C-haloalkyl, 1-4C-alkoxy, 1-4C-haloalkoxy, cyano,
  $C(O)OR^9$,
(k) heteroaryl
or
optionally $R^6$ and $R^7$ together with the nitrogen atom to which they are attached form a 6-membered ring which may contain one further heteroatom selected from the group consisting of O, S, N,
and which is optionally substituted by hydroxy-(1-6alkyl), Another aspect of the invention are compounds of formula (I), wherein
$R^7$ is hydrogen, 1-3C-alkyl, 1-3C-haloalkyl, -(1-3C-alkylen)-OH,

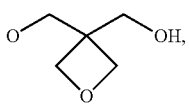

(1-3C-alkylen)-aryl, -(1-3C-alkylen)-heteroaryl, heteroaryl, —C(O)-(1-3C-alkyl), —C(O)-(1-3C-alkylen)-O-(1-3C-alkyl), —C(O)-(1-3C-alkylen)-O-(1-3C-alkylen)-O-(1-3C-alkyl), —C(O)-heterocyclyl.

Another aspect of the invention are compounds of formula (I), wherein
$R^7$ is hydrogen, 1-3C-alkyl, 1-3C-haloalkyl, 1-3C-hydroxyalkyl,

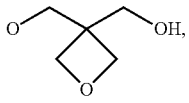

whereby * is the point of attachment,
Heteroaryl, -(1-3C-alkylen)-heteroaryl, —C(O)-heterocyclyl, —C(O)-(1-3C-alkylen)O-(1-3C-alkyl), —C(O)-(1-3C-alkyl), —C(O)CH$_2$—O-(1-3C-alkylen)-O-(1-3C-alkyl), or benzyl which is optionally substituted one or more times with halogen, cyano, 1-3C-alkyl, 1-3C-haloalkyl, 1-3C-alkoxy, 1-3C-haloalkoxy, —C(O)O(1-3-alkyl), or optionally, when $R^6$ is in position 5 of the pyrimidine ring system, $R^6$ and $R^7$ together with the nitrogen atom to which $R^7$ is attached form a 6-membered ring which may contain one further heteroatom selected from O, S or N and which in addition is optionally substituted by CH$_2$—OH or —CH$_2$—NH—CHO Another aspect of the invention are compounds of formula (I), wherein
$R^7$ is hydrogen, methyl, difluoromethyl, hydroxyethyl,

—(CH$_2$)$_2$— is tetrazolyl, pyridine-4-yl, —C(O)-tetrahydropyran-4-yl, —C(O)—CH$_2$—O—CH$_3$, —C(O)—CH$_3$, —C(O)CH$_2$—O—(CH$_2$)$_2$—O—CH$_3$ or benzyl which is optionally substituted one or more times with fluorine, chlorine, bromine, cyano, methyl, methoxy, ethoxy, difluormethoxy, trifluoromethoxy, —O—CH$_2$—CF$_3$, —C(O)OCH$_3$.

Still another aspect of the invention are compounds of formula (I), wherein
$R^7$ is hydrogen, methyl, difluoromethyl, hydroxyethyl,

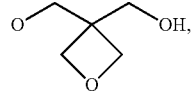

—(CH$_2$)$_2$-tetrazolyl, pyridine-4-yl, —C(O)-tetrahydropyran-4-yl, —C(O)—CH$_2$—O—CH$_3$, —C(O)—CH$_3$, —C(O)CH$_2$—O—(CH$_2$)$_2$—O—CH$_3$ or benzyl which is optionally substituted one or more times with fluorine, chlorine, cyano, methyl, methoxy, ethoxy, difluormethoxy, trifluoromethoxy, —O—CH$_2$—CF$_3$, —C(O)OCH$_3$.

Another aspect of the invention are compounds of formula (I), wherein
$R^7$ is optionally one or more times substituted benzyl, the substitutents selected from the group consisting of halogen (especially fluorine, chlorine), cyano, 1-3C-alkoxy (especially methoxy, ethoxy), 1-3C-haloalkoxy (especially —OCF$_3$, —O—CF$_2$H, —O—CH$_2$—CF$_3$).

In another aspect the benzyl group is substituted 1-, 2-, 3- or 4 times.

Another aspect of the invention are compounds of formula (I), wherein
$R^8$ is hydrogen, halogen, hydroxy, cyano, 1-6C-alkyl, 1-6C-hydroxyalkyl, 1-6C-haloalkyl, 1-6C-haloalkoxy, C(O)OR$^9$, C(O)NR$^{11}$R$^{11}$, Another aspect of the invention are compounds of formula (I), wherein
$R^8$ is hydrogen, halogen, cyano, 1-6C-haloalkyl, 1-6C-haloalkoxy, C(O)OR$^9$, C(O)NR$^{10}$R$^{11}$, Another aspect of the invention are compounds of formula (I), wherein
$R^8$ is hydrogen, cyano, 1-3C-haloalkyl, —C(O)NH$_2$, —C(O)N(1-3C-alkyl), C(O)OH, —C(O)—O(1-4C-alkyl), —C(O)-(1-3C-alkylen)-OH, especially hydrogen, cyano, CF$_3$, C(O)NH$_2$, C(O)OH, C(O)OC$_2$H$_5$, C(O)O(CH$_2$)$_2$—OH.

Another aspect of the invention are compounds of formula (I), wherein
$R^8$ is hydroxy-(1-6C-alkyl).

Another aspect of the invention are compounds of formula (I), wherein $R^8$ is hydrogen, fluorine, hydroxy, cyano, 1-3C-alkyl, 1-3C-haloalkyl, 1-3C-hydroxyalkyl, 1-3C-alkoxy, C(O)OR$^9$, C(O)NR$^{10}$R$^{11}$, especially hydrogen, fluorine, hydroxy, cyano, methyl, CF$_3$, methoxy, hydroxymethyl, COOH, COOCH$_3$, COOC$_2$H$_5$, C(O)NH$_2$, C(O)NHCH$_3$.

Still another aspect of the invention are compounds of formula (I), wherein m is 0.

Another aspect of the invention are compounds of formula (I), wherein m is 0 or 1.

Another aspect of the invention are compounds of formula (I), wherein m is selected from 0, 1 or 2.

Another aspect of the invention are compounds of formula (I), wherein $R^9$ is (a) hydrogen, (b) 1-6C-alkyl which optionally is substituted with hydroxy, Another aspect of the invention are compounds of formula (I), wherein $R^9$ is hydrogen, 1-4C-alkyl, 1-3C-hydroxyalkyl, especially hydrogen, methyl, ethyl, tert.-butyl, hydroxyethyl.

Another aspect of the invention are compounds of formula (I), wherein $R^{10}$, $R^{11}$ are independently from each other hydrogen, 1-4C-alkyl, 1-4C-hydroxyalkyl, 1-4C-alkoxy, —(CO)-(1-6C-alkyl), CHO, COOR$^9$, or together with the nitrogen atom to which they are attached form a 4-6-membered heterocyclic ring optionally containing one further heteroatom selected from the group consisting of O, S or N, and which is optionally substituted with 1-2 fluorine atoms or COOR$^9$, Another aspect of the invention are compounds of formula (I), wherein $R^{10}$/$R^{11}$ is independently from each other hydrogen, 1-3C-alkyl, 1-3C-hydroxyalkyl, especially hydrogen, methyl, hydroxyethyl, Another aspect of the invention are compounds of formula (I), wherein $R^{10}$, $R^{11}$ are independently from each other hydrogen, 1-4C-alkyl, 1-4C-hydroxyalkyl, 1-4C-alkoxy, —(CO)-(1-6C-alkyl) or together with the nitrogen atom to which they are attached form a 4-6-membered heterocyclic ring optionally containing one further heteroatom selected from the group consisting of O, S or N, which is optionally with 1-2 halogen atoms, especially fluorine atoms.

In another aspect of the invention are compounds of formula (I), wherein $R^{10}$, $R^{11}$ are independently from each other hydrogen, 1-4C-alkyl, 1-4C-hydroxyalkyl, 1-4C-alkoxy, or together with the nitrogen atom to which they are attached form a 5-6-membered heterocyclic ring optionally containing one further heteroatom selected from the group consisting of O, S or N.

Another aspect of the invention are compounds of formula (I), wherein $R^{10}$, $R^{11}$ form together with the nitrogen atom to which they are attached a 4-membered heterocyclic ring, which is optionally with 1-2 halogen atoms, especially fluorine atoms.

A further aspect of the invention are compounds of formula (I), which are present as their salts, especially as their hydrochlorides.

Another embodiment of the invention are the tautomeric forms of a hydroxypyridine which are defined to be encompassed by the claim, should the compound of formula I include such a hydroxypyridine:

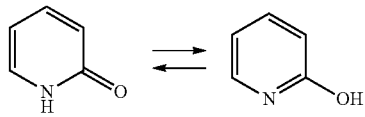 [SMILES: O=c1cccc[nH]1 ; Oc1ccccn1]

Another embodiment of the invention are compounds according to the claims as disclosed in the Claims section wherein the definitions are limited according to the preferred or more preferred definitions as disclosed below or specifically disclosed residues of the exemplified compounds and subcombinations thereof.

Definitions

Constituents which are optionally substituted as stated herein, may be substituted, unless otherwise noted, one or more times, independently from one another at any possible position. When any variable occurs more than one time in any constituent, each definition is independent.

Unless defined otherwise in the claims and in the description, the constituents defined below can optionally be substituted, one or more times, identically or differently, with a substituent selected from:

hydroxy, halogen, cyano, 1-6C-alkyl, 1-4C-haloalkyl, 1-6C-alkoxy, —NR$^{10}$R$^{11}$, cyano, (=O), —C(O)NR$^{10}$R$^{11}$, —C(O)OR$^9$, —NHC(O)R$^{11}$, —NHS(O)$_2$R$^{11}$. An alkyl constituent being multiply substituted by halogen includes also a completely halogenated alkyl moiety such as e.g. CF$_3$.

Should a constituent be composed of more than one part, e.g. —O-(1-6Calkyl)-(3-7C-cycloalkyl), the position of a possible substituent can be at any of these parts at any suitable position. A hyphen at the beginning of the constituent marks the point of attachment to the rest of the molecule. Should a ring be substituted the substitutent could be at any suitable position of the ring, also on a ring nitrogen atom if suitable.

The term "comprising" when used in the specification includes "consisting of".

If it is referred to "as mentioned above" or "mentioned above" within the description it is referred to any of the disclosures made within the specification in any of the preceding pages.

"suitable" within the sense of the invention means chemically possible to be made by methods within the knowledge of a skilled person.

"1-6C-alkyl" is a straight-chain or branched alkyl group having 1 to 6 carbon atoms. Examples are methyl, ethyl, n propyl, iso-propyl, n butyl, iso-butyl, sec-butyl and tert-butyl, pentyl, hexyl, preferably 1-4 carbon atoms (1-4C-alkyl), more preferably 1-3 carbon atoms (1-3C-alkyl). Other alkyl constituents mentioned herein having another number of carbon atoms shall be defined as mentioned above taking into account the different length of their chain. Those parts of constituents containing an alkyl chain as a bridging moiety between two other parts of the constituent which usually is called an "alkylene" moiety is defined in line with the definition for alkyl above including the preferred length of the chain e.g. methylen, ethylene, n-propylen, iso-propylen, n-butylen, isobutylene, tert-butylen.

"2-6C-Alkenyl" is a straight chain or branched alkenyl radical having 2 to 6 carbon atoms. Examples are the but-2-enyl, but-3-enyl (homoallyl), prop-1-enyl, prop-2-enyl (allyl) and the ethenyl (vinyl) radicals.

"Mono- or di-1-4C-alkylamino" radicals contain in addition to the nitrogen atom, independently one or two of the above mentioned 1-4C-alkyl radicals. Examples are the methylamino, the ethylamino, the isopropylamino, the dimethylamino, the diethylamino and the diisopropylamino radical.

"Halogen" within the meaning of the present invention is iodine, bromine, chlorine or fluorine, preferably "halogen" within the meaning of the present invention is chlorine or fluorine.

"1-6C-Haloalkyl" is a straight-chain or branched alkyl group having 1 to 6 carbon atoms in which at least one hydrogen is substituted by a halogen atom. Examples are chloromethyl or 2-bromoethyl. For a partially or completely fluorinated C1-C4-alkyl group, the following partially or completely fluorinated groups are considered, for example: fluoromethyl, difluoromethyl, trifluoromethyl, fluoroethyl, 1,1-difluoroethyl, 1,2-difluoroethyl, 1,1,1-trifluoroethyl, tetrafluoroethyl, and pentafluoroethyl, whereby difluoromethyl, trifluoromethyl, or 1,1,1-trifluoroethyl are preferred. All possible partially or completely fluorinated 1-6C-alkyl groups are considered to be encompassed by the term 1-6C-haloalkyl.

"1-6C-Hydroxyalkyl" is a straight-chain or branched alkyl group having 1 to 6 carbon atoms in which at least one hydrogen atom is substituted by a hydroxy group. Examples are hydroxymethyl, 1-hydroxyethyl, 2-hydroxyethyl, 1,2-dihydroxyethyl, 3-hydroxypropyl, 2-hydroxypropyl, 2,3-dihydroxypropyl, 3-hydroxy-2-methyl-propyl, 2-hydroxy-2-methyl-propyl, 1-hydroxy-2-methyl-propyl.

"1-6C-Alkoxy" represents radicals, which in addition to the oxygen atom, contain a straight-chain or branched alkyl radical having 1 to 6 carbon atoms. Examples which may be mentioned are the hexoxy, pentoxy, butoxy, isobutoxy, sec-butoxy, tert-butoxy, propoxy, isopropoxy, ethoxy and methoxy radicals, preferred are methoxy, ethoxy, propoxy, isopropoxy.

"1-6C-Haloalkoxy" represents radicals, which in addition to the oxygen atom, contain a straight-chain or branched alkyl radical having 1 to 6 carbon atoms in which at least one hydrogen is substituted by a halogen atom. Examples are —O—CFH2, —O—CF2H, —O—CF3, —O—CH2-CFH2, —O—CH2-CF2H, —O—CH2-CF3. Preferred are —O—CF2H, —O—CF3, —O—CH2-CF3.

"3-7C-Cycloalkyl" stands for cyclopropyl, cyclobutyl, cyclopentyl, cyclohexyl or cycloheptyl, preferably cyclopropyl.

"3-7C-Cycloalkyloxy" or "—O-(3-7C-cycloalkyl)" stands for e.g. cyclopropyloxy, cyclobutyloxy, cyclopentyloxy, cyclohexyloxy or cycloheptyloxy, preferably cyclopropyloxy.

"3-7C-Heterocyclyl", or "heterocyclyl" represents a mono- or polycyclic, preferably mono- or bicyclic, more preferably monocyclic, nonaromatic heterocyclic radical containing, 4 to 10, preferably 4 to 7, more preferably 5 to 6 ring atoms, and 1, 2 or 3, preferably 1 or 2, hetero atoms and/or hetero groups independently selected from the series consisting of N, O, S, SO, $SO_2$. The heterocyclyl radicals can be saturated or partially unsaturated and, unless stated otherwise, may be optionally substituted, one or more times, identically or differently, with a substituent selected from: 1-4C-alkyl, 1-4C-haloalkyl, 1-4C-alkoxy, hydroxy, fluorine or (=O) whereby the 1-4C-alkyl may be optionally further substituted with hydroxy and the double bonded oxygen atom leads to a carbonyl group together with the carbon atom of the heterocyclyl ring at any suitable position. Particularly preferred heterocyclic radicals are 4- to 7-membered monocyclic saturated heterocyclyl radicals having up to two hetero atoms from the series consisting of O, N and S, more preferred 5-6-membered heterocyclic radicals. The following may be mentioned by way of example and by preference: oxetanyl, tetrahydrofuranyl, tetrahydropyranyl, azetidinyl, 3-hydroxyazetidinyl, 3-fluoroazetidinyl, 3,3-difluoroazetidinyl, pyrrolidinyl, 3-hydroxypyrrolidinyl, pyrrolinyl, pyrazolidinyl, imidazolidinyl, piperidinyl, 3-hydroxypiperidinyl, 4-hydroxypiperidinyl, 3-fluoropiperidinyl, 3,3-difluoropiperidinyl, 4-fluoropiperidinyl, 4,4-difluoropiperidinyl, piperazinyl, N-methyl-piperazinyl, N-(2-hydroxyethyl)-piperazinyl, morpholinyl, thiomorpholinyl, azepanyl, homopiperazinyl, N-methyl-homopiperazinyl.

"N-heterocyclyl" represents a heterocyclic radical which is connected to the remaining molecule via its nitrogen atom contained in the heterocyclic ring.

The term "heteroaryl" represents a monocyclic 5- or 6-membered aromatic heterocycle or a fused bicyclic aromatice moiety comprising without being restricted thereto, the 5-membered heteroaryl radicals furyl, thienyl, pyrrolyl, oxazolyl, isoxazolyl, thiazolyl, isothiazolyl, imidazolyl, pyrazolyl, triazolyl (1,2,4-triazolyl, 1,3,4-triazolyl or 1,2,3-triazolyl), thiadiazolyl (1,3,4-thiadiazolyl, 1,2,5-thiadiazolyl, 1,2,3-thiadiazolyl or 1,2,4-thiadiazolyl) and oxadiazolyl (1,3,4-oxadiazolyl, 1,2,5-oxadiazolyl, 1,2,3-oxadiazolyl or 1,2,4-oxadiazolyl), as well as the 6-membered heteroaryl radicals pyridinyl, pyrimidinyl, pyrazinyl and pyridazinyl as well as the fused ring systems such as e.g. phthalidyl-, thiophthalidyl-, indolyl-, isoindolyl-, dihydroindolyl-, dihydroisoindolyl-, indazolyl-, benzothiazolyl-, benzofuranyl-, benzimidazolyl-, benzoxazinonyl-, chinolinyl-, isochinolinyl-, chinazolinyl-, chinoxalinyl-, cinnolinyl-, phthalazinyl-, 1,7- or 1,8-naphthyridinyl-, cumarinyl-, isocumarinyl-, indolizinyl-, isobenzofuranyl-, azaindolyl-, azaisoindolyl-, furanopyridyl-, furanopyrimidinyl-, furanopyrazinyl-, furanopyidazinyl-, preferred fused ring system is indazolyl. Preferred 5- or 6-membered heteroaryl radicals are furanyl, thienyl, pyrrolyl, thiazolyl, oxazolyl, thiadiazolyl, oxadiazolyl, pyridinyl, pyrimidinyl, pyrazinyl or pyridazinyl. More preferred 5- or 6-membered heteroaryl radicals are furan-2-yl, thien-2-yl, pyrrol-2-yl, thiazolyl, oxazolyl, 1,3,4-thiadiazolyl, 1,3,4-oxadiazolyl, pyridin-2-yl, pyridin-4-yl, pyrimidin-2-yl, pyrimidin-4-yl, pyrazin-2-yl or pyridazin-3-yl.

In general and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The heteroarylic, heteroarylenic, or heterocyclic groups mentioned herein may be substituted by their given substituents or parent molecular groups, unless otherwise noted, at any possible position, such as e.g. at any substitutable ring carbon or ring nitrogen atom. Analogously it is being understood that it is possible for any heteroaryl or heterocyclyl group to be attached to the rest of the molecule via any suitable atom if chemically suitable. Unless otherwise noted, any heteroatom of a heteroarylic or heteroarylenic ring with unsatisfied valences mentioned herein is assumed to have the hydrogen atom(s) to satisfy the valences. Unless otherwise noted, rings containing quaternizable amino- or amino-type ring nitrogen atoms (—N=) may be preferably not quaternized on these amino- or imino-type ring nitrogen atoms by the mentioned substituents or parent molecular groups.

The NR$^{10}$R$^{11}$ group includes, for example, NH$_2$, N(H) CH$_3$, N(CH$_3$)$_2$, N(H)CH$_2$CH$_3$ and N(CH$_3$)CH$_2$CH$_3$. In the case of —NR$^{10}$R$^{11}$, when R$^{10}$ and R$^{11}$ together with the nitrogen atom to which they are attached form a 4-6-membered heterocyclic ring optionally containing one further heteroatom selected from the group consisting of O, S or N, the term "heterocyclic ring" is defined above. Especially preferred is morpholinyl.

The C(O)NR$^{10}$R$^{11}$ group includes, for example, C(O) NH$_2$, C(O)N(H)CH$_3$, C(O)N(CH$_3$)$_2$, C(O)N(H)CH$_2$CH$_3$, C(O)N(CH$_3$)CH$_2$CH$_3$ or C(O)N(CH$_2$CH$_3$)$_2$. If R$^{10}$ or R$^{11}$ are not hydrogen, they may be substituted by hydroxy, in the case of —NR$^{10}$R$^{11}$, when R$^{10}$ and R$^{11}$ together with the nitrogen atom to which they are attached form a 4-6-membered heterocyclic, the term "heterocyclic ring" Is defined above and can be used analogously for C(O) NR$^{10}$R$^{11}$.

The C(O)OR$^9$ group includes for example C(O)OH, C(O) OCH$_3$, C(O)OC$_2$H$_5$, C(O)C$_3$H$_7$, C(O)CH(CH$_3$)$_2$, C(O) OC$_4$H$_9$, C(O)OC$_5$H$_{11}$, C(O)OC$_6$H$_{13}$; for C(O)O(1-6Calkyl), the alkyl part may be straight or branched and may be substituted.

In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or a may achieve a combination of both effects.

Salts of the compounds according to the invention include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

One aspect of the invention are salts of the compounds according to the invention including all inorganic and organic acid addition salts, especially all pharmaceutically acceptable inorganic and organic acid addition salts, particularly all pharmaceutically acceptable inorganic and organic acid addition salts customarily used in pharmacy. Another aspect of the invention are the salts with di- and tricarboxylic acids.

Examples of acid addition salts include, but are not limited to, hydrochlorides, hydrobromides, phosphates, nitrates, sulfates, salts of sulfamic acid, formates, acetates, propionates, citrates, D-gluconates, benzoates, 2-(4-hydroxybenzoyl)benzoates, butyrates, salicylates, sulfosalicylates, lactates, maleates, laurates, malates, fumarates, succinates, oxalates, malonates, pyruvates, acetoacetates, tartarates, stearates, benzensulfonates, toluenesulfonates, methanesulfonates, trifluoromethansulfonates, 3-hydroxy-2-naphthoates, benzenesulfonates, naphthalinedisulfonates and trifluoroacetates.

Examples of salts with bases include, but are not limited to, lithium, sodium, potassium, calcium, aluminum, magnesium, titanium, meglumine, ammonium, salts optionally derived from NH$_3$ or organic amines having from 1 to 16C-atoms such as e.g. ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylendiamine, N-methylpiperindine and and guanidinium salts.

The salts include water-insoluble and, particularly, water-soluble salts.

According to the person skilled in the art the compounds of formula (I) according to this invention as well as their salts may contain, e.g. when isolated in crystalline form, varying amounts of solvents. Included within the scope of the invention are therefore all solvates and in particular all hydrates of the compounds of formula (I) according to this invention as well as all solvates and in particular all hydrates of the salts of the compounds of formula (I) according to this invention.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The term "(chemotherapeutic) anti-cancer agents", includes but is not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chiormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, 1-125 seeds, ibandronic acid, ibritumomab tiuxetan, idarubicin, ifosfamide, imatinib, imiquimod, improsulfan, interferon alfa, interferon beta, interferon gamma, ipllimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

The compounds according to the invention and their salts can exist in the form of tautomers which are included in the embodiments of the invention.

The compounds of the invention may, depending on their structure, exist in different stereoisomeric forms. These forms include configurational isomers or optionally conformational isomers (enantiomers and/or diastereoisomers including those of atropisomers). The present invention therefore includes enantiomers, diastereoisomers as well as mixtures thereof. From those mixtures of enantiomers and/or disastereoisomers pure stereoisomeric forms can be isolated with methods known in the art, preferably methods of chromatography, especially high pressure liquid chromatography (HPLC) using achiral or chiral phase. The invention further includes all mixtures of the stereoisomers mentioned above independent of the ratio, including the racemates.

Some of the compounds and salts according to the invention may exist in different crystalline forms (polymorphs) which are within the scope of the invention.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

It has now been found, and this constitutes the basis of the present invention, that said compounds of the present invention have surprising and advantageous properties.

In particular, said compounds of the present invention have surprisingly been found to effectively inhibit Bub1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1 kinase, such as, for example, haemotological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The Intermediates used for the synthesis of the compounds of claims 1-6 as described below, as well as their use for the synthesis of the compounds of claims 1-6, are one further aspect of the present invention. Preferred intermediates are the Intermediate Examples as disclosed below.

General Procedures

The compounds according to the invention can be prepared according to the following schemes 1 through 6, The schemes and procedures described below illustrate synthetic routes to the compounds of general formula (I) of the invention and are not intended to be limiting. It is obvious to the person skilled in the art that the order of transformations as exemplified in the Schemes can be modified in various ways. The order of transformations exemplified in the Schemes is therefore not intended to be limiting. In addition, interconversion of any of the substituents, $R^1$, $R^2$, $R^3$, $R^4$, $R^6$, $R^7$ or $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

One route for the preparation of compounds of general formula (Ia) is described in Scheme 1. In instances where this route is not feasible, scheme 2 can be applied.

Scheme 1

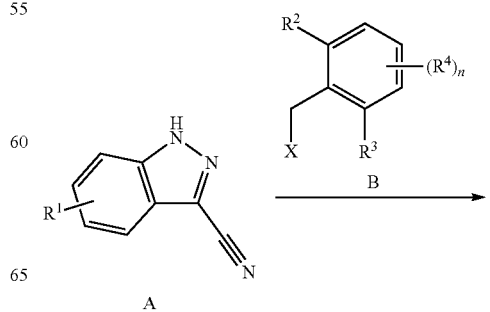

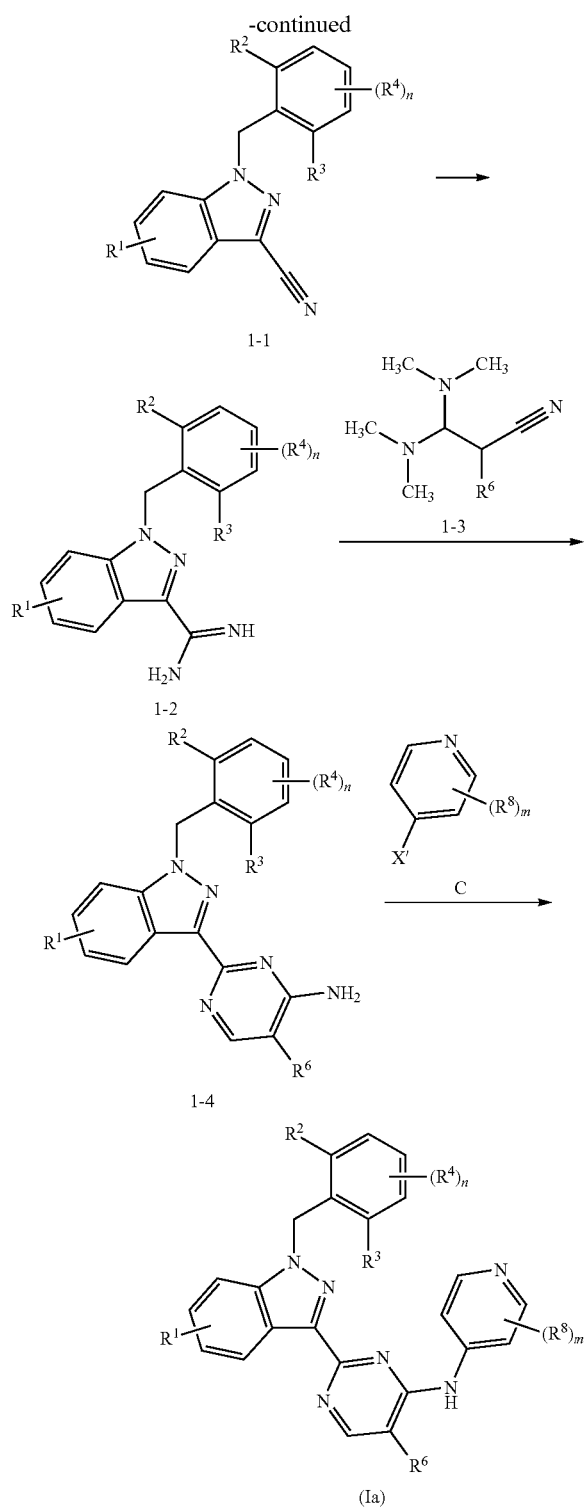

Scheme 1
Route for the preparation of compounds of general formula (Ia), wherein $R^1$, $R^2$, $R^3$, $R^4$, $R^6$, $R^8$, m and n have the meaning as given for general formula (I), supra. In addition, interconversion of any of the substituents, $R^1$, $R^2$, $R^3$, $R^4$, $R^6$ or $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Specific examples are described in the subsequent paragraphs.

Compounds A, B, and C are either commercially available or can be prepared according to procedures available from the public domain, as understandable to the person skilled in the art. Specific examples are described in the subsequent paragraphs. X represents a leaving group such as for example a Cl, Br or I, or X stands for an aryl sulfonate such as for example p-toluene sulfonate, or for an alkyl sulfonate such as for example methane sulfonate or trifluoromethane sufonate. X' represents F, Cl, Br, I, boronic acid or a boronic acid ester, such as for example 4,4,5,5-tetramethyl-2-phenyl-1,3,2-dioxaborolane (boronic acid pinacole ester).

A suitably substituted 1H-indazole-3-carbonitrile (A) can be reacted with a suitably substituted benzyl halide or benzyl sulfonate of general formula (B), such as, for example, a benzyl bromide, in a suitable solvent system, such as, for example, N,N-dimethylformamide, in the presence of a suitable base, such as, for example, cesium carbonate at temperatures ranging from −78C to room temperature, preferably the reaction is carried out at room temperature, to furnish 1-benzyl-1H-indazole-3-carbonitrile intermediates of general formula (1-1).

Intermediates of general formula (1-1) can be converted to intermediates of general formula (1-2) by reaction with a suitable alcoholate, such as, for example sodium methanolate, in a suitable solvent system, such as, for example, the corresponding alcohol, e.g. methanol, at a temperature between room temperature and the boiling point of the respective solvent, preferably the reaction is carried out at room temperature, and subsequent treatment with a suitable source of ammonium, such as for example, ammonium chloride in the presence of a suitable acid, such as for example acetic acid in a temperature range from room temperature to the boiling point of the respective solvent, preferably the reaction is carried out at 50° C.

Intermediates of general formula (1-2) are reacted with a suitably substituted 3,3-bis(dimethylamino)propanenitrile of the general formula (1-3), such as, for example 3,3-bis(dimethylamino)-2-methoxypropanenitrile, in the presence of a suitable base, such as, for example piperidine, in a suitable solvent system, such as, for example, 3-methylbutan-1-ol, in a temperature range from room temperature to the boiling point of the respective solvent, preferably the reaction is carried out at 100° C., to furnish intermediates of general formula (1-4).

Intermediates of general formula (1-4) can be reacted with a suitable 4-halopyridine of the general formula (C), such as, for example 4-bromopyridine, in the presence of a suitable base, such as, for example sodium 2-methylpropan-2-olate or potassium carbonate. Optionally, a suitable palladium catalyst, such as for example (1E,4E)-1,5-diphenylpenta-1,4-dien-3-one-palladium, and a suitable ligand, such as for example 1'-binaphthalene-2,2'-diylbis(diphenylphosphane), can be added. The reaction is carried out in a suitable solvent system, such as, for example, N,N-dimethylformamide, in a temperature range from room temperature to the boiling point of the respective solvent, preferably the reaction is carried out at 100° C. to furnish compounds of general formula (Ia). Alternatively, the following palladium catalysts can be used:

Allylpalladium chloride dimer, Dichlorobis(benzonitrile) palladium (II), Palladium (II) acetate, Palladium (II) chloride, Tetrakis(triphenylphosphine)palladium (0), Tris(dibenzylideneacetone)dipalladium (0), optionally with addition of the following ligands:

racemic-2,2'-Bis(diphenylphosphino)-1,1'-binaphthyl, rac-BINAP, 1,1'-Bis(diphenylphosphino)ferrocene, Bis(2-diphenylphosphinophenyl)ether, Di-t-butylmethylphosphonium tetrafluoroborate, 2-(Di-t-butylphosphino)biphenyl, Tri-t-butylphosphonium tetrafluoroborate, Tri-2-furylphosphine, Tris(2,4-dl-t-butylphenyl)phosphite, Tri-o-tolylphosphine, or, favourably, (9,9-dimethyl-9H-xanthene-4,5-diyl) bis(diphenylphosphine).

Alternatively, intermediates of general formula (1-4) can be reacted with a suitable boronic acid or boronic acid pinacole ester of general formula (C), such as, for example (2-fluoropyridin-4-yl)boronic acid, in the presence of a suitable base, such as, for example triethylamine, a suitable activating agent such as for example N,N-dimethylpyridin-4-amine and a suitable copper salt, such as for example copper (II) acetate, in a suitable solvent system, such as, for example, trichloromethane, in a temperature range from room temperature to the boiling point of the respective solvent, preferably the reaction is carried out at room temperature to furnish compounds of general formula (Ia).

Alternatively, intermediates of general formula (1-4) can be reacted with a suitable pyridyl fluoride of general formula (C, with X' being F), such as, for example 4-fluoro pyridine hydrochloride, in the presence of a suitable base, such as, for example sodium hydride, in a suitable solvent system, such as, for example, dimethyl formamide, in a temperature range from room temperature to the boiling point of the respective solvent, preferably the reaction is carried out at 90'C to furnish compounds of general formula (Ia).

Compounds of general formula (I) can also be synthesised according to the procedure depicted in Scheme 2.

Scheme 2

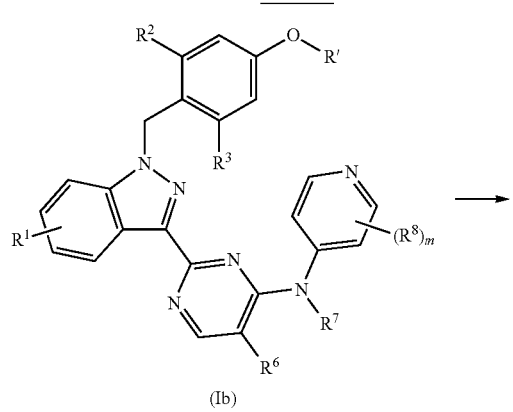

(Ib)

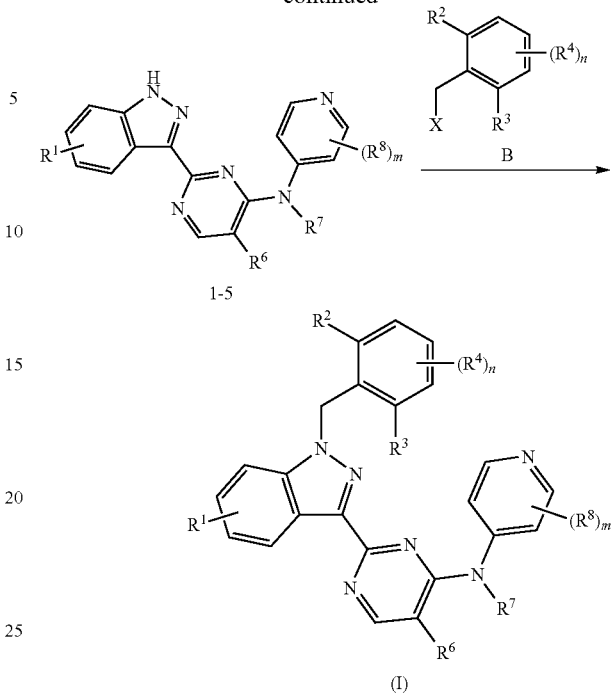

Scheme 2

Alternative route for the preparation of compounds of general formula (I), wherein $R^1$, $R^2$, $R^3$, $R^4$, $R^6$, $R^7$, $R^8$, m and n have the meaning as given for general formula (I), supra. R' is for example alkyl or benzyl, preferably methyl or ethyl. In addition, interconversion of any of the substituents, $R^1$, $R^2$, $R^3$, $R^4$, $R^6$, $R^7$ or $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Further specific examples are described in the subsequent paragraphs.

Compounds of the formula (Ib) can be prepared using the synthetic methods described in context of Scheme 1; the introduction of $R^7$ different from hydrogen may be accomplished inter alia by the methods described in Scheme 5. Compounds B are either commercially available or can be prepared according to procedures available from the public domain, as understandable to the person skilled in the art as referred to below scheme 1 above.

Compounds of general formula (Ib) are converted to intermediates of general formula (1-5) by treatment with a suitable acid system, such as, for example a mixture of trifluoroacetic acid and trifluoromethanesulfonic acid, in a suitable solvent, such as, for example, dichloroethan, in a temperature range from room temperature to the boiling point of the respective solvent, preferably the reaction is carried out at room temperature.

Intermediates of general formula (1-5) can be reacted with a suitably substituted benzyl halide or benzyl sulfonate of general formula (B), such as, for example, a benzyl bromide, in a suitable solvent system, such as, for example, tetrahydrofuran, in the presence of a suitable base, such as, for example, sodium hydride in a temperature range from room temperature to the boiling point of the respective solvent, preferably the reaction is carried out at room temperature, to furnish compounds of general formula (I). Said reaction can also result in double conversion of intermediate (1-5) if $R^7$ is hydrogen, giving rise to compounds formed alongside the target compounds, in which $R^7$ is a benzylic group identical with the benzylic moiety attached to the indazole nitrogen.

Compounds of general formula (Ia) in some instances can be advantageously prepared via a route that utilizes additional protecting groups, according to the procedure depicted in Scheme 2a, in order to avoid the aforementioned bisbenzylation. Preferably, examples 2-1-3, 2-2-3, 2-3-3, 2-4-3, 2-5-3, 2-6-3, 2-7-3, 2-8-3, 2-9-3 were prepared via this route.

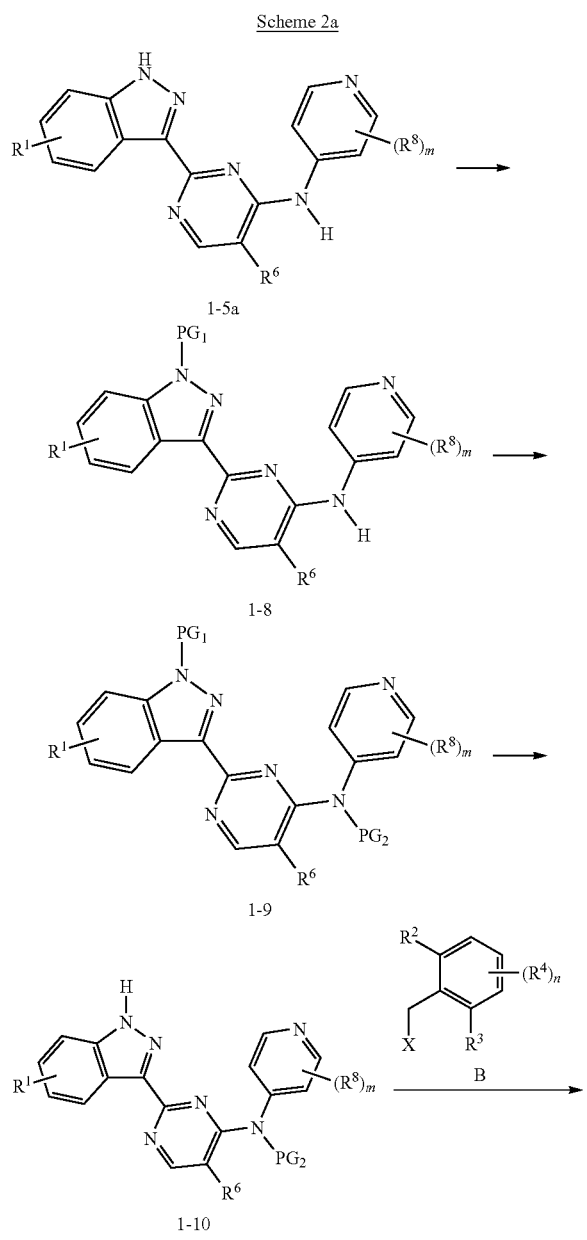

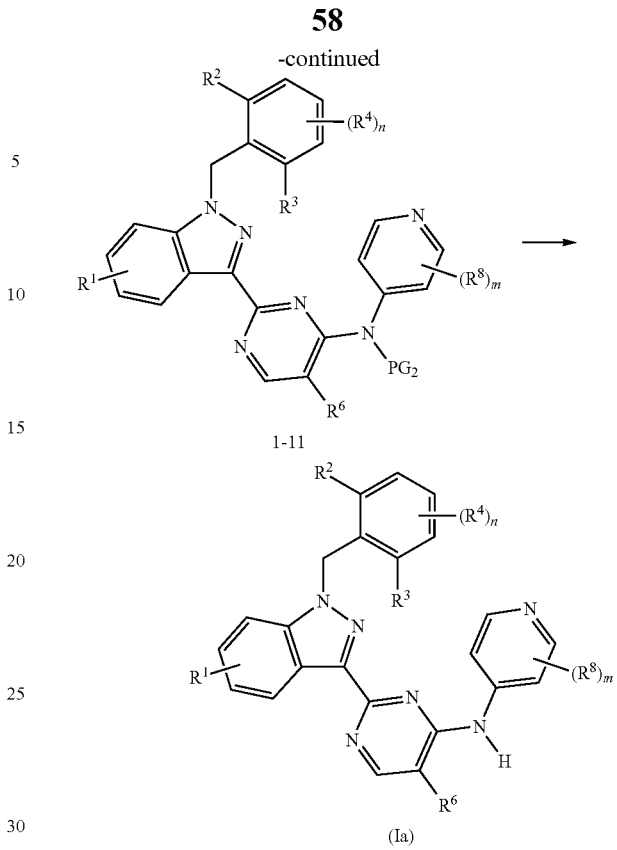

Scheme 2a

Modified route for the preparation of compounds of general formula (Ia), wherein $R^1$, $R^2$, $R^3$, $R^4$, $R^6$, $R^8$, m and n have the meaning as given for general formula (I), supra. $PG_1$ and $PG_2$ are independently from each other a protecting group, for example t-butoxycarbonyl (boc), allyloxycarbonyl (alloc) or benzoyl. In addition, interconversion of any of the substituents, $R^1$, $R^2$, $R^3$, $R^4$, $R^6$ or $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Further specific examples are described in the subsequent paragraphs.

Compounds B are either commercially available or can be prepared according to procedures available from the public domain, as understandable to the person skilled in the art as referred to below scheme 1 above.

Intermediates of general formula (1-5a), accessible in analogy to Scheme 2, can be protected by a suitable protecting group such as, for example, tertbutoxycarbonyl with a suitable reagent, such as, for example, di-tert-butyldicarbonate, in the presence of a suitable base, such as, for example, sodium hydroxide in water, in a suitable solvent system, such as, for example, methanol in a temperature range from 0° C. to room temperature, preferable the reaction is carried out at room temperature, to furnish compounds of general formula (1-8).

Intermediates of general formula (1-8) can be protected with a suitable protection group such as, for example, allyloxycarbonyl or benzoyl with a suitable reagent, such as, for example, allyl chloroformate or benzoyl chloride, in a suitable solvent system, such as, for example, pyridine, in a temperature range from room temperature to the boiling point of the respective solvent, preferably the reaction is carried out at room temperature, to furnish compounds of general formula (1-9).

Intermediates of general formula (1-9) can be deprotected under suitable conditions such as, for example, hydrochloric acid or trifluoroacetic acid, in a suitable solvent system, such as, for example, dioxane or dichloromethane, in a temperature range from 0° C. to room temperature, to furnish compounds of general formula (1-10)

Intermediates of general formula (1-10) can be reacted with a suitably substituted benzyl halide or benzyl sulfonate of general formula (B), such as, for example, a benzyl bromide, in a suitable solvent system, such as, for example, tetrahydrofuran, in the presence of a suitable base, such as, for example, sodium hydride in a temperature range from room temperature to the boiling point of the respective solvent, preferably the reaction is carried out at room temperature, to furnish compounds of general formula (1-11).

Intermediates of general formula (1-11) can be deprotected under suitable conditions such as, for example, pyrrolidine, tetrakis(triphenylphosphin)palladium or sodium hydride, or potassium hydroxide, in a suitable solvent system, such as, for example, dioxane, water, tetrahydrofuran oder ethanol, in a temperature range from 0° C. to room temperature to furnish compounds of general formula (Ia).

Compounds of general formula (Ie) and (Id) can be synthesised from compounds of general formula (Ic), according to the procedure depicted in Scheme 3.

Scheme 3

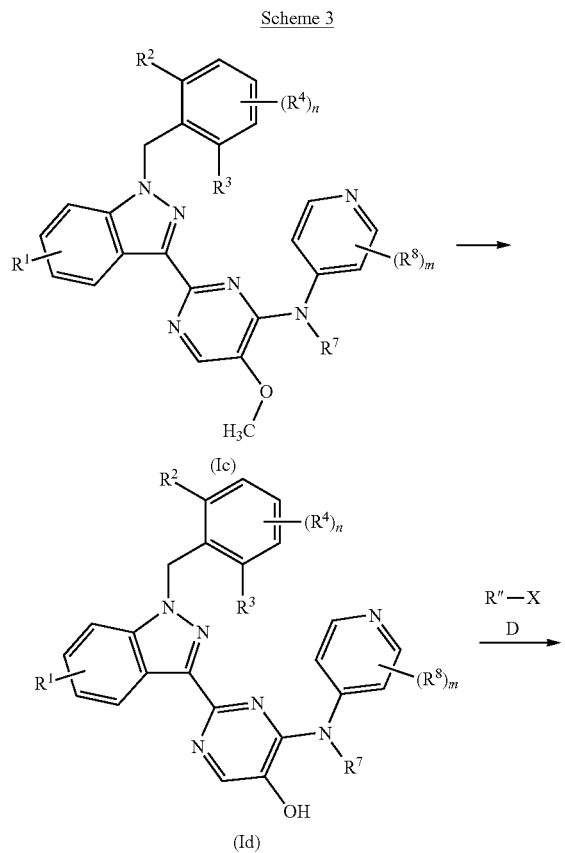

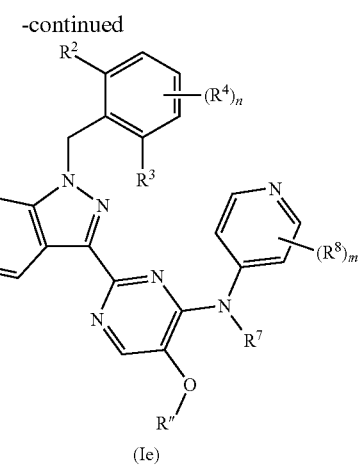

Scheme 3

Process for the preparation of compounds of general formula (Id) via de-methylation of compounds of general formula (Ic) and subsequent etherification to furnish compounds of general formula (Ie), wherein $R^1$, $R^2$, $R^3$, $R^4$, $R^7$, $R^8$, m and n have the meaning as given for general formula (I), supra. In addition, interconversion of any of the substituents, $R^1$, $R^2$, $R^3$, $R^4$, $R^7$ or $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Compounds of the formula (Ic) can be prepared using the synthetic methods described in context of Scheme 1; the introduction of $R^7$ different from hydrogen may be accomplished inter alia by the methods described in Scheme 5.

Compounds of general formula D are commercially available, wherein X represents leaving group such as for example a Cl, Br or I, or X stands for an aryl sulfonate such as for example p-toluene sulfonate, or for an alkyl sulfonate such as for example methane sulfonate or trifluoromethane sulfonate (triflate group). R"=1-6C-alkyl (independently one or more times optionally substituted with hydroxy, C(O)OR$^9$, C(O)NR$^{10}$R$^{11}$, NR$^{10}$R$^{11}$, —S-(1-6C-alkyl), —S(O)-(1-6C-alkyl), —S(O)$_2$-(1-6C-alkyl), SO$_2$NR$^{10}$R$^{11}$, heterocyclyl (which itself is optionally substituted with C(O)OR$^9$ or oxo (=O)), heteroaryl (which itself is optionally substituted one or more times with cyano, 1-4C-alkyl, 1-6C-haloalkyl, 1-6C-haloalkoxy, C(O)OR$^9$, C(O)NR$^{10}$R$^{11}$, -(2-6C-alkyl)-O-1-6C-alkyl), 3-7C-cycloalkyl, halogen, or

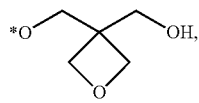

whereby the * is the point of attachment.

Compounds of general formula (Ic) are converted to compounds of general formula (Id) by treatment with a suitable demethylating agent, such as for example benzenethiol, in a suitable solvent, such as, for example, 1-methylpyrrolidin-2-one, in the presence of a suitable base, such as, for example potassium carbonate, in a temperature range from room temperature to the boiling point of the respective solvent, preferably the reaction is carried out at 190'C.

Compounds of general formula (Id) are then reacted with a compound of general formula (D) as mentioned above, in a suitable solvent, such as, for example, N,N-dimethylformamide, in the presence of a suitable base, such as, for example, potassium carbonate in a temperature range from room temperature to the boiling point of the respective solvent, preferably the reaction is carried out at room temperature, to furnish compounds of general formula (Ie).

Compounds of general formula (Id) can be converted into compounds of general formula (If) according to the procedure depicted in Scheme 4.

Scheme 4
During step 2 of this sequence the
residues might potentially undergo a modification, e.g. reduction.

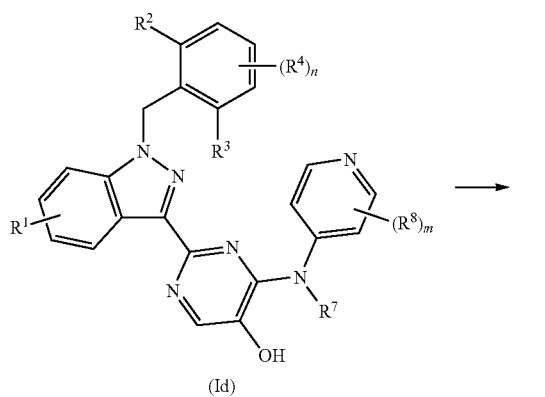

(Id)

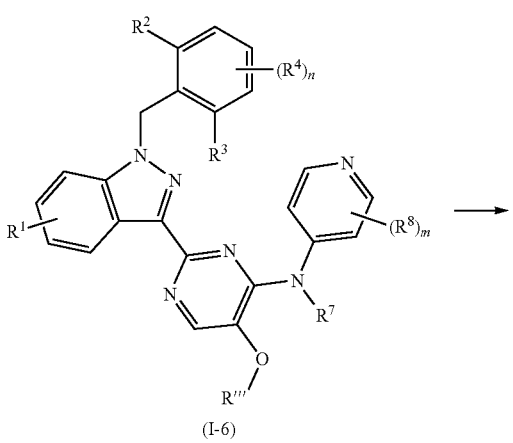

(I-6)

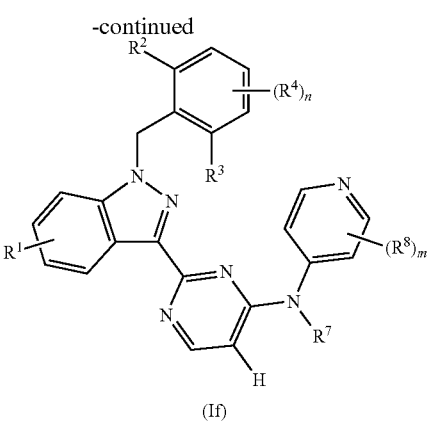

(If)

Scheme 4.

Process for the transformation of compounds of general formula (Id) into compounds of general formula (If), via an intermediate of the general formula (I-6), wherein $R^1$, $R^2$, $R^3$, $R^4$, $R^7$, $R^8$, m and n have the meaning as given for general formula (I), supra. In addition, interconversion of any of the substituents, $R^1$, $R^2$, $R^3$, $R^4$, $R^7$ or $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999).

O—R" represents a suitable leaving group, e.g. a triflate group, nonaflate group.

Compounds of general formula (Id) can be converted to intermediates of general formula (I-6) by reaction with a suitable sulfonic acid derivative, such as, for example trifluoromethanesulfonic anhydride or 1,1,2,2,3,3,4,4,4-nonafluorobutane-1-sulfonyl fluoride, in a suitable solvent, such as, for example, dichloromethane, in the presence of a suitable base, such as, for example pyridine, in a temperature range from room temperature to the boiling point of the respective solvent, preferably the reaction is carried out at room temperature.

Intermediates of general formula (I-6) are then reacted with a suitable hydride source, such as, for example, triethylsilane, in a suitable solvent such as, for example, N,N-dimethyl formamide (DMF), in the presence of a suitable Pd-catalyst, such as, for example, palladium (II) acetate together with a suitable ligand, such as, for example, propane-1,3-diylbis(diphenylphosphane) in a temperature range from room temperature to the boiling point of the respective solvent, preferably the reaction is carried out at 60° C., to furnish compounds of general formula (If).

Compounds of general formula (If') which is a compound of formula (If) wherein $R^7$=hydrogen, can be converted into compounds of general formula (Ig and Ih) according to the procedure depicted in Scheme 5.

Scheme 5

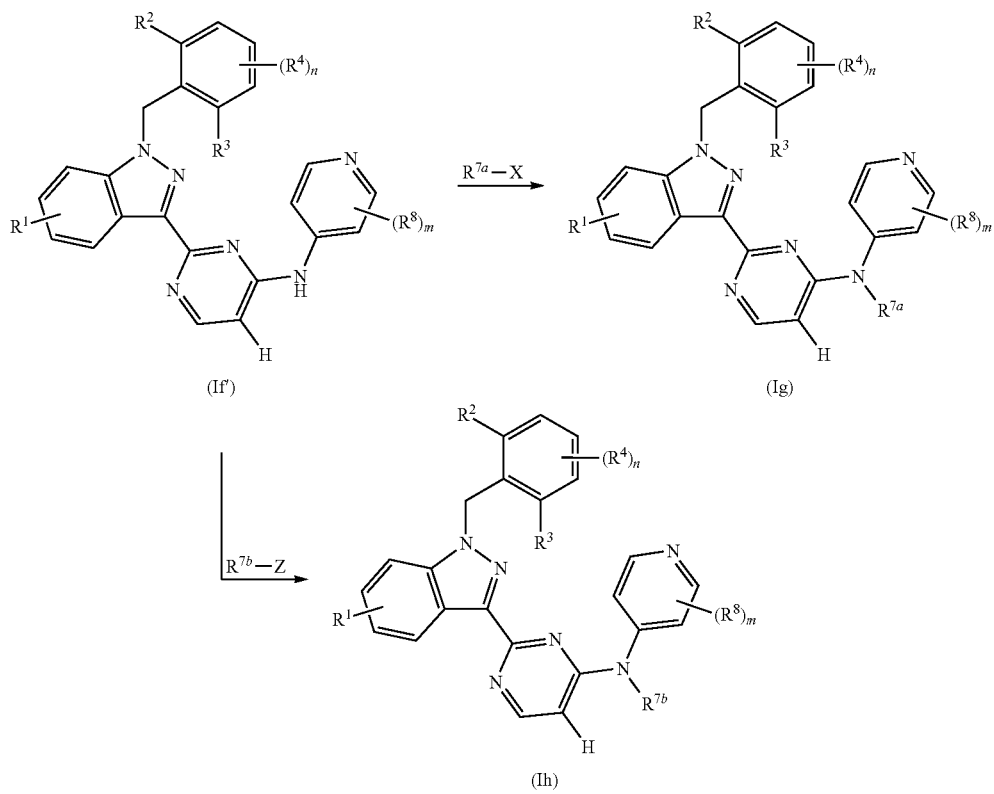

Scheme 5.

Process for the transformation of compounds of general formula (If') into compounds of general formula (Ig) and (Ih), wherein $R^1$, $R^2$, $R^3$, $R^4$, $R^8$, m and n have the meaning as given for general formula (I), supra. In addition, interconversion of any of the substituents, $R^1$, $R^2$, $R^3$, $R^4$, $R^{7a}$, $R^{7b}$ or $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999).

$R^{7a}$ represents 1-6C-alkyl, independently one or more times optionally substituted with heteroaryl, halogen, hydroxy, or $R^{7a}$ stands for

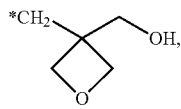

whereby the * is the point of attachment, or $R^{7a}$ represents benzyl, whereby the phenyl ring is opt. subst with 1-5 substituents independently selected from the group consisting of hydrogen, halogen, 1-4Calkyl, 1-4C-haloalkyl, 1-4C-alkoxy, 1-4C-haloalkoxy, cyano, C(O)OR$^9$. X as defined below scheme 1, supra, or for example 1,3,2-dioxathiolane 2-oxide.

$R^{7b}$ represents an acyl moiety, such as —C(O)-(1-6C-alkyl), —C(O)-(1-6C-alkylen)O-(1-6C-alkyl), —C(O)-(1-6C-alkylen)-O-(2-6C-alkylen)-O-(1-6C-alkyl), —C(O)-heterocyclyl and Z represents a halogen, hydroxy or —O—R$^{7b}$.

Compounds of general formula (If') are converted into compounds of general formula (Ig) by reaction with a suitable haloalkyl or dioxathiolane 2-oxide, such as, for example 1,3,2-dioxathiolane 2-oxide, in a suitable solvent system, such as, for example, N,N-dimethyl formamide, in the presence of a suitable base, such as, for example cesium carbonate, in a temperature range from room temperature to the boiling point of the respective solvent, preferably the reaction is carried out at 60° C.

Compounds of general formula (If') are converted into compounds of general formula (Ih) by reaction with a suitable carboxylic acid derivative, such as for example a carboxylic acid, halogenide e.g. carboxylic acid choride, or a carboxylic acid anhydride, in a suitable solvent, such as, for example, dichloromethane, in the presence of a suitable base, such as, for example N,N-diethylethanamine, in a temperature range from room temperature to the boiling point of the respective solvent, preferably the reaction is carried out at room temperature.

Compounds of general formula (Ii) and (Ij) can be synthesised according to the procedure depicted in Scheme 6.

Scheme 6

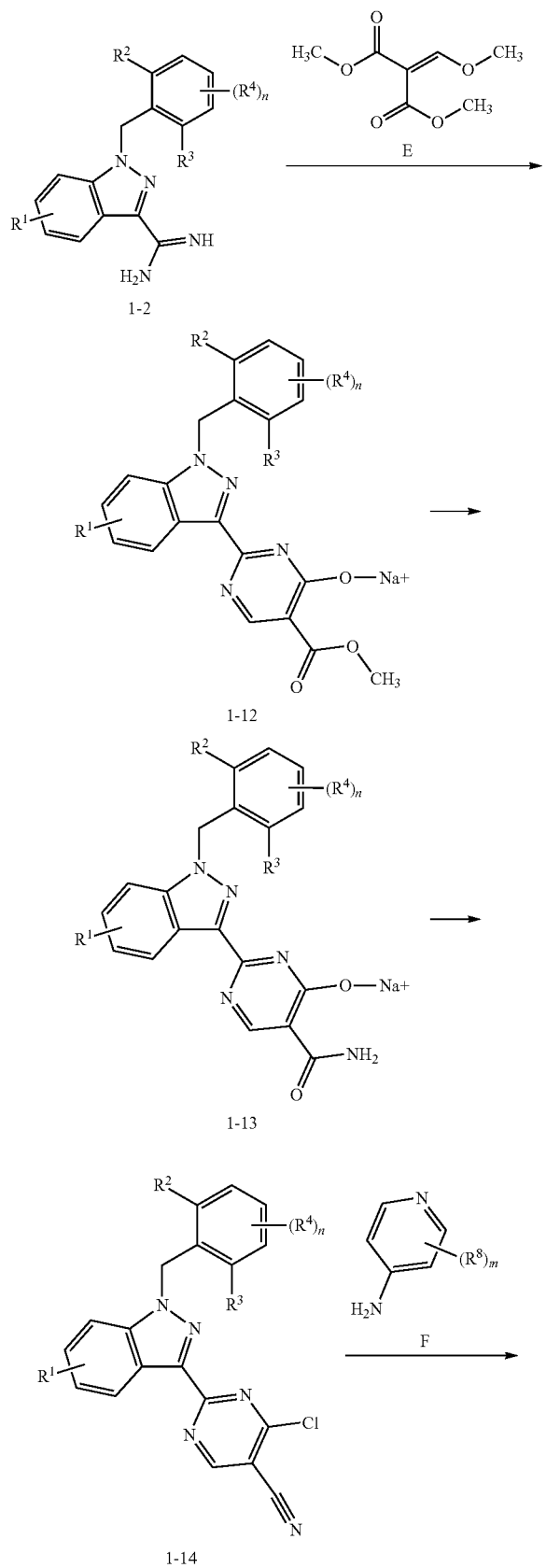

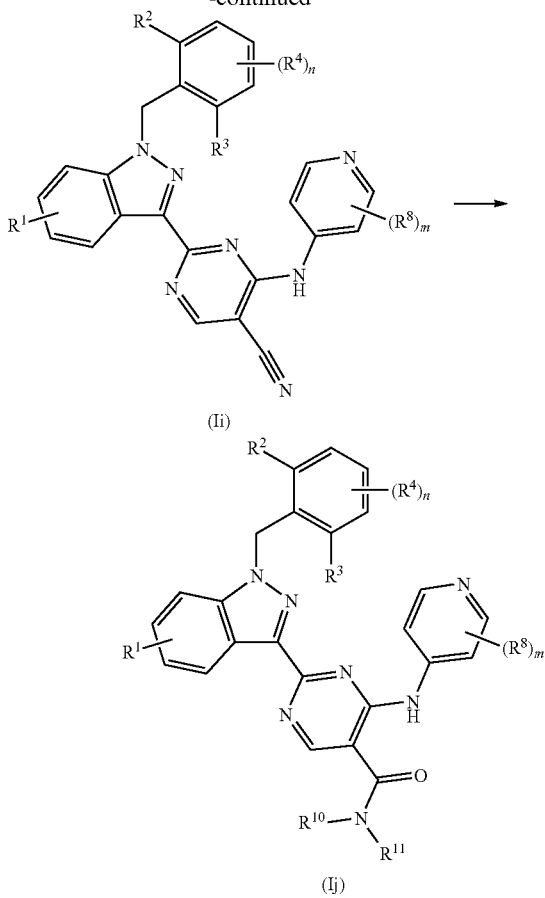

Scheme 6

Route for the preparation of compounds of general formula (Ii) and (Ij), wherein $R^1$, $R^2$, $R^3$, $R^4$, $R^8$, m and n have the meaning as given for general formula (I), supra. In addition, interconversion of any of the substituents, $R^1$, $R^2$, $R^3$, $R^4$ or $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999).

Compounds E and F are commercially available. $R^{10}$ and $R^{11}$ have the meaning as given for general formula (I), supra.

A suitably substituted carboximidamide or its respective hydrochloride of general formula (1-2), such as for example, 1-(2-fluorobenzyl)-1H-indazole-3-carboximidamide hydrochloride (1:1), can be reacted with dimethyl (methoxymethylidene)propanedioate (E), in a suitable solvent system, such as, for example, methanol, in the presence of a suitable base, such as, for example, sodium methanolate at temperatures ranging from room temperature to the boiling point of the solvent, preferably the reaction is carried out at 60'C, to furnish intermediates of general formula (1-12).

Intermediates of general formula (1-12) can be converted to intermediates of general formula (1-13) by reaction with a suitable source of ammonia, such as, for example 7N ammonia, in a suitable solvent system, such as, for example methanol, at temperatures ranging from room temperature to the boiling point of the solvent, preferably the reaction is carried out at 60° C., to furnish intermediates of general formula (1-13).

Intermediates of general formula (1-13) can be converted to intermediates of general formula (1-14) by reaction with a suitable source of chloride, such as, for example phosphoric trichloride, neat, in the presence of a suitable base, such as, for example, N,N-diethylaniline, at temperatures ranging from room temperature to the boiling point of the solvent, preferably the reaction is carried out at 90° C., to furnish intermediates of general formula (1-14).

Intermediates of general formula (1-14) can be converted to intermediates of general formula (Ii) by reaction with a suitably substituted pyridin-4-amine, such as, for example pyridin-4-amine, in a suitable solvent system, such as, for example N,N-dimethylformamide, at temperatures ranging from room temperature to the boiling point of the solvent, preferably the reaction is carried out at room temperature, to furnish compounds of general formula (Ii).

Compounds of general formula (Ii) can be converted into compounds of general formula (Ij) by treatment with a suitable acid, such as, for example concentrated sulfuric acid, at temperatures ranging from 0C to room temperature, preferably the reaction is carried out at room temperature, to furnish compounds of general formula (Ij).

One preferred aspect of the invention is the process for the preparation of the compounds of claims 1-6 according to the Examples.

A special aspect of the present invention are the following two process steps:

1. Process for the manufacture of compounds of general formula (I) according to claim 1, wherein $R^7$ is hydrogen as reflected in formula (Ia), characterized in that a compound of formula (1-4)

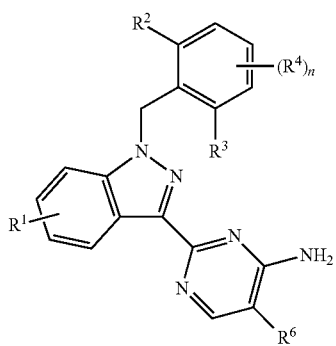

whereby $R^1$, $R^2$, $R^3$, $R^4$, $R^6$ and n have the meaning according to claim 1, is reacted with a compound of formula (C)

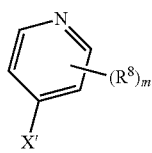

whereby $R^8$ and m have the meaning according to claim 1, and X' represents F, Cl, Br, I, boronic acid or a boronic acid ester, in the presence of a suitable base, and a suitable palladium catalyst, optionally in the presence of a suitable ligand, forming a compound of formula (Ia)

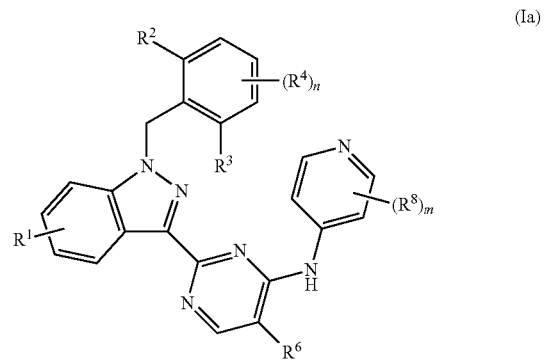

which is optionally subsequently deprotected to form a compound of general formula (I) wherein $R^7$ is hydrogen and $R^1$, $R^2$, $R^3$, $R^4$, $R^6$, $R^8$ and n and m have the meaning as defined in claim 1.

2. Process for the manufacture of compounds of general formula (I) according to claim 1, wherein a compound of formula (Ib)

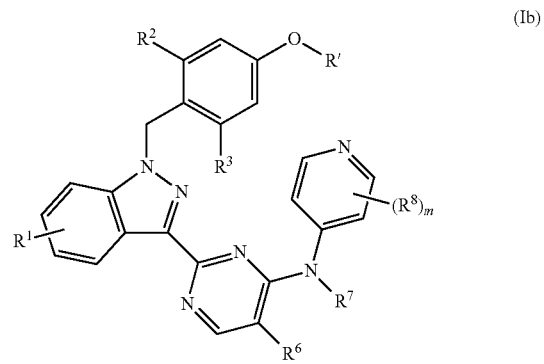

whereby $R^1$, $R^2$, $R^3$, $R^6$, $R^7$ $R^8$ and m have the meaning according to claim 1 and R' is 1-6C-alkyl or benzyl, is treated with a suitable acid system to cleave the benzylic group in order to obtain a compound of formula 1-5

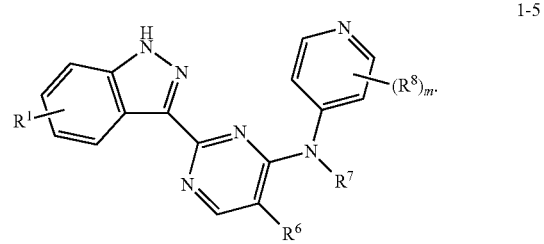

followed by reacting the compound of formula 1-5 with a compound of general formula (B),

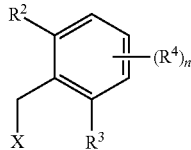

wherein $R^2$, $R^3$, $R^4$ and n have the meaning according to claim 1, and wherein X represents a leaving group, in a suitable solvent system, in the presence of a suitable base, in a temperature range from room temperature to the boiling point of the respective solvent, to furnish compounds of general formula (I).

Another aspect of the invention is the intermediate of general formula (1-5).

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present invention which possess a sufficiently basic or acidic functionality, may result in the formation of a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, solvate, inclusion complex) of a compound of the present invention as isolated as described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art. Especially preferred are hydrochlorides and the process used in the example section.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of claims 1-5 according to the examples.

Optionally, compounds of the formula (I) can be converted into their salts, or, optionally, salts of the compounds of the formula (I) can be converted into the free compounds. Corresponding processes are customary for the skilled person.

Optionally, compounds of the formula (I) can be converted into their N-oxides. The N-oxide may also be introduced by way of an intermediate. N-oxides may be prepared by treating an appropriate precursor with an oxidizing agent, such as metachloroperbenzoic acid, in an appropriate solvent, such as dichloromethane, at suitable temperatures, such as from 0° C. to 40° C., whereby room temperature is generally preferred. Further corresponding processes for forming N-oxides are customary for the skilled person.

Commercial Utility

As mentioned supra, the compounds of the present invention have surprisingly been found to effectively inhibit Bub1 finally resulting in apoptosis and cell death and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1, such as, for example, benign and malignant neoplasia, more specifically haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof, especially haematological tumours, solid tumours, and/or metastases of breast, bladder, bone, brain, central and peripheral nervous system, cervix, colon, endocrine glands (e.g. thyroid and adrenal cortex), endocrine tumours, endometrium, esophagus, gastrointestinal tumours, germ cells, kidney, liver, lung, larynx and hypopharynx, mesothelioma, ovary, pancreas, prostate, rectum, renal, small intestine, soft tissue, stomach, skin, testis, ureter, vagina and vulva as well as malignant neoplasias including primary tumors in said organs and corresponding secondary tumors in distant organs ("tumor metastases"). Haematological tumors can e.g be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

A further aspect of the invention is the use of the compounds according to formula (I) for the treatment of cervical-, breast-, non-small cell lung-, prostate-, colon- and melanoma tumors and/or metastases thereof, especially preferred for the treatment thereof as well as a method of treatment of cervical-, breast-, non-small cell lung-, prostate-, colon—and melanoma tumors and/or metastases thereof comprising administering an effective amount of a compound of formula (I).

One aspect of the invention is the use of the compounds according to formula (I) for the treatment of cervix tumors as well as a method of treatment of cervix tumors comprising administering an effective amount of a compound of formula (I).

In accordance with an aspect of the present invention therefore the invention relates to a compound of general formula I, or an N-oxide, a salt, a tautomer or a stereoisomer of said compound, or a salt of said N-oxide, tautomer or stereoisomer particularly a pharmaceutically acceptable salt thereof, or a mixture of same, as described and defined herein, for use in the treatment or prophylaxis of a disease, especially for use in the treatment of a disease.

Another particular aspect of the present invention is therefore the use of a compound of general formula I, described supra, or a stereoisomer, a tautomer, an N-oxide, a hydrate, a solvate, or a salt thereof, particularly a pharmaceutically acceptable salt thereof, or a mixture of same, for the prophylaxis or treatment of hyperproliferative disorders or disorders responsive to induction of apoptosis, especially for the treatment of hyperproliferative disorders or disorders responsive to induction of apoptosis.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, especially the treatment, wherein the diseases are haemotological tumours, solid tumours and/or metastases thereof. A preferred aspect is the use of a compound of formula (I) for the prophylaxis and/or treatment of cervical-, breast-, non-small cell lung-, prostate-, colon—and/or melanoma tumors, especially preferred for the treatment thereof.

Another aspect is the use of a compound of formula (I) is for the treatment of cervical-, breast-, non-small cell lung-, prostate-, colon—and melanoma tumors and/or metastases thereof, especially preferred for the treatment thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuro-pulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Preferably, the diseases of said method are haematological tumours, solid tumour and/or metastases thereof.

The compounds of the present invention can be used in particular in therapy and prevention i.e. prophylaxis, especially in therapy of tumour growth and metastases, especially in solid tumours of all indications and stages with or without pretreatment of the tumour growth.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease.

Therefore, the present invention includes pharmaceutical compositions that are comprised of a pharmaceutically acceptable carrier or auxiliary and a pharmaceutically effective amount of a compound, or salt thereof, of the present invention.

Another aspect of the invention is a pharmaceutical composition comprising a pharmaceutically effective amount of a compound of formula (I) and a pharmaceutically acceptable auxiliary for the treatment of a disease mentioned supra, especially for the treatment of haemotological tumours, solid tumours and/or metastases thereof.

A pharmaceutically acceptable carrier or auxiliary is preferably a carrier that is non-toxic and innocuous to a patient at concentrations consistent with effective activity of the active ingredient so that any side effects ascribable to the carrier do not vitiate the beneficial effects of the active ingredient. Carriers and auxiliaries are all kinds of additives assisting to the composition to be suitable for administration.

A pharmaceutically effective amount of compound is preferably that amount which produces a result or exerts the intended influence on the particular condition being treated.

The compounds of the present invention can be administered with pharmaceutically-acceptable carriers or auxiliaries well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing auxiliaries, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, *arachis* oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmrethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quaternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the return to release the drug. Such materials are, for example, cocoa butter and polyethylene glycol.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for administration, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal;

aerosol propellants (examples include but are not limited to carbon dioxide, $CCl_2F_2$, $F_2ClC$—$CClF_2$ and $CClF_3$)

air displacement agents—examples include but are not limited to nitrogen and argon;

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene monostearate);

encapsulating agents (examples include but are not limited to gelatin and cellulose acetate phthalate), flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to *arachis* oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas), plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan monopalmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, crosslinked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile i.v. Solution:

A 5 mg/mL solution of the desired compound of this invention can be made using sterile, injectable water, and the pH is adjusted if necessary. The solution is diluted for administration to 1-2 mg/mL with sterile 5% dextrose and is administered as an i.v. infusion over about 60 minutes.

Lyophilised Powder for i.v. Administration:

A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular Suspension:

The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:

A large number of tablets are prepared by conventional procedures so that the dosage unit is 100 mg of active ingredient, 0.2 mg. of colloidal silicon dioxide, mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules:

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" In which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. Those combined pharmaceutical agents can be other agents having antiproliferative effects such as for example for the treatment of haemotological tumours, solid tumours and/or metastases thereof and/or agents for the treatment of undesired side effects. The present invention relates also to such combinations.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, especially (chemotherapeutic) anti-cancer agents as defined supra. The combination can be a non-fixed combination or a fixed-dose combination as the case may be.

Methods of testing for a particular pharmacological or pharmaceutical property are well known to persons skilled in the art.

The example testing experiments described herein serve to illustrate the present invention and the invention is not limited to the examples given.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

EXPERIMENTAL PART

The following table lists the abbreviations used in this paragraph and in the Intermediate Examples and Examples section as far as they are not explained within the text body.

| Abbreviation | Meaning |
| --- | --- |
| aq. | aqueous |
| alloc | allyloxycarbonyl |
| boc | t-butoxycarbonyl |
| br | broad |
| CI | chemical ionisation |
| d | doublet |
| dd | doublet of doublet |
| DAD | diode array detector |
| DCM | dichloromethane |
| DMF | N,N-dimethylformamide |
| ELSD | Evaporate Light Scattering Detector |
| EtOAc | ethyl acetate |
| Eq. | equivalent |
| ESI | electrospray (ES) ionisation |
| HATU | 2-(7-aza-1H-benzotriazole-1-yl)-1,1,3,3-tetramethyluronium hexafluorophosphate (CAS number 148893-10-1) |
| HPLC | high performance liquid chromatography |
| LC-MS | liquid chromatography mass spectrometry |
| m | multiplet |
| MS | mass spectrometry |
| n-BuLi | n-butyllithium |
| NMR | nuclear magnetic rsonance spectroscopy:chemical shifts (δ) are given ppm. The chemical shifts were corrected by setting the DMSO signal to 2.50 ppm using unless otherwise stated. |
| PDA | Photo Diode Array |
| PoraPak ™; | a HPLC column obtainable from Waters |
| q | quartet |
| r.t. or rt | room temperature |
| RT | retention time (as measured either with HPLC or UPLC) in minutes |
| s | singlet |
| SM | starting material |
| SQD | Single-Quadrupol-Detector |
| t | triplet |
| THF | tetrahydrofuran |
| UPLC | ultra performance liquid chromatography |

Other abbreviations have their meanings customary per se to the skilled person. The various aspects of the invention described in this application are illustrated by the following examples which are not meant to limit the invention in any way.

Specific Experimental Descriptions NMR peak forms in the following specific experimental descriptions are stated as they appear in the spectra, possible higher order effects have not been considered. Reactions employing microwave irradiation may be run with a Biotage Initator® microwave oven optionally equipped with a robotic unit. The reported reaction times employing microwave heating are intended to be understood as fixed reaction times after reaching the indicated reaction temperature. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash $NH_2$ silica gel in combination with a Isolera® autopurifier (Biotage) and eluents such as gradients of e.g. hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated in vacuo" refers to use of a Buchi rotary evaporator at a minimum pressure of approximately 15 mm of Hg. All temperatures are reported uncorrected in degrees Celsius (C).

In order that this invention may be better understood, the following examples are set forth. These examples are for the purpose of illustration only, and are not to be construed as limiting the scope of the invention in any manner. All publications mentioned herein are incorporated by reference in their entirety.

Analytical LC-MS Conditions

LC-MS-data given in the subsequent specific experimental descriptions refer (unless otherwise noted) to the following conditions:

| | |
|---|---|
| System: | Waters Acquity UPLC-MS: Binary Solvent Manager, Sample Manager/Organizer, Column Manager, PDA, ELSD, SQD 3001 or ZQ4000 |
| Column: | Acquity UPLC BEH C18 1.7 50 × 2.1 mm |
| Solvent: | A1 = water + 0.1% vol. formic acid (99%) |
| | A2 = water + 0.2% vol. ammonia (32%) |
| | B1 = acetonitrile |
| Gradient: | 0-1.6 min 1-99% B, 1.6-2.0 min 99% B |
| Flow: | 0.8 mL/min |
| Temperature: | 60° C. |
| Injection: | 2.0 μl |
| Detection: | DAD scan range 210-400 nm → Peaktable |
| | ELSD |
| Methods: | MS ESI+, ESI– Switch → various scan ranges (Report Header) |
| | Method 1: A1 + B1 = C:\MassLynx\Mass_100_1000.flp |
| | Method 2: A1 + B1 = C:\MassLynx\Mass_160_1000.flp |
| | Method 3: A1 + B1 = C:\MassLynx\Mass_160_2000.flp |
| | Method 4: A1 + B1 = C:\MassLynx\Mass_160_1000_BasicReport.flp |
| | Method 5: A2 + B1 = C:\MassLynx\$NH_3$_Mass_100_1000.flp |
| | Method 6: A2 + B1 = C:\MassLynx\$NH_3$_Mass_100_1000_BasicReport.flp |

Preparative HPLC Conditions

"Purification by preparative HPLC" in the subsequent specific experimental descriptions refers to (unless otherwise noted) the following conditions:

Analytics (Pre- and Post Analytics: Method B):

| | |
|---|---|
| System: | Waters Acquity UPLC-MS: Binary Solvent Manager, Sample Manager/Organizer, Column Manager, PDA, ELSD, SQD 3001 |
| Column: | Acquity BEH C18 1.7 50 × 2.1 mm |
| Solvent: | A = water + 0.1% vol. formic acid (99%) |
| | B = acetonitrile |
| Gradient: | 0-1.6 min 1-99% B, 1.6-2.0 min 99% B |
| Flow: | 0.8 mL/min |
| Temperature: | 60° C. |
| Injection: | 2.0 μl |
| Detection: | DAD scan range 210-400 nm |
| | MS ESI+, ESI–, scan range 160-1000 m/z |
| | ELSD |
| Methods: | Purify_pre.flp |
| | Purify_post.flp |

Preparation:

| | |
|---|---|
| System: | Waters Autopurificationsystem: Pump 2545, Sample Manager 2767, CFO, DAD 2996, ELSD 2424, SQD 3001 |
| Column: | XBridge C18 5 μm 100 × 30 mm |
| Solvent: | A = water + 0.1% vol. formic acid (99%) |
| | B = acetonitrile |
| Gradient: | 0-1 min 1% B, 1-8 min 1-99% B, 8-10 min 99% B |
| Flow: | 50 mL/min |
| Temperature: | RT |
| Solution: | max. 250 mg/2.5 mL dimethyl sulfoxide or DMF |
| Injection: | 1 × 2.5 mL |
| Detection: | DAD scan range 210-400 nm |
| | MS ESI+, ESI–, scan range 160-1000 m/z |

Chiral HPLC Conditions

If not specified otherwise, chiral HPLC-data given in the subsequent specific experimental descriptions refer to the following conditions:

Analytics:

| | |
|---|---|
| System: | Dionex: Pump 680, ASI 100, Waters: UV-Detektor 2487 |
| Column: | Chiralpak IC 5 μm 150 × 4.6 mm |
| Solvent: | hexane/ethanol 80:20 + 0.1% diethylamine |
| Flow: | 1.0 mL/min |
| Temperature: | 25° C. |
| Solution: | 1.0 mg/mL ethanol/methanol 1:1 |
| Injection: | 5.0 μl |
| Detection: | UV 280 nm |

Preparation:

| | |
|---|---|
| System: | Agilent: Prep 1200, 2xPrep Pump, DLA, MWD, Prep FC, ESA: Corona |
| Column: | Chiralpak UC 5 μm 250 × 30 mm |
| Solvent: | hexane/ethanol 80:20 + 0.1% diethylamine |
| Flow: | 40 mL/min |
| Temperature: | RT |
| Solution: | 660 mg/5.6 mL ethanol |
| Injection: | 8 × 0.7 mL |
| Detection: | UV 280 nm |

Flash Column Chromatography Conditions

"Purification by (flash) column chromatography" as stated in the subsequent specific experimental descriptions refers to the use of a Biotage Isolera purification system. For technical specifications see "Biotage product catalogue" on www.biotage.com.

Determination of Optical Rotation Conditions

Optical rotations were measured in dimethyl sulfoxide at 589 nm wavelength, 20° C., concentration 1.0000 g/100 ml, integration time 10 s, film thickness 100.00 mm.

EXAMPLES

Synthetic Intermediates

Intermediate 1-1-1

Preparation of 1-(4-methoxybenzyl)-1H-indazole-3-carbonitrile

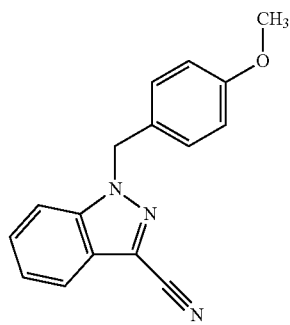 [SMILES: COc1ccc(Cn2nc(C#N)c3ccccc32)cc1]

6.47 g of 1H-indazole-3-carbonitrile (45.2 mmol, 1 eq.) were dissolved in 65 ml of dry DMF. 10 g of 1-(bromomethyl)-4-methoxybenzene (49.7 mmol, 1.1 eq.) and 17.7 g of cesium carbonate (54.2 mmol, 1.2 eq.) were added. The mixture was stirred at room temperature for 18 hours under nitrogen atmosphere. Then the reaction mixture was partitioned between water and tert-butyl methyl ether. The separated aqueous layer was extracted twice with tert-butyl methyl ether. The combined organic layers were washed with brine, dried over magnesium sulfate and concentrated in vacuo. The crystallization from methanol provided 9.25 g (35.1 mmol, 77.7%) of analytically pure target compound.

$^1$H NMR (300 MHz, DMSO-d6) δ[ppm]=3.64-3.71 (s, 3H), 5.70 (s, 2H) 6.81-6.89 (m, 2H), 7.22-7.29 (m, 2H), 7.38 (ddd, 1H), 7.55 (ddd, 1H), 7.85 (dt, 1H) 7.97 (dt, 1H)

LC-MS:
retention time: 1.27 min
MS ES$^+$: 264.31 [M+H]$^+$

The following intermediates were prepared according to the same procedure using the respective commercially available starting materials:

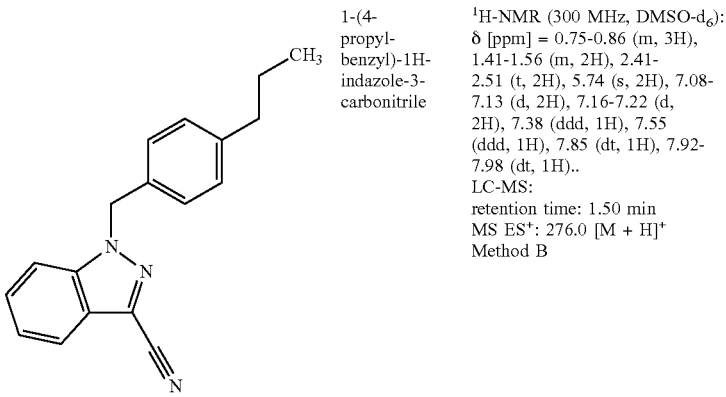

| | | |
|---|---|---|
| 1-1-2 | 1-(4-propyl-benzyl)-1H-indazole-3-carbonitrile | $^1$H-NMR (300 MHz, DMSO-d$_6$): δ [ppm] = 0.75-0.86 (m, 3H), 1.41-1.56 (m, 2H), 2.41-2.51 (t, 2H), 5.74 (s, 2H), 7.08-7.13 (d, 2H), 7.16-7.22 (d, 2H), 7.38 (ddd, 1H), 7.55 (ddd, 1H), 7.85 (dt, 1H), 7.92-7.98 (dt, 1H).. LC-MS: retention time: 1.50 min MS ES$^+$: 276.0 [M + H]$^+$ Method B |

| | | | |
|---|---|---|---|
| 1-1-3 | 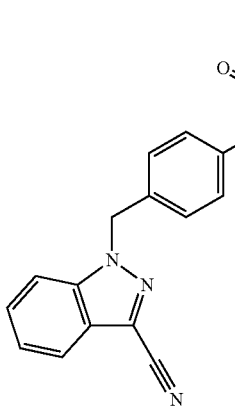 | methyl {4-[(3-cyano-1H-indazol-1-yl)methyl]phenyl} acetate | $^1$H-NMR (500 MHz, DMSO-d$_6$): δ [ppm] = 3.58 (s, 3H), 3.64 (s, 2H), 5.81 (s, 2H), 7.21-7.25 (m, 2H), 7.25-7.29 (m, 2H), 7.43 (td, 1H), 7.59 (ddd, 1H), 7.89-7.92 (m, 1H), 8.00 (d, 1H). LC-MS: retention time: 1.24 min MS ES$^+$: 306.0 [M + H]$^+$ Method B |
| 1-1-4 | 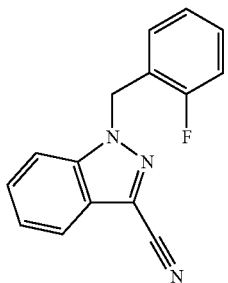 [SMILES: N#Cc1nn(Cc2ccccc2F)c2ccccc12] | 1-(2-fluoro-benzyl)-1H-indazole-3-carbnonitrile | $^1$H-NMR (300 MHz, DMSO-d6): δ [ppm] = 5.84 (s, 2H), 7.11-7.45 (m, 5H), 7.58 (ddd, 1H), 7.87 (d, 1H), 7.96 (d, 1H). LC-MS: retention time: 1.29 min MS ES$^+$: 251.9 [M + H]$^+$ Method B |
| 1-1-5 | 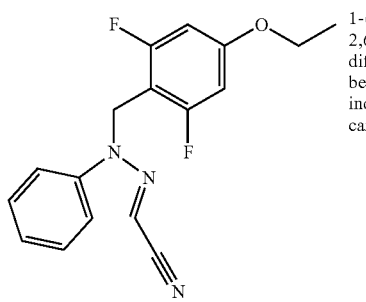 | 1-(4-ethoxy-2,6-difluoro-benzyl)-1H-indazole-3-carbonitrile | $^1$H-NMR (300 MHz, DMSO-d6): δ [ppm] = 1.26 (t, 3H), 4.01 (q, 2H), 5.72 (s, 2H), 6.70-6.76 (m, 2H), 7.34-7.47 (m, 1H), 7.56-7.67 (m, 1H), 7.80-7.88 (m, 1H), 7.91-8.01 (m, 1H). LC-MS: retention time: 1.44 min MS ES$^+$: 314.2 [M + H]$^+$ |
| 1-1-6 | 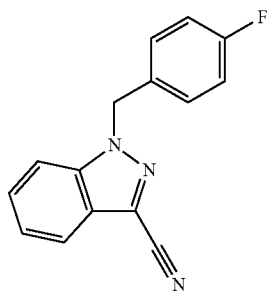 [SMILES: N#Cc1nn(Cc2ccc(F)cc2)c2ccccc12] | 1-(4-fluoro-benzyl)-1H-indazole-3-carbonitrile | $^1$H-NMR (500 MHz, DMSO-d$_6$): δ [ppm] = 5.79 (s, 2H), 7.14 (m, 2H), 7.31-7.43 (m, 3H), 7.56 (ddd, 1H), 7.87 (d, 1H), 7.98 (d, 1H). |
| 1-1-7 | 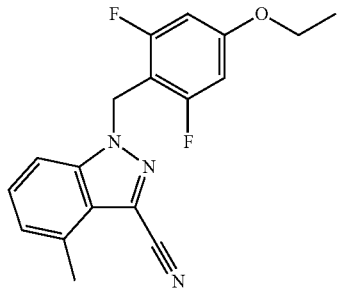 [SMILES: CCOc1cc(F)c(Cn2nc(C#N)c3c(C)cccc32)c(F)c1] | 1-(4-ethoxy-2,6-difluoro-benzyl)-4-methyl-1H-indazole-3-carbonitrile | H-NMR (400 MHz, DMSO-d6): δ [ppm] = 1.26 (t, 3H), 2.64 (s, 3H), 4.01 (q, 2H), 5.68 (s, 2H), 6.70-6.76 (m, 2H), 7.13 (d, 1H), 7.46 (dd, 1H), 7.74 (d, 1H). |

Intermediate 1-2-1

Preparation of 1-(4-methoxybenzyl)-1H-indazole-3-carboximidamide

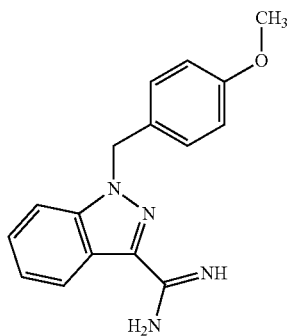 [SMILES: COc1ccc(Cn2nc(C(=N)N)c3ccccc32)cc1]

9.25 g of 1-(4-methoxybenzyl)-1H-indazole-3-carbonitrile (1-1-1, 35.1 mmol, 1 eq.) were suspended in 128 ml of dry methanol under a nitrogen atmosphere. 0,949 g (17.6 mmol, 0.5 eq.) of sodium methanolate were added. The reaction mixture was stirred for 18 hours at room temperature. To the resulting mixture were added 2.82 g (52.7 mmol, 1.5 eq.) of ammonium chloride and 1.0 ml (17.6 mmol, 0.5 eq.) of 100% acetic acid and stirred for 5 hours at 50° C. After cooling down at room temperature the mixture was concentrated in vacuo. The residue was partitioned between aq. half saturated sodium hydrogen carbonate solution and dichloromethane/isopropanol 4:1. The aqueous layer was extracted three times with dichloromethane/isopropanol 4:1. The combined organic layers were washed with brine, dried over magnesium sulfate and concentrated in vacuo. The residue was purified by flash chromatography to yield 6.45 g (23 mmol, 65.5%) of the analytically pure target compound.

$^1$H NMR (300 MHz, DMSO-d6) δ[ppm]=3.62-3.70 (s, 3H), 5.57 (s, 2H), 6.37 (br. s., 3H), 6.78-6.88 (m, 2H), 7.10-7.23 (m, 3H), 7.35 (ddd, 1H), 7.68 (d, 1H), 8.27 (d, 1H)

LC-MS:
retention time: 0.75 min
MS ES$^+$: 281.34 [M+H]$^+$

The following intermediates were prepared according to the same procedure from the indicated starting materials (SM=starting material):

| | Structure | Name | NMR / LC-MS |
|---|---|---|---|
| 1-2-2<br>SM =<br>1-1-2 | (structure) | 1-(4-propyl-benzyl)-1H-indazole-3-carboximid-amide | $^1$H-NMR (300 MHz, DMSO-d$_6$): δ [ppm] = 0.80 (t, 3H), 1.38-1.56 (m, 2H), 2.41-2.49 (t, 2H), 5.61 (s, 2H), 6.41 (br. s., 3H), 7.04-7.19 (m, 5H), 7.36 (ddd, 1H), 7.67 (d, 1H), 8.28 (d, 1H).<br>LC-MS:<br>retention time: 0.94 min<br>MS ES$^+$: 293.0 [M + H]$^+$<br>Method B |
| 1-2-3<br>SM =<br>1-1-4 | (structure) | 1-(2-fluoro-benzyl)-1H-indazole-3-carboximid-amide | $^1$H-NMR (300 MHz, DMSO-d6): δ [ppm] = 5.72 (s, 2H), 6.73 (br. s., 3H), 7.01-7.13 (m, 2H), 7.15-7.23 (m, 2H), 7.27-7.36 (m, 1H), 7.40 (ddd, 1H), 7.69 (d, 1H), 8.27 (d, 1H).<br>LC-MS:<br>retention time: 0.75 min<br>MS ES$^+$: 268.9 [M + H]$^+$<br>Method B |
| 1-2-4<br>SM =<br>1-1-5 | (structure) | 1-(4-ethoxy-2,6-difluoro-benzyl)-1H-indazole-3-carboximid-amide hydrochloride (1:1) | $^1$H-NMR (300 MHz, DMSO-d6): δ [ppm] = 1.26 (t, 3H), 4.01 (q, 2H), 5.73 (s, 2H), 6.70-6.76 (m, 2H), 7.33-7.41 (m, 1H), 7.52-7.63 (m, 1H), 7.88 (d, 1H), 7.97 (d, 1H), 9.26 (br. s., 3H).<br>LC-MS:<br>retention time: 0.87 min<br>MS ES$^+$: 332.2 [M + H]$^+$ |

| | | |
|---|---|---|
| 1-2-5 SM = 1-1-6 | 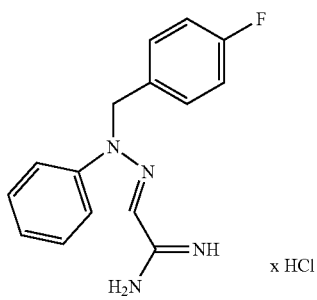 [SMILES: N=C(N)/C=N/N(Cc1ccc(F)cc1)c1ccccc1] 1-(4-fluoro-benzyl)-1H-indazole-3-carboximid-amide hydrochloride (1:1) | ¹H-NMR (400 MHz, DMSO-d6): δ [ppm] = 5.81 (s, 2H), 7.10-7.17 (m, 2H), 7.35-7.42 (m, 3H), 7.51-7.57 (m, 1H), 7.93 (d, 1H), 8.00 (d, 1H), 9.34 (br. s., 3H). LC-MS: retention time: 0.71 min MS ES⁺: 269.0 [M + H]⁺ Method B |
| 1-2-6 SM = 1-1-7 | 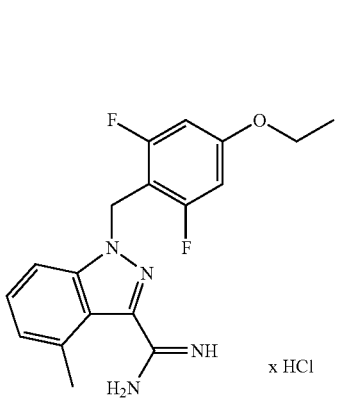 [SMILES: CCOc1cc(F)c(Cn2nc(C(=N)N)c3c(C)cccc32)c(F)c1] 1-(4-ethoxy-2,6-difluoro-benzyl)-4-methyl-1H-indazole-3-carboximid-amide hydrochloride (1:1) | ¹H-NMR (300 MHz, DMSO-d6): δ [ppm] = 1.26 (t, 3H), 2.49 (s, 3H), 3.99 (q, 2H), 5.66 (s, 2H), 6.69-6.79 (m, 2H), 7.10 (d, 1H), 7.46 (t, 1H), 7.74 (d, 1H), 7.77 (br. s., 3H). LC-MS (Method 1): retention time: 0.93 min MS ES⁺: 345.0 [M + H]⁺ |

Intermediate 1-3-1 Preparation of 3,3-bis(dimethylamino)-2-methoxypropanenitrile

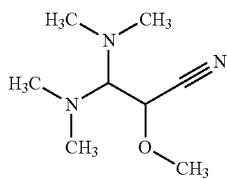

360.4 g of 1-tert-butoxy-N,N,N'N'-tetramethylmethanediamine (Bredereck's reagent) (2068 mmol, 1 eq.) and 150.0 g of methoxyacetonitrile (2068 mmol, 1 eq.) were stirred for 18 hours at 80@C. The reaction mixture was concentrated in vacuo. The residue was purified by vacuum distillation to yield 117 g (687 mmol, 33.0%) of the analytical pure target compound as a yellowish liquid.

1H-NMR (400 MHz, DMSO-d6): δ [ppm]=2.23 (s, 6H), 2.29 (s, 6H), 3.23 (d, 1H), 3.36-3.41 (s, 3H), 4.73 (d, 1H).

LC-MS:

retention time: 0.79 min

MS ES⁺: 172.09 [M+H]⁺

Intermediate 1-4-1

Preparation of 5-methoxy-2-[1-(4-methoxybenzyl)-1H-indazol-3-yl]pyrimidin-4-amine

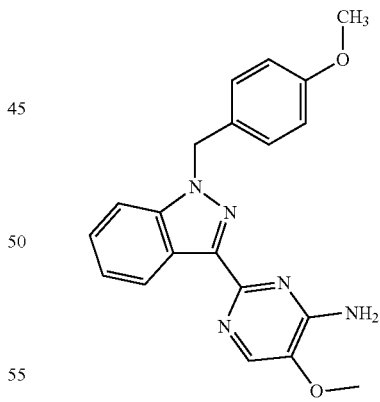

6.45 g of 1-(4-methoxybenzyl)-1H-indazole-3-carboximidamide (23.0 mmol, 1 eq.), 5.40 g of 3,3-bis(dimethylamino)-2-methoxypropanenitrile (1-2-1, 31.5 mmol, 1.37 eq.) and 0,455 ml of piperidine (4.60 mmol, 0.2 eq.) were dissolved in 82.7 ml of dry 3-methylbutan-1-ol, put under a nitrogen atmosphere and stirred at 100° C. for 3 days. The mixture was cooled down at room temperature and stirred for 18 hours for crystallization. The resulting suspension was filtered off. The crystals were washed with cold methanol and dried in vacuo at 50° C. The crystallization was repeated twice with cold methanol to receive 2 further filter cakes and a combined yield of 6.87 g (19 mmol, 82.5%) of the analytically pure target compound.

¹H-NMR (300 MHz, DMSO-d₆): δ [ppm]=3.62-3.69 (s, 3H), 3.85 (s, 3H), 5.59 (s, 2H), 6.78-6.90 (m, 4H), 7.11-7.23 (m, 3H), 7.35 (ddd, 1H), 7.68 (d, 1H), 7.95 (s, 1H), 8.53 (d, 1H).

LC-MS: Method B
retention time: 0.87 min
MS ES⁺: 362.0 [M+H]⁺

The following intermediates were prepared according to the same procedure from the indicated starting materials (SM=starting material):

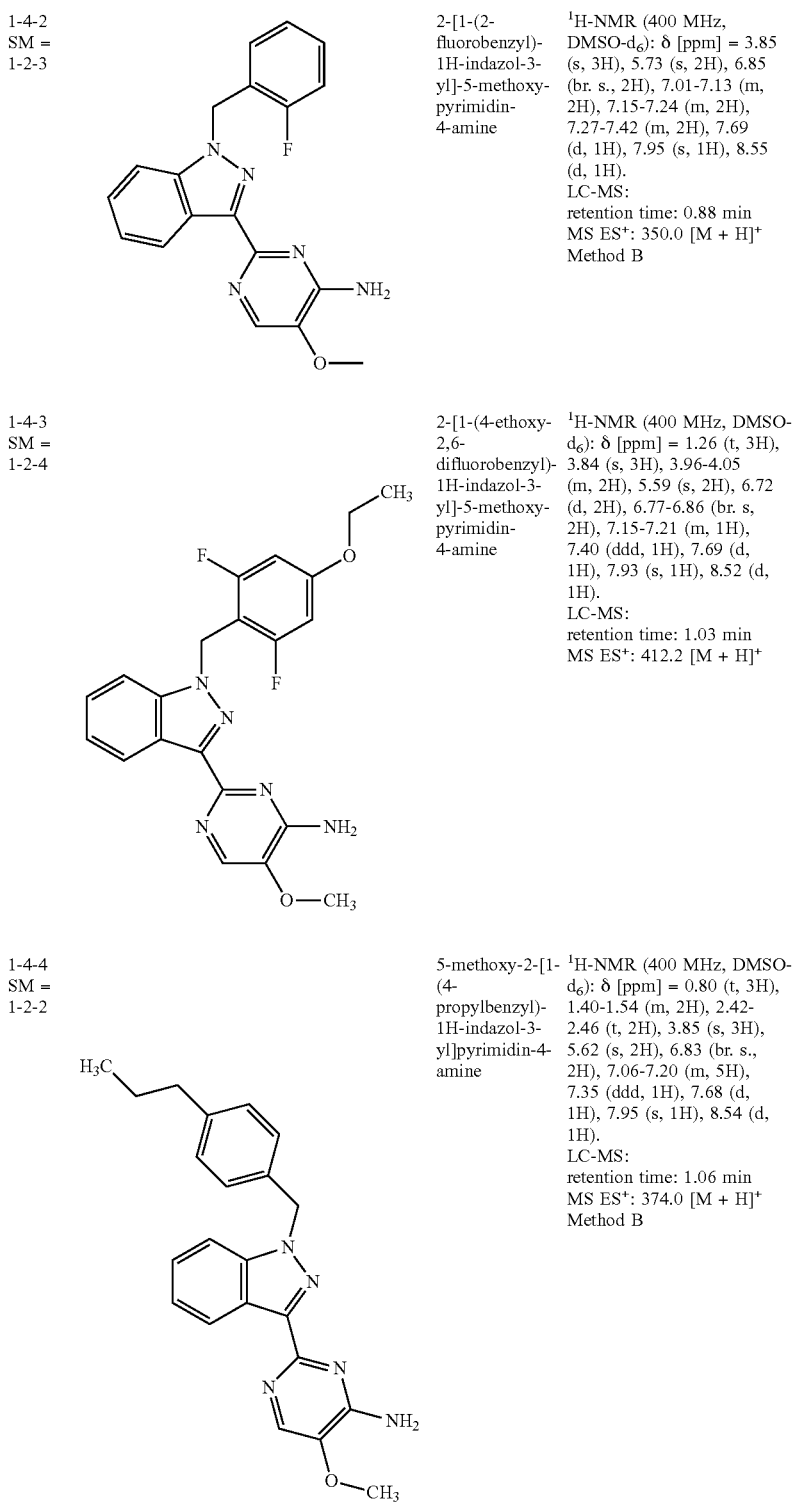

| | | | |
|---|---|---|---|
| 1-4-2<br>SM =<br>1-2-3 | | 2-[1-(2-fluorobenzyl)-1H-indazol-3-yl]-5-methoxy-pyrimidin-4-amine | ¹H-NMR (400 MHz, DMSO-d₆): δ [ppm] = 3.85 (s, 3H), 5.73 (s, 2H), 6.85 (br. s., 2H), 7.01-7.13 (m, 2H), 7.15-7.24 (m, 2H), 7.27-7.42 (m, 2H), 7.69 (d, 1H), 7.95 (s, 1H), 8.55 (d, 1H).<br>LC-MS:<br>retention time: 0.88 min<br>MS ES⁺: 350.0 [M + H]⁺<br>Method B |
| 1-4-3<br>SM =<br>1-2-4 | | 2-[1-(4-ethoxy-2,6-difluorobenzyl)-1H-indazol-3-yl]-5-methoxy-pyrimidin-4-amine | ¹H-NMR (400 MHz, DMSO-d₆): δ [ppm] = 1.26 (t, 3H), 3.84 (s, 3H), 3.96-4.05 (m, 2H), 5.59 (s, 2H), 6.72 (d, 2H), 6.77-6.86 (br. s, 2H), 7.15-7.21 (m, 1H), 7.40 (ddd, 1H), 7.69 (d, 1H), 7.93 (s, 1H), 8.52 (d, 1H).<br>LC-MS:<br>retention time: 1.03 min<br>MS ES⁺: 412.2 [M + H]⁺ |
| 1-4-4<br>SM =<br>1-2-2 | | 5-methoxy-2-[1-(4-propylbenzyl)-1H-indazol-3-yl]pyrimidin-4-amine | ¹H-NMR (400 MHz, DMSO-d₆): δ [ppm] = 0.80 (t, 3H), 1.40-1.54 (m, 2H), 2.42-2.46 (t, 2H), 3.85 (s, 3H), 5.62 (s, 2H), 6.83 (br. s., 2H), 7.06-7.20 (m, 5H), 7.35 (ddd, 1H), 7.68 (d, 1H), 7.95 (s, 1H), 8.54 (d, 1H).<br>LC-MS:<br>retention time: 1.06 min<br>MS ES⁺: 374.0 [M + H]⁺<br>Method B |

| | | | |
|---|---|---|---|
| 1-4-5 SM = 1-2-5 | 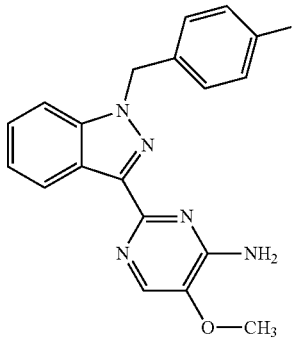 | 2-[1-(4-fluorobenzyl)-1H-indazol-3-yl]-5-methoxy-pyrimidin-4-amine | $^1$H-NMR (300 MHz, DMSO-d$_6$): δ [ppm] = 3.85 (s, 3H), 5.67 (s, 2H), 6.84 (br. s., 2H), 7.06-7.21 (m, 3H), 7.23-7.31 (m, 2H), 7.36 (td, 1H), 7.70 (d, 1H), 7.95 (s, 1H), 8.54 (d, 1H). LC-MS: retention time: 0.87 min MS ES$^+$: 350.0 [M + H]$^+$ Method B |
| 1-4-6 SM = 1-2-6 | 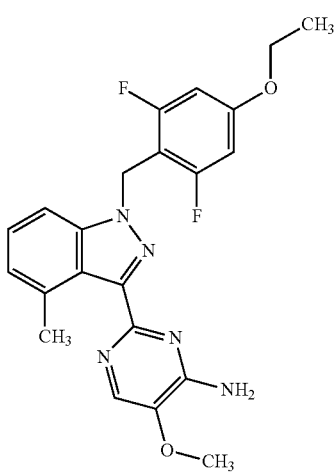 [SMILES: CCOc1cc(F)c(Cn2nc(-c3ncc(OC)c(N)n3)c3c(C)cccc32)c(F)c1] | 2-[1-(4-ethoxy-2,6-difluorobenzyl)-4-methyl-1H-indazol-3-yl]-5-methoxy-pyrimidin-4-amine | $^1$H-NMR (400 MHz, DMSO-d6): δ [ppm] = 1.26 (t, 3H), 2.34 (s, 3H), 3.85 (s, 3H), 4.00 (q, 2H), 5.52 (s, 2H), 6.63-6.74 (m, 2H), 6.78 (br s, 2H), 6.87 (d, 1H), 7.27 (dd, 1H), 7.54 (d, 1H), 7.90 (s, 1H). LC-MS: retention time: 1.32 min MS ES+: 427.08 [M + H]+ |

Intermediate 1-5-1

Preparation of 5-methoxy-2-[1-(4-methoxybenzyl)-1H-indazol-3-yl]-N-(pyridin-4-yl)pyrimidin-4-amine

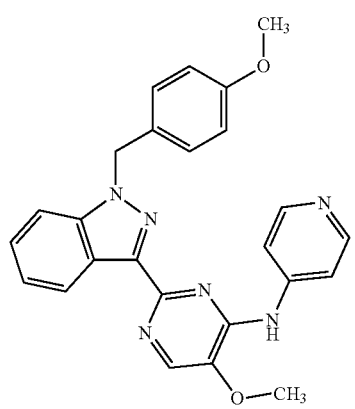 [SMILES: COc1ccc(Cn2nc(-c3ncc(OC)c(Nc4ccncc4)n3)c3ccccc32)cc1]

205 mg of 5-methoxy-2-[1-(4-methoxybenzyl)-1H-indazol-3-yl]pyrimidin-4-amine (1-4-1, 0,568 mmol, 1 eq.), 121.6 mg of 4-bromopyridine hydrochloride (1:1) (0,625 mmol, 1.1 eq.), 136.5 mg of sodium 2-methylpropan-2-olate (1.42 mmol, 2.5 eq.), 106.2 mg of 1'-binaphthalene-2,2'-diylbis(diphenylphosphane) (0,171 mmol, 0.3 eq.) and 52.0 mg of (1E,4E)-1,5-diphenylpenta-1,4-dien-3-one-palladium (3:2) (0,057 mmol, 0.1 eq.) were suspended in 3 ml of dry DMF under nitrogen atmosphere. The reaction mixture was stirred for two days at 100° C. 122 mg of 4-bromopyridine hydrochloride (1:1) (0,625 mmol, 1.1 eq.), 137 mg of sodium 2-methylpropan-2-olate (1.42 mmol, 2.5 eq.), 106 mg of 1'-binaphthalene-2,2'-diylbis(diphenylphosphane) (0,171 mmol, 0.3 eq.) and 52.0 mg of (1E,4E)-1,5-diphenylpenta-1,4-dien-3-one-palladium (3:2) (0,057 mmol, 0.1 eq.) were added and stirred for further 24 hours. The mixture was cooled down to room temperature, diluted with 10 ml dichloromethane and filtered off. The filtrate was concentrated in vacuo. The residue was purified by flash chromatography to yield 126 mg (0.23 mmol, 81%) of the analytically pure target compound.

$^1$H-NMR (300 MHz, DMSO-d$_6$): δ [ppm]=3.66 (s, 3H), 4.02 (s, 3H), 5.65 (s, 2H), 6.86 (d, 2H), 7.15-7.25 (m, 1H), 7.27-7.44 (m, 3H), 7.78 (d, 1H), 8.08-8.17 (m, 2H), 8.31-8.46 (m, 4H), 9.42 (s, 1H).

LC-MS:

retention time: 0.95 min

MS ES$^+$: 439.31 [M+H]$^+$

Method B

Intermediate 1-6-1

Preparation of 2-(1H-indazol-3-yl)-5-methoxy-N-(pyridin-4-yl)pyrimidin-4-amine

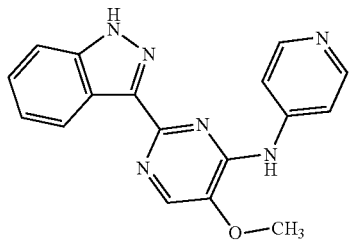 [SMILES: COc1cnc(-c2n[nH]c3ccccc23)nc1Nc1ccncc1]

13.4 g of 5-methoxy-2-[1-(4-methoxybenzyl)-1H-indazol-3-yl]-N-(pyridin-4-yl)pyrimidin-4-amine (1-5-1, 30.6 mmol, 1 eq.) was suspended in 121 ml of 1,2-dichloroethan. First 71 ml of trifluoroacetic acid (918 mmol, 30 eq.) were added dropwise, followed by 27 ml of trifluoromethanesulfonic acid (306 mmol, 10 eq.). The reaction mixture was stirred for three days under nitrogen atmosphere. The mixture was cooled with an ice bath to +3C, upon which 2M aq. sodium hydroxide solution was added until pH=12. The resulting brown suspension was stirred for 18 hours at room temperature and then the precipitate was filtered off and dried under vacuo at 70° C. to yield 9.74 g (27.7 mmol, 90.3%) of the analytically pure target compound as a light brown solid.

$^1$H-NMR (300 MHz, DMSO-d$_6$): δ [ppm]=4.02 (s, 3H), 7.11-7.26 (m, 1H), 7.37 (t, 1H), 7.56 (d, 1H), 8.17 (d, 2H), 8.32-8.53 (m, 4H), 9.39 (s, 1H), 13.39 (s, 1H).

LC-MS:
retention time: 0.68 min
MS ES$^+$: 319.0 [M+H]$^+$

Method B

Intermediate 1-7-1

Preparation of 2-[1-(2-fluorobenzyl)-1H-indazol-3-yl]-4-(pyridin-4-ylamino)pyrimidin-5-yl trifluoromethanesulfonate

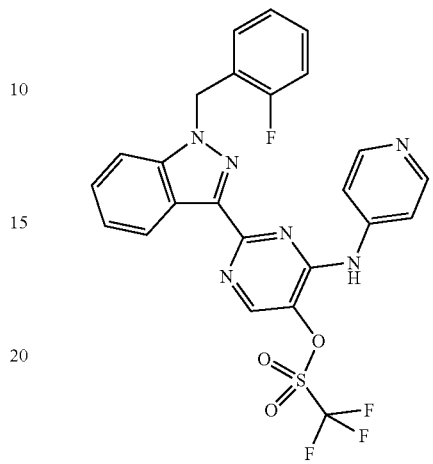

120 mg of 2-[1-(2-fluorobenzyl)-1H-indazol-3-yl]-4-(pyridin-4-ylamino)pyrimidin-5-ol (3-3, 0,291 mmol, 1 eq.) was suspended in 1.9 ml of dry dichloromethane and 0,059 ml of pyridine (0.73 mmol, 2.5 eq.) were added under nitrogen atmosphere.

The mixture was cooled with an ice bath to +3'C and 0,061 ml of trifluoromethanesulfonic anhydride (0,364 mmol, 1.25 eq.) were added dropwise. Upon completion of addition the ice bath was removed and the reaction mixture was stirred for 18 hours. The reaction mixture was cooled again with an ice bath and 0,059 ml of pyridine (0,727 mmol, 2.5 eq.) and 0,061 ml of trifluoromethanesulfonic anhydride (0,364 mmol, 1.25 eq.) were added and stirred for 3 hours. This procedure was repeated and stirred for further 24 hours. The reaction mixture was filtered off a short silica column and diluted with dichloromethane. The filtrate was concentrated in vacuo. The liquid residue was dissolved with toluene and again concentrated in vacuo. Yield=106.1 mg with 37% purity (0.07 mmol, 24.78%)

LC-MS:
retention time: 1.18 min
MS ES$^+$: 545.08 [M+H]$^+$

The following intermediate was prepared according to the same procedure using the indicated starting materials (SM=starting material):

| | | | |
|---|---|---|---|
| 1-7-2<br>SM =<br>3-1 | 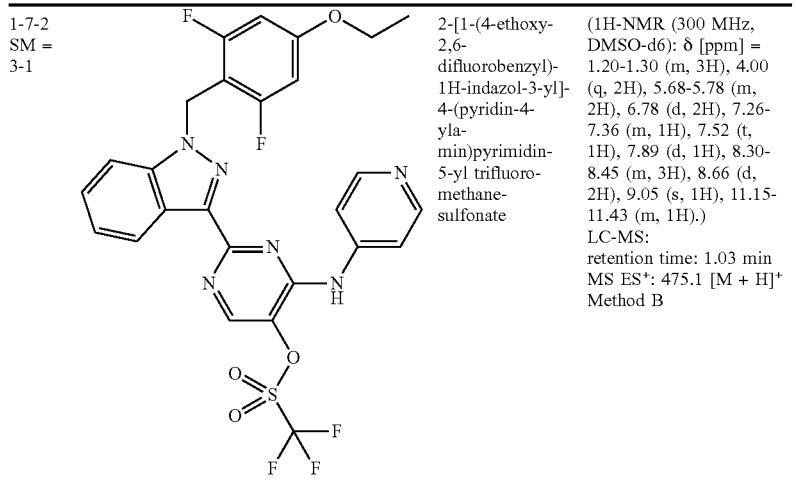 | 2-[1-(4-ethoxy-2,6-difluorobenzyl)-1H-indazol-3-yl]-4-(pyridin-4-ylamin)pyrimidin-5-yl trifluoromethanesulfonate | (1H-NMR (300 MHz, DMSO-d6): δ [ppm] = 1.20-1.30 (m, 3H), 4.00 (q, 2H), 5.68-5.78 (m, 2H), 6.78 (d, 2H), 7.26-7.36 (m, 1H), 7.52 (t, 1H), 7.89 (d, 1H), 8.30-8.45 (m, 3H), 8.66 (d, 2H), 9.05 (s, 1H), 11.15-11.43 (m, 1H).)<br>LC-MS:<br>retention time: 1.03 min<br>MS ES$^+$: 475.1 [M + H]$^+$<br>Method B |

Intermediate 1-8-1

Preparation of tert-butyl 3-[5-methoxy-4-(pyridin-4-ylamino)pyrimidin-2-yl]-1H-indazole-1-carboxylate

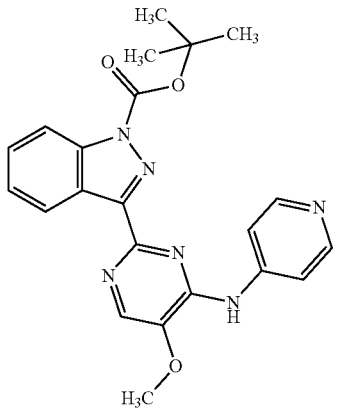 [SMILES: COc1cnc(-c2nn(C(=O)OC(C)(C)C)c3ccccc23)nc1Nc1ccncc1]

100 mg of [2-(1H-Indazol-3-yl)-5-methoxy-pyrimidin-4-yl]-pyridin-4-yl-amine (1-6-1, 0,314 mmol, 1 eq.) was dissolved in 2 ml of acetonitrile and 0,131 ml of triethylamine (0,942 mmol, 3 eq.). 3.83 mg of 4-Dimethylaminopyridin (0,031 mmol, 0.1 eq.) and 89.1 mg of di-tert-butyl dicarbonate (0,408 mmol, 1.3 eq.) dissolved in 0.5 ml of acetonitrile were added. The solution was stirred for 24 hours at room temperature under nitrogen atmosphere. The resulting suspension was filtered off and the filter cake was washed with acetonitrile to yield 100 mg (0.24 mmol, 76.1%) of the analytically pure target compound.

$^1$H-NMR (400 MHz, DMSO-d$_6$): δ [ppm]=1.68 (br. s., 9H), 4.05 (br. s., 3H), 7.43 (br. s., 1H), 7.62 (br. s., 1H), 8.18 (br. s., 3H), 8.33-8.45 (m, 3H), 8.57 (d, 1H), 9.53 (br. s., 1H).
LC-MS:
retention time: 0.97 min
MS ES$^+$: 419.1 [M+H]$^+$

Intermediate 1-9-1

Preparation of tert-butyl 3-(5-methoxy-4-{[(prop-2-en-1-yloxy)carbonyl](pyridin-4-yl)amino}pyrimidin-2-yl)-1H-indazole-1-carboxylate

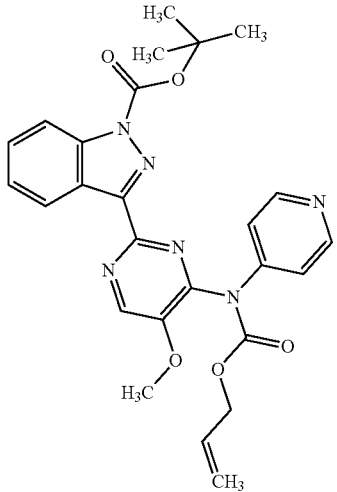 [SMILES: C=CCOC(=O)N(c1ccncc1)c1nc(-c2nn(C(=O)OC(C)(C)C)c3ccccc23)ncc1OC]

96.3 mg of tert-butyl 3-[5-methoxy-4-(pyridin-4-ylamino)pyrimidin-2-yl]-1H-indazole-1-carboxylate (1-8-1, 0.23 mmol, 1 eq.) was suspended in 7 ml of pyridine. 27.7 mg of prop-2-en-1-yl carbonochloridate (0.23 mmol, 1 eq.) were added and stirred for two hours at room temperature. Twice 27.7 mg of prop-2-en-1-yl carbonochloridate (0.23 mmol, 1 eq.) were added again and stirred the first time for 24 hours and the second time for three days at room temperature. The reaction mixture was concentrated in vacuo. To the residue was added water and acidified with 1M aq. hydrogen chloride solution. This aqueous layer was extracted three times with ethyl acetate. The combined organic layers were washed with brine, dried over a silicone filter and concentrated under vacuo. Purification by flash chromatography (ethyl acetate/methanol 0-50%) provided 50.8 mg (0.09 mmol, 39.97%) of the analytically pure target compound.

$^1$H-NMR (300 MHz, CHLOROFORM-d): δ [ppm]=1.74 (s, 9H), 4.01 (s, 3H), 4.71 (d, 2H), 5.14-5.29 (m, 2H), 5.76-5.95 (m, 1H), 7.20-7.25 (m, 2H), 7.28-7.36 (m, 1H), 7.50-7.59 (m, 1H), 8.25 (t, 2H), 8.50-8.61 (m, 2H), 8.71 (s, 1H)
LC-MS:
retention time: 1.21 min
MS ES$^+$: 503.3 [M+H]$^+$

Intermediate 1-10-1

Preparation of prop-2-en-1-yl [2-(1H-indazol-3-yl)-5-methoxypyrimidin-4-yl]pyridin-4-ylcarbamate

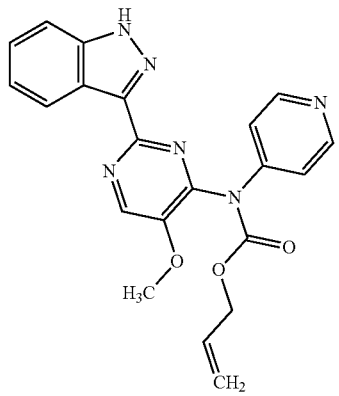 [SMILES: C=CCOC(=O)N(c1ccncc1)c1nc(-c2n[nH]c3ccccc23)ncc1OC]

1.22 g of tert-butyl 3-(5-methoxy-4-{[(prop-2-en-1-yloxy)carbonyl](pyridin-4-yl)amino}pyrimidin-2-yl)-1H-indazole-1-carboxylate (1-9-1, 2.43 mmol, 1 eq.) was suspended in 1,4-dioxane. 2.43 ml of hydrogen acid 4M in 1,4-dioxane (9,711 mmol, 4 eq.) were added dropwise. The reaction mixture was stirred for 24 hours at room temperature. 2.43 ml of hydrogen acid 4M in 1,4-dioxane (9,711 mmol, 4 eq.) were added dropwise again and stirred for further two hours. The reaction mixture was concentrated under vacuo. The residue was extracted with saturated aq. sodium hydrogen carbonate-solution and ethyl acetate. The aqueous layer was reextracted twice by ethyl acetate. The combined organic layers were dried over a silicone filter and concentrated under vacuo. Purification by flash chromatography (ethyl acetate/methanol 0-25%) provided 877 mg (1.96 mmol, 80.8%) of the analytically pure target compound.

$^1$H-NMR (400 MHz, DMSO-d$_6$): δ [ppm]=4.00 (s, 3H), 4.71-4.81 (m, 2H), 5.12-5.23 (m, 2H), 5.79-5.93 (m, 1H), 7.13-7.23 (m, 1H), 7.33-7.41 (m, 1H), 7.54-7.62 (m, 1H), 7.82-7.91 (m, 2H), 8.25-8.31 (m, 1H), 8.71-8.79 (m, 2H), 9.09 (s, 1H)

LC-MS:

retention time: 0.84 min

MS ES+: 403.3 [M+H]+

Intermediate 1-11-1

Preparation of 4-amino-2-[1-(2-fluorobenzyl)-1H-indazol-3-yl]pyrimidin-5-ol

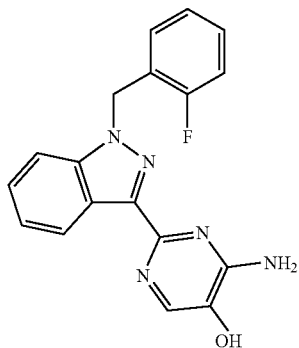 [SMILES: Nc1nc(-c2nn(Cc3ccccc3F)c3ccccc23)ncc1O]

558 mg of 2-[1-(2-fluorobenzyl)-1H-indazol-3-yl]-5-methoxypyrimidin-4-amine (1-4-2, 1.60 mmol, 1 eq.) was suspended in 10 ml of 1-methyl-2-pyrrolidon. 623 mg of sodium sulfidosodium (7.99 mmol, 5 eq.) were added and stirred for an hour at 140'C. The reaction mixture was extracted with half-saturated aq. ammonium chloride-solution and ethyl acetate. The aqueous layer was reextracted twice by ethyl acetate. The aqueous layer gave a precipitate, which was filtered off and first purified by flash chromatography (hexane/dichloro methane/methanol), followed by a HPLC purification. This provided 23.4 mg (0.07 mmol, 4.37%) of the analytically pure target compound.

$^1$H-NMR (400 MHz, DMSO-d6): δ [ppm]=5.68-5.74 (s, 2H), 6.61-6.67 (d, 1H), 7.01-7.13 (m, 2H), 7.14-7.23 (m, 2H), 7.25-7.33 (m, 2H), 7.34-7.42 (t, 1H), 7.64-7.71 (d, 1H), 7.74-7.80 (s, 1H), 8.51-8.56 (d, 1H), 9.74-9.87 (s, 1H).

LC-MS:

retention time: 0.92 min

MS ES+: 336.1 [M+H]+

Intermediate 1-12-1

Preparation of sodium 2-[1-(2-fluorobenzyl)-1H-indazol-3-yl]-5-(methoxycarbonyl)pyrimidin-4-olate

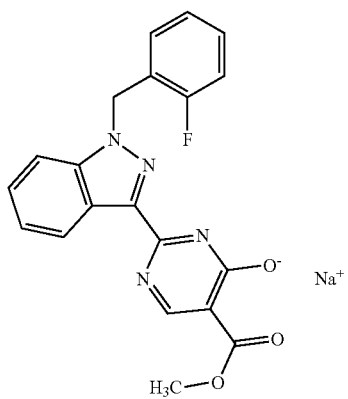 [SMILES: COC(=O)c1cnc(-c2nn(Cc3ccccc3F)c3ccccc23)nc1[O-] ; [Na+]]

2.5 g of 1-(2-fluorobenzyl)-1H-indazole-3-carboximidamide hydrochloride (1:1) (1-2-3×HCl, 8.20 mmol, 1 eq.), 1.43 g of dimethyl (methoxymethylidene)propanedioate (8.20 mmol, 1 eq.) and 50 ml of methanol and 443 mg of sodium methanolate were stirred under nitrogen atmosphere at 60'C bath temperature for 24 hours. The clear yellowish solution turned into a suspension which was filtered off. The crystals were washed with cold methanol to yield 1.64 g (4.1 mmol, 50%) of the analytically pure target compound.

$^1$H-NMR (300 MHz, DMSO-d$_6$): δ [ppm]=3.67 (s, 3H), 5.76 (s, 2H), 7.05-7.36 (m, 5H), 7.42 (ddd, 1H), 7.71 (d, 1H), 8.44-8.55 (m, 2H).

LC-MS:

retention time: 1.16 min

MS ES+: 379.1 [M+H]+

Intermediate 1-13-1

Preparation of sodium 5-carbamoyl-2-[1-(2-fluorobenzyl)-1H-indazol-3-yl]pyrimidin-4-olate

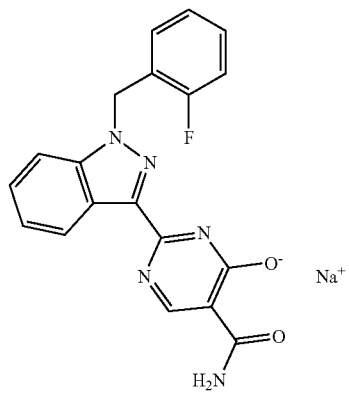 [SMILES: NC(=O)c1cnc(-c2nn(Cc3ccccc3F)c3ccccc23)nc1[O-] ; [Na+]]

100 mg of sodium 2-[1-(2-fluorobenzyl)-1H-indazol-3-yl]-5-(methoxycarbonyl)pyrimidin-4-olate (1-12-1, 0.25 mmol, 1 eq.) were dissolved in 26.8 ml of 7N ammonia in methanol (187 mmol, 750 eq.) and stirred under a nitrogen atmosphere at 60° C. bath temperature for 24 hours, then at 65° C. bath temperature for six hours and further 24 hours at 70'C bath temperature. The reaction mixture was concentrated in vacuo to yield 96 mg (0.22 mmol, 89.8%) of the analytically pure target compound.

$^1$H-NMR (400 MHz, DMSO-d6): δ [ppm]=5.82 (s, 2H), 7.07-7.26 (m, 3H), 7.27-7.42 (m, 3H), 7.47 (t; 1H), 7.77 (d, 1H), 8.47 (d, 1H), 8.58 (br. s., 1H), 9.07-9.32 (m, 1H).

LC-MS:

retention time: 1.10 min

MS ES+: 364.12 [M+H]+

Intermediate 1-14-1

Preparation of 4-chloro-2-[1-(2-fluorobenzyl)-1H-indazol-3-yl]pyrimidine-5-carbonitrile

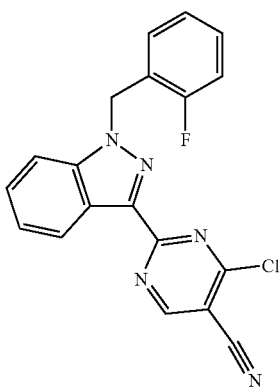 [SMILES: N#Cc1cnc(-c2nn(Cc3ccccc3F)c3ccccc23)nc1Cl]

88 mg of sodium 5-carbamoyl-2-[1-(2-fluorobenzyl)-1H-indazol-3-yl]pyrimidin-4-olate (1-13-1, 0,228 mmol, 1 eq.) were suspended in 0,915 ml of phosphoric trichloride (9.82 mmol, 43 eq.) and 69 µl of N,N-diethylaniline (0,457 mmol, 2 eq.). The suspension was stirred at 90° C. bath temperature for 24 hours and then dropped to an ice cooled saturated aqueous sodium hydrogen carbonate solution. The resulting suspension was filtered off and dried in vacuo to yield 82 mg (0.21 mmol, 93.77%) of the analytically pure target compound.

$^1$H-NMR (400 MHz, DMSO-d6): δ [ppm]=5.87-5.91 (m, 2H), 7.08-7.26 (m, 3H), 7.30-7.44 (m, 2H), 7.53 (td, 1H), 7.88 (d, 1H), 8.45 (d, 1H), 9.39 (s, 1H).

LC-MS: Method B
retention time: 1.38 min
MS ES$^+$: 364.0 [M+H]$^+$

Intermediate 1-15-1

Preparation of 2-(bromomethyl)-5-(difluoromethoxy)-1,3-difluorobenzene

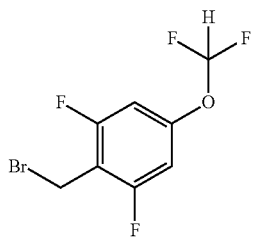 [SMILES: Fc1cc(OC(F)F)cc(F)c1CBr]

Step 1: [4-(difluoromethoxy)-2,6-difluorophenyl]methanol 1 g of 3,5-difluoro-4-(hydroxymethyl)phenol (6,245 mmol, 1 eq.) were dissolved in 16 ml of DMF 1,047 g of sodium chloro(difluoro)acetate (6.87 mmol, 1.1 eq.), 2,442 g of cesium carbonate (7,494 mmol, 1.2 eq.) and 400 µl of water were added. The mixture was stirred at 100° C. bath temperature for 2 hours under nitrogen atmosphere. Then the reaction mixture was partitioned between water and ethyl acetate. The separated aqueous layer was extracted twice with ethyl acetate. The combined organic layers were washed with brine, dried over a silicone filter and concentrated in vacuo. The residue was purified by flash chromatography to yield 763.3 mg (3.63 mmol, 58.2%) of the analytically pure target compound.

$^1$H-NMR (400 MHz, DMSO-d$_6$): δ [ppm]=4.42 (d, 2H), 5.21 (t, 1H), 6.99 (d, 2H), 7.09-7.50 (t, 1H).

Step 2: 2-(bromomethyl)-5-(difluoromethoxy)-1,3-difluorobenzene 0.76 g of [4-(difluoromethoxy)-2,6-difluorophenyl]methanol (3.62 mmol, 1 eq.) were dissolved in 1.72 ml of 33% hydrogen bromide in glacial acetic acid (9.97 mmol, 2.75 eq.) and stirred at room temperature for 2 hours. 25 ml of diethyl ether were added and the mixture was stirred at room temperature for 15 min. The reaction mixture was added dropwise to 80 ml of aqueous saturated sodium hydrogen carbonate solution and stirred again at room temperature for 15 min. The separated aqueous layer was extracted twice with diethyl ether. The combined organic layers were washed with brine, dried over a silicone filter and concentrated in vacuo to yield 991 mg (3.56 mmol, 98.4%) of the analytically pure target compound.

$^1$H-NMR (300 MHz, DMSO-d$_6$): δ [ppm]=4.60 (s, 2H), 7.08-7.14 (d, 2H), 7.08-7.59 (t, 1H).

Intermediate 1-16-1

Preparation of 7-bromomethyl-3,4-dihydro-1H-quinolin-2-one

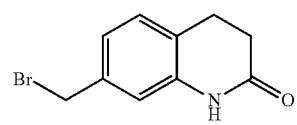

500 mg of 7-(hydroxymethyl)-3,4-dihydroquinolin-2(1H)-one (2.82 mmol, 1 eq.) were dissolved in 1.77 ml of 33% hydrogen bromide in glacial acetic acid (31.0 mmol, 11 eq.) under nitrogen atmosphere and stirred at room temperature for 30 minutes. The reaction mixture was partitioned between aq. saturated sodium hydrogen carbonate solution and dichloromethane/isopropanol 4+1. The aqueous layer was extracted three times with dichloromethane/1 isopropanol 4+1. The combined organic layers were washed with brine, dried over a silicone filter and concentrated in vacuo. The crude product was purified by flash chromatography to yield 175 mg (0.66 mmol, 23.3%) of the analytically pure target compound.

$^1$H-NMR (400 MHz, DMSO-d$_6$): δ [ppm]=2.40 (dd, 2H), 2.82 (t, 2H), 4.60 (s, 2H), 6.87 (d, 1H), 6.94 (dd, 1H), 7.10 (d, 1H).

LC-MS:
retention time: 0.91 min
MS ES$^+$: 240.2 [M+H]$^+$

The following compounds were prepared according to the same procedure from the indicated starting materials (SM=starting material):

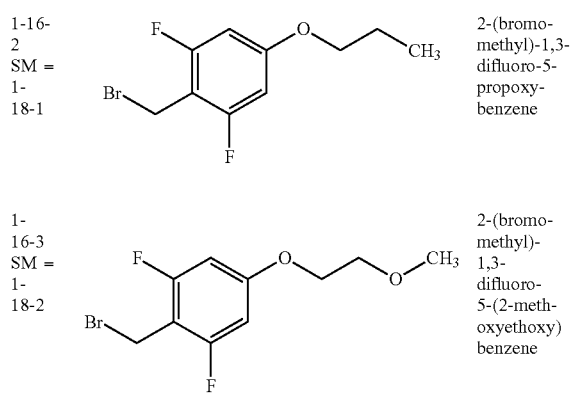

| | | |
|---|---|---|
| 1-16-2 SM = 1-18-1 | | 2-(bromomethyl)-1,3-difluoro-5-propoxybenzene |
| 1-16-3 SM = 1-18-2 | | 2-(bromomethyl)-1,3-difluoro-5-(2-methoxyethoxy)benzene |

200 mg of 3,5-difluoro-4-(hydroxymethyl)phenol (1.25 mmol, 1.0 eq.) and 184 mg 1-bromopropane (1.50 mmol, 1.2 eq.) were dissolved in 17 ml N,N-dimethylformamide. 863 mg potassium (6.25 mmol, 5.0 eq.) were added and the reaction mixture was stirred at 0° C. over night. The reaction mixture was separated between water and ethyl acetate. The aqueous layer was extracted with ethyl acetate twice. The combined organic layers were dried over a silicone filter and concentrated in vacuo. to yield 283 mg (1.19 mmol, 95%) of the crude product which was used without further purification.

$^1$H-NMR (300 MHz, DMSO-$d_6$): δ [ppm]=0.92 (t, 3H), 1.54-1.78 (m, 2H), 3.90 (t, 2H), 4.36 (s, 2H), 5.06 (br. s., 1H), 6.53-6.79 (m, 2H).

The following intermediate was prepared according to the same procedure from commercial (2-Bromethyl)-methylether and 3,5-difluoro-4-(hydroxymethyl)phenol:

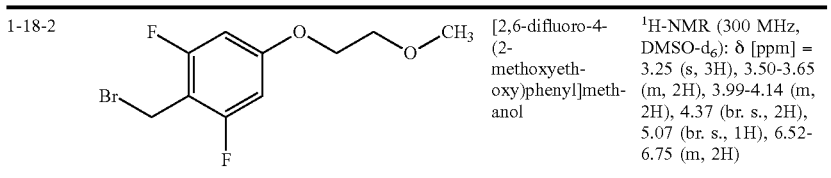

| | | | |
|---|---|---|---|
| 1-18-2 | | [2,6-difluoro-4-(2-methoxyethoxy)phenyl]methanol | $^1$H-NMR (300 MHz, DMSO-$d_6$): δ [ppm] = 3.25 (s, 3H), 3.50-3.65 (m, 2H), 3.99-4.14 (m, 2H), 4.37 (br. s., 2H), 5.07 (br. s., 1H), 6.52-6.75 (m, 2H) |

Intermediate 1-17-1

Preparation of 4-(bromomethyl)-N-cyclopropylbenzenesulfonamide

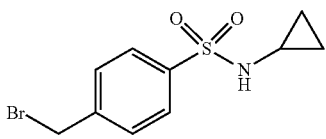 [SMILES: O=S(=O)(NC1CC1)c1ccc(CBr)cc1]

5 g of 4-(bromomethyl)benzenesulfonyl chloride (18.6 mmol, 1 eq.) were dissolved under argon atmosphere in 82.5 ml of dichloromethane and cooled down at −10C internal temperature. A solution of 1.29 ml cyclopropanamine (18.6 mmol, 1 eq.) and 2.59 ml of triethylamine (18.6 mmol, 1 eq.) in 82.5 ml of dichloromethane were added dropwise at −10° C. internal temperature and stirred at this temperature for one hour. The reaction mixture was washed once with 1 M aqueous hydrogene solution and twice with distilled water. The organic layer was dried over sodium sulfate and concentrated in vacuo. The crude product contained a mixture of bromomethyl- and chloromethyl-substituents.

Intermediate 1-18-1

Preparation of (2,6-difluoro-4-propoxyphenyl)methanol

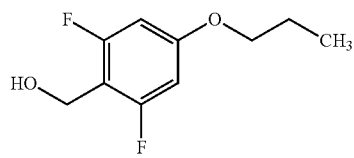

EXAMPLE COMPOUNDS

Example 2-1-1

Preparation of 2-[1-(6-chloro-2-fluoro-3-methylbenzyl)-1H-indazol-3-yl]-5-methoxy-N-(pyridin-4-yl)pyrimidin-4-amine

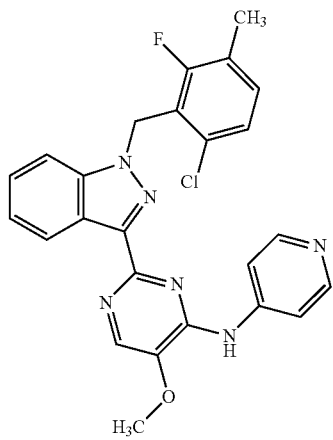 [SMILES: COc1cnc(-c2nn(Cc3c(Cl)ccc(C)c3F)c3ccccc23)nc1Nc1ccncc1]

80 mg of 2-(1H-indazol-3-yl)-5-methoxy-N-(pyridin-4-yl)pyrimidin-4-amine (1-6-1, 0.251 mmol, 1. eq.) were suspended in dry tetrahydrofuran under a nitrogen atmosphere. 30.2 mg of sodium hydride (60% purity) were added and stirred at room temperature for 10 minutes. Then 59.7 mg of 2-(bromomethyl)-1-chloro-3-fluoro-4-methylbenzene were added. The reaction mixture was stirred for 18 hours at room temperature. Then the mixture was partitioned between half saturated aq. ammonium chloride solution and dichloromethane/isopropanol 4:1. The phases were separated and the aqueous layer was extracted twice with dichloromethane/isopropanol 4:1. The combined organic layers were washed with brine, dried over a silicone filter and concentrated in vacuo. Preparative HPLC purification provided 29 mg (0.06 mmol, 24.1%) of the analytically pure target compound.

1H-NMR (300 MHz, DMSO-d6): δ [ppm]=2.19 (d, 3H), 4.00 (s, 3H), 5.80 (d, 2H), 7.17-7.37 (m, 3H), 7.42-7.53 (m, 1H), 7.89 (d, 1H), 8.13-8.22 (m, 2H), 8.29-8.40 (m, 3H), 8.46 (d, 1H), 9.39 (s, 1H).

LC-MS:
retention time: 1.01 min
MS ES+: 475.4 [M+H]$^+$

Method B

The following compounds were prepared according to the same procedure from the indicated starting materials (SM=starting material):

| | | | |
|---|---|---|---|
| 2-2-1<br>SM =<br>1-6-1 | 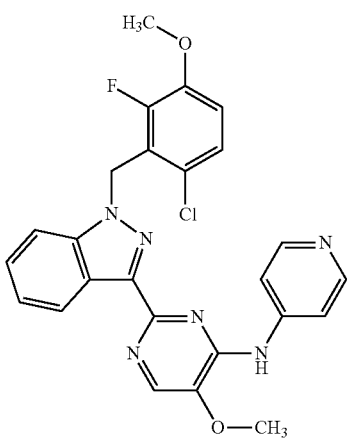 | 2-[1-(6-chloro-2-fluoro-3-methoxybenzyl)-1H-indazol-3-yl]-5-methoxy-N-(pyridin-4-yl)pyrimidin-4-amine | $^1$H-NMR (400 MHz, DMSO-d$_6$): δ [ppm] = 3.82 (s, 3H), 4.00 (s, 3H), 5.77 (d, 2H), 7.17-7.36 (m, 3H), 7.47 (ddd, 1H), 7.89 (d, 1H), 8.13-8.20 (m, 2H), 8.29-8.40 (m, 3H), 8.46 (d, 1H), 9.39 (s, 1H).<br>LC-MS:<br>retention time: 0.99 min<br>MS ES$^+$: 491.3 [M + H]$^+$<br>Method B |
| 2-3-1<br>SM =<br>1-6-1 | 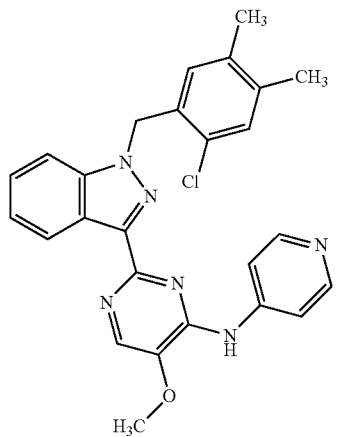 [SMILES: COc1cnc(-c2nn(Cc3cc(C)c(C)cc3Cl)c3ccccc23)nc1Nc1ccncc1] | 2-[1-(2-chloro-4,5-dimethylbenzyl)-1H-indazol-3-yl]-5-methoxy-N-(pyridin-4-yl)pyrimidin-4-amine | $^1$H-NMR (300 MHz, DMSO-d$_6$): δ [ppm] = 2.09 (s, 3H), 2.15 (s, 3H), 3.96-4.05 (m, 3H), 5.71 (s, 2H), 7.09 (s, 1H), 7.19-7.31 (m, 2H), 7.43 (s, 1H), 7.78 (d, 1H), 8.11-8.17 (m, 2H), 8.30-8.40 (m, 3H), 8.46 (d, 1H), 9.44 (s, 1H).<br>LC-MS:<br>retention time: 1.04 min<br>MS ES$^+$: 471.4 [M + H]$^+$<br>Method B |
| 2-4-1<br>SM =<br>1-6-1 | 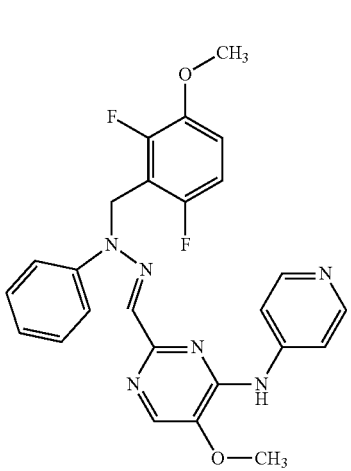 [SMILES: COc1cnc(/C=N/N(Cc2c(F)ccc(OC)c2F)c2ccccc2)nc1Nc1ccncc1] | 2-[1-(2,6-difluoro-3-methoxybenzyl)-1H-indazol-3-yl]-5-methoxy-N-(pyridin-4-yl)pyrimidin-4-amine | $^1$H-NMR (300 MHz, DMSO-d$_6$): δ [ppm] = 3.78 (s, 3H), 4.00 (s, 3H), 5.74 (s, 2H), 7.02-7.30 (m, 3H), 7.42-7.52 (m, 1H), 7.84 (d, 1H), 8.10-8.19 (m, 2H), 8.28-8.48 (m, 4H), 9.38 (s, 1H).<br>LC-MS:<br>retention time: 0.95 min<br>MS ES$^+$: 475.0 [M + H]$^+$<br>Method B |

| | | | |
|---|---|---|---|
| 2-5-1<br>SM =<br>1-6-1 | 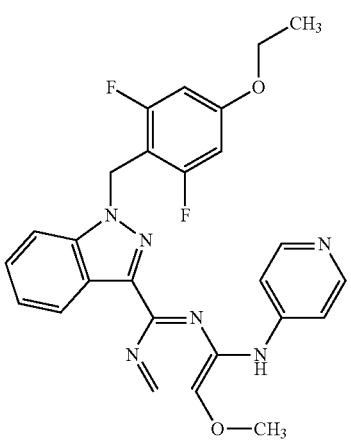 [SMILES: C=N/C(=N\C(=C\OC)Nc1ccncc1)c1nn(Cc2c(F)cc(OCC)cc2F)c2ccccc12] | 2-[1-(4-ethoxy-2,6-difluorobenzyl)-1H-indazol-3-yl]-5-methoxy-N-(pyridin-4-yl)pyrimidin-4-amine | $^1$H-NMR (300 MHz, DMSO-d$_6$): δ [ppm] = 1.25 (t, 3H), 3.93-4.09 (m, 5H), 5.64 (s, 2H), 6.68-6.82 (m, 2H), 7.23 (t, 1H), 7.40-7.51 (m, 1H), 7.81 (d, 1H), 8.11-8.20 (m, 2H), 8.29-8.48 (m, 4H), 9.37 (s, 1H).<br>LC-MS:<br>retention time: 1.05 min<br>MS ES$^+$: 489.0 [M + H ]$^+$<br>Method B |
| 2-6-1<br>SM =<br>1-6-1 | 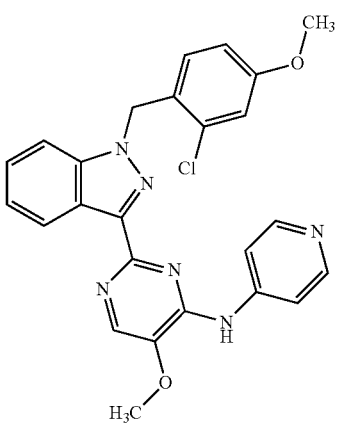 [SMILES: COc1ccc(Cn2nc(-c3ncc(OC)c(Nc4ccncc4)n3)c3ccccc32)c(Cl)c1] | 2-[1-(2-chloro-4-methoxybenzyl)-1H-indazol-3-yl]-5-methoxy-N-(pyridin-4-yl)pyrimidin-4-amine | $^1$H-NMR (300 MHz, DMSO-d$_6$): δ [ppm] = 3.72 (s, 3H), 4.01 (s, 3H), 5.72 (s, 2H), 6.90 (dd, 1H), 7.07 (d, 1H), 7.19-7.28 (m, 2H), 7.43 (t, 1H), 7.79 (d, 1H), 8.08-8.16 (m, 2H), 8.30-8.41 (m, 3H), 8.45 (d, 1H), 9.40 (s, 1H).<br>LC-MS:<br>retention time: 0.99 min<br>MS ES$^+$: 473.4 [M + H]$^+$<br>Method B |
| 2-7-1<br>SM =<br>1-6-1 | 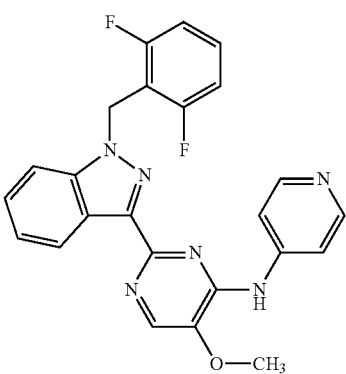 | 2-[1-(2,6-difluorobenzyl)-1H-indazol-3-yl]-5-methoxy-N-(pyridin-4-yl)pyrimidin-4-amine | $^1$H-NMR (300 MHz, DMSO-d$_6$): δ [ppm] = 4.00 (s, 3H), 5.75 (s, 2H), 7.15 (t, 1H), 7.24 (t, 1H), 7.38-7.52 (m, 2H), 7.81-7.89 (m, 1H), 7.85 (d, 1H), 8.09-8.18 (m, 2H), 8.29-8.39 (m, 3H), 8.41-8.47 (m, 1H), 9.38 (s, 1H).<br>LC-MS:<br>retention time: 0.97 min<br>MS ES$^+$: 445.0 [M + H]$^+$<br>Method B |

| | | | |
|---|---|---|---|
| 2-8-1 SM = 1-6-1 | 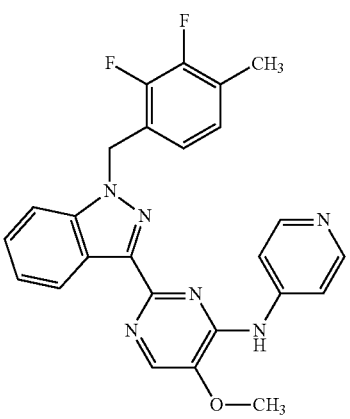 [SMILES: COc1cnc(-c2nn(Cc3ccc(C)c(F)c3F)c3ccccc23)nc1Nc1ccncc1] | 2-[1-(2,3-difluoro-4-methylbenzyl)-1H-indazol-3-yl]-5-methoxy-N-(pyidin-4-yl)pyrimidin-4-amine | $^1$H-NMR (300 MHz, DMSO-d$_6$): δ [ppm] = 2.21 (d, 3H), 4.01 (s, 3H), 5.77 (s, 2H), 7.00-7.09 (m, 2H), 7.24 (t, 1H), 7.44 (t, 1H), 7.81 (d, 1H), 8.08-8.17 (m, 2H), 8.30-8.50 (m, 4H), 9.39 (s, 1H). LC-MS: retention time: 1.01 min MS ES$^+$: 459.0 [M + H]$^+$ Method B |
| 2-9-1 SM = 1-6-1 | 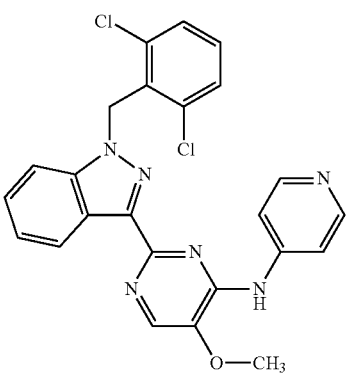 [SMILES: COc1cnc(-c2nn(Cc3c(Cl)cccc3Cl)c3ccccc23)nc1Nc1ccncc1] | 2-[1-(2,6-dichlorobenzyl)-1H-indazol-3-yl]-5-methoxy-N-(pyridin-4-yl)pyrimidin-4-amine | $^1$H-NMR (300 MHz, DMSO-d$_6$): δ [ppm] = 3.99 (s, 3H), 5.87 (s, 2H), 7.25 (t, 1H), 7.39-7.53 (m, 2H), 7.55-7.62 (m, 2H), 7.90 (d, 1H), 8.13 (d, 2H), 8.28-8.40 (m, 3H), 8.48 (d, 1H), 9.32 (s, 1H). LC-MS: retention time: 1.13 min MS ES$^+$: 477.22 [M + H]$^+$ |
| 2-10-1 SM = 1-6-1 | 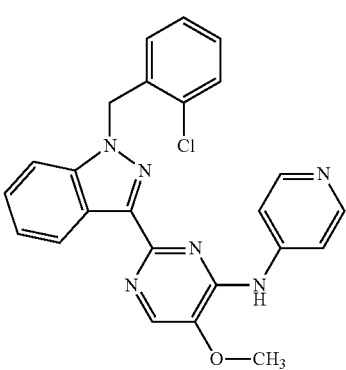 [SMILES: COc1cnc(-c2nn(Cc3ccccc3Cl)c3ccccc23)nc1Nc1ccncc1] | 2-[1-(2-chlorobenzyl)-1H-indazol-3-yl]-5-methoxy-N-(pyridin-4-yl)pyrimidin-4-amine | $^1$H-NMR (300 MHz, DMSO-d$_6$): δ [ppm] = 4.01 (s, 3H), 5.81 (s, 2H), 7.15 (dd, 1H), 7.20-7.38 (m, 3H), 7.39-7.54 (m, 2H), 7.78 (d, 1H), 8.05-8.15 (m, 2H), 8.29-8.40 (m, 3H), 8.47 (d, 1H), 9.38 (s, 1H). LC-MS: retention time: 1.00 min MS ES$^+$: 443.0 [M + H]$^+$ Method B |
| 2-11-1 SM = 1-6-1 | 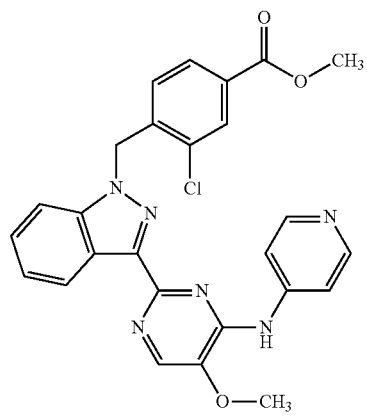 [SMILES: COC(=O)c1ccc(Cn2nc(-c3ncc(OC)c(Nc4ccncc4)n3)c3ccccc32)c(Cl)c1] | methyl 3-chloro-4-({3-[5-methoxy-4-(pyridin-4-ylamino)pyrimidin-2-yl]-1H-indazol-1-yl}methyl)benzoate | $^1$H-NMR (300 MHz, DMSO-d$_6$): δ [ppm] = 3.81 (s, 3H), 4.01 (s, 3H), 5.89 (s, 2H), 7.18-7.31 (m, 2H), 7.45 (t, 1H), 7.79 (d, 1H), 7.85 (dd, 1H), 7.98 (d, 1H), 8.06-8.13 (m, 2H), 8.30-8.39 (m, 3H), 8.48 (d, 1H), 9.40 (s, 1H). LC-MS: retention time: 0.96 min MS ES$^+$: 501.1 [M + H]$^+$ Method B |

| | | | |
|---|---|---|---|
| 2-12-1<br>SM =<br>1-6-1 | 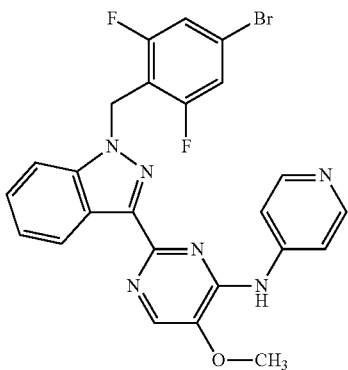 [SMILES: COc1cnc(-c2nn(Cc3c(F)cc(Br)cc3F)c3ccccc23)nc1Nc1ccncc1] | 2-[1-(4-bromo-2,6-difluorobenzyl)-1H-indazol-3-yl]-5-methoxy-N-(pyridin-4-yl)pyrimidin-4-amine | $^1$H-NMR (400 MHz, DMSO-$d_6$): δ [ppm] = 4.00 (s, 3H), 5.72 (s, 2H), 7.25 (t, 1H), 7.44-7.52 (m, 1H), 7.54-7.61 (m, 2H), 7.85 (d, 1H), 8.12-8.18 (m, 2H), 8.32 (s, 1H), 8.35-8.40 (m, 2H), 8.44 (d, 1H), 9.40 (s, 1H).<br>LC-MS:<br>retention time: 0.99 min<br>MS ES$^+$: 525.3 [M + H]+<br>Method B |
| 2-13-1<br>SM =<br>1-6-1 | 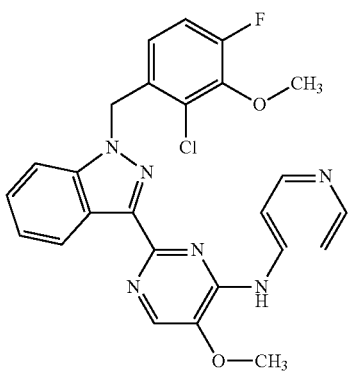 [SMILES: C=C/N=C\C=C\Nc1nc(-c2nn(Cc3ccc(F)c(OC)c3Cl)c3ccccc23)ncc1OC] | 2-[1-(2-chloro-4-fluoro-3-methoxybenzyl)-1H-indazol-3-yl]-5-methoxy-N-(pyridin-4-yl)pyrimidin-4-amine | $^1$H-NMR (400 MHz, DMSO-$d_6$): δ [ppm] = 3.85 (d, 3H), 4.01 (s, 3H), 5.79 (s, 2H), 6.91 (dd, 1H), 7.21-7.32 (m, 2H), 7.44 (td, 1H), 7.80 (d, 1H), 8.08-8.13 (m, 2H), 8.33 (s, 1H), 8.35-8.39 (m, 2H), 8.47 (d, 1H), 9.42 (s, 1H).<br>LC-MS:<br>retention time: 0.98 min<br>MS ES$^+$: 491.3 [M + H]$^+$<br>Method B |
| 2-14-1<br>SM =<br>1-6-1 | 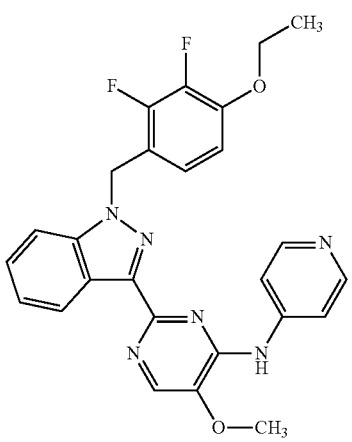 [SMILES: CCOc1ccc(Cn2nc(-c3ncc(OC)c(Nc4ccncc4)n3)c3ccccc32)c(F)c1F] | 2-[1-(4-ethoxy-2,3-difluorobenzyl)-1H-indazol-3-yl]-5-methoxy-N-(pyridin-4-yl)pyrimidin-4-amine | $^1$H-NMR (300 MHz, DMSO-$d_6$): δ [ppm] = 1.28 (t, 3H), 3.94-4.13 (m, 5H), 5.73 (s, 2H), 6.92-7.03 (m, 1H), 7.08-7.18 (m, 1H), 7.23 (t, 1H), 7.44 (t, 1H), 7.83 (d, 1H), 8.10-8.16 (m, 2H), 8.33 (s, 1H), 8.36-8.40 (m, 2H), 8.43 (d, 1H), 9.41 (s, 1H).<br>LC-MS:<br>retention time: 1.03 min<br>MS ES$^+$: 489.0 [M + H]$^+$<br>Method B |

| | | | |
|---|---|---|---|
| 2-15-1 SM = 1-6-1 | 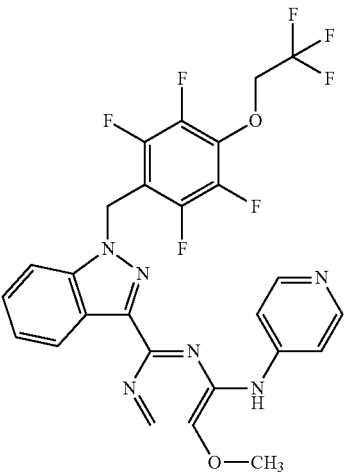 [SMILES: C=N/C(=N\C(=C\OC)Nc1ccncc1)c1nn(Cc2c(F)c(F)c(OCC(F)(F)F)c(F)c2F)c2ccccc12] | 5-methoxy-N-(pyridin-4-yl)-2-{1-[2,3,5,6-tetrafluoro-4-(2,2,2-trifluoroeth-oxy)benzyl]-1H-indazol-3-yl}pyrimidin-4-amine | $^1$H-NMR (500 MHz, DMSO-d$_6$): δ [ppm] = 4.04-4.07 (s, 3H), 4.99 (q, 2H), 5.90 (s, 2H), 7.31 (t, 1H), 7.55 (t, 1H), 7.93 (d, 1H), 8.23 (d, 2H), 8.38 (s, 1H), 8.42 (d, 2H), 8.49 (d, 1H), 9.46 (s, 1H). LC-MS: retention time: 1.21 min MS ES$^+$: 579.1 [M + H]$^+$ Method B |
| 2-16-1 SM = 1-6-1 | 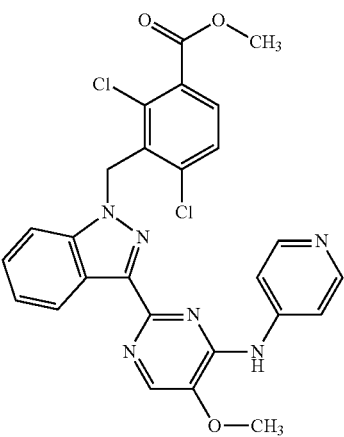 [SMILES: COC(=O)c1ccc(Cl)c(Cn2nc(-c3ncc(OC)c(Nc4ccncc4)n3)c3ccccc32)c1Cl] | methyl 2,4-dichloro-3-({3-[5-methoxy-4-(pyridin-4-yla-minO)pyrimidin-2-yl]-1H-indazol-1-yl}methyl)benzo-ate | $^1$H-NMR (400 MHz, DMSO-d$_6$): δ [ppm] = 3.85 (s, 3H), 4.02 (s, 3H), 5.96 (s, 2H), 7.29 (t, 1H), 7.48-7.55 (m, 1H), 7.73-7.78 (m, 1H), 7.80-7.84 (m, 1H), 7.94 (d, 1H), 8.11-8.16 (m, 2H), 8.34 (s, 1H), 8.38 (d, 2H), 8.52 (d, 1H), 9.34 (s, 1H). LC-MS: retention time: 1.08 min MS ES$^+$: 535.22 [M + H]$^+$ |
| 2-17-1 SM = 1-6-1 | 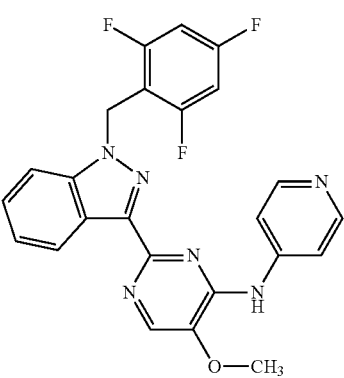 [SMILES: COc1cnc(-c2nn(Cc3c(F)cc(F)cc3F)c3ccccc23)nc1Nc1ccncc1] | 5-methoxy-N-(pyridin-4-yl)-2-[1-(2,4,6-trifluorobenzyl)-1H-indaozl-3-yl]pyrimidin-4-amine | $^1$H-NMR (300 MHz, DMSO-d$_6$): δ [ppm] = 4.00 (s, 3H), 5.68-5.76 (m, 2H), 7.20-7.34 (m, 3H), 7.43-7.51 (m, 1H), 7.84 (d, 1H), 8.12-8.18 (m, 2H), 8.32 (s, 1H), 8.37 (d, 2H), 8.44 (d, 1H), 9.35-9.40 (m, 1H). LC-MS: retention time: 1.03 min MS ES$^+$: 463.31 [M + H]$^+$ |

| | | | |
|---|---|---|---|
| 2-18-1 SM = 1-6-1 | 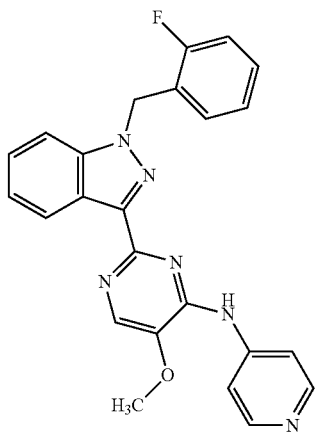 [SMILES: COc1cnc(-c2nn(Cc3ccccc3F)c3ccccc23)nc1Nc1ccncc1] | 2-[1-(2-fluorobenzyl)-1H-indazol-3-yl]-5-methoxy-N-(pyridin-4-yl)pyrimidin-4-amine | 1H-NMR (300 MHz, DMSO-d6): δ [ppm] = 4.01 (s, 3H), 5.77 (s, 2H), 7.10-7.49 (m, 6H), 7.75-7.84 (m, 1H), 8.07-8.17 (m, 2H), 8.33 (s, 1H), 8.35-8.40 (m, 2H), 8.40-8.48 (m, 1H), 9.35-9.45 (m, 1H). LC-MS: retention time: 1.01 min MS ES+: 427.19 [M + H]+ |
| 2-19-1 SM = 1-6-1 | 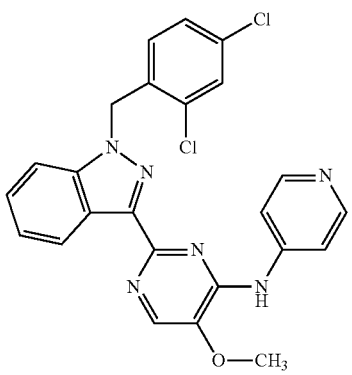 [SMILES: COc1cnc(-c2nn(Cc3ccc(Cl)cc3Cl)c3ccccc23)nc1Nc1ccncc1] | 2-[1-(2,4-dichlorobenzyl)-1H-indazol-3-yl]-5-methoxy-N-(pyridin-4-yl)pyrimidin-4-amine | $^1$H-NMR (300 MHz, DMSO-d$_6$): δ [ppm] = 4.01 (s, 3H), 5.80 (s, 2H), 7.15-7.29 (m, 2H), 7.38-7.49 (m, 2H), 7.68 (d, 1H), 7.79 (d, 1H), 8.05-8.13 (m, 2H), 8.31-8.40 (m, 3H), 8.47 (d, 1H), 9.40 (s, 1H). LC-MS: retention time: 1.07 min MS ES+: 477.35 [M + H]+ |
| 2-20-1 SM = 1-6-1 | 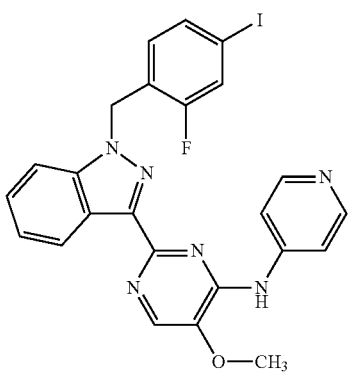 | 2-[1-(2-fluoro-4-iodobenzyl)-1H-indazol-3-yl]-5-methoxy-N-(pyridin-4-yl)pyrimidin-4-amine | $^1$H-NMR (400 MHz, DMSO-d$_6$): δ [ppm] = 4.01 (s, 3H), 5.73 (s, 2H), 7.07 (t, 1H), 7.24 (t, 1H), 7.44 (ddd, 1H), 7.55 (dd, 1H), 7.67 (dd, 1H), 7.79 (d, 1H), 8.08-8.13 (m, 2H), 8.33 (s, 1H), 8.36-8.40 (m, 2H), 8.44 (d, 1H), 9.42 (s, 1H). LC-MS: retention time: 1.00 min MS ES+: 553.3 [M + H]+ Method B |
| 2-21-1 SM = 1-6-1 | 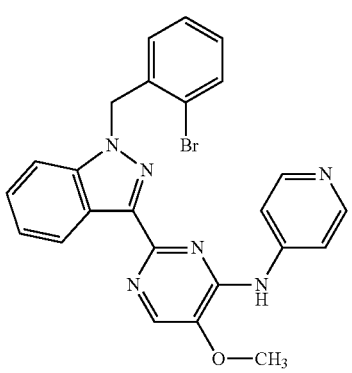 [SMILES: COc1cnc(-c2nn(Cc3ccccc3Br)c3ccccc23)nc1Nc1ccncc1] | 2-[1-(2-bromobenzyl)-1H-indazol-3-yl]-5-methoxy-N-(pyridin-4-yl)pyrimidin-4-amine | $^1$H-NMR (400 MHz, DMSO-d$_6$): δ [ppm] = 4.01 (s, 3H), 5.79 (s, 2H), 7.08 (dd, 1H), 7.22-7.28 (m, 2H), 7.30-7.36 (m, 1H), 7.44 (ddd, 1H), 7.67 (dd, 1H), 7.78 (d, 1H), 8.08-8.13 (m, 2H), 8.32-8.39 (m, 3H), 8.48 (d, 1H), 9.38 (s, 1H). LC-MS: retention time: 1.02 min MS ES+: 486.9 [M + H]+ Method B |

| | | | |
|---|---|---|---|
| 2-22-1<br>SM =<br>1-6-1 | 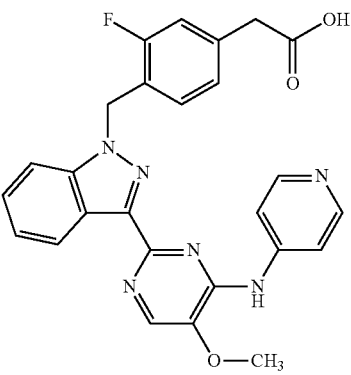 [SMILES: COc1cnc(-c2nn(Cc3ccc(CC(=O)O)cc3F)c3ccccc23)nc1Nc1ccncc1] | [3-fluoro-4-({3-[5-methoxy-4-(pyridin-4-ylamino)pyrimidin-2-yl]-1H-indazol-1-yl}methyl)phenyl]acetic acid | $^1$H-NMR (300 MHz, DMSO-$d_6$): δ [ppm] = 3.54 (s, 2H), 4.01 (s, 3H), 5.74 (s, 2H), 7.01-7.07 (m, 1H), 7.12 (d, 1H), 7.19-7.29 (m, 2H), 7.38-7.47 (m, 1H), 7.79 (d, 1H), 8.08-8.16 (m, 2H), 8.33 (s, 1H), 8.36-8.48 (m, 3H), 9.39 (s, 1H).<br>LC-MS:<br>retention time: 0.86 min<br>MS ES$^+$: 485.1 [M + H]$^+$<br>Method B |
| 2-23-1<br>SM =<br>1-6-1 | 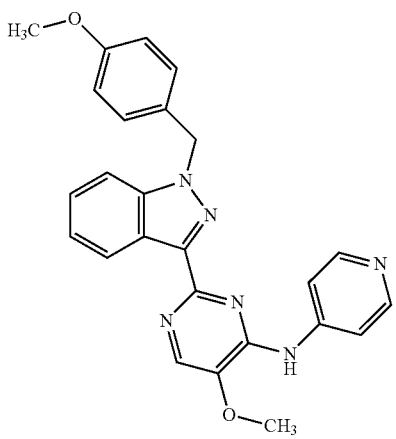 [SMILES: COc1ccc(Cn2nc(-c3ncc(OC)c(Nc4ccncc4)n3)c3ccccc32)cc1] | 5-methoxy-2-[1-(4-methoxybenzyl)-1H-indazol-3-yl]-N-(pyridin-4-yl)pyrimidin-4-amine | $^1$H-NMR (300 MHz, DMSO-$d_6$): δ [ppm] = 3.66 (s, 3H), 4.02 (s, 3H), 5.65 (s, 2H), 6.86 (d, 2H), 7.15-7.25 (m, 1H), 7.27-7.44 (m, 3H), 7.78 (d, 1H), 8.08-8.17 (m, 2H), 8.31-8.46 (m, 4H), 9.42 (s, 1H).<br>LC-MS:<br>retention time: 0.95 min<br>MS ES$^+$: 439.31 [M + H]$^+$<br>Method B |
| 2-24-1<br>SM =<br>1-6-1 | 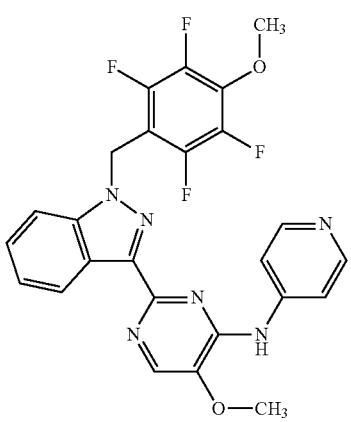 [SMILES: COc1cnc(-c2nn(Cc3c(F)c(F)c(OC)c(F)c3F)c3ccccc23)nc1Nc1ccncc1] | 5-methoxy-N-(pyridin-4-yl)-2-[1-(2,3,5,6-tetrafluoro-4-methoxybenzyl)-1H-indazol-3-yl]pyrimidin-4-amine | $^1$H-NMR (300 MHz, DMSO-$d_6$): δ [ppm] = 4.00 (s, 3H), 4.01 (s, 3H), 5.81 (s, 2H), 7.26 (t, 1H), 7.49 (t, 1H), 7.87 (d, 1H), 8.14-8.22 (m, 2H), 8.31-8.40 (m, 3H), 8.45 (d, 1H), 9.40-9.45 (m, 1H).<br>LC-MS:<br>retention time: 1.09 min<br>MS ES$^+$: 511.17 [M + H]$^+$ |

| | | | |
|---|---|---|---|
| 2-25-1 SM = 1-6-1 | 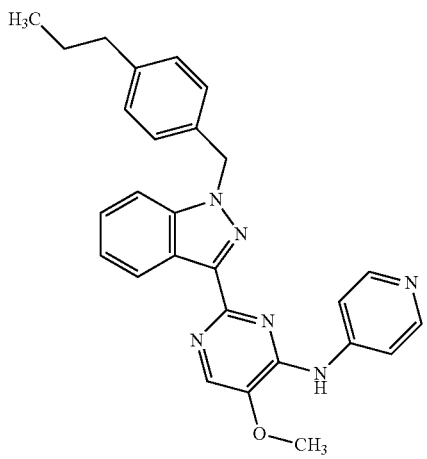 [SMILES: CCCc1ccc(Cn2nc(-c3ncc(OC)c(Nc4ccncc4)n3)c3ccccc32)cc1] | 5-methoxy-2-[1-(4-propylbenzyl)-1H-indazol-3-yl]-N-(pyridin-4-yl)pyrimidin-4-amine | $^1$H-NMR (300 MHz, DMSO-d$_6$): δ [ppm] = 0.80 (t, 3H), 1.20 (br. s., 2H), 1.40-1.57 (m, 2H), 4.02 (s, 3H), 5.68 (s, 2H), 7.12 (d, 2H), 7.17-7.30 (m, 2H), 7.40 (t, 1H), 7.78 (d, 1H), 8.12 (d, 2H), 8.21 (s, 1H), 8.32-8.46 (m, 4H), 9.42 (s, 1H). LC-MS: retention time: 1.15 min MS ES$^+$: 451.3 [M + H]$^+$ |
| 2-26-1 SM = 1-6-1 | 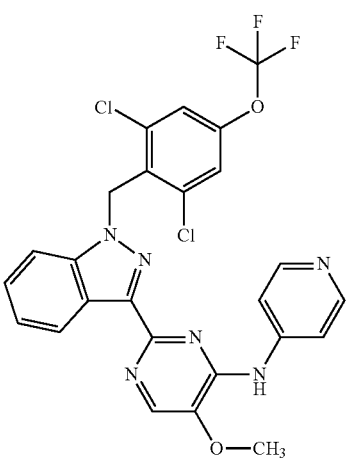 [SMILES: COc1cnc(-c2nn(Cc3c(Cl)cc(OC(F)(F)F)cc3Cl)c3ccccc23)nc1Nc1ccncc1] | 2-{1-[2,6-dichloro-4-(trifluoromethoxy)benzyl]-1H-indazol-3-yl}-5-methoxy-N-(pyridin-4-yl)pyrimidin-4-amine | $^1$H-NMR (400 MHz, DMSO-d$_6$): δ [ppm] = 4.02 (s, 3H), 5.90 (s, 2H), 7.29 (t, 1H), 7.52 (ddd, 1H), 7.83 (d, 2H), 7.94 (d, 1H), 8.12 -8.18 (m, 2H), 8.35 (s, 1H), 8.37-8.40 (m, 2H), 8.51 (d, 1H), 9.35 (s, 1H). LC-MS: retention time: 1.15 min MS ES$^+$: 561.0 [M + H]$^+$ Method B |
| 2-27-1 SM = 1-6-1 | 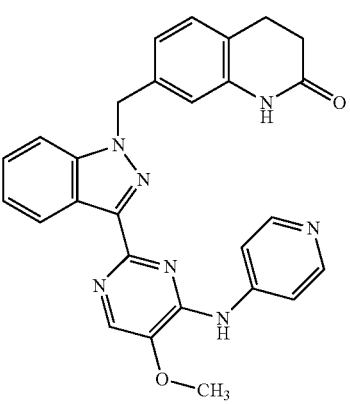 [SMILES: COc1cnc(-c2nn(Cc3ccc4c(c3)NC(=O)CC4)c3ccccc23)nc1Nc1ccncc1] | 7-({3-[5-methoxy-4-(pyridin-4-ylamino)pyrimidin-2-yl]-1H-indazol-1-yl}methyl)-3,4-dihydroquinolin-2(1H)-one | $^1$H-NMR (400 MHz, DMSO-d$_6$): δ [ppm] = 2.35 (t, 2H), 2.77 (t, 2H), 4.02 (s, 3H), 5.65 (s, 2H), 6.77 (s, 1H), 6.88 (d, 1H), 7.09 (d, 1H), 7.22 (t, 1H), 7.40 (t, 1H), 7.71 (d, 1H), 8.11 (d, 2H), 8.28-8.51 (m, 4H), 9.42 (s, 1H), 10.01 (s, 1H). LC-MS: retention time: 1.04 min MS ES$^+$: 478.1 [M + H]$^+$ Method B |

| | | | |
|---|---|---|---|
| 2-28-1<br>SM =<br>1-6-1 | 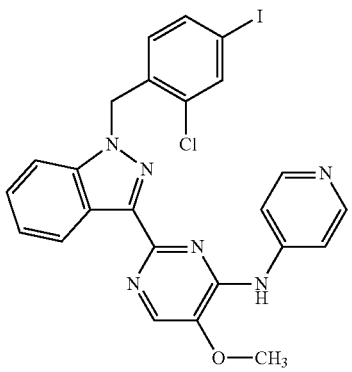 [SMILES: COc1cnc(-c2nn(Cc3ccc(I)cc3Cl)c3ccccc23)nc1Nc1ccncc1] | 2-[1-(2-chloro-4-iodobenzyl)-1H-indazol-3-yl]-5-methoxy-N-(pyridin-4-yl)pyrimidin-4-amine | $^1$H-NMR (400 MHz, DMSO-d$_6$): δ [ppm] = 4.01 (s, 3H), 5.76 (s, 2H), 6.93 (d, 1H), 7.25 (t, 1H), 7.44 (ddd, 1H), 7.68 (dd, 1H), 7.78 (d, 1H), 7.89 (d, 1H), 8.07-8.12 (m, 2H), 8.31-8.40 (m, 3H), 8.47 (d, 1H), 9.39 (s, 1H).<br>LC-MS:<br>retention time: 1.08 min<br>MS ES$^+$: 568.9 [M + H]$^+$<br>Method B. |
| 2-29-1<br>SM =<br>1-6-1 | 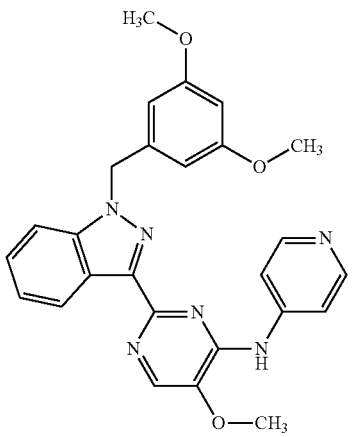 [SMILES: COc1cc(Cn2nc(-c3ncc(OC)c(Nc4ccncc4)n3)c3ccccc32)cc(OC)c1] | 2-[1-(3,5-dimethoxybenzyl)-1H-indazol-3-yl]-5-methoxy-N-(pyridin-4-yl)pyrimidin-4-amine | $^1$H-NMR (300 MHz, DMSO-d$_6$): δ [ppm] = 3.64 (s, 6H), 4.02 (s, 3H), 5.65 (s, 2H), 6.38 (s, 1H), 6.48 (d, 2H), 7.22 (t, 1H), 7.36-7.45 (m, 1H), 7.77 (d, 1H), 8.09-8.17 (m, 2H), 8.31-8.47 (m, 4H), 9.42 (s, 1H).<br>LC-MS:<br>retention time: 0.89 min<br>MS ES$^+$: 469.4 [M + H]$^+$<br>Method B |
| 2-30-1<br>SM =<br>1-6-1 | 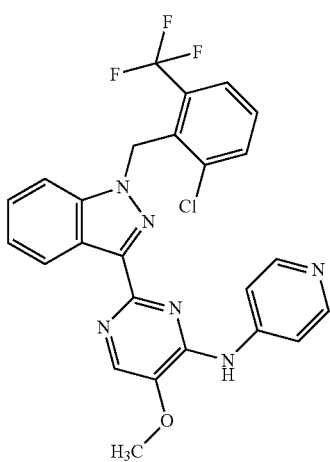 [SMILES: COc1cnc(-c2nn(Cc3c(Cl)cccc3C(F)(F)F)c3ccccc23)nc1Nc1ccncc1] | 2-{1-[2-chloro-6-(trifluoromethyl)benzyl]-1H-indazol-3-yl}-5-methoxy-N-(pyridin-4-yl)pyrimidin-4-amine | $^1$H-NMR (300 MHz, DMSO-d$_6$): δ [ppm] = 3.98 (s, 3H), 5.83 (s, 2H), 7.26 (t, 1H), 7.44-7.53 (m, 1H), 7.63-7.71 (m, 1H), 7.83-7.97 (m, 3H), 8.02-8.10 (m, 2H), 8.22-8.33 (m, 3H), 8.48 (d, 1H), 9.32 (s, 1H).<br>LC-MS:<br>retention time: 1.12 min<br>MS ES$^+$: 511.36 [M + H]$^+$ |

| | | | |
|---|---|---|---|
| 2-31-1<br>SM =<br>1-6-1 | 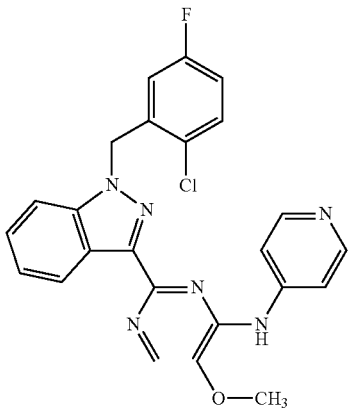 [SMILES: C=N/C(=N\C(=C\OC)Nc1ccncc1)c1nn(Cc2cc(F)ccc2Cl)c2ccccc12] | 2-[1-(2-chloro-5-fluorobenzyl)-1H-indazol-3-yl]-5-methoxy-N-(pyridin-4-yl)pyrimidin-4-amine | ¹H-NMR (400 MHz, DMSO-d₆): δ [ppm] = 4.01 (s, 3H), 5.80 (s, 2H), 7.11 (dd, 1H), 7.20-7.29 (m, 2H), 7.42-7.50 (m, 1H), 7.56 (dd, 1H), 7.83 (d, 1H), 8.07-8.15 (m, 2H), 8.31-8.40 (m, 3H), 8.47 (d, 1H), 9.42 (s, 1H).<br>LC-MS:<br>retention time: 1.02 min<br>MS ES⁺: 461.0 [M + H]⁺<br>Method B |
| 2-32-1<br>SM =<br>1-6-1 | 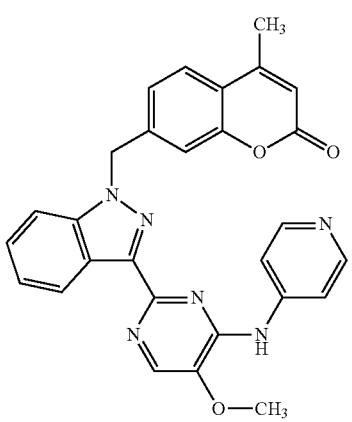 [SMILES: COc1cnc(-c2nn(Cc3ccc4c(C)cc(=O)oc4c3)c3ccccc23)nc1Nc1ccncc1] | 7-({3-[5-methoxy-4-(pyridin-4-ylamino)pyrimidin-2-yl]-1H-indazol-1-yl}methyl)-4-methyl-2H-chromen-2-one | ¹H-NMR (300 MHz, DMSO-d₆): δ [ppm] = 2.34 (d, 3H), 4.02 (s, 3H), 5.86 (s, 2H), 6.32 (d, 1H), 7.19-7.31 (m, 2H), 7.34 (s, 1H), 7.42 (t, 1H), 7.71 (d, 1H), 7.81 (d, 1H), 8.07-8.15 (m, 2H), 8.31-8.48 (m, 4H), 9.41 (s, 1H).<br>LC-MS:<br>retention time: 0.89 min<br>MS ES⁺: 491.0 [M + H]⁺<br>Method B |
| 2-33-1<br>SM =<br>1-6-1 | 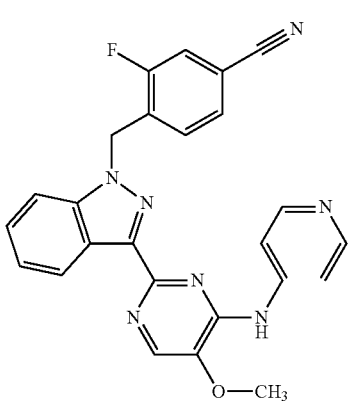 [SMILES: C=C/N=C\C=C\Nc1nc(-c2nn(Cc3ccc(C#N)cc3F)c3ccccc23)ncc1OC] | 3-fluoro-4-({3-[5-methoxy-4-(pyridin-4-ylamino)pyrimidin-2-yl]-1H-indazol-1-yl}methyl)benzonitrile | ¹H-NMR (300 MHz, DMSO-d₆): δ [ppm] = 4.01 (s, 3H), 5.87 (s, 2H), 7.21-7.30 (m, 1H), 7.38 (t, 1H), 7.42-7.50 (m, 1H), 7.67 (dd, 1H), 7.81 (d, 1H), 7.90 (dd, 1H), 8.04-8.12 (m, 2H), 8.33 (s, 1H), 8.37 (d, 2H), 8.45 (d, 1H), 9.37-9.43 (m, 1H).<br>LC-MS:<br>retention time: 0.92 min<br>MS ES⁺: 452.0 [M + H]⁺<br>Method B |

| | | |
|---|---|---|
| 2-34-1<br>SM =<br>1-6-1<br>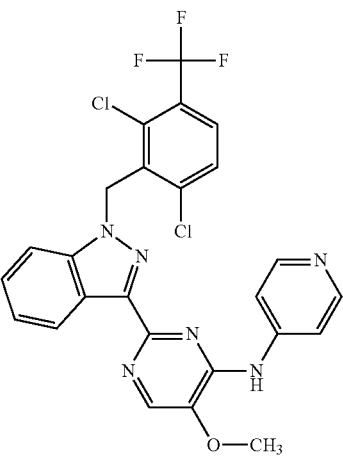 [SMILES: COc1cnc(-c2nn(Cc3c(Cl)ccc(C(F)(F)F)c3Cl)c3ccccc23)nc1Nc1ccncc1] | 2-{1-[2,6-dichloro-4-(trifluoromethyl)benzyl]-1H-indazol-3-yl}-5-methoxy-N-(pyridin-4-yl)pyrimidin-4-amine | $^1$H-NMR (400 MHz, DMSO-$d_6$): δ [ppm] = 3.99 (s, 3H), 5.97 (s, 2H), 7.27 (t, 1H), 7.48-7.54 (m, 1H), 7.83-7.89 (m, 1H), 7.93 (d, 2H), 8.08-8.13 (m, 2H), 8.31-8.36 (m, 3H), 8.49 (d, 1H), 9.35 (s, 1H).<br>LC-MS:<br>retention time: 1.17 min<br>MS ES$^+$: 545.0 [M + H]$^+$<br>Method B |
| 2-35-1<br>SM =<br>1-6-1<br>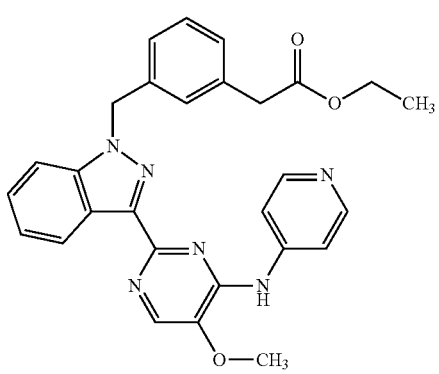 [SMILES: CCOC(=O)Cc1cccc(Cn2nc(-c3ncc(OC)c(Nc4ccncc4)n3)c3ccccc32)c1] | ethyl [3-({3-[5-methoxy-4-(pyridin-4-ylamino)pyrimidin-2-yl]-1H-indazol-1-yl}methyl)phenyl]acetate | $^1$H-NMR (300 MHz, DMSO-$d_6$): δ [ppm] = 0.28 (t, 3H), 2.72-2.77 (m, 2H), 3.20 (q, 2H), 4.05 (s, 3H), 4.92 (s, 2H), 6.30-6.49 (m, 5H), 6.54-6.63 (m, 1H), 6.69-6.77 (m, 1H), 7.21-7.27 (m, 2H), 7.45 (s, 1H), 7.53-7.61 (m, 2H), 7.65 (d, 1H).<br>LC-MS:<br>retention time: 0.97 min<br>MS ES$^+$: 495.39 [M + H]$^+$ |
| 2-36-1<br>SM =<br>1-6-1<br>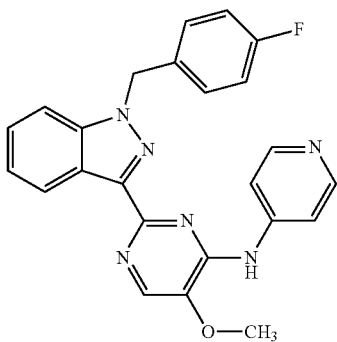 [SMILES: COc1cnc(-c2nn(Cc3ccc(F)cc3)c3ccccc23)nc1Nc1ccncc1] | 2-[1-(4-fluorobenzyl)-1H-indazol-3-yl]-5-methoxy-N-(pyridin-4-yl)pyrimidin-4-amine | $^1$H-NMR (400 MHz, DMSO-$d_6$): δ [ppm] = 4.02 (s, 3H), 5.73 (s, 2H), 7.10-7.18 (m, 2H), 7.19-7.27 (m, 1H), 7.35-7.46 (m, 3H), 7.80 (d, 1H), 8.08-8.14 (m, 2H), 8.34 (s, 1H), 8.37-8.44 (m, 3H), 9.43 (s, 1H).<br>LC-MS:<br>retention time: 0.92 min<br>MS ES$^+$: 427.0 [M + H]$^+$<br>Method B |

| | | | |
|---|---|---|---|
| 2-37-1<br>SM =<br>1-6-1 | 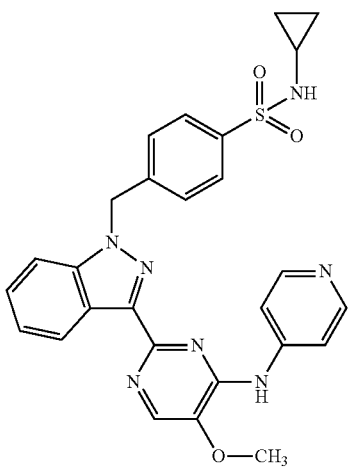 [SMILES: COc1cnc(-c2nn(Cc3ccc(S(=O)(=O)NC4CC4)cc3)c3ccccc23)nc1Nc1ccncc1] | N-cyclopropyl-4-({3-[5-methoxy-4-(pyridin-4-ylamino)pyrimidin-2-yl]-1H-indazol-1-yl}methyl)benzenesulfonamide | ¹H-NMR (300 MHz, DMSO-d₆): δ [ppm] = 0.31 (d, 2H), 0.38 (d, 2H), 1.91-2.06 (m, 1H), 4.02 (s, 3H), 5.86 (s, 2H), 7.24 (t, 1H), 7.37-7.46 (m, 1H), 7.51 (d, 2H), 7.68-7.81 (m, 3H), 7.84 (br. s., 1H), 8.10 (d, 2H), 8.32-8.41 (m, 3H), 8.45 (d, 1H), 9.37-9.44 (m, 1H).<br>LC-MS:<br>retention time: 0.90 min<br>MS ES⁺: 528.24 [M + H]⁺ |
| 2-38-1<br>SM =<br>1-6-1 | 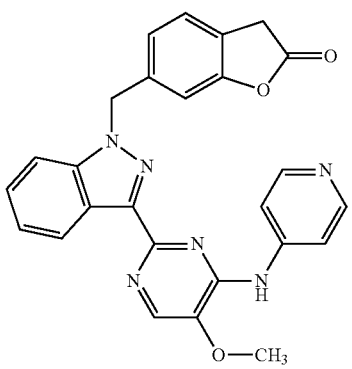 [SMILES: COc1cnc(-c2nn(Cc3ccc4c(c3)OC(=O)C4)c3ccccc23)nc1Nc1ccncc1] | 6-({3-[5-methoxy-4-(pyridin-4-ylamino)pyrimidin-2-yl]-1H-indazol-1-yl}methyl)-1-benzofuran-2(3H)-one | ¹H-NMR (400 MHz, DMSO-d₆): δ [ppm] = 4.05 (s, 3H), 5.34 (s, 2H), 5.95 (s, 2H), 7.26 (t, 1H), 7.45 (t, 1H), 7.52-7.58 (m, 2H), 7.83 (t, 2H), 8.10-8.15 (m, 2H), 8.37 (s, 1H), 8.39-8.43 (m, 2H), 8.48 (d, 1H), 9.43 (s, 1H).<br>LC-MS:<br>retention time: 0.81 min<br>MS ES⁺: 465.0 [M + H]⁺<br>Method B |
| 2-39-1<br>SM =<br>1-6-1 | 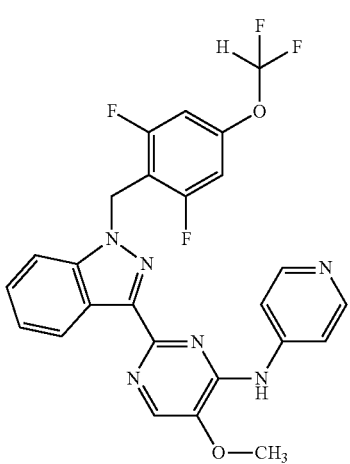 [SMILES: COc1cnc(-c2nn(Cc3c(F)cc(OC(F)F)cc3F)c3ccccc23)nc1Nc1ccncc1] | 2-{1-[4-(difluoromethoxy)-2,6-difluorobenzyl]-1H-indazol-3-yl}-5-methoxy-N-(pyridin-4-yl)pyrimidin-4-amine | ¹H-NMR (300 MHz, DMSO-d6): δ [ppm] = 3.93-4.05 (s, 3H), 5.73 (s, 2H), 7.13 (d, 2H), 7.20-7.28 (m, 1H), 7.30 (t, 1H), 7.47 (t, 1H), 7.84 (d, 1H), 8.15 (d, 2H), 8.32 (s, 1H), 8.38 (d, 2H), 8.44 (d, 1H), 9.38 (s, 1H).<br>LC-MS:<br>retention time: 1.01 min<br>MS ES⁺: 511.0 [M + H]⁺<br>Method B |

| | | | |
|---|---|---|---|
| 2-40-1 SM = 1-6-1 | 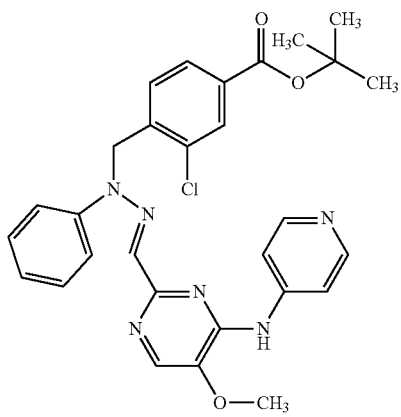 [SMILES: COc1cnc(/C=N/N(Cc2ccc(C(=O)OC(C)(C)C)cc2Cl)c2ccccc2)nc1Nc1ccncc1] | tert-butyl 3-chloro-4-({3-[5-methoxy-4-(pyridin-4-ylamino)pyrimidin-2-yl]-1H-indazol-1-yl}methyl)benzoate | ¹H-NMR (400 MHz, DMSO-d₆): δ [ppm] = 1.52 (s, 9H), 4.04 (s, 3H), 5.90 (s, 2H), 7.25-7.33 (m, 2H), 7.44-7.51 (m, 1H), 7.78-7.86 (m, 2H), 7.93 (d, 1H), 8.07-8.12 (m, 2H), 8.33-8.40 (m, 3H), 8.47-8.52 (m, 1H), 9.40 (s, 1H). LC-MS: retention time: 1.18 min MS ES⁺: 543.1 [M + H]⁺ Method B |
| 2-41-1 SM = 1-6-1 | 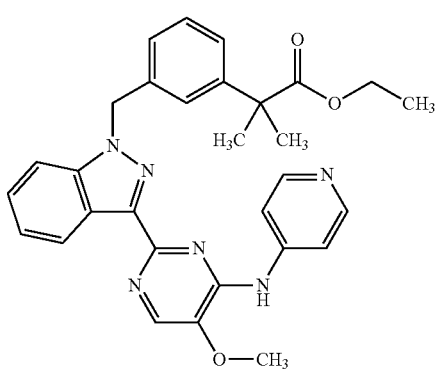 [SMILES: CCOC(=O)C(C)(C)c1cccc(Cn2nc(-c3ncc(OC)c(Nc4ccncc4)n3)c3ccccc32)c1] | ethyl 2-[3-({3-[5-methoxy-4-(pyridin-4-ylamino)pyrimidin-2-yl]-1H-indazol-1-yl}methyl)phenyl]-2-methylpropanoate | ¹H-NMR (300 MHz, DMSO-d₆): δ [ppm] = 0.89 (t, 3H), 1.39 (s, 6H), 3.87 (d, 2H), 4.02 (s, 3H), 5.74 (s, 2H), 7.14-7.31 (m, 5H), 7.40 (t, 1H), 7.77 (d, 1H), 8.08-8.16 (m, 2H), 8.31-8.47 (m, 4H), 9.41 (s, 1H). LC-MS: retention time: 1.04 min MS ES⁺: 523.88 [M + H]⁺ |
| 2-42-1 SM = 1-6-1 | 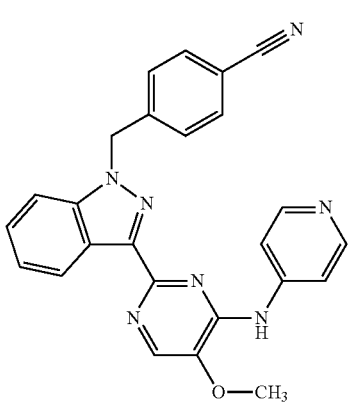 [SMILES: COc1cnc(-c2nn(Cc3ccc(C#N)cc3)c3ccccc23)nc1Nc1ccncc1] | 4-({3-[5-methoxy-4-(pyridin-4-ylamino)pyrimidin-2-yl]-1H-indazol-1-yl}methyl)benzonitrile | ¹H-NMR (300 MHz, DMSO-d₆): δ [ppm] = 4.02 (s, 3H), 5.86 (s, 2H), 7.20-7.28 (m, 1H), 7.41-7.48 (m, 3H), 7.73-7.83 (m, 3H), 8.06-8.12 (m, 2H), 8.31-8.49 (m, 4H), 9.42 (s, 1H). LC-MS: retention time: 0.82 min MS ES⁺: 434.4 [M + H]⁺ Method B |

| | | | |
|---|---|---|---|
| 2-43-1<br>SM =<br>1-6-1 | 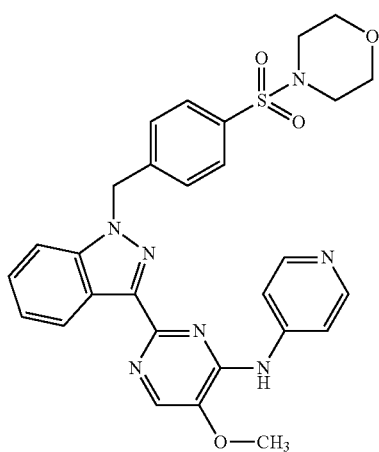 [SMILES: COc1cnc(-c2nn(Cc3ccc(S(=O)(=O)N4CCOCC4)cc3)c3ccccc23)nc1Nc1ccncc1] | 5-methoxy-2-{1-[4-(morpholin-4-ylsulfonyl)benzyl]-1H-indazol-3-yl}-N-(pyridin-4-yl)pyrimidin-4-amine | $^1$H-NMR (300 MHz, DMSO-d$_6$): δ [ppm] = 2.73-2.83 (m, 4H), 3.50-3.59 (m, 4H), 4.02 (s, 3H), 5.89 (s, 2H), 7.20-7.28 (m, 1H), 7.43 (t, 1H), 7.54 (d, 2H), 7.70 (d, 2H), 7.79 (d, 1H), 8.06-8.14 (m, 2H), 8.32-8.49 (m, 4H), 9.39-9.43 (m, 1H).<br>LC-MS:<br>retention time: 0.90 min<br>MS ES$^+$: 558.23 [M + H]$^+$ |
| 2-44-1<br>SM =<br>1-6-1 | 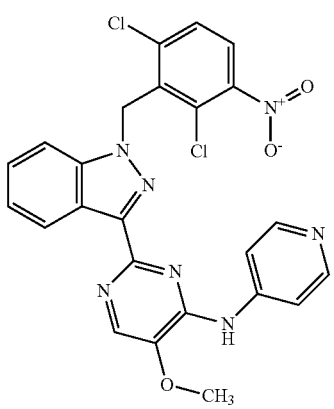 [SMILES: COc1cnc(-c2nn(Cc3c(Cl)ccc([N+](=O)[O-])c3Cl)c3ccccc23)nc1Nc1ccncc1] | 2-[1-(2,6-dichloro-3-nitrobenzyl)-1H-indazol-3-yl]-5-methoxy-N-(pyridin-4-yl)pyrimidin-4-amine | $^1$H-NMR (300 MHz, DMSO-d$_6$): δ [ppm] = 3.99 (s, 3H), 5.96 (s, 2H), 7.20-7.34 (m, 1H), 7.46-7.56 (m, 1H), 7.86-7.99 (m, 2H), 8.06-8.16 (m, 3H), 8.29-8.39 (m, 3H), 8.50 (d, 1H), 9.36 (s, 1H).<br>LC-MS:<br>retention time: 1.03 min<br>MS ES$^+$: 522.1 [M + H]$^+$ |
| 2-45-1<br>SM =<br>1-6-1 | 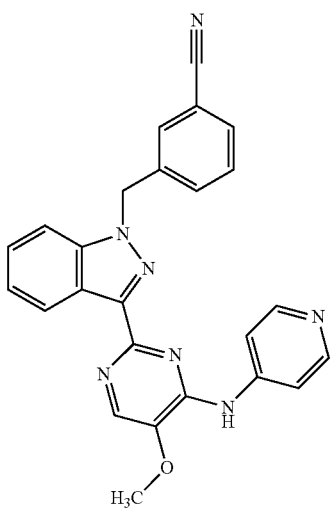 [SMILES: COc1cnc(-c2nn(Cc3cccc(C#N)c3)c3ccccc23)nc1Nc1ccncc1] | 3-({3-[5-methoxy-4-(pyridin-4-ylamino)pyrimidin-2-yl]-1H-indazol-1-yl}methyl)benzonitrile | $^1$H-NMR (400 MHz, METHANOL-d$_4$): δ [ppm] = 4.08 (s, 3H), 5.79 (s, 2H), 7.20-7.28 (m, 1H), 7.41-7.50 (m, 2H), 7.55-7.63 (m, 3H), 7.70 (s, 1H), 8.06 (d, 2H), 8.27 (s, 1H), 8.36-8.42 (m, 2H), 8.47 (s, 1H).<br>LC-MS:<br>retention time: 0.94 min<br>MS ES$^+$: 434.44 [M + H]$^+$ |

| | | |
|---|---|---|
| 2-46-1<br>SM =<br>1-6-1<br>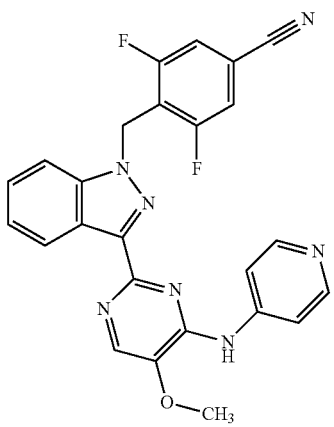 [SMILES: COc1cnc(-c2nn(Cc3c(F)cc(C#N)cc3F)c3ccccc23)nc1Nc1ccncc1] | 3,5-difluoro-4-({3-[5-methoxy-4-(pyridin-4-ylamino)pyrimidin-2-yl]-1H-indazol-1-yl}methyl)benzonitrile | $^1$H-NMR (300 MHz, DMSO-$d_6$): δ [ppm] = 4.00 (s, 3H), 5.82 (s, 2H), 7.25 (t, 1H), 7.49 (t, 1H), 7.85-7.94 (m, 3H), 8.08-8.20 (m, 2H), 8.32 (s, 1H), 8.37-8.46 (m, 3H), 9.41 (s, 1H).<br>LC-MS:<br>retention time: 0.99 min<br>MS ES$^+$: 470.35 [M + H]$^+$ |
| 2-47-1<br>SM =<br>1-6-1<br>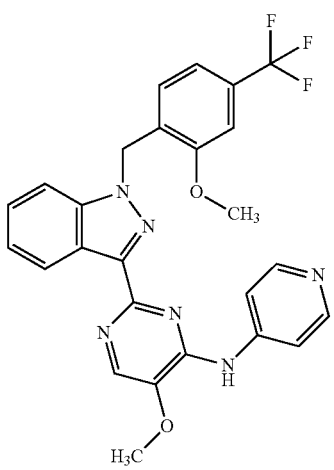 [SMILES: COc1cc(C(F)(F)F)ccc1Cn1nc(-c2ncc(OC)c(Nc3ccncc3)n2)c2ccccc21] | 5-methoxy-2-{1-[2-methoxy-4-(trifloromethyl)benzyl]-1H-indazol-3-yl}-N-(pyridin-4-yl)pyrimidin-4-amine | $^1$H-NMR (300 MHz, DMSO-$d_6$): δ [ppm] = 3.93 (s, 3H), 4.12 (s, 3H), 5.61 (s, 2H), 7.17-7.26 (m, 1H), 7.34-7.45 (m, 3H), 7.58 (d, 1H), 7.63-7.70 (m, 1H), 8.42-8.50 (m, 1H), 8.51-8.68 (m, 6H).<br>LC-MS:<br>retention time: 1.03 min<br>MS ES$^+$: 507.42 [M + H]$^+$ |
| 2-48-1<br>SM =<br>1-6-1<br>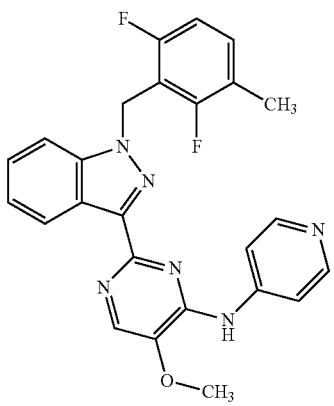 [SMILES: COc1cnc(-c2nn(Cc3c(F)ccc(C)c3F)c3ccccc23)nc1Nc1ccncc1] | 2-[1-(2,6-difluoro-3-methylbenzyl)-1H-indazol-3-yl]-5-methoxy-N-(pyridin-4-yl)pyrimidin-4-amine | $^1$H-NMR (400 MHz, DMSO-$d_6$): δ [ppm] = 2.16 (s, 3H), 4.00 (s, 3H), 5.74 (s, 2H), 7.06 (t, 1H), 7.21-7.34 (m, 2H), 7.47 (t, 1H), 7.85 (d, 1H), 8.07-8.20 (m, 2H), 8.28-8.50 (m, 4H), 9.40 (br. s., 1H).<br>LC-MS:<br>retention time: 1.03 min<br>MS ES$^+$: 459.2 [M + H]$^+$ |

| | | | |
|---|---|---|---|
| 2-49-1 SM = 1-6-1 | 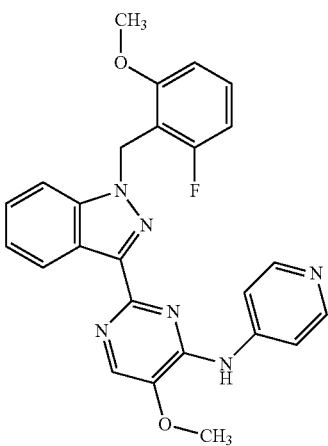 [SMILES: COc1cnc(-c2nn(Cc3c(F)cccc3OC)c3ccccc23)nc1Nc1ccncc1] | 2-[1-(2-fluoro-6-methoxybenzyl)-1H-indazol-3-yl]-5-methoxy-N-(pyridin-4-yl)pyrimidin-4-amine | $^1$H-NMR (400 MHz, DMSO-d$_6$): δ [ppm] = 3.80 (s, 3H), 3.85 (s, 3H), 5.09 (s, 2H), 6.85-6.99 (m, 4H), 7.06 (t, 1H), 7.31 (t, 1H), 7.36-7.48 (m, 1H), 7.51 (d, 1H), 7.62 (d, 2H), 8.16 (s, 1H), 8.39 (d, 1H), 13.15 (br.s., 1H). LC-MS: retention time: 0.90 min MS ES$^+$: 457.2 [M + H]$^+$ |
| 2-50-1 SM = 1-6-1 | 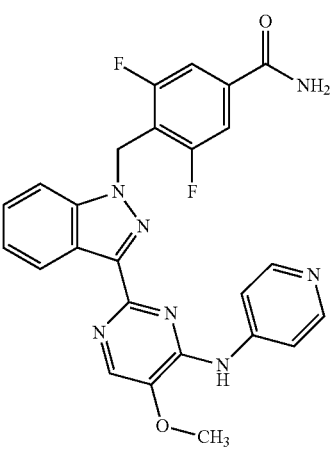 [SMILES: COc1cnc(-c2nn(Cc3c(F)cc(C(N)=O)cc3F)c3ccccc23)nc1Nc1ccncc1] | 3,5-difluoro-4-({3-[5-methoxy-4-(pyridin-4-ylamino)pyrimidin-2-yl]-1H-indazol-1-yl}methyl)benzamide | $^1$H-NMR (400 MHz, Methanol-d$_4$): δ [ppm] = 4.07 (s, 3H), 5.81 (s, 2H), 7.25 (t, 1H), 7.47 (t, 1H), 7.50-7.58 (m, 2H), 7.72 (d, 1H), 8.18 (s, 1H), 8.27-8.38 (m, 3H), 8.39-8.49 (m, 3H) LC-MS: retention time: 0.87 min MS ES$^+$: 488.39 [M + H]$^+$ |
| 2-51-1 SM = 1-6-1 | 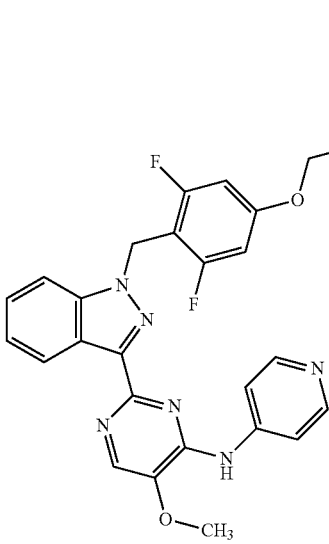 | 2-[3,5-difluoro-4-({3-[5-methoxy-4-(pyridin-4-ylamino)pyrimidin-2-yl]-1H-indazol-1-yl}methyl)phenoxy]ethyl acetate | $^1$H-NMR (600 MHz, DMSO-d$_6$): δ [ppm] = 2.00 (s, 3H), 4.04 (s, 3H), 4.21 (t, 2H), 4.29 (t, 2H), 5.69 (s, 2H), 6.80-6.94 (m, 2H), 7.19-7.34 (m, 1H), 7.42-7.55 (m, 1H), 7.79-7.90 (m, 1H), 8.10-8.25 (m, 2H), 8.35 (s, 1H), 8.39-8.44 (m, 2H), 8.44-8.51 (m, 1H), 9.41 (s, 1H). LC-MS (Method 5): retention time: 1.22 min MS ES$^+$: 547.3 [M + H]$^+$ |

| | | | |
|---|---|---|---|
| 2-52-1<br>SM =<br>1-6-1 | 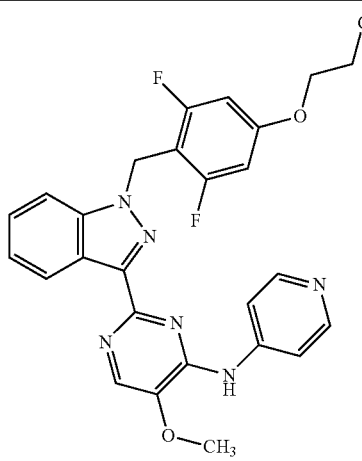 | 2-[1-(2,6-difluoro-4-propoxybenzyl)-1H-indazol-3-yl]-5-methoxy-N-(pyridin-4-yl)pyrimidin-4-amine | $^1$H-NMR (300 MHz, DMSO-d$_6$): δ [ppm] = 0.93 (t, 3H), 1.59-1.79 (m, 2H), 3.94 (t, 2H), 4.04 (s, 3H), 5.68 (s, 2H), 6.74-6.94 (m, 2H), 7.21-7.35 (m, 1H), 7.42-7.62 (m, 1H), 7.80-7.90 (m, 1H), 8.15-8.26 (m, 2H), 8.36 (s, 1H), 8.37-8.43 (m, 2H), 8.43-8.51 (m, 1H), 9.44 (s, 1H).<br>LC-MS:<br>retention time: 1.14 min<br>MS ES$^+$: 503.37 [M + H]$^+$ |

The following compound was also isolated from the reaction leading to 2-5-1:

| | | | |
|---|---|---|---|
| 2-53-1<br>SM =<br>1-6-1 | 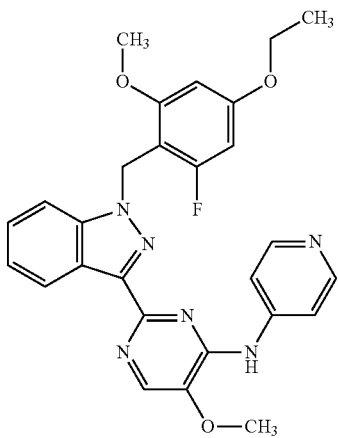 [SMILES: CCOc1cc(F)c(Cn2nc(-c3ncc(OC)c(Nc4ccncc4)n3)c3ccccc32)c(OC)c1] | 2-[1-(4-ethoxy-2-fluoro-6-methoxybenzyl)-1H-indazol-3-yl]-5-methoxy-N-(pyridin-4-yl)pyrimidin-4-amine | $^1$H-NMR (300 MHz, DMSO-d$_6$): δ [ppm] = 1.26 (t, 3H), 3.72 (s, 3H), 3.92-4.10 (m, 5H), 5.54 (s, 2H), 6.40 (s, 1H), 6.50 (dd, 1H), 7.13-7.27 (m, 1H), 7.37-7.49 (m, 1H), 7.79 (d, 1H), 8.16 (d, 2H), 8.31 (s, 1H), 8.35-8.47 (m, 3H), 9.38 (s, 1H). |

The following bis-benzyl compounds were also formed during the above described procedure using the indicated starting materials (SM=starting material):

| | | | |
|---|---|---|---|
| 2-4-2<br>SM =<br>1-6-1 | 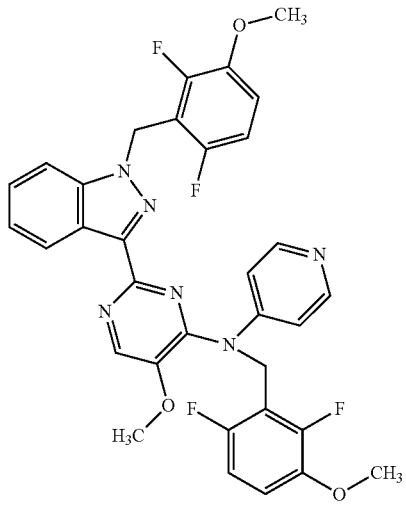 [SMILES: COc1cnc(-c2nn(Cc3c(F)ccc(OC)c3F)c3ccccc23)nc1N(Cc1c(F)ccc(OC)c1F)c1ccncc1] | N-(2,6-difluoro-3-methoxybenzyl)-2-[1-(2,6-difluoro-3-methoxybenzyl)-1H-indazol-3-yl]-5-methoxy-N-(pyridin-4-yl)pyrimidin-4-amine | $^1$H-NMR (300 MHz, DMSO-d$_6$): δ [ppm] = 3.77 (d, 6H), 3.82 (s, 3H), 5.22 (s, 2H), 5.69 (S, 2H), 6.86 (d, 2H), 6.97-7.06 (m, 1H), 7.06-7.19 (m, 3H), 7.21-7.30 (m, 1H), 7.41 (t, 1H), 7.57 (d, 2H), 7.74 (d, 1H), 8.12 (s, 1H), 8.37 (d, 1H).<br>LC-MS:<br>retention time: 1.16 min<br>MS ES$^+$: 631.24 [M + H]$^+$ |

| | | | |
|---|---|---|---|
| 2-5-2 SM = 1-6-1 | 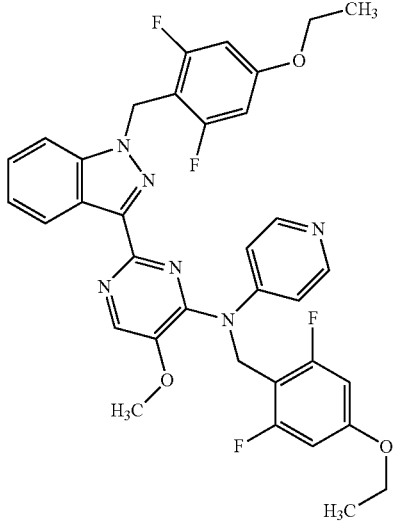 [SMILES: CCOc1cc(F)c(CN(c2ccncc2)c2nc(-c3nn(Cc4c(F)cc(OCC)cc4F)c4ccccc34)ncc2OC)c(F)c1] | N-(4-ethoxy-2,6-difluorobenzyl)-2-[1-(4-ethoxy-2,6-difluorobenzyl)-1H-indazol-3-yl]-5-methoxy-N-(pyridin-4-yl)pyrimidin-4-amine | $^1$H-NMR (300 MHz, DMSO-$d_6$): δ [ppm] = 1.21-1.32 (m, 6H), 3.78 (s, 3H), 4.02 (dq, 4H), 5.13 (s, 2H), 5.59 (s, 2H), 6.69 (d, 2H), 6.78-6.93 (m, 4H), 7.09 (t, 1H), 7.39 (t, 1 H), 7.56 (d, 2H), 7.71 (d, 1H), 8.12 (s, 1H), 8.37 (d, 1H). LC-MS: retention time: 1.26 min MS ES$^+$: 659.0 [M + H]$^+$ Method B |
| 2-7-2 SM = 1-6-1 | 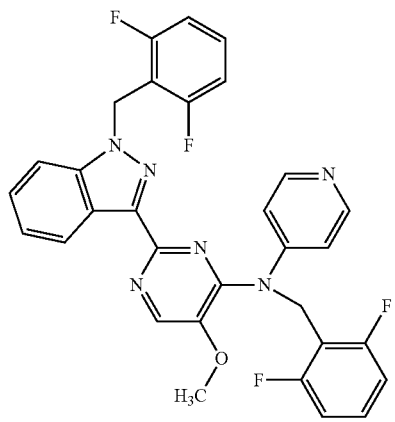 [SMILES: COc1cnc(-c2nn(Cc3c(F)cccc3F)c3ccccc23)nc1N(Cc1c(F)cccc1F)c1ccncc1] | N-(2,6-difluorobenzyl)-2-[1-(2,6-difluorobenzyl)-1H-indazol-3-yl]-5-methoxy-N-(pyridin-4-yl)pyrimidin-4-amine | $^1$H-NMR (300 MHz, DMSO-$d_6$): δ [ppm] = 3.77 (s, 3H), 5.24 (s, 2H), 5.69 (s, 2H), 6.89 (d, 2H), 7.03-7.15 (m, 3H), 7.22 (t, 3H), 7.36-7.46 (m, 2H), 7.58 (d, 2H), 7.75 (d, 1H), 8.12 (s, 1H), 8.38 (d, 1H). LC-MS: retention time: 1.13 min MS ES$^+$: 571.18 [M + H]$^+$ |
| 2-8-2 SM = 1-6-1 | 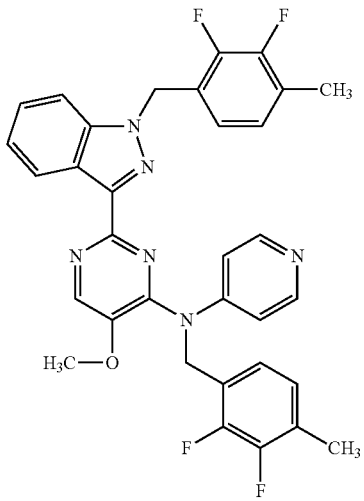 [SMILES: COc1cnc(-c2nn(Cc3ccc(C)c(F)c3F)c3ccccc23)nc1N(Cc1ccc(C)c(F)c1F)c1ccncc1] | N-(2,3-difluoro-4-methylbenzyl)-2-[1-(2,3-difluoro-4-methylbenzyl)-1H-indazol-3-yl]-5-methoxy-N-(pyridin-4-yl)pyrimidin-4-amine | $^1$H-NMR (300 MHz, DMSO-$d_6$): δ [ppm] = 2.19 (d, 3H), 2.25 (d, 3H), 3.79 (s, 3H), 5.19 (s, 2H), 5.68-5.77 (s, 2H), 6.77-6.87 (m, 3H), 6.98 (t, 1H), 7.03-7.19 (m, 3H), 7.38 (t, 1H), 7.61-7.74 (m, 3H), 8.11-8.17 (m, 1H), 8.37-8.45 (m, 1H). LC-MS: retention time: 1.20 min MS ES$^+$: 599.25 [M + H]$^+$ |

| | | | |
|---|---|---|---|
| 2-9-2<br>SM =<br>1-6-1 | 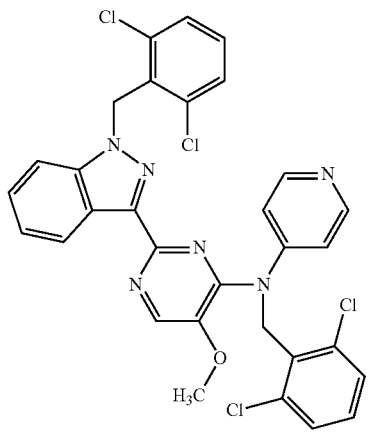 [SMILES: COc1cnc(-c2nn(Cc3c(Cl)cccc3Cl)c3ccccc23)nc1N(Cc1c(Cl)cccc1Cl)c1ccncc1] | N-(2,6-dichlorobenzyl)-2-[1-(2,6-dichlorobenzyl)-1H-indazol-3-yl]-5-methoxy-N-(pyridin-4-yl)pyrimidin-4-amine | $^1$H-NMR (400 MHz, DMSO-d$_6$): δ [ppm] = 3.78 (s, 3H), 5.43 (s, 2H), 5.79 (s, 2H), 7.09-7.18 (m, 3H), 7.30-7.45 (m, 4H), 7.50-7.60 (m, 3H), 7.63-7.68 (d, 2H), 7.77 (d, 1H), 8.12 (s, 1H), 8.42 (d, 1H).<br>LC-MS:<br>retention time: 1.26 min<br>MS ES$^+$: 637.09 [M + H]$^+$ |
| 2-10-2<br>SM =<br>1-6-1 | 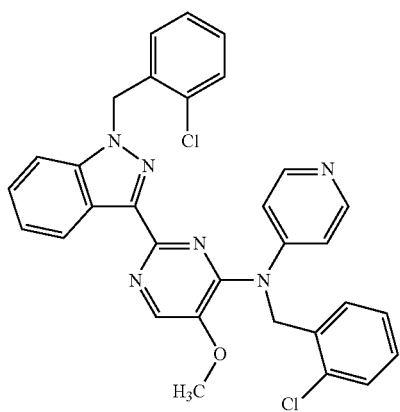 [SMILES: COc1cnc(-c2nn(Cc3ccccc3Cl)c3ccccc23)nc1N(Cc1ccccc1Cl)c1ccncc1] | N-(2-chlorobenzyl)-2-(1-(2-chlorobenzyl)-1H-indazol-3-yl]-5-methoxy-N-(pyridin-4-yl)pyrimidin-4-amine | $^1$H-NMR (400 MHz, DMSO-d$_6$): δ [ppm] = 3.81 (s, 3H), 5.23 (s, 2H), 5.76 (s, 2H), 6.81-6.89 (m, 3H), 7.12 (t, 1H), 7.19 (td, 1H), 7.23-7.30 (m, 2H), 7.34-7.42 (m, 3H), 7.47 (dd, 1H), 7.54 (dd, 1H), 7.63-7.69 (m, 3H), 8.15 (s, 1H), 8.47 (d, 1H).<br>LC-MS:<br>retention time: 1.12 min<br>MS ES$^+$: 567.2 [M + H]$^+$ |
| 2-11-2<br>SM =<br>1-6-1 | 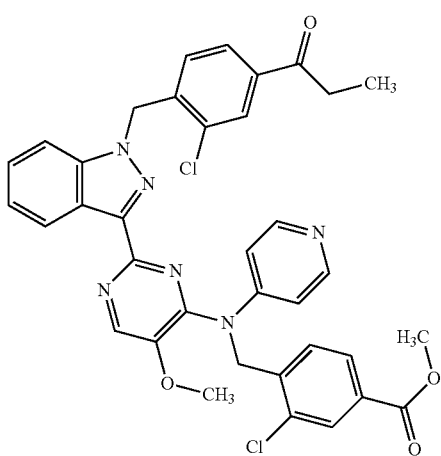 [SMILES: CCC(=O)c1ccc(Cn2nc(-c3ncc(OC)c(N(Cc4ccc(C(=O)OC)cc4Cl)c4ccncc4)n3)c3ccccc32)c(Cl)c1] | methyl 3-chloro-4-{[(2-{1-[2-chloro-4-(methoxycarbonyl)benzyl]-1H-indazol-3-yl}-5-methoxy-pyrimidin-4-yl)(pyridin-4-yl)amino]methyl}benzoate | $^1$H-NMR (400 MHz, DMSO-d$_6$): δ [ppm] = 3.79 (s, 3H), 3.85 (s, 3H), 3.97 (s, 3H), 5.60 (s, 2H), 5.87 (s, 2H), 7.00 (d, 1H), 7.23 (t, 1H), 7.33 (d, 1H), 7.40-7.46 (m, 1H), 7.71-7.80 (m, 2H), 7.90-7.97 (m, 3H), 8.01 (d, 1H), 8.25 (s, 1H), 8.29 (d, 2H), 8.42-8.50 (m, 2H).<br>LC-MS:<br>retention time: 1.17 min<br>MS ES$^+$: 683.1 [M + H]$^+$<br>Method B |

| | | | |
|---|---|---|---|
| 2-14-2<br>SM =<br>1-6-1 | 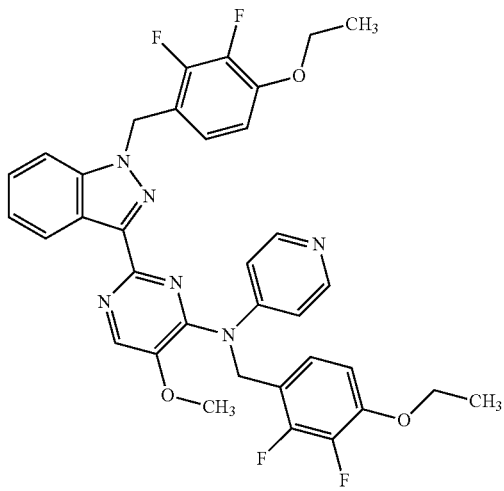 [SMILES: CCOc1ccc(CN(c2ccncc2)c2nc(-c3nn(Cc4ccc(OCC)c(F)c4F)c4ccccc34)ncc2OC)c(F)c1F] | N-(4-ethoxy-2,3-difluorobenzyl)-2-[1-(4-ethoxy-2,3-difluorobenzyl)-1H-indazol-3-yl]-5-methoxy-N-(pyridin-4-yl)pyrimidin-4-amine | $^1$H-NMR (300 MHz, DMSO-d$_6$): δ [ppm] = 1.22-1.36 (m, 6H), 3.79 (s, 3H), 3.99-4.18 (m, 4H), 5.14 (s, 2H), 5.68 (s, 2H), 6.81 (d, 2H), 6.92 (d, 2H), 7.00-7.22 (m, 3H), 7.38 (t, 1H), 7.61-7.74 (m, 3H), 8.14 (s, 1H), 8.40 (d, 1H).<br>LC-MS:<br>retention time: 1.22 min<br>MS ES$^+$: 659.0 [M + H]$^+$<br>Method B |
| 2-15-2<br>SM =<br>1-6-1 | 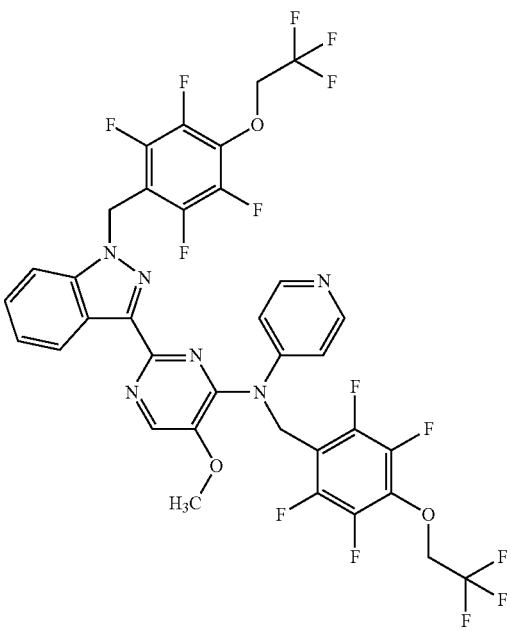 [SMILES: COc1cnc(-c2nn(Cc3c(F)c(F)c(OCC(F)(F)F)c(F)c3F)c3ccccc23)nc1N(Cc1c(F)c(F)c(OCC(F)(F)F)c(F)c1F)c1ccncc1] | 5-methoxy-N-(pyridin-4-yl)-N-[2,3,5,6-tetrafluoro-4-(2,2,2-trifluoroethoxy)benzyl]-2-{1-[2,3,5,6-tetrafluoro-4-(2,2,2-trifluoroethoxy)benzyl]-1H-indazol-3-yl}pyrimidin-4-amine | $^1$H-NMR (400 MHz, DMSO-d$_6$): δ [ppm] = 4.00 (s, 3H), 4.93 (qd, 4H), 5.31 (s, 2H), 5.63 (s, 2H), 7.21 (t, 1H), 7.36 (ddd, 1H), 7.64 (d, 1H), 8.04-8.11 (m, 2H), 8.27-8.33 (m, 2H), 8.43 (d, 1H), 9.35 (s, 1H).<br>LC-MS:<br>retention time: 1.42 min<br>MS ES$^+$: 837.1 [M + H]$^+$<br>Method B |
| 2-17-2<br>SM =<br>1-6-1 | 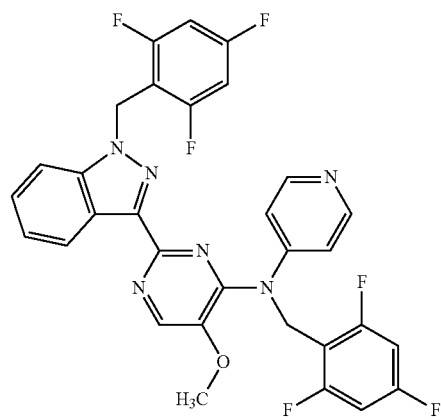 [SMILES: COc1cnc(-c2nn(Cc3c(F)cc(F)cc3F)c3ccccc23)nc1N(Cc1c(F)cc(F)cc1F)c1ccncc1] | 5-methoxy-N-(pyridin-4-yl)-N-(2,4,6-trifluorobenzyl)-2-[1-(2,4,6-trifluorobenzyl)-1H-indazol-3-yl]pyrimidin-4-amine | $^1$H-NMR (300 MHz, DMSO-d$_6$): δ [ppm] = 3.78 (s, 3H), 5.20 (s, 2H), 5.66 (s, 2H), 6.86 (d, 2H), 7.07-7.26 (m, 3H), 7.29-7.46 (m, 3H), 7.58 (d, 2H), 7.75 (d, 1H), 8.13 (s, 1H), 8.38 (d, 1H).<br>LC-MS:<br>retention time: 1.12 min<br>MS ES$^+$: 608.17 [M + H]$^+$ |

| | | | |
|---|---|---|---|
| 2-21-2 SM = 1-6-1 | 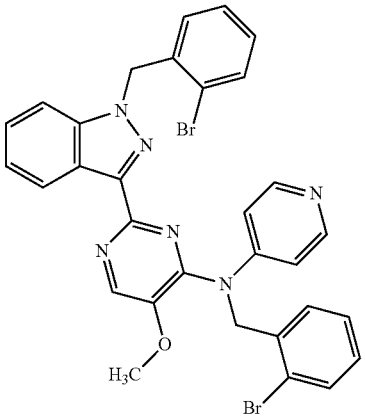 [SMILES: COc1cnc(-c2nn(Cc3ccccc3Br)c3ccccc23)nc1N(Cc1ccccc1Br)c1ccncc1] | N-(2-bromobenzyl)-2-[1-(2-bromobenzyl)-1H-indazol-3-yl]-5-methoxy-N-(pyridin-4-yl)pyrimidln-4-amine | $^1$H-NMR (300 MHz, DMSO-d$_6$): δ [ppm] = 3.81 (s, 3H), 5.20 (s, 2H), 5.73 (s, 2H), 6.69-6.76 (m, 1H), 6.87 (d, 2H), 7.08-7.26 (m, 4H), 7.28-7.48 (m, 3H), 7.60-7.73 (m, 5H), 8.15 (s, 1H), 8.48 (d, 1H). LC-MS: retention time: 1.30 min MS ES$^+$: 657.04 [M + H]$^+$ |
| 2-26-2 SM = 1-6-1 | 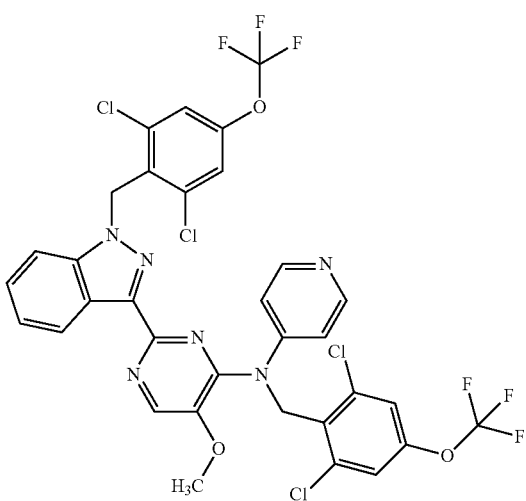 [SMILES: COc1cnc(-c2nn(Cc3c(Cl)cc(OC(F)(F)F)cc3Cl)c3ccccc23)nc1N(Cc1c(Cl)cc(OC(F)(F)F)cc1Cl)c1ccncc1] | N-[2,6-dichloro-4-(trifluoromethoxy)benzyl]-2-{1-[2,6-dichloro-4-(trifluoromethoxy)benzyl]-1H-indazol-3-yl}-5-methoxy-N-(pyridin-4-yl)pyrimidin-4-amine | $^1$H-NMR (300 MHz, DMSO-d$_6$): δ [ppm] = 3.78 (s, 3H), 5.40 (s, 2H), 5.81 (s, 2H), 6 99 (d. 2H), 7.12 (t, 1H), 7.42 (t, 1H), 7.55 (d, 2H), 7.64 (s, 2H), 7.76-7.85 (m, 3H), 8.12 (s, 1H), 8.42 (d, 1H). LC-MS: retention time: 1.39 min MS ES$^+$: 804.9 [M + H]$^+$ Method B |
| 2-33-2 SM = 1-6-1 | 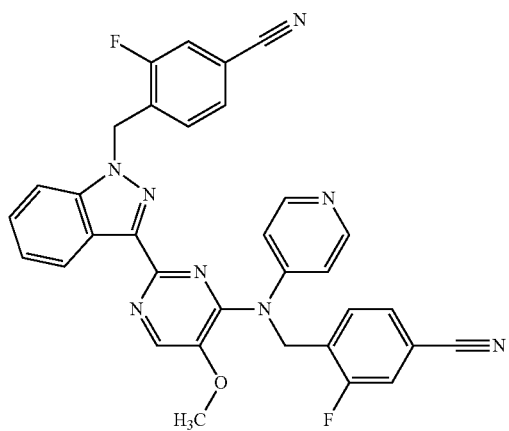 [SMILES: COc1cnc(-c2nn(Cc3ccc(C#N)cc3F)c3ccccc23)nc1N(Cc1ccc(C#N)cc1F)c1ccncc1] | 4-{[{2-[1-(4-cyano-2-fluorobenzyl)-1H-indazol-3-yl]-5-methoxy pyrimidin-4-yl}(pyridin-4-yl)amino]methyl}-3-fluoro-benzonitrile | $^1$H-NMR (300 MHz, DMSO-d$_6$): δ [ppm] = 3.80 (s, 3H), 5.28 (s, 2H), 5.84 (s, 2H), 6.83 (d, 2H), 7.09-7.19 (m, 2H), 7.43 (dt, 2H), 7.56-7.79 (m, 5H), 7.84-7.98 (m, 2H), 8.17 (s, 1H), 8.44 (d, 1H). LC-MS: retention time: 1.01 min MS ES$^+$: 586.2 [M + H]$^+$ |

| | | | |
|---|---|---|---|
| 2-39-2<br>SM =<br>1-6-1 | 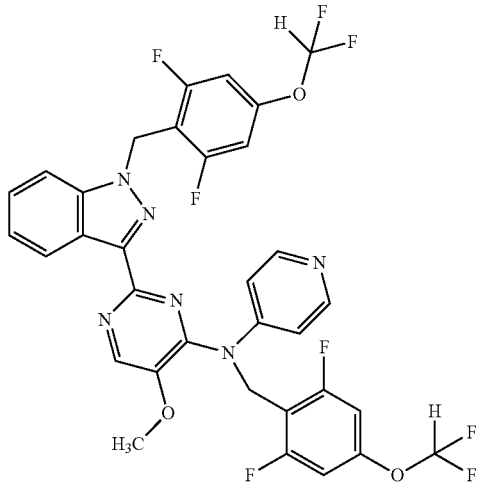 [SMILES: COc1cnc(-c2nn(Cc3c(F)cc(OC(F)F)cc3F)c3ccccc23)nc1N(Cc1c(F)cc(OC(F)F)cc1F)c1ccncc1] | N-[4-(difluoromethoxy)-2,6-difluorobenzyl]-2-{1-[4-(difluoromethoxy)-2,6-difluorobenzyl]-1H-indazol-3-yl}-5-methoxy-N-(pyridin-4-yl)pyrimidin-4-amine | $^1$H-NMR (300 MHz, DMSO-d$_6$): δ [ppm] = 3.78 (s, 3H), 5.20 (s, 2H), 5.67 (s, 2H), 6.84 (d, 2H), 7.01-7.21 (m, 5H), 7.31 (d, 1H), 7.41 (t, 1H), 7.51-7.60 (m, 3H), 7.75 (d, 1H), 8.13 (s, 1H), 8.38 (d, 1H).<br>LC-MS:<br>retention time: 1.17 min<br>MS ES$^+$: 703.1 [M + H]$^+$<br>Method B |

The following compounds were prepared following the procedure described in scheme 2a using the indicated starting materials (SM=starting material):

| | | | |
|---|---|---|---|
| 2-1-3<br>SM =<br>1-10-1 | 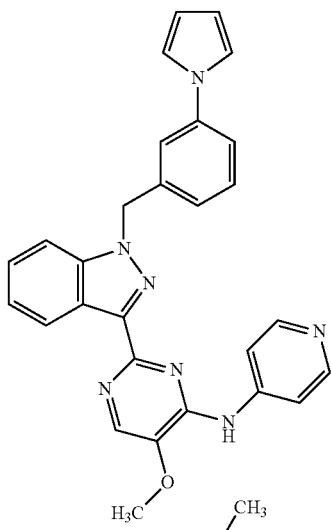 | 5-methoxy-N-(pyridin-4-yl)-2-{1-[3-(1H-pyrrol-1-yl)benzyl]-1H-indazol-3-yl}pyrimidin-4-amine | H-NMR (300 MHz, METHANOL-d4): δ [ppm] = 4.06 (s, 3H), 5.77 (s, 2H), 6.16-6.25 (m, 2H), 7.09 (s, 3H), 7.18-7.27 (m, 1H), 7.30-7.37 (m, 2H), 7.37-7.49 (m, 2H), 7.57-7.64 (m, 1H), 8.05-8.14 (m, 2H), 8.24-8.41 (m, 3H), 8.42-8 51 (m, 1H)<br>LC-MS:<br>retention time:<br>1.07 min<br>MS ES$^+$: 474.4 [M + H]$^+$<br>Method B |
| 2-2-3<br>SM =<br>1-10-1 | 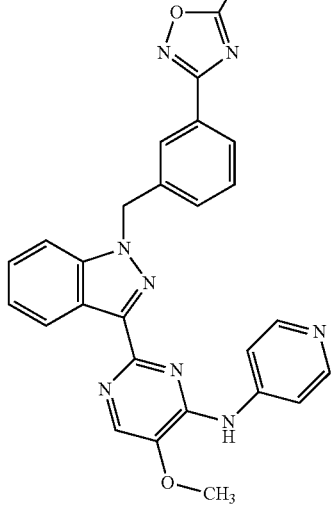 | 5-methoxy-2-{1-[3-(5-methyl-1,2,4-oxadiazol-3-yl)benzyl]-1H-indazol-3-yl}-N-(pyridin-4-yl)pyrimidin-4-amine | $^1$H-NMR (400 MHz, CHLOROFORM-d): δ [ppm] = 2.64 (s, 3H), 4.08 (s, 3H), 5.82 (s, 2H), 7.35-7.45 (m, 5H), 7.82-7.90 (m, 2H), 7.94-8.01 (m, 1H), 8.12 (s, 1H), 8.25 (s, 1H), 8.52-8.63 (m, 3H)<br>LC-MS:<br>retention time:<br>0.95 min<br>MS ES$^+$: 491.3 [M + H]$^+$ |

| | | | |
|---|---|---|---|
| 2-3-3<br>SM =<br>1-10-1 | 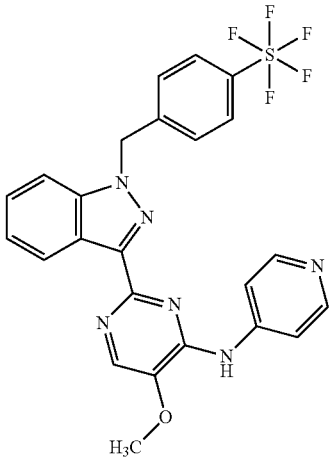 [SMILES: COc1cnc(-c2nn(Cc3ccc(S(F)(F)(F)(F)F)cc3)c3ccccc23)nc1Nc1ccncc1] | 5-methoxy-2-{1-[4-(pentafluoro-λ⁶-sulfanyl)benzyl]-1H-indazol-3-yl}-N-(pyridin-4-yl)pyrimidin-4-amine | ¹H-NMR (300 MHz, CHLOROFORM-d): δ [ppm] = 4.08 (s, 3H), 5.79 (s, 2H), 7.28-7.50 (m, 5H), 7.66 (d, 2H), 7.80-7.89 (m, 2H), 8.24 (s, 1H), 8.53-8.66 (m, 3H)<br>LC-MS: retention time: 1.07 min<br>MS ES⁺: 535.2 [M + H]⁺ |
| 2-4-3<br>1-10-1 | 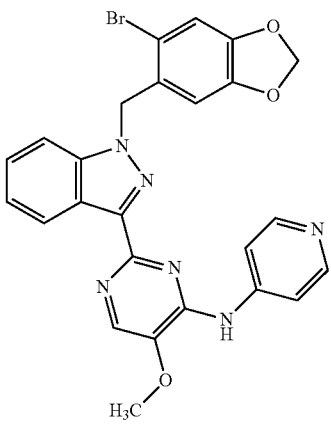 | 2-{1-[(6-bromo-1,3-benzodioxol-5-yl)methyl]-1H-indazol-3-yl}-5-methoxy-N-(pyridin-4-yl)pyrimidin-4-amine | 1H-NMR (300 MHz, CHLOROFORM-d): δ [ppm] = 4.08 (s, 3H), 5.76 (s, 2H), 5.89 (s, 2H), 6.45 (s, 1H), 7.04 (s, 1H), 7.41-7.43 (m, 3H), 7.79-7.90 (m, 2H), 8.24 (s, 1H), 8.47-8.65 (m, 3H)<br>LC-MS: retention time: 1.09 min<br>MS ES⁺: 509.1 [M + H]⁺<br>Method B |
| 2-5-3<br>SM =<br>1-10-1 | 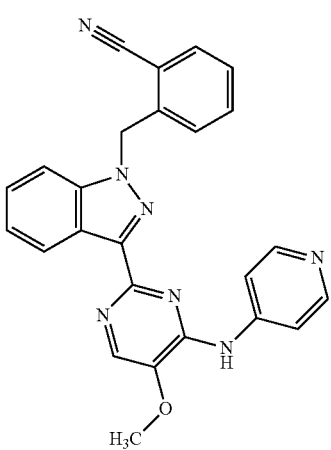 [SMILES: COc1cnc(-c2nn(Cc3ccccc3C#N)c3ccccc23)nc1Nc1ccncc1] | 2-({3-[5-methoxy-4-(pyridin-4-ylamino)pyrimidin-2-yl]-1H-indazol-1-yl}methyl)benzonitrile | ¹H-NMR (300 MHz, CHLOROFORM-d): δ [ppm] = 4.08 (s, 3H), 5.98 (s, 2H), 7.13-7.22 (m, 1H), 7.30-7.53 (m, 5H), 7.67-7.77 (m, 1H), 7.79-7.94 (m, 2H), 8.25 (s, 1H), 8.51-8.70 (m, 3H)<br>LC-MS: retention time: 0.90 min<br>MS ES⁺: 434.2 [M + H]⁺ |

| | | | |
|---|---|---|---|
| 2-6-3 SM = 1-10-1 | 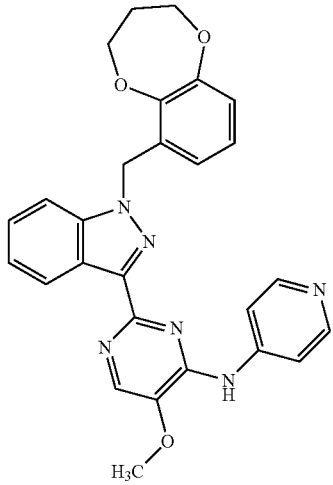 [SMILES: COc1cnc(-c2nn(Cc3cccc4c3OCCCO4)c3ccccc23)nc1Nc1ccncc1] | 2-[1-(3,4-dihydro-2H-1,5-benzodioxepin-6-ylmethyl)-1H-indazol-3-yl]-5-methoxy-N-(pyridin-4-yl)pyrimidin-4-amine | $^1$H-NMR (300 MHz, CHLOROFORM-d): δ [ppm] = 2.20 (quint, 2H), 4.06 (s, 3H), 4.14 (t, 2H), 4.19 (t, 2H), 5.76 (s, 2H), 6.73-6.83 (m, 2H), 6.87-6.96 (m, 1H), 7.33-7.54 (m, 3H), 7.80-7.91 (m, 2H), 8.23 (s, 1H), 8.54-8.58 (m, 3H) LC-MS: retention time: 0.95 min MS ES$^+$: 481.3 [M + H]$^+$ |
| 2-7-3 SM = 1-10-1 | 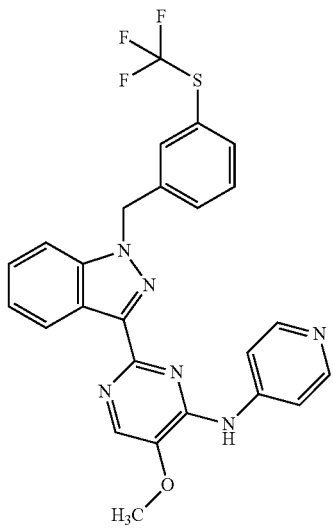 [SMILES: COc1cnc(-c2nn(Cc3cccc(SC(F)(F)F)c3)c3ccccc23)nc1Nc1ccncc1] | 5-methoxy-N-(pyridin-4-yl)-2-(1-{3-[(trifluoromethyl)sulfanyl]benzyl}-1H-indazol-3-yl)pyrimidin-4-amine | 1H-NMR (300 MHz, CHLOROFORM-d): δ [ppm] = 4.08 (s, 3H), 5.77 (s, 2H), 7.30-7.42 (m, 5H), 7.51-7.66 (m, 2H), 7,83 (d, 2H), 8.24 (s, 1H), 8.55-8.61 (m, 3H) LC-MS: retention time: 1.08 min MS ES$^+$: 509.2 [M + H]$^+$ |
| 2-8-3 SM = 1-10-1 | 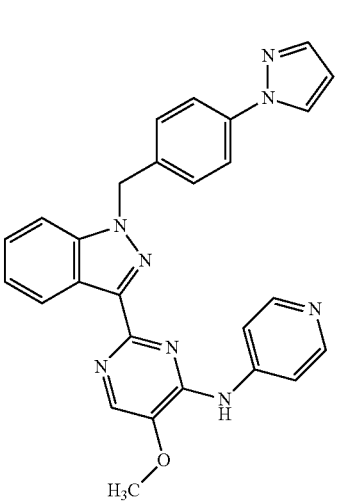 [SMILES: COc1cnc(-c2nn(Cc3ccc(-n4cccn4)cc3)c3ccccc23)nc1Nc1ccncc1] | 5-methoxy-2-pyrazol-1-yl)benzyl]-1H-indazol-3-yl}-N-(pyridin-4-yl)pyrimidin-4-amine | LC-MS: retention time: 0.98 min MS ES$^+$: 475.42 [M + H]$^+$ |

-continued

| | | | |
|---|---|---|---|
| 2-9-3<br>SM =<br>1-10-1 | 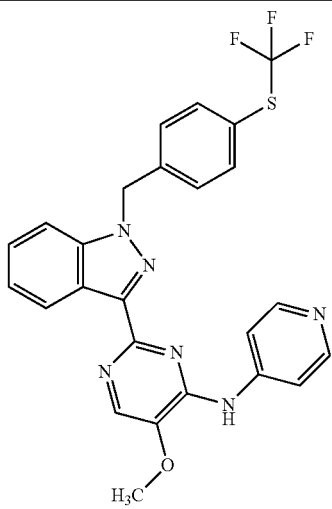 | 5-methoxy-N-(pyridin-4-yl)-2-(1-{4-[(trifluoro-methyl)sulfanyl]benzyl}-1H-indazol-3-yl)pyrimidin-4-amine | H-NMR (300 MHz, METHANOL-d4): δ [ppm] = 4.09 (s, 3H), 5.82 (s, 2H), 7.21-7.30 (m, 1H), 7.34-7.49 (m, 2H), 7.49-7.73 (m, 4H), 8.01-8.09 (m, 2H), 8.28 (s, 1H), 8.35-8.43 (m, 2H), 8.50 (d, 1H)<br>LC-MS:<br>retention time: 1.16 min<br>MS ES+: 509:39 [M + H]+ |

Example 3-1

Preparation of 2-[1-(4-ethoxy-2,6-difluorobenzyl)-1H-indazol-3-yl]-4-(pyridin-4-ylamino)pyrimidin-ol

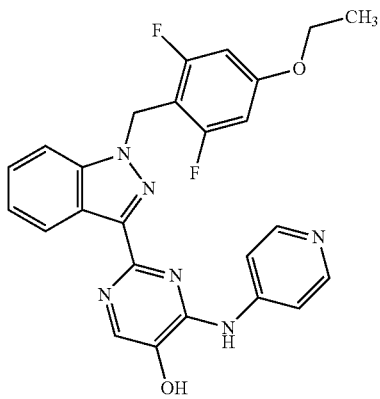 [SMILES: CCOc1cc(F)c(Cn2nc(-c3ncc(O)c(Nc4ccncc4)n3)c3ccccc32)c(F)c1]

1.32 g of 2-[1-(4-ethoxy-2,6-difluorobenzyl)-1H-indazol-3-yl]-5-methoxy-N-(pyridin-4-yl)pyrimidin-4-amine (2-5-1, 2.70 mmol, 1. eq.) were dissolved in 117 ml of dry 1-methylpyrrolidin-2-one. 142 mg of potassium carbonate were added under nitrogen atmosphere. Then 0.42 ml of benzenethiol were added dropwise. The reaction mixture was stirred for an hour at 190° C. and cooled over the weekend at room temperature. Then the mixture was portioned between half saturated aq. ammonium chloride solution and dichloromethane/isopropanol 4:1. The phases were separated and the aqueous layer was extracted twice with dichloromethane/isopropanol 4:1. The combined organic layers were washed with brine, dried over a silicone filter and concentrated in vacuo. The residue was purified by flash chromatography to yield 781 mg (1.65 mmol, 60.9%) of the analytically pure target compound.

$^1$H-NMR (300 MHz, DMSO-d$_6$): δ [ppm]=1.25 (t, 3H), 4.00 (q, 2H), 5.63 (s, 2H), 6.71-6.81 (m, 2H), 7.21 (t, 1H), 7.44 (td, 1H), 7.80 (d, 1H), 8.09-8.18 (m, 3H), 8.33-8.38 (m, 2H), 8.42 (d, 1H), 9.28 (s, 1H), 10.78 (br. s., 1H).

LC-MS:

retention time: 0.97 min

MS ES+: 475.59 [M+H]+

The following compounds were prepared according to the same procedure using the indicated starting materials (SM=starting material):

| | | | |
|---|---|---|---|
| 3-2<br>SM =<br>1-5-1 | 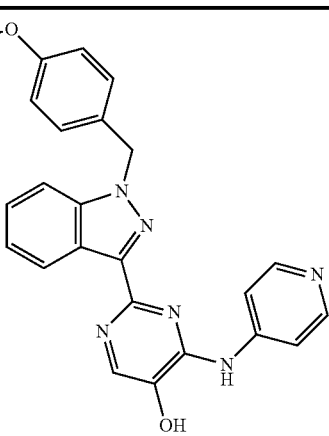 | 2-[1-(4-methoxy-benzyl)-1H-indazol-3-yl]-4-(pyridin-4-ylamino)pyrimidin-5-ol | $^1$H-NMR (400 MHz, DMSO-d$_6$): δ [ppm] = 3.66 (s, 3H), 5.64 (s, 2H), 6.83-6.88 (m, 2H), 7.19 (t, 1H), 7.27-7.33 (m, 2H), 7.38 (ddd, 1H), 7.76 (d, 1H), 8.10-8.15 (m, 3H), 8.34-8.43 (m, 2H), 9.31 (s, 1H).<br>LC-MS:<br>retention time: 0.83 min<br>MS ES+: 425.1 [M + H]+<br>Method B |

| | | | |
|---|---|---|---|
| 3-3 SM = 2-18-1 | 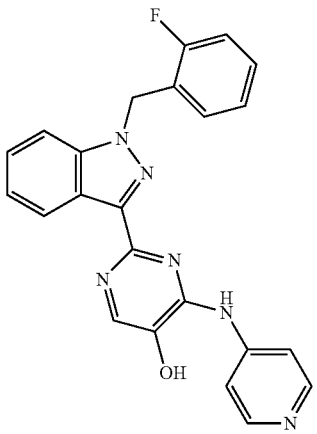 [SMILES: Oc1cnc(-c2nn(Cc3ccccc3F)c3ccccc23)nc1Nc1ccncc1] | 2-[1-(2-fluorobenzyl)-1H-indazol-3-yl]-4-(pyridin-4-ylamino)pyrimidin-5-ol | $^1$H-NMR (400 MHz, DMSO-d$_6$): δ [ppm] = 5.76 (s, 2H), 7.12-7.18 (m, 1H), 7.19-7.38 (m, 4H), 7.43 (ddd, 1H), 7.78 (d, 1H), 8.09-8.14 (m, 3H), 8.33-8.37 (m, 2H), 8.43 (d, 1H), 9.30 (s, 1H), 10.71-10.92 (s, 1H). LC-MS: retention time: 0.86 min MS ES$^+$: 413.2 [M + H]$^+$ |
| 3-4 SM = 2-36-1 | 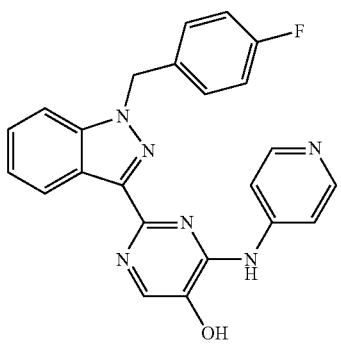 [SMILES: Oc1cnc(-c2nn(Cc3ccc(F)cc3)c3ccccc23)nc1Nc1ccncc1] | 2-[1-(4-fluorobenzyl)-1H-indazol-3-yl]-4-(pyridin-4-ylamino)pyrimidin-5-ol | $^1$H-NMR (400 MHz, DMSO-d$_6$): δ [ppm] = 5.70-5.73 (m, 2H), 7.10-7.23 (m, 3H), 7.34-7.44 7.78 (d, 1H), 8.07-8.14 (m, 3H), 8.34-8.39 (m, 2H), 8.42 (d, 1H), 9.31 (s, 1H), 10.83-11.18 (m, 1H). LC-MS: retention time: 0.85 min MS ES$^+$: 413.0 [M + H]$^+$ Method B |

Example 4-1

Preparation of {3-[({2-[1-(4-ethoxy-2,6-difluorobenzyl)-1H-indazol-3-yl]-4-(pyridin-4-ylamino)pyrimidin-5-yl}oxy)methyl]oxetan-3-yl}methano

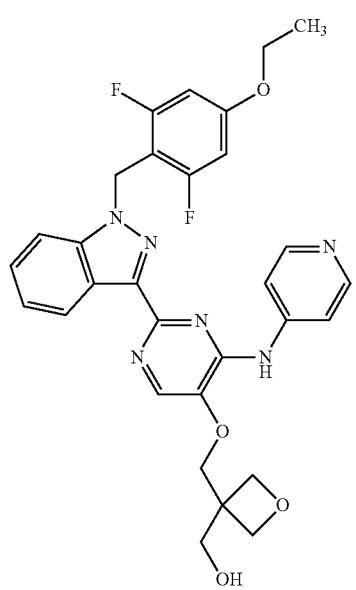 [SMILES: CCOc1cc(F)c(Cn2nc(-c3ncc(OCC4(CO)COC4)c(Nc4ccncc4)n3)c3ccccc32)c(F)c1]

100 mg of 2-[1-(4-ethoxy-2,6-difluorobenzyl)-1H-indazol-3-yl]-4-(pyridin-4-ylamino)pyrimidin-5-ol (3-1, 0.21 mmol, 1. eq.) were dissolved in 1.6 ml of DMF under a nitrogen atmosphere, then 87 mg of potassium carbonate (0.63 mmol, 3 eq.) and 40 mg of [3-(bromomethyl)oxetan-3-yl]methanol (0.21 mmol, 1 eq.) were added. The resulting mixture was stirred at room temperature for 18 hours. 6.0 mg of [3-(bromomethyl)oxetan-3-yl]methanol (0,032 mmol, 0.15 eq.) were added and stirred again for 24 hours. Then the mixture was partitioned between half saturated aq. ammonium chloride solution and dichloromethane/isopropanol 4:1. The phases were separated and the aqueous layer was extracted twice with dichloromethane/isopropanol 4:1. The combined organic layers were washed with brine, dried over a silicone filter and concentrated in vacuo. The residue was purified by flash chromatography to yield 75 mg (0.13 mmol, 61.9%) of the analytically pure target compound.

$^1$H-NMR (400 MHz, DMSO-d$_6$): δ [ppm]=1.26 (t, 3H), 3.83 (d, 2H), 4.01 (q, 2H), 4.39-4.50 (m, 6H), 5.06 (t, 1H), 5.65 (s, 2H), 6.72-6.81 (m, 2H), 7.23 (t, 1H), 7.46 (ddd, 1H), 7.82 (d, 1H), 8.01-8.09 (m, 2H), 8.38-8.46 (m, 4H), 8.90 (s, 1H).

LC-MS:

retention time: 1.00 min

MS ES$^+$: 574.82 [M+H]$^+$

The following compounds were prepared according to the same procedure using the indicated starting materials (SM=starting material):

| | | | |
|---|---|---|---|
| 4-2-1 SM = 3-3 | 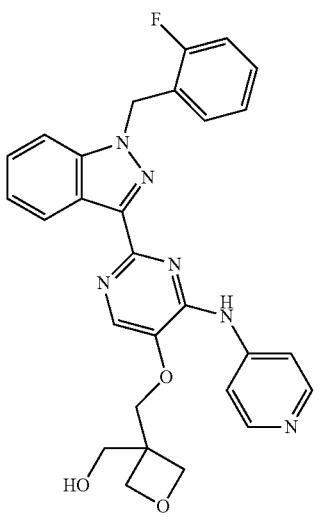 [SMILES: OCC1(COc2cnc(-c3nn(Cc4ccccc4F)c4ccccc34)nc2Nc2ccncc2)COC1] | {3-[({2-[1-(2-fluorobenzyl)-1H-indazol-3-yl]-4-(pyridin-4-ylamino)pyrimidin-5-yl}oxy)methyl]oxetan-3-yl}methanol | $^1$H-NMR (300 MHz, DMSO-d$_6$): δ [ppm] = 3.83 (br. s., 2H), 4.39-4.48 (m, 6H), 5.06 (br. s., 1H), 5.78 (s, 2H), 7.11-7.38 (m, 5H), 7.40-7.49 (m, 1H), 7.80 (d, 1H), 8.00 (d, 2H), 8.37-8.46 (m, 4H), 8.92 (br. s., 1H). LC-MS: retention time: 0.92 min MS ES$^+$: 513.25 [M + H]$^+$ |
| 4-2-2 SM = 3-3 | 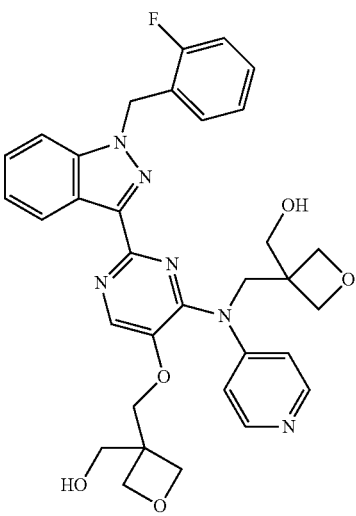 [SMILES: OCC1(COc2cnc(-c3nn(Cc4ccccc4F)c4ccccc34)nc2N(CC2(CO)COC2)c2ccncc2)COC1] | (3-{[(2-[1-(2-fluorobenzyl)-1H-indazol-3-yl]-5-{[3-(hydroxy-methyl)oxetan-3-yl]methoxy}pyrimidin-4-yl)(pyridin-4-yl)amino]methyl}oxetan-3-yl)methanol | LC-MS: retention time: 0.93 min MS ES$^+$: 613.26 [M + H]$^+$ |
| 4-3 SM = 3-3 | 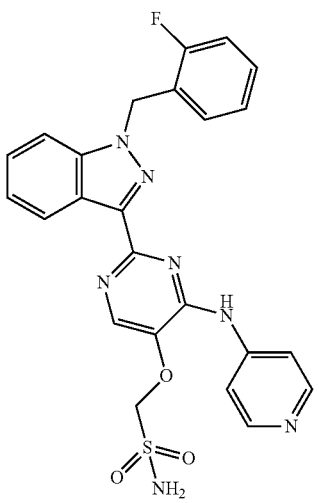 [SMILES: NS(=O)(=O)COc1cnc(-c2nn(Cc3ccccc3F)c3ccccc23)nc1Nc1ccncc1] | 1-({2-[1-(2-fluorobenzyl)-1H-indazol-3-yl]-4-(pyridin-4-ylamino)pyrimidin-5-yl}oxy)methanesulfonamide | $^1$H-NMR (400 MHz, DMSO-d$_6$): δ [ppm] = 5.30 (s, 2H), 5.79 (s, 2H), 7.12-7.38 (m, 5H), 7.41-7.48 (m, 3H), 7.82 (d, 1H), 8.03-8.09 (m, 2H), 8.39-8.45 (m, 3H), 8.56 (s, 1H), 9.18-9.22 (m, 1H). LC-MS (Method 2): retention time: 1.32 min MS ES$^+$: 506.00 [M + H]$^+$ |

| | | | |
|---|---|---|---|
| 4-4 SM = 3-3 | 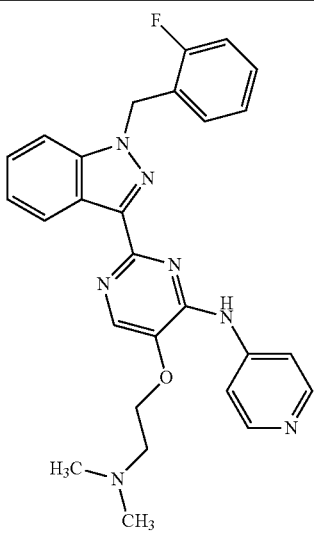 | 5-[2-(dimethyl-amino)ethoxy]-2-[1-(2-fluorobenzyl)-1H-indazol-3-yl]-N-(pyridin-4-yl)pyrimidin-4-amine | $^1$H-NMR (400 MHz, DMSO-d$_6$): δ [ppm] = 2.25 (s, 6H), 2.68-2.75 (m, 2H), 4.29 (t, 2H), 5.78 (s, 2H), 7.12-7.38 (m, 5H), 7.44 (ddd, 1H), 7.80 (d, 1H), 8.01-8.06 (m, 2H), 8.37-8.46 (m, 4H), 9.42 (s, 1H). LC-MS: retention time: 0.77 min MS ES$^+$: 484.3 [M + H]$^+$ |
| 4-5-1 SM = 3-3 | 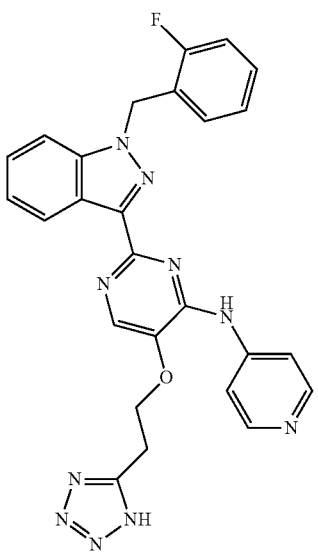 [SMILES: Fc1ccccc1Cn1nc(-c2ncc(OCCc3nnn[nH]3)c(Nc3ccncc3)n2)c2ccccc21] | 2-[1-(2-fluorobenzyl)-1H-indazol-3-yl]-N-(pyridin-4-yl)-5-[2-(1H-tetrazol-5-yl)ethoxy]pyrimidin-4-amine | $^1$H-NMR (300 MHz, DMSO-d$_6$): δ [ppm] = 3.17-3.24 (m, 4H), 4.41 (t, 2H), 5.79 (s, 2H), 7.12-7.39 (m, 5H), 7.40-7.49 (m, 1H), 7.80 (d, 1H), 8.39-8.49 (m, 6H). LC-MS: retention time: 0.91 min MS ES$^+$. 509.36 [M + H]$^+$ |
| 4-5-2 SM = 3-3 | 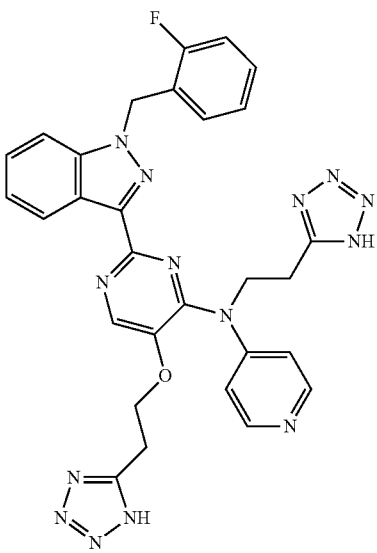 [SMILES: Fc1ccccc1Cn1nc(-c2ncc(OCCc3nnn[nH]3)c(N(CCc3nnn[nH]3)c3ccncc3)n2)c2ccccc21] | 2-[1-(2-fluorobenzyl)-1H-indazol-3-yl]-N-(pyridin-4-yl)-5-[2-(1H-tetrazol-5-yl)ethoxy]-N-[2-(1H-tetrazol-5-yl)ethyl]pyrimidin-4-amine | LC-MS: retention time: 0.95 min MS ES$^+$: 605.32 [M + H]$^+$ |

| | | | |
|---|---|---|---|
| 4-6 SM = 3-4 | 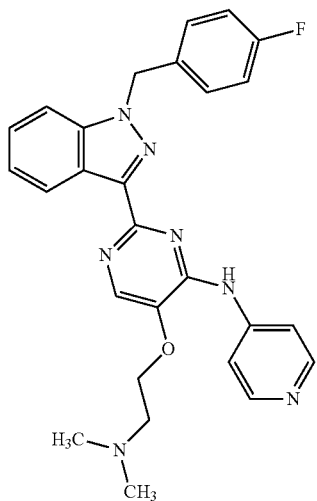 [SMILES: CN(C)CCOc1cnc(-c2nn(Cc3ccc(F)cc3)c3ccccc23)nc1Nc1ccncc1] | 5-[2-(dimethyl-amino)ethoxy]-2-(1-(4-fluorobenzyl)-1H-indazol-3-yl]-N-(pyridin-4-yl)pyrimidin-4-amine | $^1$H-NMR (300 MHz, DMSO-$d_6$): δ [ppm] = 2.24 (s, 6H), 2.65-2.75 (m, 2H), 4.29 (s, 2H), 5.73 (s, 2H), 7.09-7.30 (m, 4H), 7.35-7.45 (m, 2H), 7.74-7.83 (m, 1H), 8.03 (d, 2H), 8.36-8.46 (m, 4H), 9.41-9.47 (m, 1H). LC-MS: retention time: 0.88 min MS ES$^+$: 484.0 [M + H]$^+$ Method B |
| 4-7 SM = 3-3 | 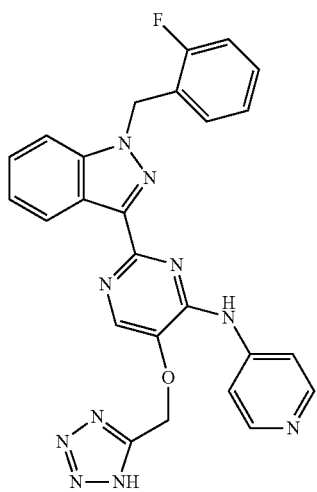 [SMILES: Fc1ccccc1Cn1nc(-c2ncc(OCc3nnn[nH]3)c(Nc3ccncc3)n2)c2ccccc21] | 2-[1-(2-fluorobenzyl)-1H-indazol-3-yl]-N-(pyridin-4-yl)-5-(1H-tetrazol-5-ylmethoxy)pyrimidin-4-amine | $^1$H-NMR (300 MHz, DMSO-$d_6$): δ [ppm] = 5.70 (s, 2H), 5.79 (s, 2H), 7.11-7.39 (m, 5H), 7.45 (t, 1H), 7.81 (d, 1H), 8.19 (d, 2H), 8.39-8.50 (m, 3H), 8.59 (s, 1H), 9.61 (br.s., 1H). LC-MS: retention time: 0.92 min MS ES$^+$: 495.2 [M + H]$^+$ |
| 4-8 SM = 3-1 | 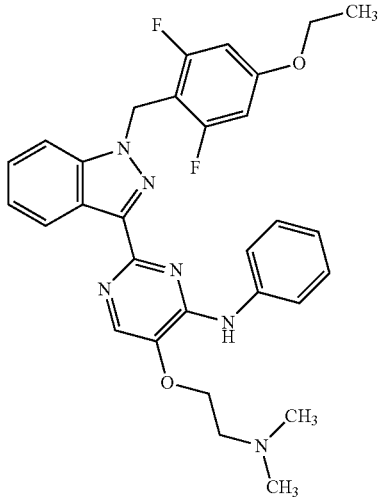 [SMILES: CCOc1cc(F)c(Cn2nc(-c3ncc(OCCN(C)C)c(Nc4ccccc4)n3)c3ccccc32)c(F)c1] | 5-[2-(dimethyl-amino)ethoxy]-2-[1-(4-ethoxy-2,6-difluorobenzyl)-1H-indazol-3-yl]-N-(pyridin-4-yl)pyrimidin-4-amine | $^1$H-NMR (400 MHz, DMSO-$d_6$): δ [ppm] = 1.25 (t, 3H), 2.24 (s, 6H), 2.69 (t, 2H), 4.01 (q, 2H), 4.20 (t, 2H), 5.56 (s, 2H), 6.76 (d, 2H), 7.23 (t, 1H), 7.46 (td, 1H), 7.82 (d, 1H), 8.07 (dd, 2H), 8.36-8.45 (m, 4H), 9.38 (s, 1H). LC-MS: retention time: 0.80 min MS ES$^+$: 546.2 [M + H]$^+$ |

| | | |
|---|---|---|
| 4-9<br>SM =<br>3-1 | 1-({2-[1-(4-ethoxy-2,6-difluorobenzyl)-1H-indazol-3-yl]-4-(pyridin-4-ylamino)pyrimidin-5-yl}oxy)-3-(piperidin-1-yl)propan-2-ol | $^1$H-NMR (500 MHz, DMSO-$d_6$): δ [ppm] = 1.30 (t, 3H), 1.38 (m, 2H), 1.50 (m, 4H), 2.37 (m, 1H), 2.38-2.54 (m, 4H), 2.65 (m, 1H), 4.06 (q, 2H), 4.09 (br. d, 1H), 4.11 (br. s, 1H), 4.29 (br. d, 1H), 5.19 (br. d, 1H), 5.70 (s, 2H), 6.81 (d, 2H), 7.28 (t, 1H), 7.50 (br. t, 1H), 7.86 (d, 1H), 8.12 (br. d, 2H), 8.38 (s, 1H), 8.45-8.48 (m, 3H), 9.14 (s, 1H).<br>LC-MS (Method 5): retention time: 1.45 min<br>MS ES$^+$: 616.3 [M + H]$^+$ |
| | 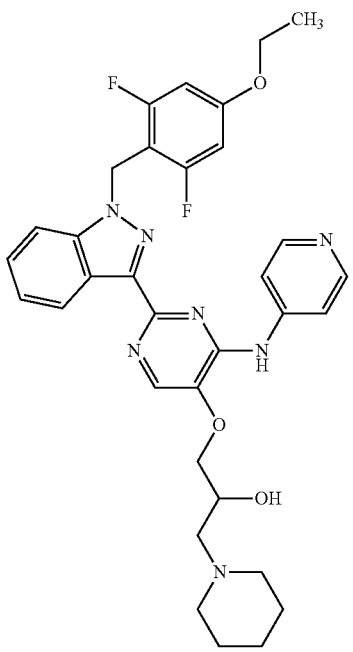 [SMILES: CCOc1cc(F)c(Cn2nc(-c3ncc(OCC(O)CN4CCCCC4)c(Nc4ccncc4)n3)c3ccccc32)c(F)c1] | |
| 4-10<br>SM =<br>3-1 | 2-[1-(4-ethoxy-2,6-difluorobenzyl)-1H-indazol-3-yl]-5-(2-methoxyethoxy)-N-(pyridin-4-yl)pyrimidin-4-amine | 1H-NMR (300 MHz, DMSO-d6): δ [ppm] = 1.25 (t, 3H), 3.32 (s, 3H), 3.76 (m, 2H), 4.01 (q, 2H), 4.36 (m, 2H), 5.65 (s, 2H), 6.76 (m, 2H), 7.23 (t, 1H), 7.46 (br. t, 1H), 7.82 (d, 1H), 8.12 (br. d, 2H), 8.35-8.45 (m, 4H), 9.13 (s, 1H). |
| | 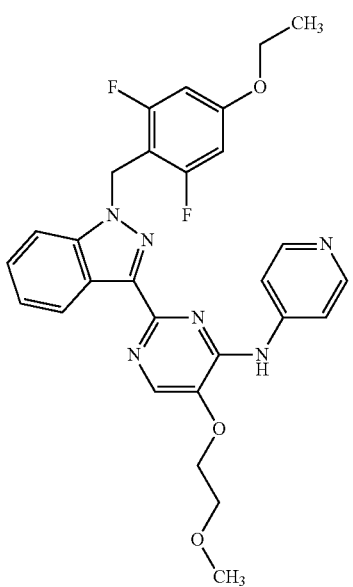 [SMILES: CCOc1cc(F)c(Cn2nc(-c3ncc(OCCOC)c(Nc4ccncc4)n3)c3ccccc32)c(F)c1] | |

| | | | |
|---|---|---|---|
| 4-11 SM = 3-1 | 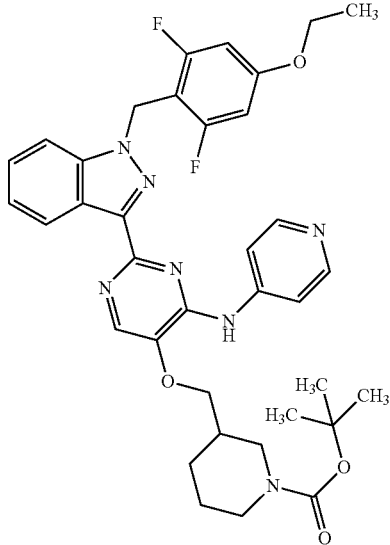 [SMILES: CCOc1cc(F)c(Cn2nc(-c3ncc(OCC4CCCN(C(=O)OC(C)(C)C)C4)c(Nc4ccncc4)n3)c3ccccc32)c(F)c1] | tert-butyl 2-[({2-[1-(4-ethoxy-2,6-difluorobenzyl)-1H-indazol-3-yl]-4-(pyridin-4-ylamino)pyrimidin-5-yl}oxy)methyl]morpholine-4-carboxylate | 1H-NMR (300 MHz, DMSO-d6): δ [ppm] = 1.25 (t, 3H), 1.37 (s, 9H), 2.91 (m, 2H), 3.45 (br. t, 1H), 3.70 (br. d, 1H), 3.80-4.06 (m, 5H), 4.27 (d, 2H), 5.65 (s, 2H), 6.76 (m, 2H), 7.23 (t, 1H), 7.46 (t, 1H), 7.82 (d, 1H), 8.11 (br. d, 2H), 8.35-8.45 (m, 4H), 9.10 (s, 1H). |
| 4-12 SM = 3-1 | 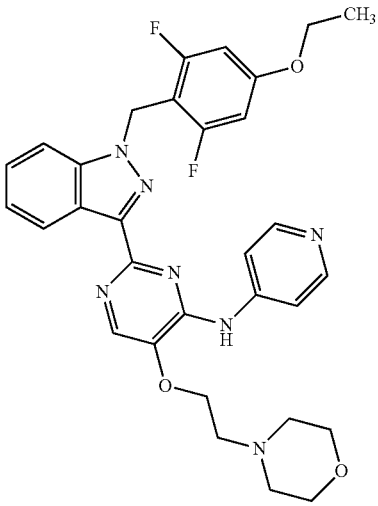 [SMILES: CCOc1cc(F)c(Cn2nc(-c3ncc(OCCN4CCOCC4)c(Nc4ccncc4)n3)c3ccccc32)c(F)c1] | 2-[1-(4-ethoxy-2,6-difluorobenzyl)-1H-indazol-3-yl]-5-[2-(morpholin-4-yl)ethoxy]-N-(pyridin-4-yl)pyrimidin-4-amine | 1H-NMR (300 MHz, DMSO-d6): δ [ppm]= 1.25 (t, 3H), 2.79 (t, 2H), 3.51 (m, 4H), 3.70 (br. d, 1H), 4.01 (q, 2H), 4.34 (t, 2H), 5.65 (s, 2H), 6.76 (m, 2H), 7.23 (t, 1H), 7.46 (t, 1H), 7.82 (d, 1H), 8.12 (br. d, 2H), 8.35-8.45 (m, 4H), 9.08 (s, 1H). LC-MS (Method 5): retention time: 1.14 min MS ES+: 588.2 [M + H]+ |
| 4-13 SM = 3-3 | 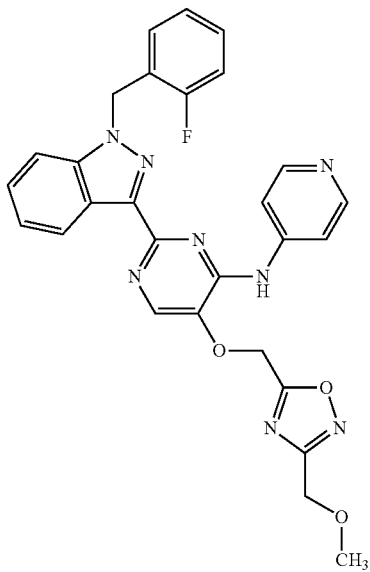 [SMILES: COCc1noc(COc2cnc(-c3nn(Cc4ccccc4F)c4ccccc34)nc2Nc2ccncc2)n1] | 2-[1-(2-fluorobenzyl)-1H-indazol-3-yl]-5-{[3-(methoxymethyl)-1,2,4-oxadiazol-5-yl]methoxy}-N-(pyridin-4-yl)pyrimidin-4-amine | 1H-NMR (300 MHz, DMSO-d6): δ [ppm] = 3.30 (s, 3H), 4.55 (s, 2H), 5.78 (s, 4H), 7.12-7.39 (m, 5H), 7.44 (br. t, 1H), 7.81 (d, 1H), 8.12 (br. d, 2H), 8.37-8.47 (m, 4H), 9.50 (s, 1H). LC-MS (Method 5): retention time: 1.20 min MS ES+: 539.3 [M + H]+ |

| | | | |
|---|---|---|---|
| 4-14 SM = 3-1 | 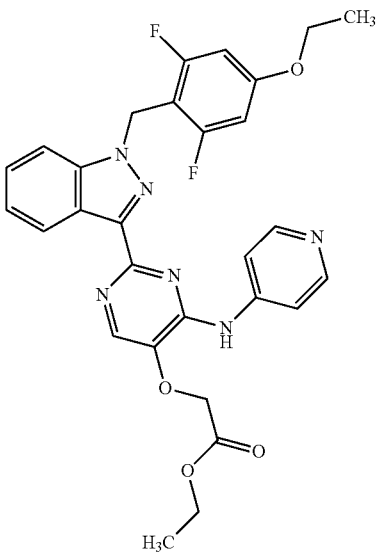 [SMILES: CCOC(=O)COc1cnc(-c2nn(Cc3c(F)cc(OCC)cc3F)c3ccccc23)nc1Nc1ccncc1] | ethyl ({2-[1-(4-ethoxy-2,6-difluorobenzyl)-1H-indazol-3-yl]-4-(pyridin-4-ylamino)pyrimidin-5-yl}oxy)acetate | LC-MS (Method 5): retention time: 1.38 min MS ES+: 561.2 [M + H]+ |
| 4-15 SM = 3-1 | 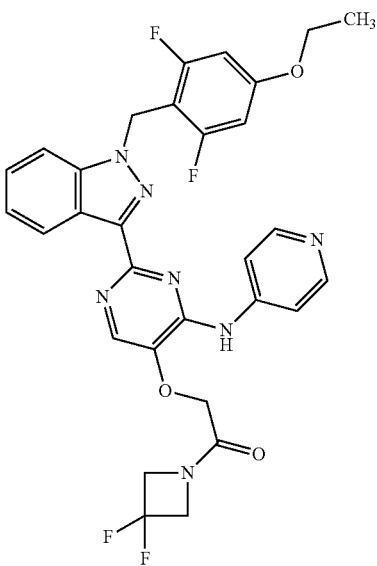 [SMILES: CCOc1cc(F)c(Cn2nc(-c3ncc(OCC(=O)N4CC(F)(F)C4)c(Nc4ccncc4)n3)c3ccccc32)c(F)c1] | 1-(3,3-difluoroazetidin-1-yl)-2-({2-[1-(4-ethoxy-2,6-difluorobenzyl)-1H-indazol-3-yl]-4-(pyridin-4-ylamino)pyrimidin-5-yl}oxy)ethanone | 1H-NMR (300 MHz, DMSO-d6): δ [ppm] = 1.25 (t, 3H), 4.01 (q, 2H), 4.39 (br. t, 2H), 4.73 (br. t, 2H), 4.98 (s, 2H), 5.66 (s, 2H), 6.76 (m, 2H), 7.23 (t, 1H), 7.46 (t, 1H), 7.82 (d, 1H), 8.17 (d, 2H), 8.30 (s, 1H), 8.38-8.45 (m, 3H), 9.56 (s, 1H). LC-MS (Method 5): retention time: 1.31 min MS ES+: 608.2 [M + H]+ |
| 4-16 SM = 3-1 | 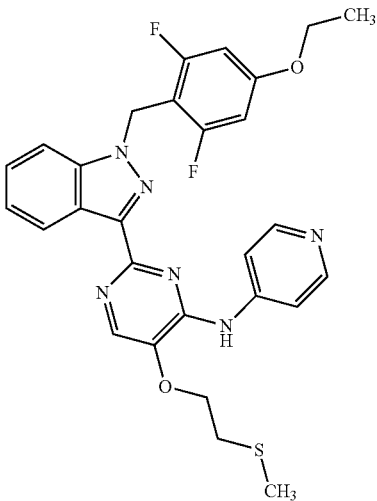 [SMILES: CCOc1cc(F)c(Cn2nc(-c3ncc(OCCSC)c(Nc4ccncc4)n3)c3ccccc32)c(F)c1] | 2-[1-(4-ethoxy-2,6-difluorobenzyl)-1H-indazol-3-yl]-5-[2-(methylsulfanyl)ethoxy]-N-(pyridin-4-yl)pyrimidin-4-amine | 1H-NMR (300 MHz, DMSO-d6): δ [ppm] = 1.25 (t, 3H), 2.15 (s, 3H), 2.96 (t, 2H), 4.01 (q, 2H), 4-39 (t, 2H), 5.56 (s, 2H), 6.76 (m, 2H), 7.23 (t, 1H), 7.46 (t, 1H), 7.82 (d, 1H), 8.12 (d, 2H), 8.37-8.45 (m, 4H), 9.11 (s, 1H). LC-MS (Method 5): retention time: 1.42 min MS ES+: 550.5 [M + H]+ |

| | | | |
|---|---|---|---|
| 4-17<br>SM =<br>3-1 | 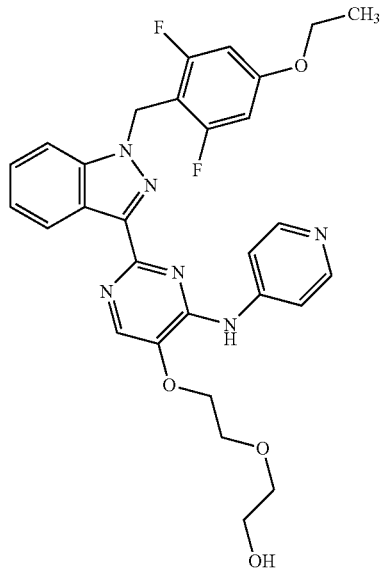 [SMILES: CCOc1cc(F)c(Cn2nc(-c3ncc(OCCOCCO)c(Nc4ccncc4)n3)c3ccccc32)c(F)c1] | 2-[2-({2-[1-(4-ethoxy-2,6-difluorobenzyl)-1H-indazol-3-yl]-4-(pyridin-4-ylamino)pyrimidin-5-yl}oxy)ethoxy]ethanol | 1H-NMR (300 MHz, DMSO-d6): δ [ppm] = 1.26 (t, 3H), 3.52 (s, 4H), 3.85 (m, 2H), 4.01 (q,2H), 4.36 (m, 2H), 4.63 (m, 1H), 5.56 (s, 2H), 6.76 (m, 2H), 7.23 (t, 1H), 7.46 (t, 1H), 7.82 (d, 1H), 8.12 (d, 2H), 8.35-8.45 (m, 4H), 9.10 (s, 1H).<br>LC-MS (Method 5): retention time: 1.24 min<br>MS ES+: 561.4 [M + H]+ |
| 4-18<br>SM =<br>3-1 | 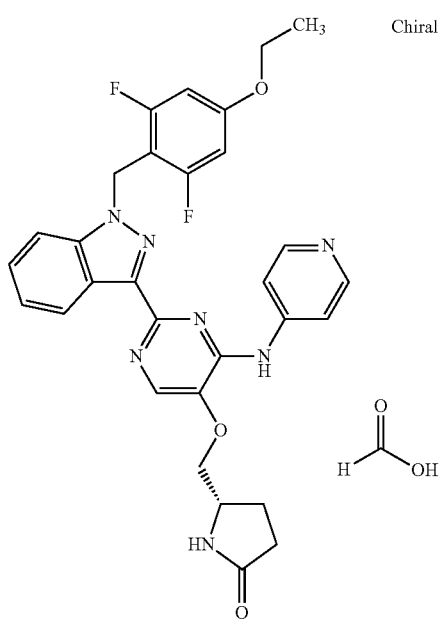 [SMILES: CCOc1cc(F)c(Cn2nc(-c3ncc(OC[C@@H]4CCC(=O)N4)c(Nc4ccncc4)n3)c3ccccc32)c(F)c1 ; O=CO] Chiral | formic acid-(5S)-5-[({2-[1-(4-ethoxy-2,6-difluorobenzyl)-1H-indazol-3-yl]-4-(pyridin-4-ylamino)pyrimidin-5-yl}oxy)methyl]pyrrolidin-2-one (1:1) | 1H-NMR (400 MHz, DMSO-d6): δ [ppm] = 1.25 (t, 3H), 1.64-1.85 (m, 1H), 2.13-2.29 (m, 3H), 3.86-4.09 (m, 4H), 4.28-4.38 (m, 1H), 5.65 (s, 2H), 6.71-6.88 (m, 2H), 7.23 (t, 1H), 7.43-7.48 (m, 1H), 7.81 (d, 1H), 8.00-8.15 (m, 3H), 8.23-8.35 (m, 2H), 8.37-8.50 (m, 3H), 8.90 (s, 1H).<br>LC-MS:<br>retention time: 0.96 min<br>MS ES+: 572.3 [M + H]+ |

| | | | |
|---|---|---|---|
| 4-19 SM = 3-1 | 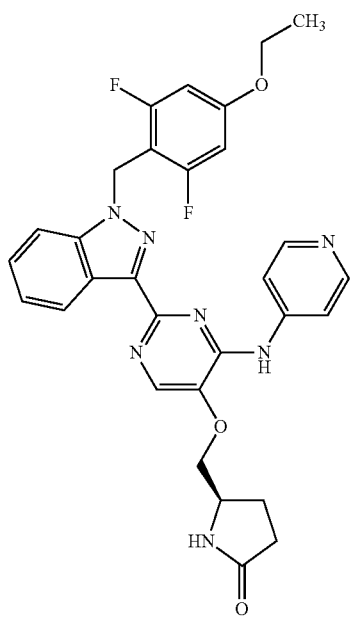 | (5R)-5-[({2-[1-(4-ethoxy-2,6-difluorobenzyl)-1H-indazol-3-yl]-4-(pyridin-4-ylamino)pyrimidin-5-yl}oxy)methyl]pyrrolidin-2-one | 1H-NMR (300 MHz, DMSO-d6): δ [ppm] = 1.26 (t, 3H), 2.14-2.28 (m, 4H), 3.88-4.06 (m, 2H), 4.01 (q, 2H), 4.32 (br. d, 1H), 5.65 (s, 2H), 6.76 (m, 2H), 7.23 (t, 1H), 7.46 (t, 1H), 7.82 (d, 1H), 8.07 (d, 2H), 8.26-8.33 (m, 2H), 8.39-8.46 (m, 3H), 8.90 (s, 1H). LC-MS (Method 5): retention time: 1.22 min MS ES+: 572.3 [M + H]+ |
| 4-20 SM = 3-3 | 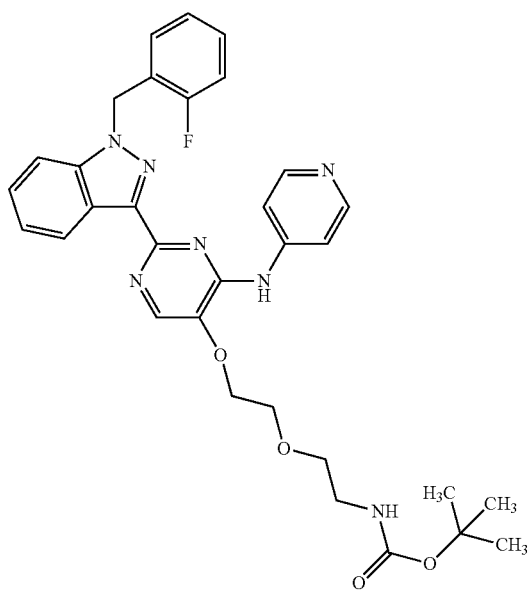 [SMILES: CC(C)(C)OC(=O)NCCOCCOc1cnc(-c2nn(Cc3ccccc3F)c3ccccc23)nc1Nc1ccncc1] | tert-butyl {2-[2-({2-[1-(2-fluorobenzyl)-1H-indazol-3-yl]-4-(pyridin-4-ylamino)pyrimidin-5-yl}oxy)ethoxy]ethyl}carbamate | 1H-NMR (400 MHz, DMSO-d6): δ [ppm] = 1.31 (s, 9H), 3.03-3.13 (m, 2H), 3.46 (t, 2H), 3.77-3.87 (m, 2H), 4.31-4.42 (m, 2H), 5.78 (s, 2H), 6.76-6.85 (m, 1H), 7.12-7.38 (m, 5H), 7.40-7.48 (m, 1H), 7.80 (d, 1H), 8.08-8.12 (m, 2H), 8.35-8.47 (m, 4H), 9.18 (s, 1H) LC-MS: retention time: 1.07 min MS ES+: 600.3 [M + H]+ |

| | | |
|---|---|---|
| 4-21 SM = 3-1 | 2-({2-[1-(4-ethoxy-2,6-difluorobenzyl)-1H-indazol-3-yl]-4-(pyridin-4-ylamino)pyrimidin-5-yl}oxy)-1-(3-fluoroazetidin-1-yl)ethanone | 1H-NMR (300 MHz, DMSO-d6): δ [ppm] = 1.25 (t, 3H), 3.90-3.97 (m, 1 H), 4.01 (q, 2H), 4.29 (m, 2H), 4.56 (m, 1H), 4.91 (s, 2H), 5.29-5.54 (m, 1H), 5.66 (s, 2H), 6.76 (m, 2H), 7.24 (t, 1H), 7.46 (t, 1H), 7.82 (d, 1H), 8.16 (d, 2H), 8.26 (s, 1H), 8.38-8.45 (m, 3H), 9.61 (s, 1H). LC-MS (Method 5): retention time: 1.29 min MS ES+: 590.4 [M + H]+ |
| 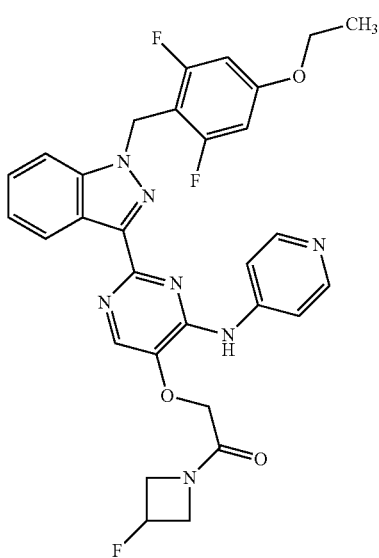 [SMILES: CCOc1cc(F)c(Cn2nc(-c3ncc(OCC(=O)N4CC(F)C4)c(Nc4ccncc4)n3)c3ccccc32)c(F)c1] | | |
| 4-22 SM = 3-1 | (5S)-5-[({2-[1-(4-ethoxy-2,6-difluorobenzyl)-1H-indazol-3-yl]-4-(pyridin-4-ylamino)pyrimidin-5-yl}oxy)methyl]pyrrolidin-2-one | 1H-NMR (300 MHz, DMSO-d6): δ [ppm] = 1.25 (t, 3H), 1.64-1.88 (m, 1H), 2.15-2.28 (m, 3H), 3.84-4.09 (m, 4H), 4.32 (dd, 1H), 5.65 (s, 2H), 6.73-6.81 (m, 2H), 7.24 (t, 1H), 7.46 (t, 1H), 7.82 (d, 1H), 8.07 (d, 2H), 8.24-8.50 (m, 5H), 8.94 (s, 1H). LC-MS: retention time: 1.21 min MS ES+: 572.3 [M + H]+ |
| 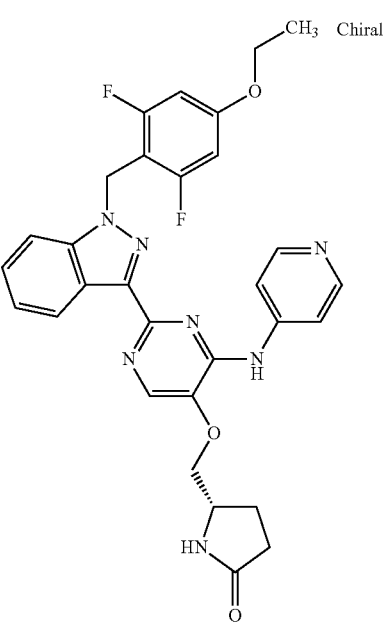 [SMILES: CCOc1cc(F)c(Cn2nc(-c3ncc(OC[C@@H]4CCC(=O)N4)c(Nc4ccncc4)n3)c3ccccc32)c(F)c1] | | |

-continued

| | | | |
|---|---|---|---|
| 4-23 SM = 3-1 | 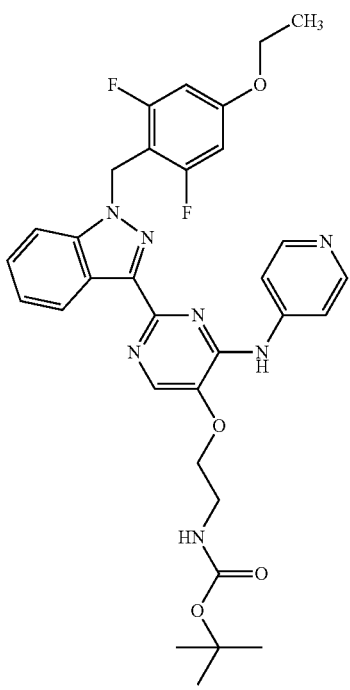 [SMILES: CCOc1cc(F)c(Cn2nc(-c3ncc(OCCNC(=O)OC(C)(C)C)c(Nc4ccncc4)n3)c3ccccc32)c(F)c1] | tert-butyl [2-({2-[1-{4-ethoxy-2,6-difluorobenzyl)-1H-indazol-3-yl]-4-(pyridin-4-ylamino)pyrimidin-5-yl}oxy)ethyl] carbamate | LC-MS (Method 5): retention time: 1.43 min MS ES+: 618.3 [M+H]+ |

35

The following compound was formed according to the same procedure using 5-chloromethyl-2-oxazolidinone and the indicated starting material (SM=starting material):

| | | |
|---|---|---|
| 4-24 SM = 3-1 | 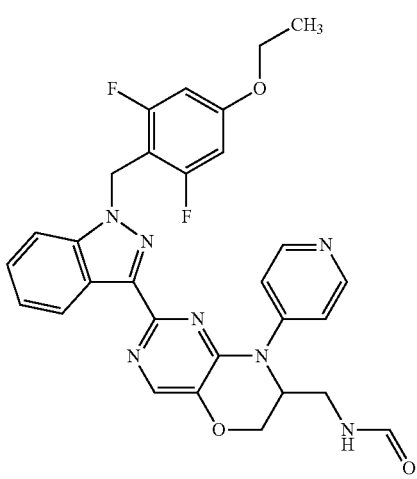 [SMILES: CCOc1cc(F)c(Cn2nc(-c3ncc4c(n3)N(c3ccncc3)C(CNC=O)CO4)c3ccccc32)c(F)c1] | N-({2-[1-(4-ethoxy-2,6-difluorobenzyl)-1H-indazol-3-yl]-8-(pyridin-4-yl)-7,8-dihydro-6H-pyrimido[5,4-b][1,4]oxazin-7-yl}methyl)formamide |

Example 5-1

Preparation of 2-[1-(4-ethoxy-2,6-difluorobenzyl)-1H-indazol-3-yl]-N-(pyridin-4-yl)pyrimidin-4-amine

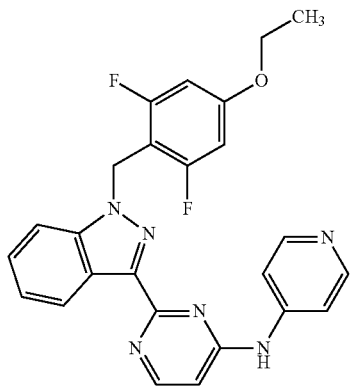 [SMILES: CCOc1cc(F)c(Cn2nc(-c3nccc(Nc4ccncc4)n3)c3ccccc32)c(F)c1]

100 mg of 2-[1-(4-ethoxy-2,6-difluorobenzyl)-1H-indazol-3-yl]-4-(pyridin-4-ylamino)pyrimidin-5-yl trifluoromethanesulfonate (1-7-2, 0.165 mmol, 1. eq.), 0.74 mg of palladium (II) acetate (0,003 mmol, 0.02 eq.) and 1.36 mg of propane-1,3-diylbis(diphenylphosphane) were dissolved in 1 ml of DMF under a nitrogen atmosphere. The mixture was heated to 60° C. bath temperature. Then 0.66 ml of triethylsilane (0.41 mmol, 2.5 eq.) were added. The resulting mixture was stirred at 60° C. bath temperature for 18 hours. Then the mixture was partitioned between saturated aq. sodium hydrogen carbonate solution and dichloromethane. The phases were separated and the aqueous layer was extracted twice with dichloromethane. The combined organic layers were washed with brine, dried over a silicone filter and concentrated in vacuo. Preparative HPLC purification provided 16 mg (0.03 mmol, 20.1%) of the analytically pure target compound.

$^1$H-NMR (300 MHz, DMSO-$d_6$): δ [ppm]=1.25 (t, 3H), 4.00 (q, 2H), 5.68 (s, 2H), 6.70-6.86 (m, 3H), 7.26 (t, 1H), 7.42-7.53 (m, 1H), 7.78-7.97 (m, 2H), 8.11 (s, 1H), 8.38 (br. s., 2H), 8.44-8.57 (m, 2H), 10.07 (s, 1H).

LC-MS:
retention time: 0.97 min
MS ES$^+$: 459.1 [M+H]$^+$

Method B

The following compounds were prepared according to the same procedure using the indicated starting materials (SM=starting material):

| | | | |
|---|---|---|---|
| 5-2 | 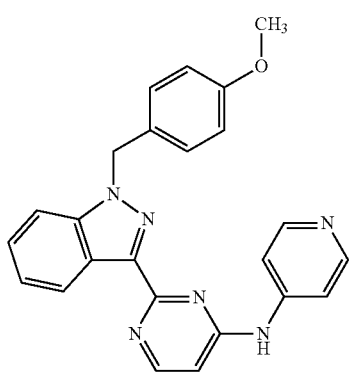 [SMILES: COc1ccc(Cn2nc(-c3nccc(Nc4ccncc4)n3)c3ccccc32)cc1] | 2-[1-(4-methoxy-benzyl)-1H-indazol-3-yl]-N-(pyridin-4-yl)pyrimidin-4-amine | $^1$H NMR (400 MHz, DMSO-$d_6$): δ [ppm] = 3.70 (s, 3H), 5.72 (s, 2H), 6.90 (d, 3H), 7.28 (t, 1H), 7.35 (d, 2H), 7.45 (t, 1H), 7.83 (d, 1H), 7.92 (br. s., 2H), 8.37-8.55 (m, 3H), 8.58 (d, 1H), 10.13 (s, 1H). LC-MS: retention time: 0.86 min MS ES$^+$: 409.1 [M + H]$^+$ Method B |
| 5-3 SM = 1-7-1 | 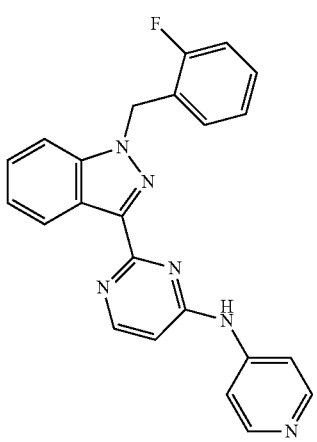 [SMILES: Fc1ccccc1Cn1nc(-c2nccc(Nc3ccncc3)n2)c2ccccc21] | 2-[1-(2-fluorobenzyl)-1H-indazol-3-yl]-N-(pyridin-4-yl)pyrimidin-4-amine | $^1$H NMR (400 MHz, DMSO-$d_6$): δ [ppm] = 5.81 (s, 2H), 6.84 (d, 1H), 7.13-7.39 (m, 5H), 7.43-7.49 (m, 1H), 7.79-7.89 (m, 3H), 8.38 (d, 2H), 8.49 (d, 1H), 8.53 (d, 1H), 10.07 (s, 1H). LC-MS: retention time: 0.93 min MS ES$^+$: 397.25 [M + H]$^+$ |

Example 6-1

Preparation of 2-[1-(4-cyclopropyl-2,6-difluorobenzyl)-1H-indazol-3-yl]-5-methoxy-N-(pyridin-4-yl)pyrimidin-4-amine

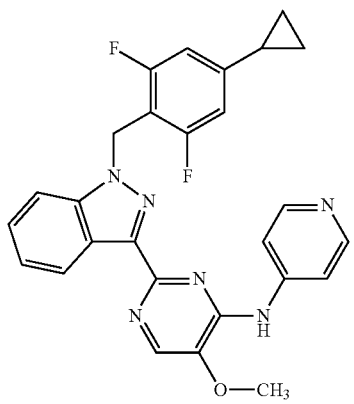 [SMILES: COc1cnc(-c2nn(Cc3c(F)cc(C4CC4)cc3F)c3ccccc23)nc1Nc1ccncc1]

100 mg of 2-[1-(4-bromo-2,6-difluorobenzyl)-1H-indazol-3-yl]-5-methoxy-N-(pyridin-4-yl)pyrimidin-4-amine (2-12-1, 0.191 mmol, 1. eq.) were suspended in 3 ml of dry toluene. 21.3 mg of cyclopropylboronic acid (0,248 mmol, 1.3 eq.) 5.36 mg of tricyclohexylphosphane (0,019 mmol, 0.1 eq.), 142 mg of potassium phosphate (0,669 mmol, 3.5 eq.) and 50 µl of water were added. Then 2.15 mg of palladium (II) acetate (0.01 mmol, 0.05 eq.) were added under a nitrogen atmosphere. The mixture was stirred at 100° C. bath temperature for 5 hours. Upon the mixture was cooled to room temperature it was partitioned between water and dichloromethane/isopropanol 4:1. The phases were separated and the aqueous layer was extracted twice with dichloromethane/isopropanol 4:1. The combined organic layers were dried over magnesium sulfate and concentrated in vacuo. Preparative HPLC purification provided 28.7 mg (0.06 mmol, 31%) of the analytically pure target compound.

$^1$H-NMR (400 MHz, DMSO-$d_6$): δ [ppm]=0.66-0.74 (m, 2H), 0.89-0.98 (m, 2H), 1.93 (m, 1H), 4.00 (s, 3H), 5.67 (s, 2H), 6.85-6.92 (m, 2H), 7.23 (t, 1H), 7.46 (t, 1H), 7.83 (d, 1H), 8.13-8.20 (m, 2H), 8.32 (s, 1H), 8.34-8.40 (m, 2H), 8.43 (d, 1H), 9.41 (s, 1H).

LC-MS:
retention time: 1.06 min
MS ES$^+$: 485.1 [M+H]$^+$

Method B

The following compounds were prepared according to the same procedure using the indicated starting materials (SM=starting material):

| | | | |
|---|---|---|---|
| 6-2<br>SM =<br>2-12-1 | 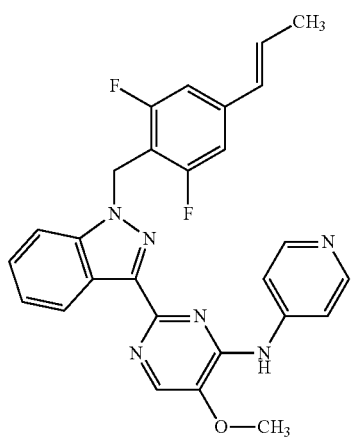 [SMILES: C/C=C/c1cc(F)c(Cn2nc(-c3ncc(OC)c(Nc4ccncc4)n3)c3ccccc32)c(F)c1] | 2-(1-{2,6-difluoro-4-[(1E)-prop-1-en-1-yl]benzyl}-1H-indazol-3-yl)-5-methoxy-N-(pyridin-4-yl)pyrimidin-4-amine | $^1$H NMR (400 MHz, DMSO-$d_6$): δ [ppm] = 1.82 (d, 3H), 4.03 (s, 3H), 5.73 (s, 2H), 6.33-6.55 (m, 2H), 7.17-7.30 (m, 3H), 7.45-7.53 (m, 1H), 7.86 (d, 1H), 8.14-8.22 (m, 2H), 8.34 (s, 1H), 8.37-8.42 (m, 2H), 8.46 (d, 1H), 9.40 (s, 1H).<br>LC-MS:<br>retention time: 8.67 min<br>MS ES$^+$: 485.1 [M + H]$^+$ |

Example 7-1

Preparation of 1-[3,5-difluoro-4-({3-[5-methoxy-4-(pyridin-4-ylamino)pyrimidin-2-yl]-1H-indazol-1-yl}methyl)phenyl]ethanone

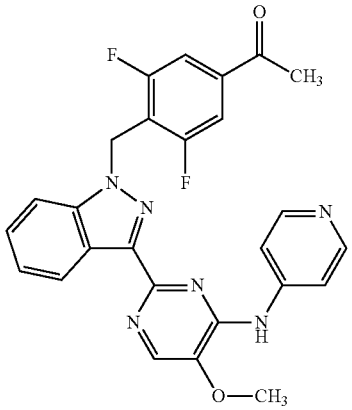 [SMILES: COc1cnc(-c2nn(Cc3c(F)cc(C(C)=O)cc3F)c3ccccc23)nc1Nc1ccncc1]

Step 1: 2-{1-[4-(1-ethoxyethenyl)-2,6-difluorobenzyl]-1H-indazol-3-yl}-5-methoxy-N-(pyridin-4-yl)pyrimidin-4-amine 100 mg of 2-[1-(4-bromo-2,6-difluorobenzyl)-1H-indazol-3-yl]-5-methoxy-N-(pyridin-4-yl)pyrimidin-4-amine (2-12-1, 0,191 mmol, 1 eq.) was suspended in dry toluol. 1.34 mg of dichloropalladium-triphenylphosphane (1:2) (0,002 mmol, 0.01 eq.) and 71 µl of tributyl(1-ethoxyethenyl)stannane (0.21 mmol, 1.2 eq.) were added. The mixture was stirred for 5 hours at 100° C. bath temperature and for 18 hours at 120'C bath temperature. 5 mg of dichloropalladium-triphenylphosphane (1:2) (0,007 mmol, 0.035 eq.) and 140 µl of tributyl(1-ethoxyethenyl)stannane (0.42 mmol, 2.4 eq.) and 1 ml of 1-methylpyrrolidin-2-one were added. The solution was stirred for 3 days at 100'C bath temperature. 5 mg of dichloropalladium-triphenylphosphane (1:2) (0,007 mmol, 0.035 eq.) and 140 µl of tributyl(1-ethoxyethenyl)stannane (0.42 mmol, 2.4 eq.) were added and stirred at 100° C. again for 22 hours. The reaction mixture was concentrated in vacuo and purified by flash chromatography to yield 119 mg (0.2 mmol, 107%) of the analytically pure target compound.

$^1$H-NMR (300 MHz, DMSO-d6): δ [ppm]=1.25-1.33 (t, 3H), 3.78-3.89 (m, 2H), 4.00 (s, 3H), 4.34-4.41 (d, 1H), 4.91-4.97 (d, 1H), 5.74 (s, 2H), 7.24 (t, 1H), 7.37 (d, 1H), 7.43-7.64 (m, 2H), 7.84 (d, 1H), 8.09-8.18 (dd, 2H), 8.32 (s, 1H), 8.34-8.39 (dd, 2H), 8.44 (d, 1H), 9.32-9.41 (s, 1H).
LC-MS:
retention time: 1.09 min
MS ES$^+$: 515.1 [M+H]$^+$ Method B Step 2: 1-[3,5-difluoro-4-({3-[5-methoxy-4-(pyridin-4-ylamino)pyrimidin-2-yl]-1H-indazol-1-yl})methyl)phenyl]ethanone 119 mg of 2-{1-[4-(1-ethoxyethenyl)-2,6-difluorobenzyl]-1H-indazol-3-yl}-5-methoxy-N-(pyridin-4-yl)pyrimidin-4-amine (0,231 mmol, 1 eq.) and 66 mg of 4-methylbenzenesulfonic acid hydrate (1:1) (0,347 mmol, 1.5 eq.) were dissolved in 2.4 ml of ethanol and 0.6 ml of water. The mixture was stirred for one hour at 80'C bath temperature. The reaction mixture was concentrated in vacuo. The residue was partitioned between ethyl acetate and saturated sodium hydrogen carbonate solution. The phases were separated and the aqueous layer was extracted twice with ethyl acetate. The combined organic layers were dried over magnesium sulfate and concentrated in vacuo. The residue was purified by flash chromatography and preparative HPLC purification to yield 26 mg (0.05 mmol, 22.7%) of the analytically pure target compound.

$^1$H-NMR (300 MHz, DMSO-d$_6$): δ [ppm]=2.54 (s, 3H), 4.00 (s, 3H), 5.82 (s, 2H), 7.25 (t, 1H), 7.49 (t, 1H), 7.69 (d, 2H), 7.87 (d, 1H), 8.14 (d, 2H), 8.31 (s, 1H), 8.37 (d, 2H), 8.44 (d, 1H), 9.38 (s, 1H).
LC-MS:
retention time: 0.95 min
MS ES$^+$: 487.1 [M+H]$^+$ Method B

Example 8-1

Preparation of [2,4-dichloro-3-({3-[5-methoxy-4-(pyridin-4-ylamino)pyrimidin-2-yl]-1H-indazol-1-yl}methyl)phenyl]methanol

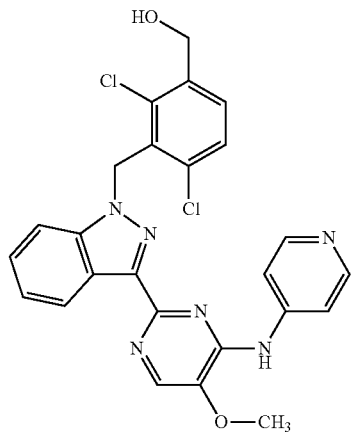 [SMILES: COc1cnc(-c2nn(Cc3c(Cl)ccc(CO)c3Cl)c3ccccc23)nc1Nc1ccncc1]

80 mg of methyl 2,4-dichloro-3-({3-[5-methoxy-4-(pyridin-4-ylamino)pyrimidin-2-yl]-1H-indazol-1-yl}methyl)benzoate (2-16-1, 0.149 mmol, 1. eq.) was suspended in 2.4 ml of dry tetrahydrofuran under nitrogen atmosphere. The suspension was cooled with an ice bath to +3° C., upon which 254 µl of a 1 M lithium aluminium hydride solution in tetrahydrofuran (0,254 mmol, 1.7 eq.) were added dropwise. The ice bath was remove and the mixture was stirred at room temperature for 30 minutes. Then the mixture was acidified by 2 M sulfuric acid. The mixture formed a suspension which was filtered off and washed with water. The precipitate was dried in vacuo at 60° C. for 18 hours to yield 60 mg (0.11 mmol, 74.4%) of the analytically pure target compound.

$^1$H-NMR (300 MHz, DMSO-d$_6$): δ [ppm]=4.02 (s, 3H), 4.51 (s, 2H), 5.47-5.57 (m, 1H), 5.90 (s, 2H), 7.26 (t, 1H), 7.49 (t, 1H), 7.54-7.67 (m, 2H), 7.91 (d, 1H), 8.34-8.41 (m, 2H), 8.42-8.49 (m, 4H), 9.98 (s, 1H).
LC-MS:
retention time: 0.91 min
MS ES$^+$: 507.3 [M+H]$^+$ Method B The following compounds were prepared according to the same procedure using the indicated starting materials (SM=starting material):

| | | | |
|---|---|---|---|
| 8-2<br>SM =<br>2-35-1 | 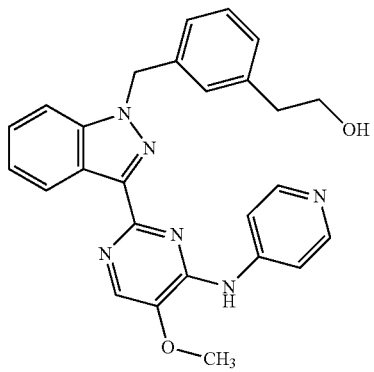 [SMILES: COc1cnc(-c2nn(Cc3cccc(CCO)c3)c3ccccc23)nc1Nc1ccncc1] | 2-[3-({3-[5-methoxy-4-(pyridin-4-ylamino)pyrimidin-2-yl]-1H-indazol-1-yl}methyl)phenyl]ethanol | $^1$H-NMR (300 MHz, DMSO-$d_6$): δ [ppm] = 2.59-2.67 (m, 2H), 3.51 (d, 2H), 4.02 (s, 3H), 4.58 (s, 1H), 5.69 (s, 2H), 7.06-7.14 (m, 2H), 7.16-7.26 (m, 3H), 7.40 (t, 1H), 7.77 (d, 1H), 8.12 (dd, 2H), 83.1-8.46 (m, 4H), 9.42 (s, 1H).<br>LC-MS:<br>retention time: 0.87 min<br>MS ES$^+$: 453.22<br><br>[M + H]$^+$ |
| 8-3<br>SM =<br>2-41-1 | 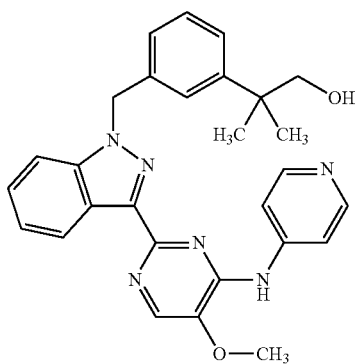 [SMILES: COc1cnc(-c2nn(Cc3cccc(C(C)(C)CO)c3)c3ccccc23)nc1Nc1ccncc1] | 2-[3-({3-[5-methoxy-4-(pyridin-4-ylamino)pyrimidin-2-yl]-1H-indazol-1-yl}methyl)phenyl]-2-methylpropan-1-ol | $^1$H-NMR (300 MHz, DMSO-$d_6$): δ [ppm] = 1.13 (s, 6H), 4.05 (s, 3H), 4.57-4.66 (m, 1H), 5.69-5.76 (m, 4H), 7.03 (d, 1H), 7.15-7.27 (m, 3H), 7.37-7.48 (m, 2H), 7.79 (d, 1H), 8.32-8.54 (m, 6H), 9.97-10.04 (m, 1H).<br>LC-MS:<br>retention time: 0.87 min<br>MS ES$^+$: 481.4<br><br>[M + H]$^+$<br>Method B |
| 8-4<br>SM =<br>39-1 | 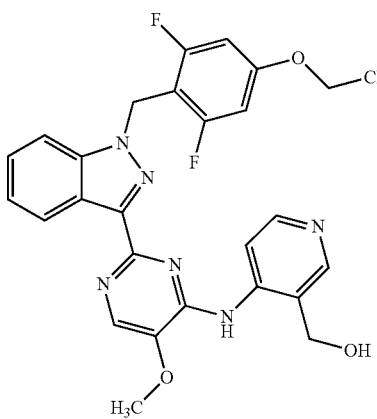 | [4-({2-[1-(4-ethoxy-2,6-difluorobenzyl)-1H-indazol-3-yl]-5-methoxypyrimidin-4-yl}amino)pyridin-3-yl]methanol | 1H-NMR (300 MHz, DMSO-d6): δ [ppm] = 1.25 (t, 3H), 3.99 (s, 3H), 4.01 (q, 2H), 4.67 (d, 2H), 5.64 (s, 2H), 5.96 (t, 1H), 6.76 (m, 2H), 7.23 (t, 1H), 7.45 (t, 1H), 7.81 (d, 1H), 8.32-8.44 (m, 4H), 8.82 (d, 1H), 9.52 (s, 1H).<br>LC-MS (Method 1):<br>retention time: 1.03 min<br>MS ES$^+$: 481.4<br>[M + H]$^+$ |

Example 9-1

Preparation of 2-[3-chloro-4-({3-[5-methoxy-4-(pyridin-4-ylamino)pyrimidin-2-yl]-1H-indazol-1-yl}methyl)phenyl]propan-2-ol

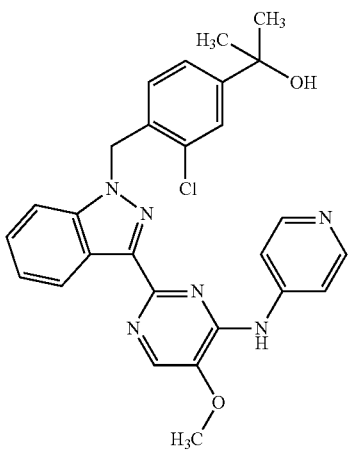 [SMILES: COc1cnc(-c2nn(Cc3ccc(C(C)(C)O)cc3Cl)c3ccccc23)nc1Nc1ccncc1]

36 mg of methyl 3-chloro-4-({3-[5-methoxy-4-(pyridin-4-ylamino)pyrimidin-2-yl]-1H-indazol-1-yl}methyl)benzoate (2-11-1, 0.072 mmol, 1. eq.) were suspended in 583 µl of dry tetrahydrofuran under nitrogen atmosphere. The suspension was cooled with a freezing mixture to −75° C. Then 90 µl of 1.6 M methyllithium solution in diethyl ether (0,144 mmol, 2 eq.) were added dropwise. The freezing mixture was removed and the reaction mixture was stirred at room temperature for 24 hours. The reaction mixture was cooled with a freezing mixture to −75° C. 90 µl of 1.6 M methyllithium solution in diethyl ether (0,144 mmol, 2 eq.) were added dropwise again. The freezing mixture was removed and the reaction mixture was stirred at room temperature for further 24 hours. Then the mixture was partitioned between water and dichloromethane/isopropanol 4:1. The phases were separated and the aqueous layer was extracted twice with dichloromethane/isopropanol 4:1. The combined organic layers were washed with brine, dried over a silicone filter and concentrated in vacuo. The residue was purified by preparative TLC to yield 3.5 mg (0.01 mmol, 9.3%) of the analytically pure target compound.

$^1$H-NMR (400 MHz, DMSO-$d_6$): δ [ppm]=1.34 (s, 6H), 4.01 (s, 3H), 5.11 (s, 1H), 5.77 (s, 2H), 7.13 (d, 1H), 7.21-7.27 (m, 1H), 7.34 (dd, 1H), 7.44 (ddd, 1H), 7.54 (d, 1H), 7.79 (d, 1H), 8.10-8.15 (m, 2H), 8.34 (s, 1H), 8.35-8.40 (m, 2H), 8.46 (d, 1H), 9.41 (s, 1H).

LC-MS:
retention time: 0.99 min
MS ES$^+$: 501.2 [M+H]$^+$

The following compounds were prepared according to the same procedure using the indicated starting materials (SM=starting material):

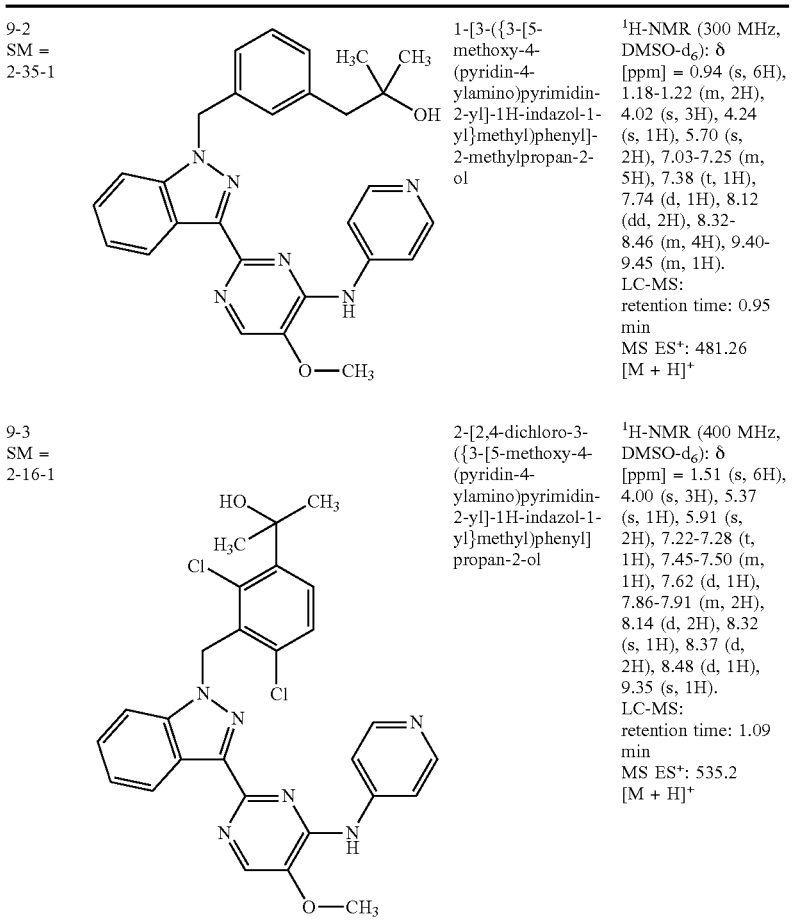

| | | | |
|---|---|---|---|
| 9-2 SM = 2-35-1 | | 1-[3-({3-[5-methoxy-4-(pyridin-4-ylamino)pyrimidin-2-yl]-1H-indazol-1-yl}methyl)phenyl]-2-methylpropan-2-ol | $^1$H-NMR (300 MHz, DMSO-$d_6$): δ [ppm] = 0.94 (s, 6H), 1.18-1.22 (m, 2H), 4.02 (s, 3H), 4.24 (s, 1H), 5.70 (s, 2H), 7.03-7.25 (m, 5H), 7.38 (t, 1H), 7.74 (d, 1H), 8.12 (dd, 2H), 8.32-8.46 (m, 4H), 9.40-9.45 (m, 1H). LC-MS: retention time: 0.95 min MS ES$^+$: 481.26 [M + H]$^+$ |
| 9-3 SM = 2-16-1 | | 2-[2,4-dichloro-3-({3-[5-methoxy-4-(pyridin-4-ylamino)pyrimidin-2-yl]-1H-indazol-1-yl}methyl)phenyl]propan-2-ol | $^1$H-NMR (400 MHz, DMSO-$d_6$): δ [ppm] = 1.51 (s, 6H), 4.00 (s, 3H), 5.37 (s, 1H), 5.91 (s, 2H), 7.22-7.28 (t, 1H), 7.45-7.50 (m, 1H), 7.62 (d, 1H), 7.86-7.91 (m, 2H), 8.14 (d, 2H), 8.32 (s, 1H), 8.37 (d, 2H), 8.48 (d, 1H), 9.35 (s, 1H). LC-MS: retention time: 1.09 min MS ES$^+$: 535.2 [M + H]$^+$ |

Example 10-1

Preparation of 5-(difluoromethoxy)-2-[1-(4-ethoxy-2,6-difluorobenzyl)-1H-indazol-3-yl]-N-(pyridin-4-yl)pyrimidin-4-amine

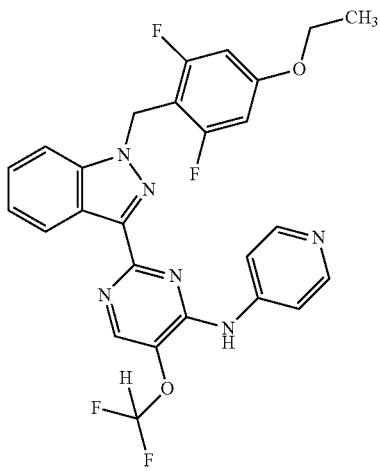 [SMILES: CCOc1cc(F)c(Cn2nc(-c3ncc(OC(F)F)c(Nc4ccncc4)n3)c3ccccc32)c(F)c1]

100 mg of 2-[1-(4-ethoxy-2,6-difluorobenzyl)-H-indazol-3-yl]-4-(pyridin-4-ylamino)pyrimidin-5-ol (3-1, 0.211 mmol, 1. eq.) were suspended in 843 µl of 30% aq. potassium hydroxide solution (5.72 mmol, 27 eq.) and 843 µl of acetonitrile. The suspension was cooled with a freezing mixture to −75° C. 93 µl of 2-chloro-2,2-difluoro-1-phenylethanone (0,632 mmol, 3 eq.) were added dropwise. The freezing mixture was removed. The reaction mixture was stirred at 80° C. bath temperature for 4 hours. Then the mixture was partitioned between water and dichloromethane/isopropanol 4:1. The phases were separated and the aqueous layer was extracted twice with dichloromethane/isopropanol 4:1. The combined organic layers were washed with brine, dried over a silicone filter and concentrated in vacuo. Preparative HPLC purification provided 4 mg (0.01 mmol, 3.2%) of the analytically pure target compound.

$^1$H-NMR (500 MHz, DMSO-$d_6$): δ [ppm]=1.30 (t, 3H), 4.05 (q, 2H), 5.73 (s, 2H), 6.81 (d, 2H), 7.16-7.48 (m, 2H), 7.50-7.57 (m, 1H), 7.90 (d, 1H), 8.12-8.17 (m, 2H), 8.44-8.49 (m, 3H), 8.54 (s, 1H), 9.71 (s, 1H).

LC-MS:

retention time: 1.65 min

MS ES$^+$: 525.02 [M+H]$^+$

The following compounds were also formed during the same procedure:

| | | | |
|---|---|---|---|
| 10-2 SM = 3-1 | (structure) | 5-(difluoromethoxy)-N-(difluoromethyl)-2-[1-(4-ethoxy-2,6-difluorobenzyl)-1H-indazol-3-yl]-N-(pyridin-4-yl)pyrimidin-4-amine | $^1$H-NMR (300 MHz, DMSO-$d_6$): δ [ppm] = 1.25 (t, 3H), 4.00 (q, 2H), 5.65 (s, 2H), 6.72 (d, 2H), 6.91 (d, 1H), 7.16-7.25 (m, 1H), 6.97-7.47 (t, 2H), 7.34-7.60 (m, 2H), 7.76 (d, 1H), 7.91 (d, 2H), 8.36 (d, 1H), 8.46 (s, 1H). LC-MS: retention time: 1.15 min MS ES$^+$: 575.1 [M + H]$^+$ |
| 10-3 SM = 3-1 | (structure) | 4-[(difluoromethyl)(pyridin-4-yl)amino]-2-[1-(4-ethoxy-2,6-difluorobenzyl)-1H-indazol-3-yl]pyrimidin-5-ol | 1H-NMR (600 MHz, DMSO-d6): δ [ppm]= 1.29 (t, 4H), 4.04 (q, 3H), 5.63 (s, 2H), 6.71-6.79 (m, 2H), 7.04 (br. s., 1H), 7.20 (t, 1H), 7.44 (td, 1H), 7.49-7.71 (m, 1H), 7.74 (d, 1H), 7.91 (d, 2H), 8.15 (s, 1H), 8.41 (s, 1H). LC-MS: retention time: 1.10 min MS ES+: 525.0 [M + H]+ |

Example 11-1

Preparation of 2-[1-(4-methoxybenzyl)-1H-indazol-3-yl]-N-(pyridin-4-yl)-5-(2,2,2-trifluoroethoxy)pyrimidin-4-amine

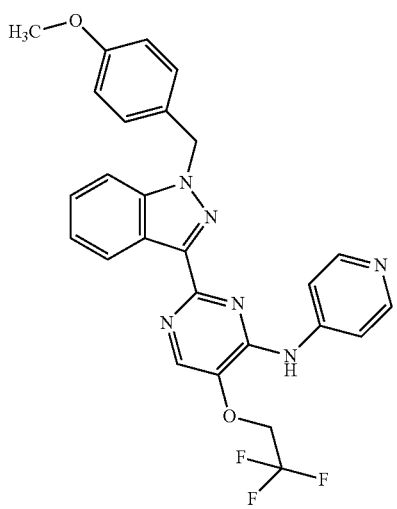 [SMILES: COc1ccc(Cn2nc(-c3ncc(OCC(F)(F)F)c(Nc4ccncc4)n3)c3ccccc32)cc1]

143 mg of 2-[1-(4-methoxybenzyl)-1H-indazol-3-yl]-4-(pyridin-4-ylamino)pyrimidin-5-ol (3-2, 0.337 mmol, 1. eq.) were dissolved in 500 μl of dry DMF. Then 117 mg of 2,2,2-trifluoroethyl trifluoromethanesulfonate (0,505 mmol, 1.5 eq.), 93.1 mg of potassium carbonate (0,674 mmol, 2 eq.) and 24 μl of acetonitrile were added. The resulting mixture was stirred at 150° C. for 30 minutes in a microwave. Then the mixture was partitioned between water and dichloromethane/isopropanol 4:1. The phases were separated and the aqueous layer was extracted twice with dichloromethane/isopropanol 4:1. The combined organic layers were washed with brine, dried over a silicone filter and concentrated in vacuo. The residue was purified by flash chromatography and preparative TLC to yield 7.7 mg (0.01 mmol, 3.9%) of the analytically pure target compound.

$^1$H-NMR (300 MHz, DMSO-$d_6$): δ [ppm]=3.66 (s, 3H), 4.95-5.08 (m, 2H), 5.65 (s, 2H), 6.83-6.90 (m, 2H), 7.16-7.24 (m, 1H), 7.30 (d, 2H), 7.36-7.45 (m, 1H), 7.78 (d, 1H), 8.00-8.11 (m, 2H), 8.35-8.52 (m, 4H), 9.32 (s, 1H).

LC-MS:
retention time: 1.03 min
MS ES+: 507.1 [M+H]+

Method B

The following compounds were prepared according to the same procedure using the indicated starting materials (SM=starting material):

| | | | |
|---|---|---|---|
| 11-2<br>SM =<br>3 -1 | 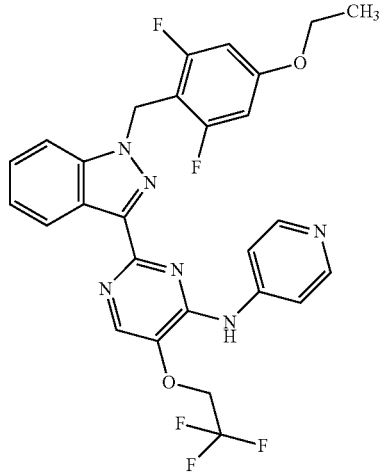 [SMILES: CCOc1cc(F)c(Cn2nc(-c3ncc(OCC(F)(F)F)c(Nc4ccncc4)n3)c3ccccc32)c(F)c1] | 2-[1-(4-ethoxy-2,6-difluorobenzyl)-1H-indazol-3-yl]-N-(pyridin-4-yl)-5-(2,2,2-trifluoroethoxy)pyrimidin-4-amine | $^1$H-NMR (400 MHz, DMSO-$d_6$): δ [ppm] = 1.28 (t, 3H), 4.04 (q, 2H), 5.03 (q, 2H), 5.69 (s, 2H), 6.79 (d, 2H), 7.22-7.30 (m, 1H), 7.49 (ddd, 1H), 7.85 (d, 1H), 8.10-8.16 (m, 2H), 8.40-8.46 (m, 3H), 8.50 (s, 1H), 9.32 (s, 1H).<br>LC-MS:<br>retention time: 1.11 min<br>MS ES+: 557.1 [M + H]+<br>Method B |

Example 12-1

Preparation of 3-({2-[1-(2-fluorobenzyl)-1H-indazol-3-yl]-4-(pyridin-4-ylamino)pyrimidin-5-yl}oxy)propane-1,2-diol

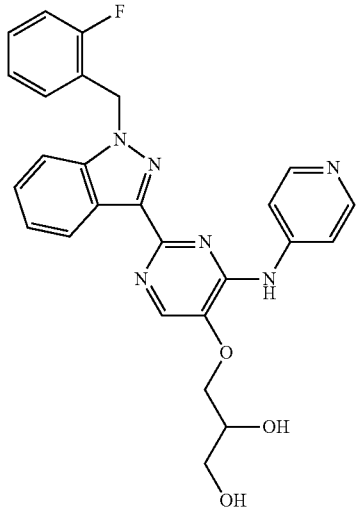 [SMILES: OCC(O)COc1cnc(-c2nn(Cc3ccccc3F)c3ccccc23)nc1Nc1ccncc1]

25.0 mg of 2-[1-(2-fluorobenzyl)-1H-indazol-3-yl]-4-(pyridin-4-ylamino)pyrimidin-5-ol (3-3, 0.06 mmol, 1 eq.), 28.2 mg of 3-bromo-propane-1,2-diol (0.18 mmol, 3 eq.) and 41.9 mg of potassium carbonate (0.30 mmol, 5 eq.) were suspended in 466 µl of dry DMF. The reaction mixture was stirred at 100 Cc oil bath temperature for 18 hours. Then the mixture was partitioned between half saturated aq. sodium chloride solution and ethyl acetate. The phases were separated and the aqueouse layer was extracted once more with ethyl acetate and once with dichloromethane/isopropanol 4:1. The combined organic layers were dried over magnesium sulfate and concentrated in vacuo. The residue was purified by preparative thin layer chromatography to yield 2.60 mg (5.34 µmol, 9%) of the analytically pure target compound.

LC-MS:
retention time: 1.00 min
MS ES$^+$: 487.41 [M+H]$^+$

Example 12-2

Preparation of (2R)-3-({2-[1-(2-fluorobenzyl)-1H-indazol-3-yl]-4-(pyridin-4-ylamino)pyrimidin-5-yl}oxy)propane-1,2-diol

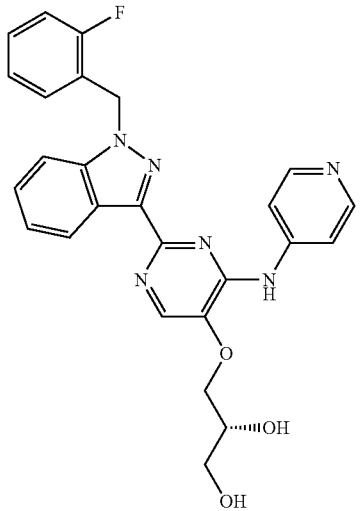 [SMILES: OC[C@@H](O)COc1cnc(-c2nn(Cc3ccccc3F)c3ccccc23)nc1Nc1ccncc1]

Step 1: 5-{[(4S)-2,2-dimethyl-1,3-dioxolan-4-yl]methoxy}-2-[1-(2-fluorobenzyl)-1H-indazol-3-yl]-N-(pyridin-4-yl)pyrimidin-4-amine 200 mg of 2-[1-(2-fluorobenzyl)-1H-indazol-3-yl]-4-(pyridin-4-ylamino)pyrimidin-5-ol (3-3, 0.49 mmol, 1 eq.), 94.6 mg of 2,2-dimethyl-4(R)-4-bromomethyl-1,3-dioxalane (0.49 mmol, 1 eq.) and 134 mg of potassium carbonate (0.97 mmol, 2 eq.) were suspended in 3.7 ml of dry DMF. The reaction mixture was stirred at 50° C. oil bath temperature for 18 hours. 201 mg of potassium carbonate (1.46 mmol, 3 eq.) were added and the mixture was stirred at 90° C. oil bath temperature for further 24 hours. Then the mixture was partitioned between half saturated aq. ammonium chloride solution and dichloromethane/isopropanol 4:1. The phases were separated and the aqueous layer was extracted twice with dichloromethane/isopropanol 4:1. The combined organic layers were washed with brine, dried over a silicone filter and concentrated in vacuo. The residue was purified by flash chromatography to yield 126 mg (0.27 mmol, 44%) of the analytically pure target compound.

$^1$H-NMR (400 MHz, DMSO-d$_6$): δ [ppm]=1.29 (s, 3H), 1.34 (s, 3H), 3.86 (dd, 1H), 4.15 (dd, 1H), 4.27 (dd, 2H), 4.54 (m, 1H), 5.78 (s, 2H), 7.12-7.38 (m, 5H), 7.40-7.47 (m, 1H), 7.80 (d, 1H), 8.04-8.09 (m, 2H), 8.38-8.46 (m, 4H), 9.11 (s, 1H).

LC-MS:
retention time: 1.00 min
MS ES$^+$: 527.39 [M+H]$^+$

Step 2: (2R)-3-({2-[1-(2-fluorobenzyl)-1H-Indazol-3-yl]-4-(pyridine-4-ylamino)pyrimidin-5-yl}oxy)propane-1,2-diol hydrochloride (1:1)

124 mg of 5-{[(4S)-2,2-dimethyl-1,3-dioxolan-4-yl]methoxy}-2-[1-(2-fluorobenzyl)-1H-indazol-3-yl]-N-(pyridin-4-yl)pyrimidin-4-amine (0.24 mmol, 1. eq.) were dissolved in 12 ml of acetonitrile. 515 µl of conc. hydrogen chloride (6.00 mmol, 20.8 eq.) were added dropwise. The reaction mixture was stirred at room temperature for 18 hours. The suspension was filtered off and washed with acetonitrile. The precipitate was dried at 45° C. under vacuo to yield 119 mg (0.23 mmol, 97%) of the analytically pure target compound.

$^1$H-NMR (600 MHz, DMSO de): δ [ppm]=3.49 (m, 2H), 3.94 (m, 1H), 4.14 (dd, 1H), 4.34 (dd, 1H), 4.73 (br. s, 2H), 5.82 (s, 2H), 7.15 (td, 1H), 7.19-7.30 (m, 2H), 7.34 (m, 1H), 7.46 (td, 1H), 7.49 (ddd, 1H), 7.80 (d, 1H), 8.41 (d, 1H), 8.58 (s, 1H), 8.65 (d, 2H), 8.75 (d, 2H), 10.72 (s, 1H), 14.82 (br. s., 1H).

LC-MS:
retention time: 0.86 min
MS ES$^+$: 487.34 [M+H]$^+$

Step 3: (2R)-3-({2-[1-(2-fluorobenzyl)-1H-indazol-3-yl]-4-(pyridin-4-ylamino)pyrimidin-5-yl}oxy)propane-1,2-diol 84.5 mg of (2R)-3-({2-[1-(2-fluorobenzyl)-1H-indazol-3-yl]-4-(pyridin-4-ylamino)pyrimidin-5-yl}oxy)propane-1,2-diol hydrochloride (1:1) was dissolved in water. 2M aq. sodium hydroxide solution was added. The mixture was stirred at room temperature for 3 hours. The resulting suspension was filtered off and washed with water to yield 52.9 mg (0.11 mmol, 67%) of the analytically pure target compound.

$^1$H-NMR (300 MHz, DMSO-d$_6$): δ [ppm]=3.50 (d, 2H), 3.85-3.97 (m, 1H), 4.01-4.13 (m, 1H), 4.23-4.30 (m, 1H), 4.79 (s, 1H), 5.20-5.27 (m, 1H), 5.78 (s, 2H), 7.11-7.39 (m, 5H), 7.44 (t, 1H), 7.80 (d, 1H), 7.99-8.07 (m, 2H), 8.33 (s, 1H), 8.39-8.46 (m, 3H), 9.14 (s, 1H).

LC-MS (chiral):
retention time: 0.85 min
MS ES$^+$: 487.35 [M+H]$^+$

The following enatiomer was prepared according to the same procedure using the indicated starting material (SM=starting material) and 2,2-dimethyl-4(S)-4-bromomethyl-1,3-dioxalane:

| 12-3 SM = 3-3 | 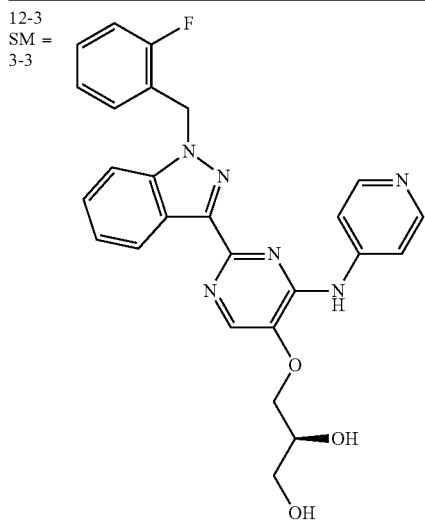 | (2S)-3-({2-[1-(2-fluorobenzyl)-1H-indazol-3-yl]-4-(pyridin-4-ylamino)pyrimidin-5-yl}oxy)propane-1,2-diol | $^1$H-NMR (300 MHz, DMSO-d$_6$): δ [ppm] = 3.50 (d, 2H), 3.86-3.98 (m, 1H), 4.08 (s, 1H), 4.19-4.30 (m, 1H), 4.79 (s, 1H), 5.25 (d, 1H), 5.78 (s, 2H), 7.11-7.39 (m, 5H), 7.44 (t, 1H), 7.80 (d, 1H), 8.01-8.07 (m, 2H), 8.33 (s, 1H), 8.39-8.47 (m, 3H), 9.14 (s, 1H). LC-MS (chiral): retention time: 0.90 min MS ES$^+$: 487.21 [M + H]$^+$ |

Example 13-1

Preparation of 2-({2-[1-(4-ethoxy-2,6-difluorobenzyl)-1H-indazol-3-yl]-4-(pyridin-4-ylamino)pyrimidin-5-yl}oxy)ethanol

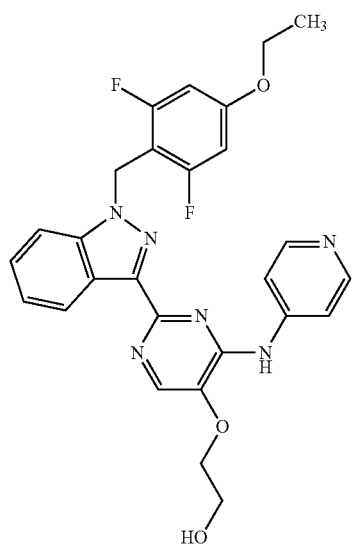 [SMILES: CCOc1cc(F)c(Cn2nc(-c3ncc(OCCO)c(Nc4ccncc4)n3)c3ccccc32)c(F)c1]

Step 1

182 mg of 2-[1-(4-ethoxy-2,6-difluorobenzyl)-1H-indazol-3-yl]-4-(pyridin-4-ylamino)pyrimidin-5-ol (3-1, 0,383 mmol, 1 eq.), 110 mg of (2-bromoethoxy)(tertbutyl)dimethylsilane (0,459 mmol, 1.2 eq.) and 159 mg of potassium carbonate were suspended in 3 ml of dry DMF under nitrogen atmosphere and stirred for 3 days at room temperature. Then the mixture was partitioned between water and dichloromethane. The phases were separated and the aqueous layer was extracted twice with dichloromethane. The combined organic layers were washed with half saturated aq. sodium chloride solution, dried over a silicone filter and concentrated in vacuo to yield 224 mg (0.32 mmol, 82.3%) of the analytically pure target compound.

$^1$H-NMR (300 MHz, DMSO-d$_6$): δ [ppm]=0.00 (s, 6H), 0.79 (s, 9H), 1.25 (t, 3H), 4.01 (d, 4H), 4.30-4.39 (m, 2H), 5.65 (s, 2H), 6.77 (d, 2H), 7.23 (t, 1H), 7.46 (t, 1H), 7.82 (d, 1H), 8.07-8.14 (m, 2H), 8.34-8.45 (m, 4H), 9.07-9.14 (m, 1H).

LC-MS:
retention time: 1.70 min
MS ES$^+$: 633.4 [M+H]$^+$

Step 2

224 mg of 5-(2-{[tert-butyl(dimethyl)silyl]oxy}ethoxy)-2-[1-(4-ethoxy-2,6-difluorobenzyl)-1H-Indazol-3-yl]-N-(pyridin-4-yl)pyrimidin-4-amine (0.337 mmol, 1. eq.) were dissolved in 3 ml of dry dioxane under nitrogen atmosphere. 442 µl of 4 M hydrogen chloride solution in dioxane were added and gave immediately a suspension. This suspension was stirred for 30 minutes. Then 10 ml of a aq. saturated sodium hydrogen carbonate solution were added. The suspension was filtered off and washed with water to yield 210 mg (0.34 mmol, 97.0%) of the analytically pure target compound.

$^1$H-NMR (400 MHz, DMSO-d$_6$): δ [ppm]=1.28 (t, 3H), 3.83 (d, 2H), 4.04 (q, 2H), 4.24 (t, 2H), 5.11 (br. s., 1H), 5.68 (s, 2H), 6.75-6.84 (m, 2H), 7.26 (t, 1H), 7.45-7.52 (m, 1H), 7.85 (d, 1H), 8.09-8.14 (m, 2H), 8.36 (s, 1H), 8.41-8.48 (m, 3H), 9.12 (s, 1H).

LC-MS:
retention time: 0.95 min
MS ES$^+$: 519.4 [M+H]$^+$

Method B

The following compounds were prepared according to the same two-step procedure using the indicated starting materials (SM=starting material):

| | | | |
|---|---|---|---|
| 13-2<br>SM =<br>3-3 | 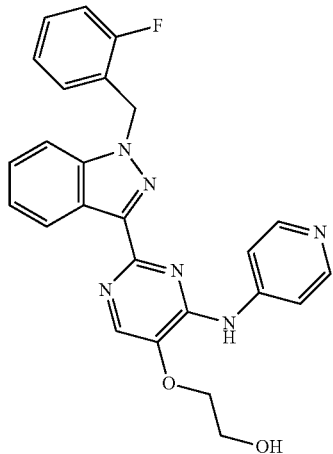 [SMILES: OCCOc1cnc(-c2nn(Cc3ccccc3F)c3ccccc23)nc1Nc1ccncc1] | 2-({2-[1-(2-fluorobenzyl)-1H-indazol-3-yl]-4-(pyridin-4-ylamino)pyrimidin-5-yl}oxy)ethanol | $^1$H-NMR (400 MHz, DMSO-$d_6$): δ [ppm] = 3.77-3.85 (m, 2H), 4.22 (t, 2H), 5.10 (t, 1H), 5.78 (s, 2H), 7.12-7.39 (m, 5H), 7.44 (td, 1H), 7.80 (d, 1H), 8.04-8.09 (m, 2H), 8.35 (s, 1H), 8.40-8.46 (m, 3H), 9.17 (s, 1H).<br>LC-MS:<br>retention time: 0.95 min<br>MS ES$^+$: 457.32 [M + H]$^+$ |
| 13-3<br>SM =<br>30-3 | 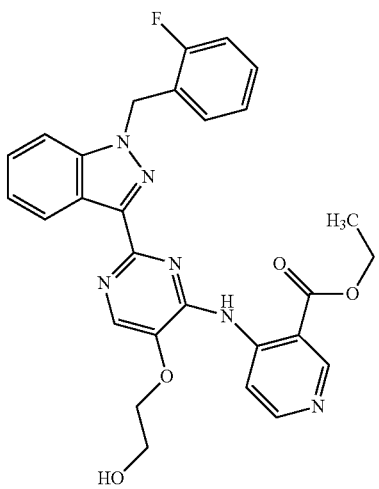 [SMILES: CCOC(=O)c1cnccc1Nc1nc(-c2nn(Cc3ccccc3F)c3ccccc23)ncc1OCCO] | ethyl 4-({2-[1-(2-fluorobenzyl)-1H-indazol-3-yl]-5-(2-hydroxyethoxy)pyrimidin-4-yl}amino)pyridine-3-carboxylate | $^1$H-NMR (400 MHz, DMSO-$d_6$): δ [ppm] = 1.35 (t, 3H), 3.83 (q, 2H), 4.33 (t, 2H), 4.40 (q, 2H), 4.90 (t, 1H), 5.79 (s, 2H), 7.12-7.39 (m, 5H), 7.46 (t, 1H), 7.82 (d, 1H), 8.45 (d, 1H), 8.50 (s, 1H), 8.58 (d, 1H), 9.02-9.09 (m, 1H), 9.29 (d, 1H), 11.23 (s, 1H).<br>LC-MS:<br>retention time: 1.12 min<br>MS ES$^+$: 529.0 [M + H]$^+$<br>Method B |
| 13-4<br>SM =<br>13-3 | 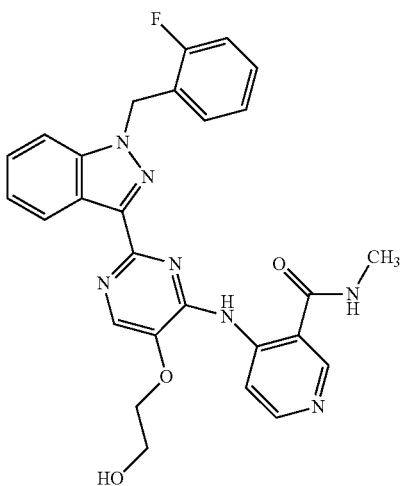<br>(derived from 13-3 via amidation and subsequent desilylation) | 4-({2-[1-(2-fluorobenzyl)-1H-indazol-3-yl]-5-(2-hydroxyethoxy)pyrimidin-4-yl}amino)-N-methylpyridine-3-carboxamide | $^1$H-NMR (400 MHz, DMSO-$d_6$): δ [ppm]= 2.81 (d, 3H), 3.83 (q, 2H), 4.29 (t, 2H), 4.83 (t, 1H), 5.79 (s, 2H), 7.12-7.38 (m, 5H), 7.41-7.49 (m, 1H), 7.81 (d, 1H), 8.42-8.47 (m, 2H), 8.50 (d, 1H), 8.84 (s, 1H), 8.91 (d, 1H), 9.15 (d, 1H), 11.91 (s, 1H).<br>LC-MS:<br>retention time: 0.93 min<br>MS ES$^+$: 514.4 [M + H]$^+$<br>Method B |

| | | | |
|---|---|---|---|
| 13-5 SM = 30-1 | 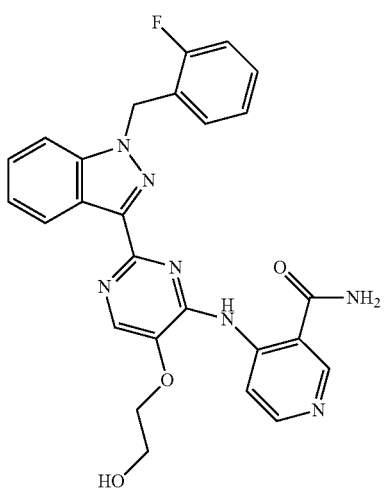 [SMILES: NC(=O)c1cnccc1Nc1nc(-c2nn(Cc3ccccc3F)c3ccccc23)ncc1OCCO] | 4-({2-[1-(2-fluorobenzyl)-1H-indazol-3-yl]-5-(2-hydroxyethoxy)pyrimidin-4-yl}amino)pyridine-3-carboxamide | LC-MS: retention time: 0.96 min MS ES$^+$: 500.1 [M + H]$^+$ Method B |
| 13-6 SM = 30-2 | 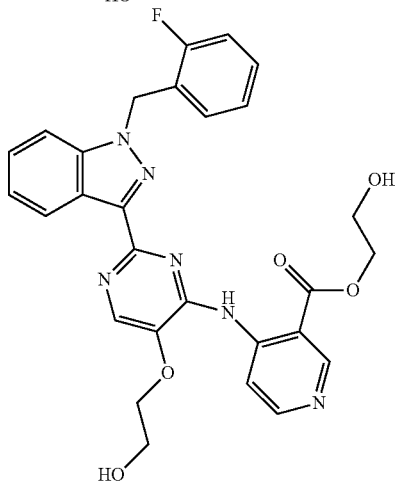 | 2-hydroxyethyl 4-({2-[1-(2-fluorobenzyl)-1H-indazol-3-yl]-5-(2-hydroxyethoxy)pyrimidin-4-yl}amino)pyridine-3-carboxylate | $^1$H-NMR (300 MHz, DMSO-d6): δ [ppm] = 3.69-3.77 (m, 2H), 3.79-3.88 (m, 2H), 4.28-4.40 (m, 4H), 4.86-4.94 (m, 1H), 4.96-5.04 (m, 1H), 5.76-5.83 (m, 2H), 7.13-7.40 (m, 5H), 7.46 (t, 1H), 7.82 (d, 1H), 8.45 (d, 1H), 8.51 (s, 1H), 8.59 (d, 1H), 9.15 (s, 1H), 9.30 (d, 1H), 11.22-11.27 (m, 1H). LC-MS: retention time: 1.15 min MS ES$^+$: 545.0 [M + H]$^+$ Method B |

Example 14-1

Preparation of 5-(cyclopropyloxy)-2-[1-(4-methoxybenzyl)-1H-indazol-3-yl]-N-(pyridin-4-yl)pyrimidin-4-amine

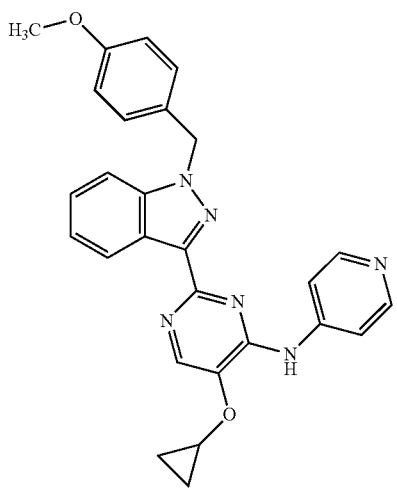 [SMILES: COc1ccc(Cn2nc(-c3ncc(OC4CC4)c(Nc4ccncc4)n3)c3ccccc32)cc1]

100 mg of 2-[1-(4-methoxybenzyl)-1H-indazol-3-yl]-4-(pyridin-4-ylamino)pyrimidin-5-ol (3-2, 0.236 mmol, 1. eq.), 34.2 mg of bromocyclopropane (0,283 mmol, 1.2 eq.), 44.9 mg of copper (1) chloride (0,236 mmol, 1 eq.) and 154 mg of cesium carbonate (0,471 mmol, 2 eq.) were suspended in 3 ml of dry DMF. The reaction mixture was stirred at 60° C. bath temperature for 18 hours. Then the mixture was partitioned between half saturated aq. ammonium chloride solution and dichloromethane/isopropanol 4:1. The phases were separated and the aqueous layer was extracted twice with dichloromethane/isopropanol 4:1. The combined organic layers were washed with brine including a precipitate which was separated with filtering it off. The precipitate was purified by preparative HPLC to yield 2.58 mg (0.047 mmol, 2%) of the analytically pure target compound.

$^1$H-NMR (300 MHz, DMSO-d$_6$): δ [ppm]=3.65 (s, 3H), 4.90 (d, 2H), 5.19-5.40 (m, 2H), 5.60 (s, 2H), 6.01-6.18 (m, 1H), 6.85 (d, 2H), 7.09-7.18 (m, 1H), 7.26 (d, 2H), 7.34 (t, 1H), 7.65 (d, 1H), 7.94 (s, 1H), 8.28 (br. s., 1H), 8.43 (dd, 3H), 8.57 (br. s., 2H).

LC-MS:
retention time: 0.95 min
MS ES$^+$: 465.1 [M+H]$^+$ Method B

Example 15-1

Preparation of 2-[1-(4-ethoxy-2,6-difluorobenzyl)-1H-indazol-3-yl]-5-methoxy-N-(pyridin-4-yl)pyrimidin-4-amine hydrochloride (1:1)

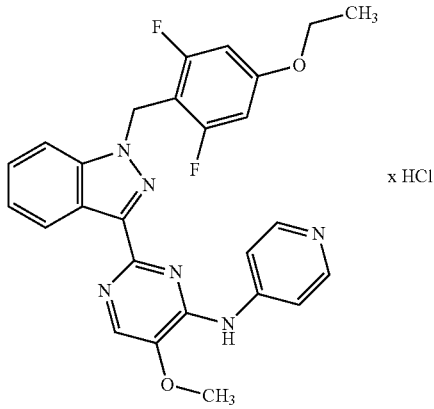 [SMILES: CCOc1cc(F)c(Cn2nc(-c3ncc(OC)c(Nc4ccncc4)n3)c3ccccc32)c(F)c1]

x HCl 150 mg of 2-[1-(4-ethoxy-2,6-difluorobenzyl)-1H-indazol-3-yl]-5-methoxy-N-(pyridin-4-yl)pyrimidin-4-amine (2-5-1, 0.307 mmol, 1. eq.) were dissolved in a mixture of 5.9 ml of dry dichloromethane and 2.5 ml of dry methanol. 0.25 ml of 1.25 M hydrogen chloride solution in methanol were added. The mixture was stirred at room temperature for 1 hour. Then the mixture was concentrated in vacuo to yield 161 mg (0.29 mmol, 95.9%) of the analytically pure target compound.

$^1$H-NMR (300 MHz, DMSO-$d_6$): δ [ppm]=1.25 (t, 3H), 3.93-4.08 (m, 5H), 5.66 (s, 2H), 6.72-6.82 (m, 2H), 7.24 (t, 1H), 7.42-7.51 (m, 1H), 7.82 (d, 1H), 8.34 (d, 2H), 8.39-8.48 (m, 4H), 9.85 (s, 1H).

LC-MS:
retention time: 1.08 min
MS ES$^+$: 489.1 [M+H]$^+$

Method B

| | SM | Product | Analytics |
|---|---|---|---|
| 15-2 | SM = 12-2 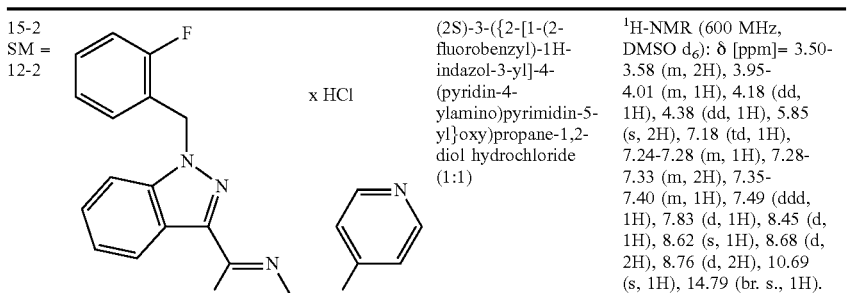 | (2S)-3-({2-[1-(2-fluorobenzyl)-1H-indazol-3-yl]-4-(pyridin-4-ylamino)pyrimidin-5-yl}oxy)propane-1,2-diol hydrochloride (1:1) | $^1$H-NMR (600 MHz, DMSO $d_6$): δ [ppm]= 3.50-3.58 (m, 2H), 3.95-4.01 (m, 1H), 4.18 (dd, 1H), 4.38 (dd, 1H), 5.85 (s, 2H), 7.18 (td, 1H), 7.24-7.28 (m, 1H), 7.28-7.33 (m, 2H), 7.35-7.40 (m, 1H), 7.49 (ddd, 1H), 7.83 (d, 1H), 8.45 (d, 1H), 8.62 (s, 1H), 8.68 (d, 2H), 8.76 (d, 2H), 10.69 (s, 1H), 14.79 (br. s., 1H). LC-MS: retention time: 0.87 min MS ES$^+$: 487.45 [M + H]$^+$ |
| 15-3 | SM = 13-1 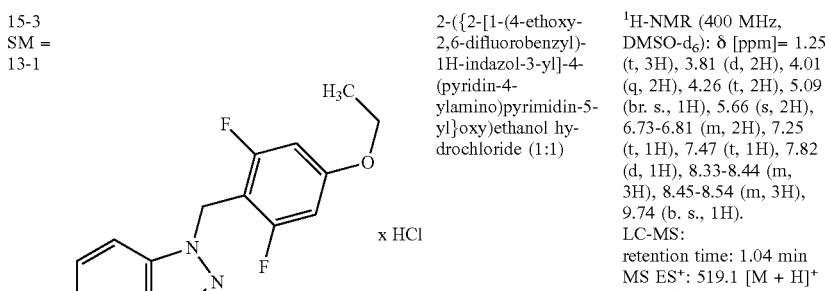 | 2-({2-[1-(4-ethoxy-2,6-difluorobenzyl)-1H-indazol-3-yl]-4-(pyridin-4-ylamino)pyrimidin-5-yl}oxy)ethanol hydrochloride (1:1) | $^1$H-NMR (400 MHz, DMSO-$d_6$): δ [ppm]= 1.25 (t, 3H), 3.81 (d, 2H), 4.01 (q, 2H), 4.26 (t, 2H), 5.09 (br. s., 1H), 5.66 (s, 2H), 6.73-6.81 (m, 2H), 7.25 (t, 1H), 7.47 (t, 1H), 7.82 (d, 1H), 8.33-8.44 (m, 3H), 8.45-8.54 (m, 3H), 9.74 (b. s., 1H). LC-MS: retention time: 1.04 min MS ES$^+$: 519.1 [M + H]$^+$ Method B |

| | | | |
|---|---|---|---|
| 15-4 SM = 2-9-1 | 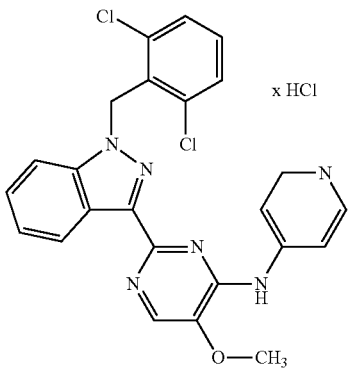 x HCl | 2-[1-(2,6-dichlorobenzyl)-1H-indazol-3-yl]-5-methoxy-N-(pyridin-4-yl)pyrimidin-4-amine hydrochloride (1:1) | $^1$H-NMR (300 MHz, DMSO-d$_6$): δ [ppm] = 4.01 (s, 3H), 5.88 (s, 2H), 7.26 (t, 1H), 7.39-7.53 (m, 2H), 7.56-7.62 (m, 2H), 7.91 (d, 1H), 8.27 (d, 2H), 8.37-8.43 (m, 3H), 8.47 (d, 1H), 9.69 (s, 1H). LC-MS: retention time: 1.05 min MS ES$^+$: 476.9 [M + H]$^+$ |
| 15-5 SM = 8-1 | 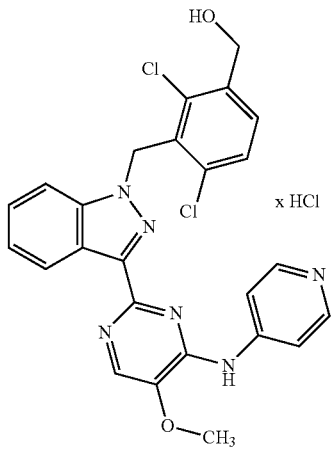 x HCl | [2,4-dichloro-3-({3-[5-methoxy-4-(pyridin-4-ylamino)pyrimidin-2-yl]-1H-indazol-1-yl}methyl)phenyl]methanol hydrochloride (1:1) | $^1$H-NMR (300 MHz, DMSO-d$_6$): δ [ppm]= 3.96-4.02 (m, 3H), 4.52 (s, 2H), 5.47-5.55 (m, 1H), 5.89 (s, 2H), 7.25 (t, 1H), 7.48 (t, 1H), 7.55-7.66 (m, 2H), 7.90 (d, 1H), 8.09-8.15 (m, 2H), 8.31 (s, 1H), 8.34-8.39 (m, 2H), 8.48 (d, 1H), 9.32 (s, 1H). LC-MS: retention time: 0.99 min MS ES$^+$: 507.0 [M + H]$^+$ Method B |
| 15-6 SM = 12-3 | 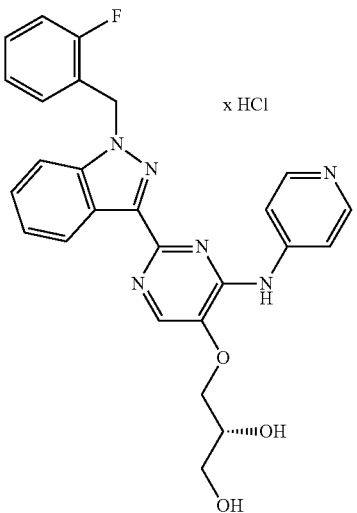 x HCl | (2R)-3-({2-[1-(2-fluorobenzyl)-1H-indazol-3-yl]-4-(pyridin-4-ylamino)pyrimidin-5-yl}oxy)propane-1,2-diol hydrochloride (1:1) | $^1$H-NMR (400 MHz, DMSO-d$_6$): δ [ppm] = 3.43-3.54 (m, 2H), 3.90-3.98 (m, 1H), 4.14 (dd, 1H), 4.34 (dd, 1H), 5.82 (s, 2H), 7.11-7.18 (m, 1H), 7.19-7.38 (m, 4H), 7.46 (ddd, 1H), 7.80 (d, 1H), 8.41 (d, 1H), 8.58 (s, 1H), 8.65 (d, 2H), 8.74 (d, 2H), 10.72 (s, 1H). LC-MS: retention time: 0.86 min MS ES$^+$: 487.34 [M + H]$^+$ |

Example 16-1

Preparation of N-{2-[1-(4-ethoxy-2,6-difluorobenzyl)-1H-indazol-3-yl]pyrimidin-4-yl}-N-(pyridin-4-yl)acetamide

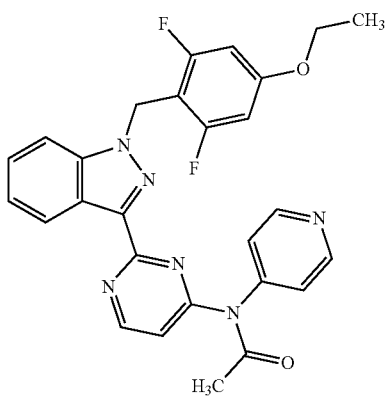 [SMILES: CCOc1cc(F)c(Cn2nc(-c3nccc(N(C(C)=O)c4ccncc4)n3)c3ccccc32)c(F)c1]

100 mg of 2-[1-(4-ethoxy-2,6-difluorobenzyl)-1H-indazol-3-yl]-N-(pyridin-4-yl)pyrimidin-4-amine (5-1-1, 0.218 mmol, 1. eq.) was dissolved in 2 ml of dry dichloromethane. First 94 µl of dry N,N-diethylethanamine (0.676 mmol, 3.1 eq.) and then 23 µl of acetyl chloride (0,327 mmol, 1.5 eq.) were added under nitrogen atmosphere. The reaction mixture was stirred at room temperature for 18 hours. Then the mixture was partitioned between water and dichloromethane. The phases were separated and the aqueous layer was extracted twice with dichloromethane. The combined organic layers were washed with brine, dried over a silicon filter and concentrated in vacuo. The residue was purified by flash chromatography and preparative TLC to yield 29.8 mg (0.06 mmol, 26.8%) of the analytically pure target compound.

$^1$H-NMR (300 MHz, DMSO-$d_6$): δ [ppm]=1.25 (t, 3H), 2.08 (s, 3H), 4.00 (q, 2H), 5.61 (s, 2H), 6.63-6.75 (m, 2H), 6.85-6.93 (m, 1H), 7.09 (d, 1H), 7.36 (ddd, 1H), 7.52-7.57 (m, 2H), 7.70 (d, 1H), 7.93 (d, 1H), 8.73-8.83 (m, 3H).

LC-MS:
retention time: 1.21 min
MS ES$^+$: 501.1 [M+H]$^+$

Method B

The following compounds were prepared according to the same procedure using the indicated starting materials (SM=starting material):

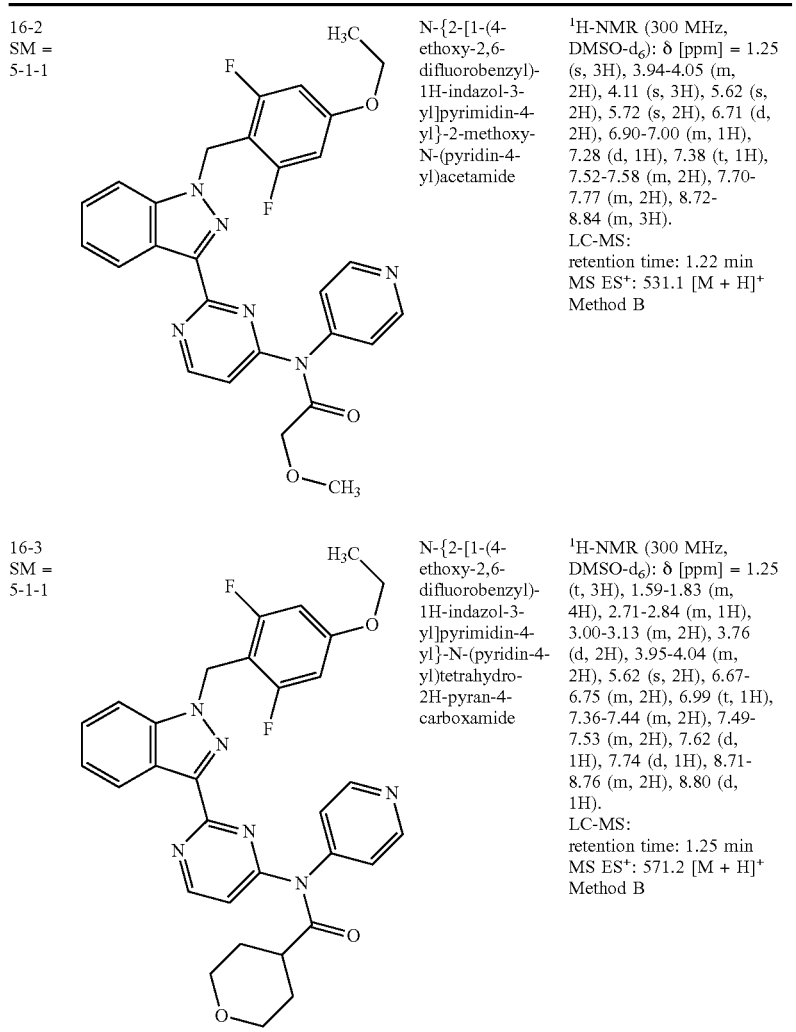

| | | | |
|---|---|---|---|
| 16-2 SM = 5-1-1 | | N-{2-[1-(4-ethoxy-2,6-difluorobenzyl)-1H-indazol-3-yl]pyrimidin-4-yl}-2-methoxy-N-(pyridin-4-yl)acetamide | $^1$H-NMR (300 MHz, DMSO-$d_6$): δ [ppm] = 1.25 (s, 3H), 3.94-4.05 (m, 2H), 4.11 (s, 3H), 5.62 (s, 2H), 5.72 (s, 2H), 6.71 (d, 2H), 6.90-7.00 (m, 1H), 7.28 (d, 1H), 7.38 (t, 1H), 7.52-7.58 (m, 2H), 7.70-7.77 (m, 2H), 8.72-8.84 (m, 3H). LC-MS: retention time: 1.22 min MS ES$^+$: 531.1 [M + H]$^+$ Method B |
| 16-3 SM = 5-1-1 | | N-{2-[1-(4-ethoxy-2,6-difluorobenzyl)-1H-indazol-3-yl]pyrimidin-4-yl}-N-(pyridin-4-yl)tetrahydro-2H-pyran-4-carboxamide | $^1$H-NMR (300 MHz, DMSO-$d_6$): δ [ppm] = 1.25 (t, 3H), 1.59-1.83 (m, 4H), 2.71-2.84 (m, 1H), 3.00-3.13 (m, 2H), 3.76 (d, 2H), 3.95-4.04 (m, 2H), 5.62 (s, 2H), 6.67-6.75 (m, 2H), 6.99 (t, 1H), 7.36-7.44 (m, 2H), 7.49-7.53 (m, 2H), 7.62 (d, 1H), 7.74 (d, 1H), 8.71-8.76 (m, 2H), 8.80 (d, 1H). LC-MS: retention time: 1.25 min MS ES$^+$: 571.2 [M + H]$^+$ Method B |

| | | |
|---|---|---|
| 16-4<br>SM =<br>5-1-1 | 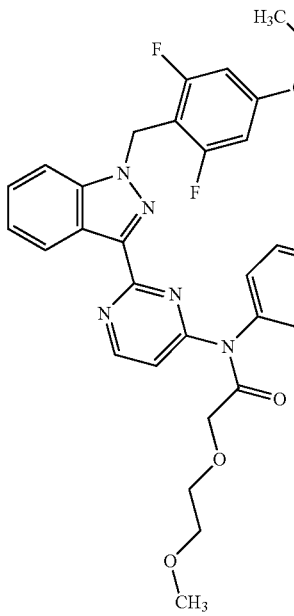<br>N-{2-[1-(4-ethoxy-2,6-difluorobenzyl)-1H-indazol-3-yl]pyrimidin-4-yl}-2-(2-methoxyethoxy)-N-(pyridin-4-yl)acetamide | $^1$H-NMR (300 MHz, DMSO-$d_6$): δ [ppm] = 1.18-1.31 (m, 3H), 3.12-3.16 (m, 3H), 3.34 (dd, 2H), 3.51 (dd, 2H), 4.00 (d, 2H), 4.19 (s, 2H), 5.62 (s, 2H), 6.71 (d, 2H), 6.95 (t, 1H), 7.28 (d, 1H), 7.34-7.42 (m, 1H), 7.51-7.56 (m, 2H), 7.69-7.77 (m, 2H), 8.74-8.77 (m, 2H), 8.80 (d, 1H).<br>LC-MS:<br>retention time: 1.22 min<br>MS ES$^+$: 575.2 [M + H]$^+$<br>Method B |

Example 17-1

Preparation of 2-[{2-[1-(4-ethoxy-2,6-difluorobenzyl)-1H-indazol-3-yl]pyrimidin-4-s yl}(pyridin-4-yl) amino]ethanol

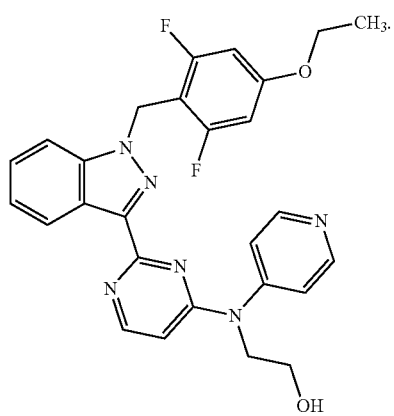 [SMILES: CCOc1cc(F)c(Cn2nc(-c3nccc(N(CCO)c4ccncc4)n3)c3ccccc32)c(F)c1]

120 mg of 2-[1-(4-ethoxy-2,6-difluorobenzyl)-1H-indazol-3-yl]-N-(pyridin-4-yl)pyrimidin-4-amine (5-1-1, 0.262 mmol, 1. eq.) were suspended in 12 ml of dry DMF. 426 mg of cesium carbonate (1.31 mmol, 5 eq.) and 142 mg of 1,3,2-dioxathiolane 2-oxide (1.31 mmol, 5 eq.) were added under nitrogen atmosphere. The reaction mixture was stirred at 60° C. bath temperature for 18 hours. 142 mg of 1,3,2-dioxathiolane 2-oxide (1.31 mmol, 5 eq.) were added and the mixture was stirred at 60° C. bath temperature for further 22 hours. Then the mixture was partitioned between water and dichloromethane/isopropanol 4:1. The phases were separated and the aqueous layer was extracted twice with dichloromethane/isopropanol 4:1. The combined organic layers were dried over magnesium sulfate and concentrated in vacuo. The residue was purified by flash chromatography and preparative TLC to yield 14.2 mg (0.03 mmol, 10.5%) of the analytically pure target compound.

$^1$H-NMR (300 MHz, DMSO-$d_6$): δ [ppm]=1.26 (t, 3H), 3.64-3.76 (m, 2H), 4.01 (q, 2H), 4.11 (t, 2H), 4.91 (t, 1H), 5.64 (s, 2H), 6.66-6.80 (m, 3H), 7.13 (t, 1H), 7.42 (t, 1H), 7.47-7.53 (m, 2H), 7.75 (d, 1H), 8.16 (d, 1H), 8.37 (d, 1H), 8.54-8.62 (m, 2H).

LC-MS:

retention time: 0.96 min

MS ES$^+$: 503.1 [M+H]$^+$

Method B

The following compounds were prepared according to the same procedure using the indicated starting materials (SM=starting material):

| | | | |
|---|---|---|---|
| 17-2<br>SM =<br>5-1-1 | 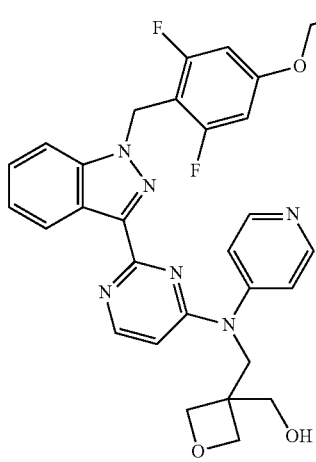 | (3-{[{2-[1-(4-ethoxy-2,6-difluorobenzyl)-1H-indazol-3-yl]pyrimidin-4-yl}(pyridin-4-yl)amino]methyl}oxetan-3-yl)methanol | $^1$H-NMR (500 MHz, DMSO-d6): δ [ppm] = 1.29 (t, 3H), 3.65 (d, 2H), 4.03 (q, 2H), 4.35 (d, 2H), 4.57 (d, 2H), 4.83 (s, 2H), 5.39 (t, 1H), 5.75 (s, 2H), 6.79-6.86 (m, 2H), 7.08 (d, 1H), 7.33 (t, 1H), 7.54 (ddd, 1H), 7.90 (d, 1H), 8.38-8.55 (m, 3H), 8.63 (d, 2H), 8.81 (d, 1H), 11.45 (br. s., 1H). |

Example 18-1

Preparation of 2-{1-[4-bromo-2-fluoro-6-(2,2,2-trifluoroethoxy)benzyl]-1H-indazol-3-yl}-5-methoxy-N-(pyridin-4-yl)pyrimidin-4-amine

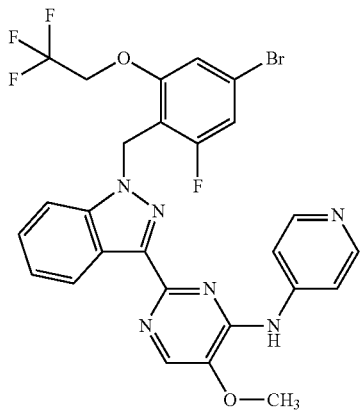 [SMILES: COc1cnc(-c2nn(Cc3c(F)cc(Br)cc3OCC(F)(F)F)c3ccccc23)nc1Nc1ccncc1]

38.2 mg of 2,2,2-trifluoroethanol (0.382 mmol, 2 eq.) were dissolved in 1.5 ml of dry DMF under nitrogen atmosphere. 16.8 mg of 60% sodium hydrid in paraffin oil (0.42 mmol, 2.2 eq.) were added. The suspension was stirred at room temperature for 15 minutes. 100 mg of 2-[1-(4-bromo-2,6-difluorobenzyl)-1H-Indazol-3-yl]-5-methoxy-N-(pyridin-4-yl)pyrimidin-4-amine (2-12-1, 0,191 mmol, 1 eq.) were added. The reaction mixture was stirred at room temperature for 18 hours. Water was added dropwise. The suspension was filtered off. The precipitate was dried at 50° C. under vacuo. The precipitate was purified by preparative HPLC to yield 34 mg (0.05 mmol, 28%) of the analytically pure target compound.

$^1$H-NMR (400 MHz, DMSO-d$_6$): δ [ppm]=4.00 (s, 3H), 4.82 (q, 2H), 5.60 (s, 2H), 7.22 (t, 1H), 7.30 (s, 1H), 7.39-7.46 (m, 1H), 7.74 (d, 1H), 8.10-8.16 (m, 3H), 8.32 (s, 1H), 8.35-8.39 (m, 2H), 8.42 (d, 1H), 9.38 (s, 1H).

LC-MS:

retention time: 1.05 min

MS ES$^+$: 605.0 [M+H]$^+$

As a second product the following compound was obtained:

| | | | |
|---|---|---|---|
| 18-2<br>SM =<br>2-12-1 | 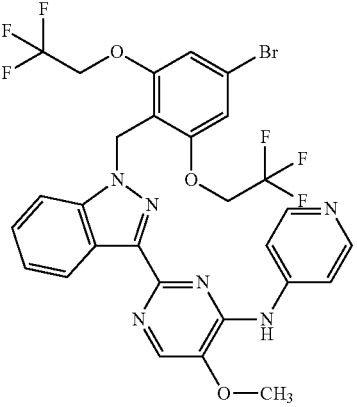 [SMILES: COc1cnc(-c2nn(Cc3c(OCC(F)(F)F)cc(Br)cc3OCC(F)(F)F)c3ccccc23)nc1Nc1ccncc1] | 2-{1-[4-bromo-2,6-bis(2,2,2-trifluoroethoxy)benzyl]-1H-indazol-3-yl}-5-methoxy-N-(pyridin-4-yl)pyrimidin-4-amine | $^1$H-NMR (400 MHz, DMSO-d$_6$): δ [ppm]= 4.00 (s, 3H), 4.82 (q, 4H), 5.55 (s, 2H), 7.16-7.22 (t, 1H), 7.26 (s, 2H), 7.38 (ddd, 1H), 7.68 (d, 1H), 8.02-8.06 (m, 2H), 8.29-8.34 (m, 3H), 8.41 (d. 1H), 9.33 (s, 1H).<br>LC-MS:<br>retention time: 1.12 min<br>MS ES$^+$: 685.0 [M + H]$^+$<br>Method B |

Example 19-1

Preparation of 2,4-dichloro-3-({3-[5-methoxy-4-(pyridin-4-ylamino)pyrimidin-2-yl]-1H-indazol-1-yl}methyl)benzoic acid

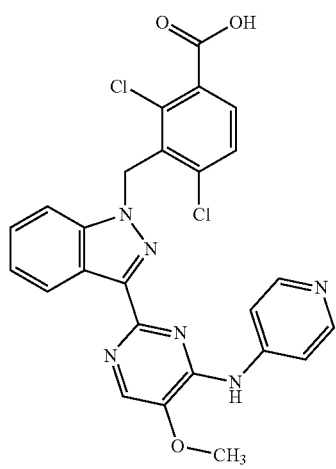 [SMILES: COc1cnc(-c2nn(Cc3c(Cl)ccc(C(=O)O)c3Cl)c3ccccc23)nc1Nc1ccncc1]

1 g of methyl 2,4-dichloro-3-({3-[5-methoxy-4-(pyridin-4-ylamino)pyrimidin-2-yl]-1H-indazol-1-yl}methyl)benzoate (2-16-1, 1.868 mmol, 1. eq.) were dissolved in 19 ml of dry THF and 2.2 ml of methanol. 4.67 ml of 2 M aqueous sodium hydroxide solution (9.34 mmol, 5 eq.) were added. The mixture was stirred for three hours at room temperature. The reaction mixture was partitioned between citric acid (pH 3) and ethyl acetate. This process dropped out a white precipitate which was filtered off and dried for three days to yield 992 mg (1.86 mmol, 99.8%) of the analytically pure target compound.

$^1$H-NMR (400 MHz, DMSO-d6): δ [ppm]=3.99 (s, 3H), 5.91 (s, 2H), 7.26 (t, 1H), 7.44-7.54 (m, 1H), 7.62-7.66 (m, 2H), 7.84-7.94 (m, 1H), 8.07-8.16 (m, 2H), 8.32 (s, 1H), 8.35-8.42 (m, 2H), 8.49 (d, 1H), 9.33 (s, 1H) LC-MS:
retention time: 0.96 min
MS ES$^+$: 521.1 [M+H]$^+$ The following compound was obtained according to the same procedure using the indicated starting material (SM):

Example 20-1

Preparation of 2,4-dichloro-3-({3-[5-methoxy-4-(pyridin-4-ylamino)pyrimidin-2-yl]-1H-indazol-1-yl}methyl)-N-methylbenzamide

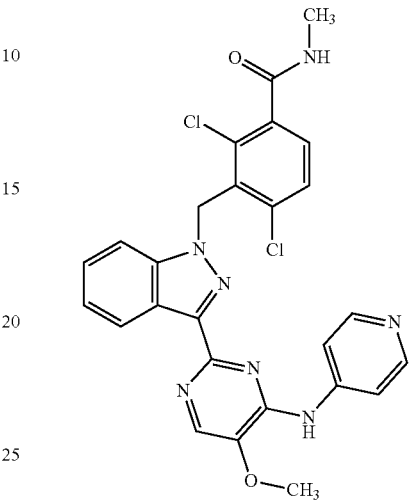

100 mg of 2,4-dichloro-3-({3-[5-methoxy-4-(pyridin-4-ylamino)pyrimidin-2-yl]-1H-indazol-1-yl}methyl)benzoic acid (19-1, 0.192 mmol, 1. eq.) were dissolved in 0,953 ml of dry dimethyl sulfoxide. 80.2 mg of N-[(dimethylamino)(3H-[1,2,3]triazolo[4,5-b]pyridin-3-yloxy)methylidene]-N-methylmethanaminium hexafluorophosphate (0.211 mmol, 1.1 eq.), 67 µl of N-ethyl-N-(propan-2-yl)propan-2-amine (0,384 mmol, 2 eq.) and 96 µl of 2 N methyl amine in tetrahydrofuran were added in this sequence. The reaction mixture was stirred at room temperature for 18 hours. 80.2 mg of N-[(dimethylamino)(3H-[1,2,3]triazolo[4,5-b]pyridin-3-yloxy)methylidene]-N-methylmethanaminium hexafluorophosphate (0.211 mmol, 1.1 eq.), 67 µl of N-ethyl-N-(propan-2-yl)propan-2-amine (0,384 mmol, 2 eq.) and 96 µl of 2 N methyl amine in tetrahydrofuran were added in this sequence again twice and stirred each time at room temperature for 24 hours. The reaction mixture was stirred at 50° C. bath temperature for further 2 hours. Then the mixture was filtered off purified by preparative HPLC to

| | | | |
|---|---|---|---|
| 19-2<br>SM =<br>4-14 | 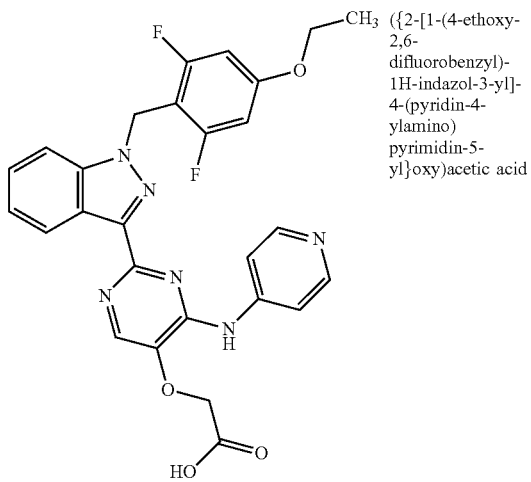 | ({2-[1-(4-ethoxy-2,6-difluorobenzyl)-1H-indazol-3-yl]-4-(pyridin-4-ylamino)pyrimidin-5-yl}oxy)acetic acid | 1H-NMR (300 MHz, DMSO-d6): δ [ppm] = 1.24 (t, 3H), 4.00 (q, 2H), 5.04 (d, 2H), 5. 68 (s, 2H), 6. 78 (m, 2H), 7.26 (t, 1H), 7.48 (t, 1H), 7.83 (d, 1H), 8.39 (d, 1H), 8.51 (s, 1H), 8.53-8.63 (m, 4H), 10.58 (s, 1H), 14.33 (br. s, 1H).<br>LC-MS (Method 1):<br>retention time: 1.03 min<br>MS ES+: 481.4 [ | yield 15 mg (0.03 mmol, 14.3%) of the analytically pure target compound.

¹H-NMR (300 MHz, DMSO-d6): δ [ppm]=2.68 (d, 3H), 3.99 (s, 3H), 5.91 (s, 2H), 7.19-7.32 (m, 1H), 7.42-7.51 (m, 2H), 7.63-7.72 (m, 1H), 7.87-7.98 (m, 1H), 8.07-8.23 (m, 2H), 8.32-8.50 (m, 5H), 9.33 (s, 1H)

LC-MS:

retention time: 0.92 min

MS ES⁺: 534.2 [M+H]⁺

The following compounds were obtained according to the same procedure using the indicated starting materials (SM):

| | | | |
|---|---|---|---|
| 20-2 SM = 19-1 | (structure) | 2,4-dichloro-3-({3-[5-methoxy-4-(pyridin-4-ylamino)pyrimidin-2-yl]-1H-indazol-1-yl}methyl)benzamide | ¹H-NMR (400MHz, DMSO-d₆): δ [ppm] = 4.00 (s, 3H), 5.91 (s, 2H), 7.19-7.33 (m, 1H), 7.39-7.54 (m, 2H), 7.56-7.63 (m, 1H), 7.63-7.71 (m, 1H), 7.85-7.97 (m, 2H), 8.06-8.22 (m, 2H), 8.32 (s, 4H), 9.23-9.42 (m, 1H) LC-MS: retention time: 0.91 min MS ES⁺: 520.1 [M + H]⁺ |
| 20-3 SM = 19-1 | (structure) | 2,4-dichloro-3-({3-[5-methoxy-4-(pyridin-4-ylamino)pyrimidin-2-yl]-1H-indazol-1-yl}methyl)-N,N-dimethyl-benzamide | ¹H-NMR (300 MHz, DMSO-d₆): δ [ppm] = 2.64 (s, 3H), 2.92 (s, 3H), 3.99 (s, 3H), 5.77-6.01 (m, 2H), 7.25 (t, 1H), 7.40 (d, 1H), 7.44-7.53 (m, 1H), 7.68 (d, 1H), 7.84-7.96 (m, 1H), 8.06-8.18 (m, 2H), 8.26-8.41 (m, 3H), 8.49 (d, 1H), 9.31 (s, 1H) LC-MS: retention time: 0.98 min MS ES⁺: 548.2 [M + H]⁺ |
| 20-4 SM = 19-1 | (structure) | 2,4-dichloro-N-(2-hydroxyethyl)-3-({3-[5-methoxy-4-(pyridin-4-ylamino)pyrimidin-2-yl]-1H-indazol-1-yl}methyl)benzamide | ¹H-NMR (400 MHz, Chloroform-d): δ [ppm] = 3.62-3.73 (m, 2H), 3.81-3.91 (m, 2H), 4.03 (s, 3H), 5.90 (s, 2H), 6.69-6.81 (m, 1H), 7.31 (t, 1H), 7.37-7.45 (m, 2H), 7.45-7.56 (m, 2H), 7.66 (d, 1H), 7.97 (d, 2H), 8.18 (s, 1H), 8.48 (d, 2H), 8.64 (d, 1H) LC-MS: retention time: 0.89 min MS ES⁺: 564.2 [M + H]⁺ |

| | | | |
|---|---|---|---|
| 20-5<br>SM =<br>19-1 | 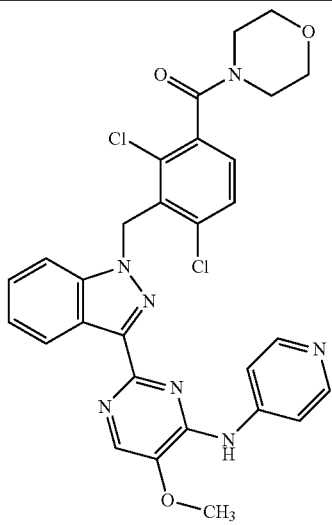 | [2,4-dichloro-3-({3-[5-methoxy-4-(pyridin-4-ylamino)pyrimidin-2-yl]-1H-indazol-1-yl}methyl)phenyl](morpholin-4-yl)methanone | $^1$H-NMR (300 MHz, DMSO-d$_6$): δ [ppm] = 2.99-3.11 (m, 2H), 3.37-3.45 (m, 2H), 3.56-3.64 (m, 4H), 4.03 (s, 3H), 5.91 (s, 2H), 7.28 (t, 1H), 7.45 (d, 1H), 7.47-7.55 (m, 1H), 7.69 (d, 1H), 7.92 (d, 1H), 8.36-8.44 (m, 2H), 8.46-8.50 (m, 4H), 10.08 (br. s., 1H)<br>LC-MS:<br>retention time: 0.95 min<br>MS ES$^+$: 590.1 [M + H]$^+$ |
| 20-6<br>SM =<br>19-1 | 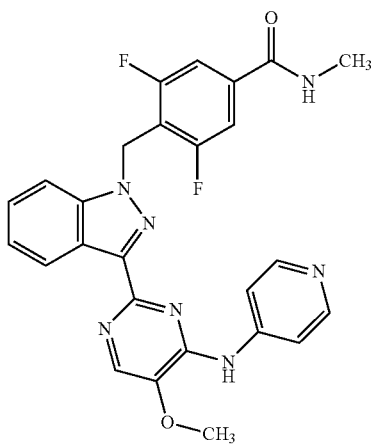 [SMILES: CNC(=O)c1cc(F)c(Cn2nc(-c3ncc(OC)c(Nc4ccncc4)n3)c3ccccc32)c(F)c1] | 3,5-difluoro-4-({3-[5-methoxy-4-(pyridin-4-ylamino)pyrimidin-2-yl]-1H-indazol-1-yl}methyl)-N-methylbenzamide | $^1$H-NMR (300 MHz, METHANOL-d$_4$): δ [ppm] = 2.91 (s, 3H), 4.13 (s, 3H), 5 77-5.82 (m, 2H), 7.20-7.28 (m, 1H), 7.44 (td, 1H), 7.60 (d, 3H), 8.47 (d, 1H), 8.56 (s, 1H), 8.59-8.67 (m, 4H).<br>LC-MS:<br>retention time: 0.80 min<br>MS ES$^+$: 502.1 [M + H]$^+$ |

Example 21-1

Preparation of 2-[1-(4-ethynyl-2-fluorobenzyl)-1H-indazol-3-yl]-5-methoxy-N-(pyridin-4-yl)pyrimidin-4-amine

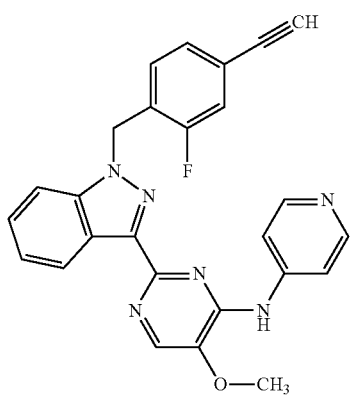 [SMILES: C#Cc1ccc(Cn2nc(-c3ncc(OC)c(Nc4ccncc4)n3)c3ccccc32)c(F)c1]

Step 1: 2-(1-{2-fluoro-4-[(trimethylsilyl)ethynyl]benzyl}-1H-indazol-3-yl)-5-methoxy-N-(pyridin-4-yl)pyrimidin-4-amine 144.7 mg of 2-[1-(2-fluoro-4-iodobenzyl)-1H-indazol-3-yl]-5-methoxy-N-(pyridin-4-yl)pyrimidin-4-amine (2-201, 0,262 mmol, 1 eq.), 6.02 mg of (1E,4E)-1,5-diphenylpenta-1,4-dien-3-one-palladium (2:1) (0.01 mmol, 0.04 eq.), 2.0 mg of copper (I) iodide (0.01 mmol, 0.04 eq.), and 13.7 mg of triphenylphosphane (0,052 mmol, 0.2 mmol) were suspended in 2.6 ml of dry N,N-diethylethanamine and purged with nitrogen. Then 3.86 ml of ethynyl(trimethyl)silane (1.57 mmol, 6 eq.) were added and the reaction mixture was stirred at 60° C. for 18 hours. The mixture was concentrated under vacuo. The crude product was used without further purification in step 2.
LC-MS:
retention time: 1.14 min
MS ES$^+$: 523.4 [M+H]$^+$ Method B Step 2: 2-[1-(4-ethynyl-2-fluorobenzyl)-1H-indazol-3-yl]-5-methoxy-N-(pyridin-4-yl)pyrimidin-4-amine 37.3 mg of 2-(1-{2-fluoro-4-[(trimethylsilyl)ethynyl]benzyl}-1H-indazol-3-yl)-5-methoxy-N-(pyridin-4-yl)pyrimidin-4-amine (0.071 mmol, 1. eq.) were dissolved in 1.0 ml of dry tetrahydrofuran. 71 μl of a 1 M N,N,N-tributylbutan-1-ammonium fluoride in tetrahydrofuran (0,071 mmol, 1 eq.) were added under nitrogen atmosphere and stirred at room temperature for 18 hours. Then the mixture was partitioned between a aqueous half saturated sodium hydrogen carbonate solution and dichloromethane/isopropanol 4:1. The phases were separated and the aqueous layer was extracted twice with dichloromethane/isopropanol 4:1. The combined organic layers were dried over magnesium sulfate and concentrated in vacuo. The residue was purified by preparative TLC in ethyl acetate/methanol 7:3 to yield 23.2 mg (0.05 mmol, 68.4%) of the analytically pure target compound.

$^1$H-NMR (300 MHz, DMSO-$d_6$): δ [ppm]=4.01 (s, 3H), 4.28 (s, 1H), 5.79 (s, 2H), 7.20-7.31 (m, 3H), 7.34-7.48 (m, 2H), 7.80 (d, 1H), 8.07-8.13 (m, 2H), 8.33 (s, 1H), 8.35-8.40 (m, 2H), 8.44 (d, 1H), 9.41 (s, 1H).

LC-MS:
retention time: 0.91 min
MS ES$^+$: 451.4 [M+H]$^+$

Method B

Example 22-1

Preparation of {2-[1-(2-fluorobenzyl)-1H-indazol-3-yl]-8-(pyridin-4-yl)-7,8-dihydro-6H-pyrimido[5,4-b][1,4]oxazin-7-yl}methanol

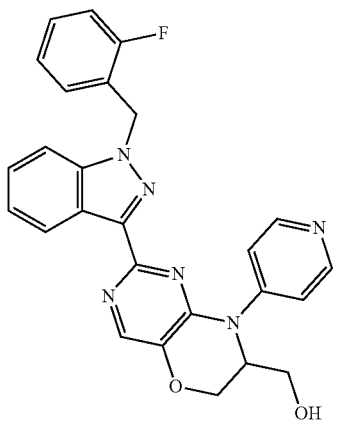 [SMILES: OCC1COc2cnc(-c3nn(Cc4ccccc4F)c4ccccc34)nc2N1c1ccncc1]

25 mg of 2-[1-(2-fluorobenzyl)-1H-indazol-3-yl]-4-(pyridin-4-ylamino)pyrimidin-5-ol (3-3, 0.061 mmol, 1. eq.), 28.2 mg of 3-bromopropane-1,2-diol (0,182 mmol, 3 eq.) and 41.9 mg of potassium carbonate (0,303 mmol, 5 eq.) were suspended in 470 μl of dry DMF under nitrogen atmosphere. The reaction mixture was stirred at 100° C. bath temperature for 18 hours. Then the mixture was partitioned between aqueous half saturated sodium chloride solution and ethyl acetate. The phases were separated and the aqueous layer was extracted once with ethyl acetate and once with dichloromethane/isopropanol 4:1. The combined organic layers were dried over magnesium sulfate and concentrated in vacuo. The residue was purified by preparative TLC in dichloromethane/methanol 9:1 to yield 6.26 mg (0.01 mmol, 19.8%) of the analytically pure target compound.

$^1$H-NMR (300 MHz, DMSO-$d_6$): δ [ppm]=3.53-3.67 (m, 2H), 4.14-4.23 (m, 1H), 4.25-4.32 (m, 1H), 4.53-4.61 (m, 1H), 5.26-5.33 (m, 1H), 5.73 (s, 2H), 7.01-7.24 (m, 4H), 7.27-7.42 (m, 2H), 7.68-7.78 (m, 3H), 8.13 (d, 1H), 8.26 (s, 1H), 8.50-8.57 (m, 2H).

LC-MS:
retention time: 0.89 min
MS ES$^+$: 469.0 [M+H]$^+$

Method B

Example 23-1

Preparation of 2-[1-(2-fluorobenzyl)-1H-indazol-3-yl]-5-methoxy-N-methyl-N-(pyridin-4-yl)pyrimidin-4-amine

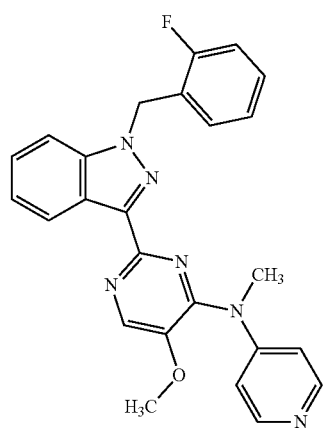 [SMILES: COc1cnc(-c2nn(Cc3ccccc3F)c3ccccc23)nc1N(C)c1ccncc1]

135 mg of 2-[1-(2-fluorobenzyl)-1H-indazol-3-yl]-5-methoxy-N-(pyridin-4-yl)pyrimidin-4-amine (2-18-1, 0.316 mmol, 1. eq.) were dissolved in 3 ml of 1-methylpyrrolidin-2-one and 514 mg of cesium carbonate (1.58 mmol, 5 eq.) were added. The reaction mixture was stirred at 190° C. bath temperature for 18 hours. After cooling at room temperature the mixture was partitioned between water and butan-2-one. The phases were separated and the aqueous layer was extracted twice with butan-2-one. The combined organic layers were washed with brine and dried over magnesium sulfate and concentrated in vacuo. The residue was purified by flash chromatography and preparative TLC to yield 10.9 mg (0.02 mmol, 7.2%) of the analytically pure target compound.

$^1$H-NMR (400 MHz, DMSO-$d_6$): δ [ppm]=3.77 (s, 3H), 3.89 (s, 3H), 5.80 (s, 2H), 7.15-7.19 (m, 3H), 7.21-7.29 (m, 3H), 7.34-7.41 (m, 2H), 7.44 (ddd, 1H), 7.75 (d, 1H), 7.79 (br. s., 1H), 8.23 (s, 1H), 8.50 (d, 1H).

LC-MS:
retention time: 1.02 min
MS ES$^+$: 441.53 [M+H]$^+$

Example 24-1

Preparation of 4-({2-[1-(2-fluorobenzyl)-1H-indazol-3-yl]-5-methoxypyrimidin-4-yl}amino)pyridine-3-carbonitrile

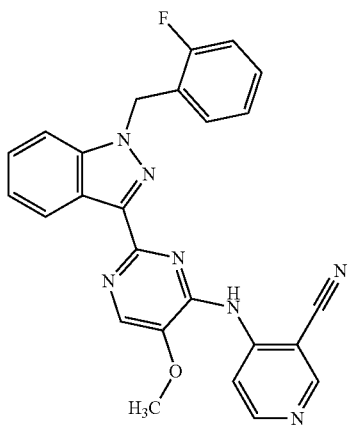 [SMILES: COc1cnc(-c2nn(Cc3ccccc3F)c3ccccc23)nc1Nc1ccncc1C#N]

175 mg of 2-[1-(2-fluorobenzyl)-1H-indazol-3-yl]-5-methoxypyrimidin-4-amine (1-11-1, 0.501 mmol, 1. eq.), 101 mg of 4-bromopyridine-3-carbonitrile (0.551 mmol, 1.1 eq.), 115 mg of Tris(dibenzylideneacetone)dipalladium (0) (0.125 mmol, 0.25 eq.), 156 mg of 1,1'-binaphthalene-2,2'-diylbis(diphenylphosphane) (0.25 mmol, 0.5 eq), 144 mg of sodium 2-methylpropan-2-olate (97%) (1.503 mmol, 3 eq.) and 52 ml of N,N-dimethylformamide were stirred under nitrogen atmosphere for 30 minutes at 100° C. and 300 W in a CEM microwave. The reaction mixture was washed with half-saturated aqueous sodium chloride solution. The organic layer was extracted twice with ethyl acetate. The combined organic layers were washed with brine and dried over sodium sulfate and concentrated in vacuo. The residue was purified by flash chromatography (hexane/dichloromethane/methanol) and preparative HPLC. A crystallisation from dichloromethane/methanol gave 5.8 mg (0.01 mmol, 2.6%) of the analytically pure target compound.

$^1$H-NMR (300 MHz, DMSO-$d_6$): δ [ppm]=4.04 (s, 3H), 5.76 (s, 2H), 7.08-7.26 (m, 4H), 7.28-7.46 (m, 2H), 7.75 (d, 1H), 8.20-8.31 (m, 2H), 8.45 (s, 1H), 8.68 (d, 1H), 8.88 (s, 1H), 9.23 (s, 1H).

LC-MS:
retention time: 1.28 min
MS ES$^+$: 452.33 [M+H]

The following compounds were prepared according to the same procedure using the indicated starting materials (SM=starting material), and the respective halopyridines:

| | | | |
|---|---|---|---|
| 24-2 SM = 1-4-2 | (structure) | methyl 4-({2-[1-(2-fluorobenzyl)-1H-indazol-3-yl]-5-methoxypyrimidin-4-yl}amino)pyridine-3-carboxylate | $^1$H-NMR (300 MHz, DMSO-$d_6$): δ [ppm] = 4.05 (s, 3H), 4.11 (s, 3H), 5.80-5.85 (m, 2H), 7.10-7.40 (m, 6H), 7.49-7.59 (m, 2H), 7.86 (d, 1H), 8.06 (d, 1H), 8.39 (dd, 1H), 8.95-9.06 (m, 2H). LC-MS: retention time: 0.91 min MS ES$^+$: 485.11 [M + H]$^+$ |
| 24-3 SM = 1-4-2 | (structure) | 2-[1-(2-fluorobenzyl)-1H-indazol-3-yl]-5-methoxy-N-(pyridin-4-yl)pyrimidin-4-amine | 1H-NMR (300 MHz, DMSO-d6): δ [ppm] = 4.01 (s, 3H), 5.77 (s, 2H), 7.10-7.49 (m, 6H), 7.75-7.84 (m, 1H), 8.07-8.17 (m, 2H), 8.33 (s, 1H), 8.35-8.40 (m, 2H), 8.40-8.48 (m, 1H), 9.35-9.45 (m, 1H). LC-MS: retention time: 1.01 min MS ES$^+$: 427.19 [M + H]$^+$ Method B |

The following compound was also formed during the reaction leading to 24-3:

| | | | |
|---|---|---|---|
| 24-4<br>SM =<br>1-4-2 | 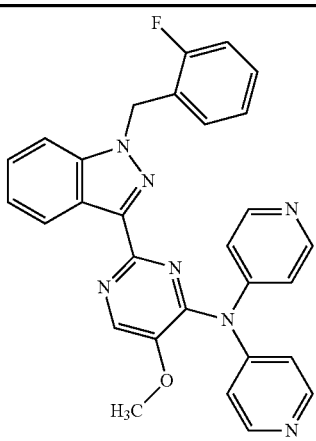 | 2-[1-(2-fluorobenzyl)-1H-indazol-3-yl]-5-methoxy-N,N-di(pyridin-4-yl)pyrimidin-4-amine | $^1$H-NMR (300 MHz, DMSO-d$_6$): δ [ppm] = 3.74 (s, 3H), 5.75 (s, 2H), 6.92 (t, 1H), 6.99-7.12 (m, 6H), 7.13-7.23 (m, 1H), 7.26-7.38 (m, 2H), 7.65 (dd, 2H), 8.41-8.50 (m, 4H), 8.71 (s, 1H).<br>LC-MS:<br>retention time: 0.90 min<br>MS ES$^+$: 504.57 [M + H]$^+$ |

The following compounds were prepared according to the same procedure using the indicated starting materials (SM=starting material), and the respective halopyridines/halopyridones:

| | | | |
|---|---|---|---|
| 24-5<br>SM =<br>1-4-3 | 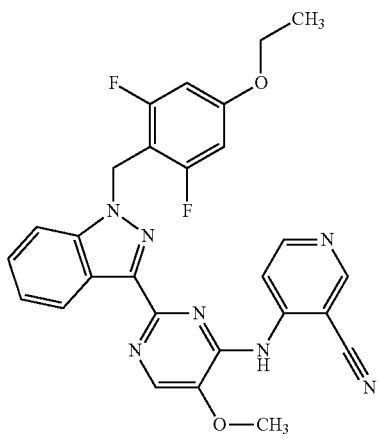 [SMILES: CCOc1cc(F)c(Cn2nc(-c3ncc(OC)c(Nc4ccncc4C#N)n3)c3ccccc32)c(F)c1] | 4-({2-[1-(4-ethoxy-2,6-difluorobenzyl)-1H-indazol-3-yl]-5-methoxypyrimidin-4-yl}amino)pyridine-3-carbonitrile | 1H-NMR (500 MHz, DMSO-d6): δ [ppm] = 1.30 (t, 3H), 4.05 (q, 2H), 4.07 (s, 3H), 5. 67 (s, 2H), 6.80 (m, 2H), 7.22 (t, 1H), 7.48 (t, 1H), 7 83 (d, 1H), 8.32 (d, 1H), 8.45 (br. s, 1H), 8.68 (br. s, 1H), 8.90 (br. s, 1H), 9.15 (br. s, 1H).<br>Ein H fehlt<br>LC-MS (Method 5):<br>retention time: 1.43 min<br>MS ES$^+$: 514.2 [$^5$ |
| 24-6<br>SM =<br>1-4-3 | 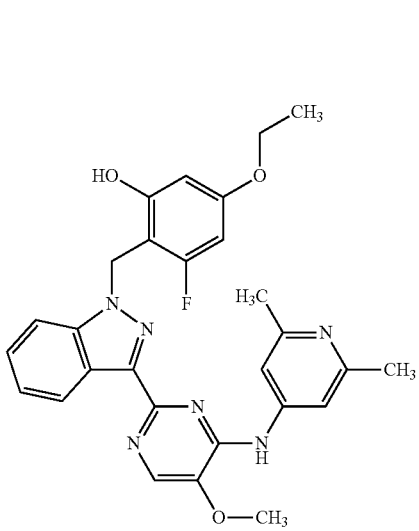 [SMILES: CCOc1cc(O)c(Cn2nc(-c3ncc(OC)c(Nc4cc(C)nc(C)c4)n3)c3ccccc32)c(F)c1] | 2-[{3-{4-[(2,6-dimethylpyridin-4-yl)amino]-5-methoxypyrimidin-2-yl}-1H-indazol-1-yl)methyl]-5-ethoxy-3-fluorophenol | 1H-NMR (400 MHz, DMSO-d6): δ [ppm] = 1.24 (t, 3H), 2.36 (s, 6H), 3.90 (q, 2H), 3.99 (s, 3H), 5.54 (s, 2H), 6. 20 (br. s, 1H), 6. 24 (br. d, 1H), 7.18 (t, 1H), 7.39 (t, 1H), 7.78 (s, 1H), 7.78 (d, 1H), 8.28 (s, 1H), 8.44 (d, 1H), , 9.09 (s, 1H), 10.26 (br. s, 1H).<br>LC-MS (Method 5):<br>retention time: 0.68 min<br>MS ES$^+$: 515.2 |

| | | | |
|---|---|---|---|
| 24-7 SM = 1-4-1 | 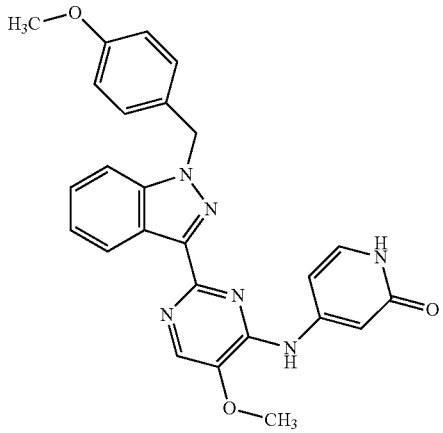 [SMILES: COc1ccc(Cn2nc(-c3ncc(OC)c(Nc4cc[nH]c(=O)c4)n3)c3ccccc32)cc1] | 4-({5-methoxy-2-[1-(4-methoxybenzyl)-1H-indazol-3-yl]pyrimidin-4-yl}amino)pyridin-2(1H)-one | $^1$H-NMR (300 MHz, DMSO-d$_6$): δ [ppm] = 3.65 (s, 3H), 4.00 (s, 3H), 5.62 (s, 2H), 6.79-6 87 (m, 3H), 7.13-7.27 (m, 2H), 7.27-7.45 (m, 4H), 7.76 (d, 1H), 8.33 (s, 1H), 8.42 (d, 1H), 9.06 (s, 1H), 11.03 (br. s., 1H). LC-MS: retention time: 0.97 min MS ES$^+$: 455.2 [M + H]$^+$ |
| 24-8 SM = 1-4-3 | 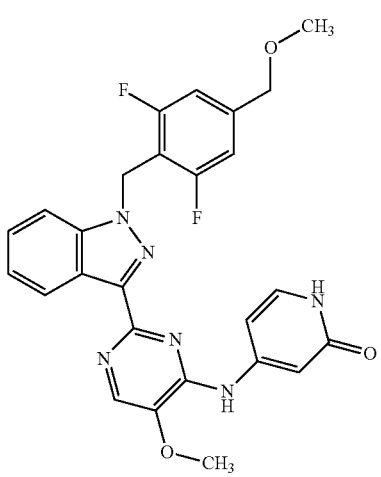 [SMILES: COCc1cc(F)c(Cn2nc(-c3ncc(OC)c(Nc4cc[nH]c(=O)c4)n3)c3ccccc32)c(F)c1] | 4-({2-[1-(4-ethoxy-2,6-difluorobenzyl)-1H-indazol-3-yl]-5-methoxypyrimidin-4-yl}amino)pyridin-2(1H)-one | 1H-NMR (300 MHz, DMSO-d6): δ [ppm] = 1.25 (t, 3H), 3.98 (s, 3H), 4.00 (q, 2H), 5. 63 (s, 2H), 6.72 (m, 2H), 6. 97 (br. s, 1H), 7.05 (br. d, 1H), 7.20 (m, 1H), 7.44 (t, 1H), 7.75 (m, 2H), 8.31 (s, 1H), 8.41 (d, 1H), 9.06 (s, 1H), 11.02 (br. s, 1H). LC-MS (Method 2): retention time: 0.94 min MS ES$^+$: 505.0 |
| 24-9 SM = 1-4-4 | 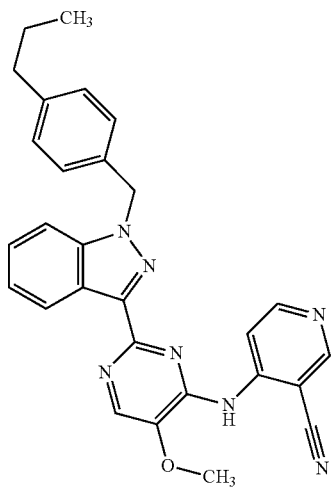 [SMILES: CCCc1ccc(Cn2nc(-c3ncc(OC)c(Nc4ccncc4C#N)n3)c3ccccc32)cc1] | 4-({5-methoxy-2-[1-(4-propylbenzyl)-1H-indazol-3-yl]pyrimidin-4-yl}amino) nicotinonitrile | LC-MS: retention time: 1.51 min MS ES$^+$: 476.27 [M + H]$^+$ |

Example 25-1

Preparation of 4-({2-[1-(2-fluorobenzyl)-1H-indazol-3-yl]-5-methoxypyrimidin-4-yl}amino)pyridine-3-carboxamide

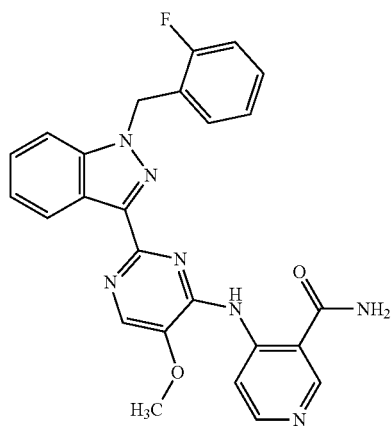 [SMILES: COc1cnc(-c2nn(Cc3ccccc3F)c3ccccc23)nc1Nc1ccncc1C(N)=O]

54 mg of 4-({2-[1-(2-fluorobenzyl)-1H-indazol-3-yl]-5-methoxypyrimidin-4-yl}amino)pyridine-3-carbonitrile (24-1, 0.12 mmol, 1. eq.) were dissolved in 1.6 ml of dimethyl sulfoxide under nitrogene atmosphere. 42 µl of 3 M aqueous sodium hydroxide solution (0.126 mmol, 1.05 eq.) were added. The mixture was oilbath heated to 63° C. bath temperature. At this temperature 302 µl hydrogen peroxide (30% in water) (9.87 mmol, 82.2 eq.) were added dropwise. The reaction mixture was stirred at 65° C. bath temperature for 3 hours and at room temperature for 24 hours. After stirring the mixture one hour with ice-water it was extracted three times with dichloromethane/isopropanol 4:1. The combined organic layers were dried over magnesium sulfate and concentrated in vacuo. The residue was purified by preparative TLC (dichloromethane/methanol 9:1) to yield 12.0 mg (0.02 mmol, 20.5%) of the analytically pure target compound.

$^1$H-NMR (300 MHz, DMSO-$d_6$): δ [ppm]=4.01 (s, 3H), 5.79 (s, 2H), 7.10-7.39 (m, 5H), 7.45 (t, 1H), 7.81 (d, 2H), 8.34-8.55 (m, 4H), 8.91 (s, 1H), 9.22 (d, 1H), 12.10-12.19 (m, 1H).

LC-MS:

retention time: 1.01 min

MS ES$^+$: 470.1 [M+H]$^+$

Method B

The following compounds were obtained according to the same procedure using the indicated starting materials (SM=starting material):

| | | |
|---|---|---|
| 25-2<br>SM =<br>24-9 | 4-{{5-methoxy-2-[1-(4-propylbenzyl)-7H-indazol-3-yl]pyrimidin-4-yl}amino)pyridine-3-carboxamide | $^1$H-NMR (400 MHz, DMSO-$d_6$): δ [ppm] = 0.81 (t, 3H), 1.43-1.55 (m, 2H), 2.44-2.56 (m, 2H), 4.02 (s, 3H), 5.70 (s, 2H), 7.12 (d, 2H), 7.21-7.29 (m, 3H), 7.41 (ddd, 1H), 7.78 (d, 1H), 7.86 (br. s., 1H), 8.38-8.46 (m, 3H), 8.54 (d, 1H), 8.92 (s, 1H), 9.25 (d, 1H), 12.19 (s, 1H).<br>LC-MS:<br>retention time: 1.24 min<br>MS ES$^+$: 494.3 [M + H]$^+$ |

The following compound was prepared according to the following alternative method:

105 mg of 4-({2-[1-(4-ethoxy-2,6-difluorobenzyl)-1H-indazol-3-yl]-5-methoxypyrimidin-4-yl}amino)pyridine-3-carbonitrile (24-5, 0,204 mmol) was dissolved in 311 µl conc. sulphuric acid (5.83 mmol) and stirred at room temperature for 18 hours. The mixture was poured in ice water and then 2M sodium hydroxid was added until a basic pH was reached. The aqueous phase was extracted 3 times with CH2Cl2/isopropanol 4:1, dried over magnesium sulphate, filtered off and concentrated in vacuo. The residue was purified by preparative TLC (dichloromethane/methanol 9:1) to yield 6.9 mg (0.01 mmol, 6.3%) of the analytically pure target compound.

| | | | |
|---|---|---|---|
| 25-3<br>SM =<br>24-5 | 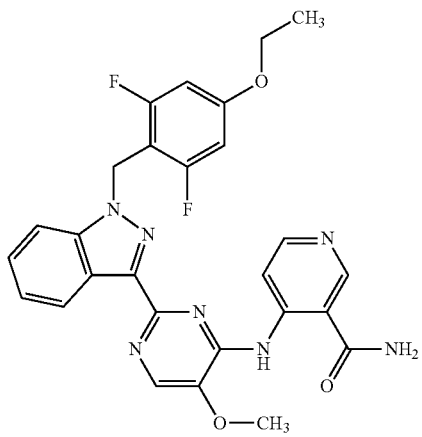 [SMILES: CCOc1cc(F)c(Cn2nc(-c3ncc(OC)c(Nc4ccncc4C(N)=O)n3)c3ccccc32)c(F)c1] | 4-({2-[1-(4-ethoxy-2,6-difluorobenzyl)-1H-indazol-3-yl]-5-methoxypyrimidin-4-yl}amino)pyridine-3-carboxamide | ¹H-NMR (400 MHz, DMSO-d₆): δ [ppm] = 1.26 (t, 3H), 3.94-4.08 (m, 5H), 5.65 (s, 2H), 6.77 (d, 2H), 7.19-7.32 (m, 1H), 7.40-7.53 (m, 1H), 7.74-7.87 (m, 2H), 8.29-8.55 (m, 4H), 8.92 (s, 1H). 9.20-9.30 (m, 1H), 12.17 (s, 1H).<br>LC-MS:<br>retention time: 1.13 min<br>MS ES⁺: 532.3 [M + H]⁺ |

The following compound was also formed during the same reaction:

| | | | |
|---|---|---|---|
| 25-4<br>SM =<br>24-5 | 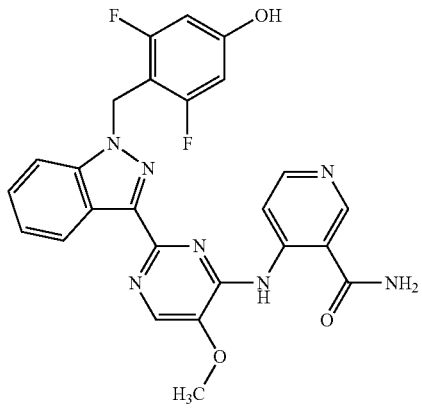 [SMILES: COc1cnc(-c2nn(Cc3c(F)cc(O)cc3F)c3ccccc23)nc1Nc1ccncc1C(N)=O] | 4-({2-[1-(2,6-difluoro-4-hydroxybenzyl)-1H-indazol-3-yl]-5-methoxypyrimidin-4-yl}amino)pyridine-3-carboxamide | ¹H-NMR (500 MHz, DMSO-d₆): δ [ppm] = 4.05 (s. 3H), 5.66 (s, 2H), 6.54 (m. 2H), 7.30 (t, 1H), 7.51 (t, 1H), 7.85-7.88 (m, 2H), 8.42 (s, 1H), 8.46 (br. s, 1H), 8.48 (s, 1H), 8.49 (s, 1H), 8.53 (d, 1H), 8.96 (s, 1H), 9 33 (d, 1H), 10.56 (br. s, 1H).<br>LC-MS (Method 5):<br>retention time: 0.75 min<br>MS ES⁺: 504.2 [M + H]⁺ |

Example 26-1

Preparation of 4-({2-[1-(2-fluorobenzyl)-H-indazol-3-yl]-5-hydroxypyrimidin-4-yl}amino)pyridine-3-carbonitrile

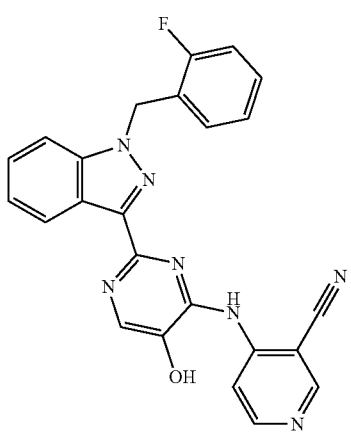 [SMILES: N#Cc1cnccc1Nc1nc(-c2nn(Cc3ccccc3F)c3ccccc23)ncc1O]

50 mg of 4-amino-2-[1-(2-fluorobenzyl)-1H-indazol-3-yl]pyrimidin-5-ol (1-11-1, 0.149 mmol, 1. eq.) were dissolved in 3 ml of N,N-dimethylformamide. 103 mg of potassium carbonate (0.746 mmol, 5 eq.) and 32.8 mg of 4-bromopyridine-3-carbonitrile (0.179 mmol, 1.2 eq.) were added. The reaction mixture was stirred at 100° C. bath temperature for 18 hours. After cooling at room temperature the mixture was filtered off and washed with dichloromethane. The filtrate was concentrated in vacuo. The residue was purified by preparative HPLC and preparative TLC to yield 4.21 mg (0.01 mmol, 6.1%) of the analytically pure target compound.

¹H-NMR (400 MHz, DMSO-d₆): δ [ppm]=5.75 (s, 2H), 7.10-7.25 (m, 4H), 7.29 is 7.37 (m, 1H), 7.41 (ddd, 1H), 7.76 (d, 1H), 8.21 (s, 1H), 8.30 (d, 1H), 8.48 (d, 1H), 8.65 (d, 1H), 8.86 (s, 1H), 8.90-9.03 (m, 1H), 11.09-11.44 (m, 1H).

LC-MS:

retention time: 1.13 min

MS ES⁺: 438.32 [M+H]⁺

The following compound was formed during the same procedure using the indicated starting material (SM=starting material):

| | | | |
|---|---|---|---|
| 26-2 SM = 1-11-1 | 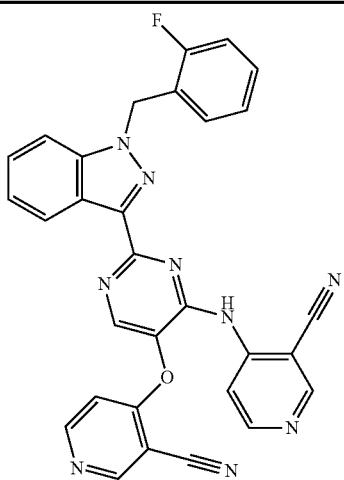 | 4-({4-[(3-cyanopyridin-4-yl)amino]-2-[1-(2-fluorobenzyl)-7H-indazol-3-yl]pyrimidin-5-yl}oxy)pyridine-3-carbonitrile | LC-MS: retention time: 1.10 min MS ES$^+$: 540.30 [M + H]$^+$ |

Example 27-1

Preparation of 5-methoxy-2-[1-(4-methoxybenzyl)-1H-indazol-3-yl]-N-[3-(trifluoromethyl)pyridin-4-yl]pyrimidin-4-amine

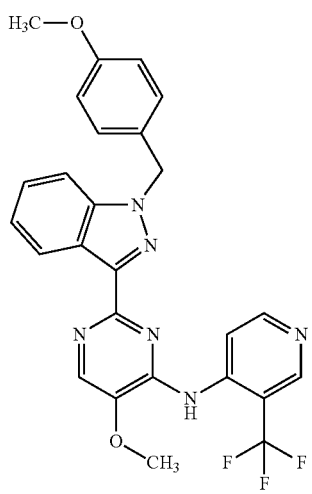 [SMILES: COc1ccc(Cn2nc(-c3ncc(OC)c(Nc4ccncc4C(F)(F)F)n3)c3ccccc32)cc1]

1 g of 5-methoxy-2-[1-(4-methoxybenzyl)-1H-indazol-3-yl]pyrimidin-4-amine (1-4-1, 2.77 mmol, 1. eq.), 938 mg of 4-bromo-3-(trifluoromethyl)pyridine (4.15 mmol, 1.5 eq.), 127 mg of Tris(dibenzylideneacetone)dipalladium (0) (0.138 mmol, 0.05 eq.), 345 mg of 1,1'-binaphthalene-2,2'-diylbis(diphenylphosphane) (0.553 mmol, 0.2 eq), 1.06 g of sodium 2-methylpropan-2-olate (97%) (11.1 mmol, 4 eq.) and 15 ml of N,N-dimethylformamide were stirred under nitrogen atmosphere for 24 hours at 100° C. bath temperature in a pressure pipe. The reaction mixture was washed with half-saturated aqueous ammonium chloride solution. The organic layer was extracted three times with dichloromethane. The combined organic layers were washed with brine and dried over magnesium sulfate and concentrated in vacuo. The residue was purified twice by flash chromatography (hexane/ethyl acetate/methanol) and preparative TLC. A crystallisation gave 56.9 mg (0.1 mmol, 3.73%) of the analytically pure target compound.

$^1$H-NMR (400 MHz, DMSO-d$_6$): δ [ppm]=3.66 (s, 3H), 4.05 (s, 3H), 5.65 (s, 2H), 6.81-6.89 (m, 2H), 7.17 (t, 1H), 7.28 (d, 2H), 7.34-7.42 (m, 1H), 7.76 (d, 1H), 8.18-8.28 (m, 2H), 8.45 (s, 1H), 8.76-8.89 (m, 3H).

LC-MS:
retention time: 1.39 min
MS ES$^+$: 507.0 [M+H]$^+$

Example 28-1

Preparation of 3-chloro-4-({3-[5-methoxy-4-(pyridin-4-ylamino)pyrimidin-2-yl]-1H-indazol-1-yl}methyl)benzoic acid

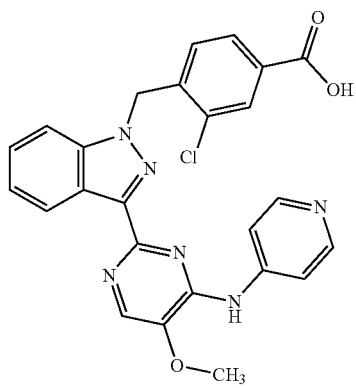 [SMILES: COc1cnc(-c2nn(Cc3ccc(C(=O)O)cc3Cl)c3ccccc23)nc1Nc1ccncc1]

150 mg of methyl 3-chloro-4-({3-[5-methoxy-4-(pyridin-4-ylamino)pyrimidin-2-yl]-1H-indazol-1-yl}methyl)benzoate (2-11-1, 0.299 mmol, 1. eq.) were dissolved in 0,364 ml of methanol. 60 mg of sodium hydroxid (1.50 mmol, 5 eq.) were added. The reaction mixture was stirred at room temperature for 3 hours. The resulting suspension was neutralised with acetic acid. The solution was diluted with ethyl acetate. The occurred precipitate was filtered off and washed with ethyl acetate and was dried in vacuo at 50° C. to yield 138 mg (0.28 mmol, 92.8%) of the analytically pure target compound.

$^1$H-NMR (400 MHz, DMSO-d$_6$): δ [ppm]=4.01 (s, 3H), 5.88 (s, 2H), 7.20 (d, 1H), 7.26 (t, 1H), 7.45 (td, 1H), 7.76-7.85 (m, 2H), 7.95 (d, 1H), 8.07-8.11 (m, 2H), 8.32-8.37 (m, 3H), 8.48 (d, 1H), 9.39 (s, 1H).

LC-MS:

retention time: 0.93 min

MS ES⁺: 487.2 [M+H]⁺

Example 29-1

Preparation of formic acid—3-chloro-4-({3-[5-methoxy-4-(pyridin-4-ylamino)pyrimidin-2-yl]-1H-indazol-1-yl}methyl)-N-methylbenzamide (1:1)

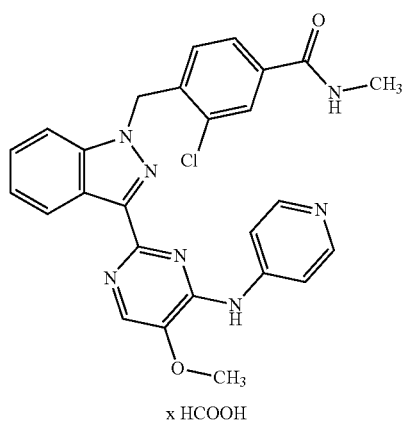 [SMILES: CNC(=O)c1ccc(Cn2nc(-c3ncc(OC)c(Nc4ccncc4)n3)c3ccccc32)c(Cl)c1]

x HCOOH 130.9 mg of 3-chloro-4-({3-[5-methoxy-4-(pyridin-4-ylamino)pyrimidin-2-yl]-1H-indazol-1-yl}methyl)benzoic acid (28-1, 0.269 mmol, 1. eq.), 1.1 ml of dimethylsulfoxide, 269 µl of 2 M methanamine in tetrahydrofuran (0.538 mmol, 2 eq.), 225 mg of N-[(dimethylamino)(3H-[1,2,3]triazolo[4,5-b]pyridin-3-yloxy)methylidene]-N-methylmethanaminium hexafluorophosphate (HATU; 0.591 mmol, 2.2 eq.) and 140 µl of N-ethyl-N-(propan-2-yl)propan-2-amine (0.806 mmol, 3 eq.) were stirred at 50° C. bath temperature for 5 hours. The reaction mixture was filtered off and purified by preparative HPLC to yield 91 mg (0.17 mmol, 62%) of the analytically pure target compound.

¹H-NMR (300 MHz, DMSO-d₆): δ [ppm]=2.72 (d, 3H), 4.01 (s, 3H), 5.85 (s, 2H), 7.19-7.29 (m, 2H), 7.40-7.48 (m, 1H), 7.73 (dd, 1H), 7.79 (d, 1H), 7.92 (d, 1H), 8.06-8.13 (m, 3H), 8.31-8.39 (m, 3H), 8.44-8.54 (m, 2H), 9.39 (s, 1H).

LC-MS:

retention time: 0.82 min

MS ES⁺: 500.1 [M+H]⁺

Method B

The compound was treated with base to form the salt free analogon:

| | | | |
|---|---|---|---|
| 29-2<br>SM =<br>28-1 | | 3-chloro-4-({3-[5-methoxy-4-(pyridin-4-ylamino)pyrimidin-2-yl]-1H-indazol-1-yl}methyl)-N-methylbenzamide | ¹H-NMR (300 MHz, DMSO-d₆): δ [ppm] = 2.72 (d, 3H), 4.01 (s, 3H), 5.85 (s, 2H), 7.20-7.28 (m, 2H), 7.44 (td, 1H), 7.73 (dd, 1H), 7.79 (d, 1H), 7.92 (d, 1H), 8.10 (dd, 2H), 8.32-8.39 (m, 3H), 8.45-8.54 (m, 2H), 9.38 (s, 1H). |
| | 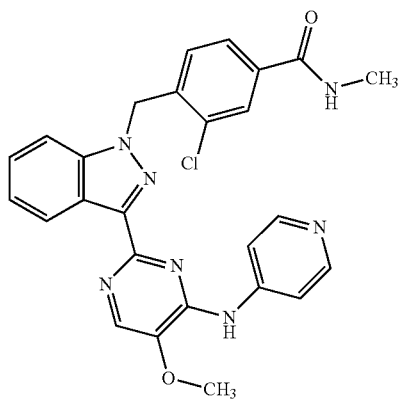 [SMILES: CNC(=O)c1ccc(Cn2nc(-c3ncc(OC)c(Nc4ccncc4)n3)c3ccccc32)c(Cl)c1] | | |

Example 30-1

Preparation of 4-({2-[1-(2-fluorobenzyl)-H-indazol-3-yl]-5-hydroxypyrimidin-4-yl}amino)pyridine-3-carboxamide

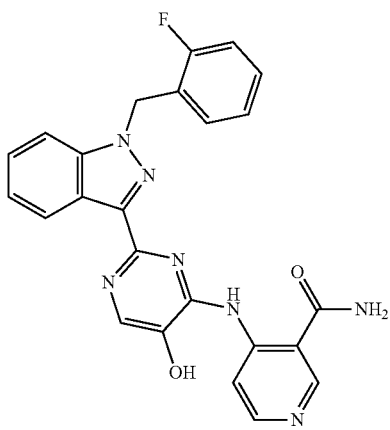 [SMILES: NC(=O)c1cnccc1Nc1nc(-c2nn(Cc3ccccc3F)c3ccccc23)ncc1O]

25 mg of 4-amino-2-[1-(2-fluorobenzyl)-1H-indazol-3-yl]pyrimidin-5-ol (1-11-1, 0.075 mmol, 1. eq.) were dissolved in 1.5 ml of N,N-dimethylformamide. 51.52 mg of potassium carbonate (0.373 mmol, 5 eq.) and 23.35 mg of 4-chloropyridine-3-s carboxamide (0.149 mmol, 2 eq.) were added. The reaction mixture was stirred at 100° C. bath temperature in a pressure pipe for 48 h ours. The reaction mixture was filtered off. The residue was purified by preparative HPLC to yield 2.07 mg (0.004 mmol, 5.6%) of the analytically pure target compound.

$^1$H-NMR (300 MHz, DMSO-$d_6$): δ [ppm]=5.77 (s, 2H), 7.11-7.37 (m, 5H), 7.40-7.48 (m, 1H), 7.74-7.83 (m, 2H), 8.18 (s, 1H), 8.38 (br. s., 1H), 8.41-8.50 (m, 2H), 8.89 (s, 1H), 9.20 (d, 1H), 10.90 (br. s., 1H), 11.94 (s, 1H).

LC-MS:

retention time: 0.94 min

MS ES$^+$: 456.2 [M+H]$^+$

The following compound was formed during the same procedure using the indicated starting material (SM=starting material):

| | | | |
|---|---|---|---|
| 30-2<br>SM =<br>1-11-1 | 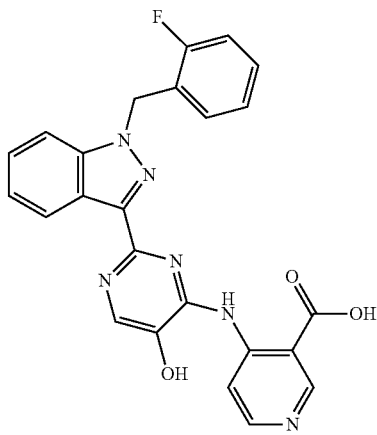 [SMILES: O=C(O)c1cnccc1Nc1nc(-c2nn(Cc3ccccc3F)c3ccccc23)ncc1O] | 4-({2-[1-(2-fluorobenzyl)-1H-indazol-3-yl]-5-hydroxypyrimidin-4-yl}amino)pyridine-3-carboxylic acid | $^1$H-NMR (300 MHz, DMSO-$d_6$): δ [ppm] = 5.78 (s, 2H), 7.12-7.39 (m, 6H), 7.44 (t, 1H), 7.79 (d, 1H), 8.23 (s, 1H), 8.44 (d, 1H), 8.50 (d, 1H), 8.98 (s, 1H), 9.33 (d, 1H), 11.02 (br. s., 1H), 13.66- 14.11 (br. s., 1H).<br>LC-MS:<br>retention time: 0.95 min<br>MS ES$^+$: 456.9 [M + H]$^+$<br>Method B |
| 30-3<br>SM =<br>1-11-1 | 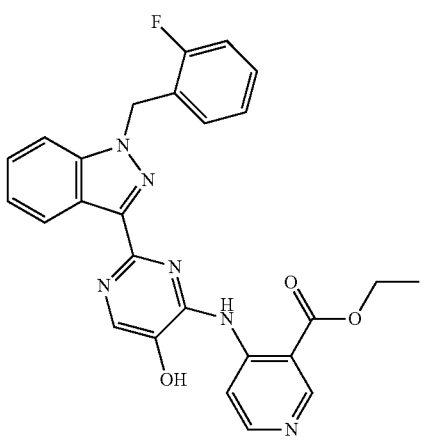 [SMILES: CCOC(=O)c1cnccc1Nc1nc(-c2nn(Cc3ccccc3F)c3ccccc23)ncc1O] | ethyl 4-({2-[1-(2-fluorobenzyl)-1H-indazol-3-yl]-5-hydroxypyrimidin-4-yl}amino)pyridine-3-carboxylate | $^1$H-NMR (300 MHz, DMSO-$d_6$): δ [ppm] = 1.36 (t, 3H), 4.35 (q, 2H), 5.68 (s, 2H), 7.07-7.38 (m, 7H), 7.47 (s, 1H), 7.63 (d, 1H), 8.32-8.42 (m, 1H), 8.43-8.53 (m, 1H), 8.90 (s, 1H), 9.43 (d, 1H), 11.26 (s, 1H).<br>LC-MS:<br>retention time: 1.09 min<br>MS ES$^+$: 485.21 [M + H]$^+$ |

Example 31-1

Preparation of 2-[1-(2-fluorobenzyl)-1H-indazol-3-yl]-4-(pyridin-4-ylamino)pyrimidine-5-carbonitrile

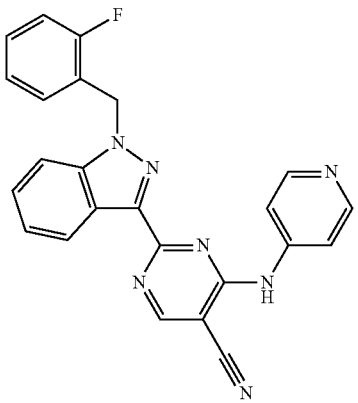 [SMILES: N#Cc1cnc(-c2nn(Cc3ccccc3F)c3ccccc23)nc1Nc1ccncc1]

73 mg of 4-chloro-2-[1-(2-fluorobenzyl)-1H-indazol-3-yl]pyrimidine-5-carbonitrile (1-14-1, 0.201 mmol, 1. eq.), 22.66 mg of pyridin-4-amine (0.241 mmol, 1.2 eq.), 42 µl of N-ethyl-N-(propan-2-yl)propan-2-amine (0.241 mmol, 1.2 eq.) and 1 ml of N,N-dimethylformamide were stirred at room temperature for 24 hours. The reaction mixture was partitioned between half-saturated aqueous sodium hydrogen carbonate solution and dichloromethane/isopropanol 4:1. The aqueous layer was extracted twice with dichloromethane/isopropanol 4:1. The combined organic layers were washed with brine, dried over a silicon filter and concentrated in vacuo. The residue was purified by flash chromatography and preparative HPLC to yield 24.4 mg (0.06 mmol, 28.9%) of the analytically pure target compound.

$^1$H-NMR (300 MHz, DMSO-$d_6$): δ [ppm]=5.83 (s, 2H), 7.08-7.40 (m, 5H), 7.47 (td, 1H), 7.82-7.92 (m, 3H), 8.34 (d, 1H), 8.46 (d, 2H), 8.99 (s, 1H), 10.16-10.37 (m, 1H).

LC-MS:

retention time: 1.00 min

MS ES$^+$: 422.2 [M+H]$^+$

Example 32-1

Preparation of 2-[1-(2-fluorobenzyl)-1H-indazol-3-yl]-4-(pyridin-4-ylamino)pyrimidine-5-carboxamide

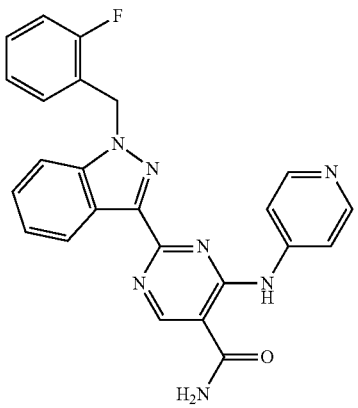 [SMILES: NC(=O)c1cnc(-c2nn(Cc3ccccc3F)c3ccccc23)nc1Nc1ccncc1]

20.7 mg of 2-[1-(2-fluorobenzyl)-1H-indazol-3-yl]-4-(pyridin-4-ylamino)pyrimidine-5-carbonitrile (31-1, 0.049 mmol, 1 eq.) were added to ice bath cooled conc. sulfuric acid (1.84 mmol, 37.5 eq.) and stirred for five minutes at 5° C. and further 24 hours at room temperature. Ice was added to the suspension. The suspension was filtered off, washed with water and the filter cake was dried under vacuo at 50° C. to yield 23.0 mg (0.05 mmol, 106%) of the analytically pure target compound.

$^1$H-NMR (300 MHz, DMSO-$d_6$): δ [ppm]=5.86 (s, 2H), 7.13-7.27 (m, 2H), 7.29-7.41 (m, 3H), 7.46-7.55 (m, 1H), 7.88 (d, 1H), 8.07 (br. s., 1H), 8.28 (d, 2H), 8.46 (d, 1H), 8.57 (d, 3H), 9.19 (s, 1H), 12.07 (s, 1H).

LC-MS:

retention time: 1.02 min

MS ES$^+$: 440.37 [M+H]$^+$

Example 33-1

Preparation of 4-({2-[1-(2-fluorobenzyl)-1H-indazol-3-yl]-5-(2-hydroxyethoxy)pyrimidin-4-yl}amino)pyridine-3-carboxylic acid hydrochloride (1:1)

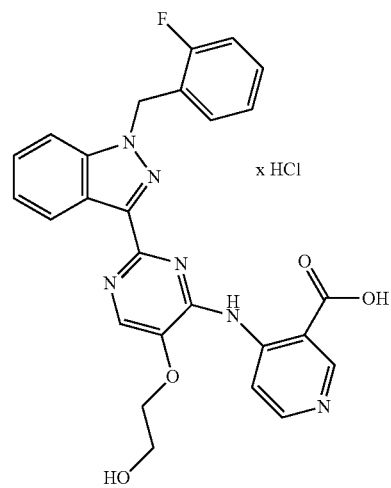 [SMILES: O=C(O)c1cnccc1Nc1nc(-c2nn(Cc3ccccc3F)c3ccccc23)ncc1OCCO]

183 mg of 4-({5-(2-{[tert-butyl(dimethyl)silyl]oxy}ethoxy)-2-[1-(2-fluorobenzyl)-1H-indazol-3-yl]pyrimidin-4-yl}amino)pyridine-3-carboxylic acid (derived from 30-3 as SM via step 1 of the procedure described in 13-1 and subsequent ester hydrolysis) 0.297 mmol, 1. eq.) were dissolved in 10 ml of 4 M hydrogen chloride solution in dioxane and stirred at room temperature for 24 hours. The precipitate was filtered off, washed with dichloromethane and the filter cake was dried under vacuo to yield 157 mg (0.26 mmol, 88.4%) of the analytically pure target compound.

$^1$H-NMR (300 MHz, DMSO-$d_6$): δ [ppm]=3.52 (s, 2H), 3.79-3.88 (m, 2H), 4.35 (t, 2H), 5.82 (s, 2H), 7.08-7.38 (m, 5H), 7.46 (t, 1H), 7.81 (d, 1H), 8.43 (d, 1H), 8.65-8.70 (m, 1H), 8.76 (d, 1H), 9.11 (s, 1H), 9.66 (d, 1H), 12.53 (s, 1H).

LC-MS:

retention time: 0.98 min

MS ES$^+$: 501.33 [M+H]$^+$

Example 34-1

Preparation of N-(2-fluoropyridin-4-yl)-5-methoxy-2-[1-(4-methoxybenzyl)-1H-indazol-3-yl]pyrimidin-4-amine

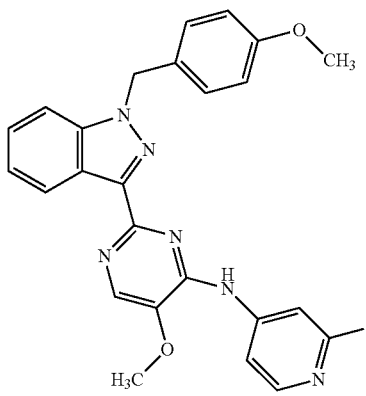

100 mg of 5-methoxy-2-[1-(4-methoxybenzyl)-1H-indazol-3-yl]pyrimidin-4-amine (1-4-1, 0.277 mmol, 1. eq.), 78.0 mg of (2-fluoropyridin-4-yl)boronic acid (0.553 mmol, 2 eq.) and 205 mg of copper (II) acetate were suspended in 4 ml of trichloromethane. 154 µl of triethylamine (1.11 mmol, 4 eq.) and 16.9 mg of N,N-dimethylpyridin-4-amine (138 mmol, 0.5 eq.) were added. The reaction mixture was stirred at room temperature for 24 hours. The reaction mixture was filtered off over Celite 545 and washed with dichloromethane. The filtrate was concentrated in vacuo. The residue was purified by flash chromatography and preparative HPLC to yield 13 mg (0.03 mmol, 10.9%) of the analytically pure target compound.

$^1$H-NMR (300 MHz, DMSO-d6): δ [ppm]=3.66 (s, 3H), 4.03 (s, 3H), 5.63 (br. s., 2H), 6.85 (d, 2H), 7.23 (d, 1H), 7.29-7.48 (m, 3H), 7.75-7.92 (m, 2H), 8.05 (d, 1H), 8.26 (s, 1H), 8.42 (d, 2H), 9.75 (s, 1H).

LC-MS:

retention time: 1.25 min

MS ES$^+$: 457.2 [M+H]$^+$

The following compound was formed according to the same procedure using the indicated starting material (SM):

| | | | |
|---|---|---|---|
| 34-2<br>SM =<br>1-4-1 | 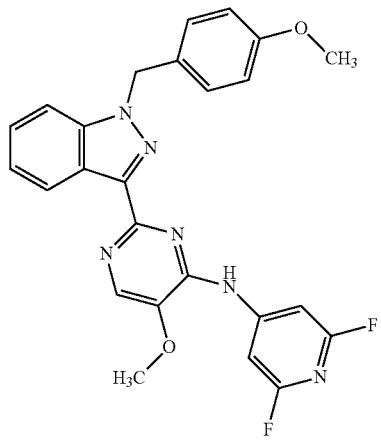 [SMILES: COc1ccc(Cn2nc(-c3ncc(OC)c(Nc4cc(F)nc(F)c4)n3)c3ccccc32)cc1] | N-(2,6-difluoropyridin-4-yl)-5-methoxy-2-[1-(4-methoxybenzyl)-1H-indazol-3-yl]pyrimidin-4-amine | $^1$H-NMR (400 MHz, DMSO-d6): δ [ppm] = 3.66 (s, 3H), 4 04 (s, 3H), 5.63 (s, 2H), 6.84 (d, 2H), 7.22 (t, 1H), 7.36 (d, 2H), 7.40 (d, 1H), 7.83 (d, 1H), 7.98 (s, 2H), 8.38-8.49 (m, 2H), 10.04 (s, 1H).<br>LC-MS:<br>retention time: 1.40 min<br>MS ES$^+$: 475.3 [M + H]$^+$<br>Method B |
| 34-3<br>SM =<br>1-4-1 | 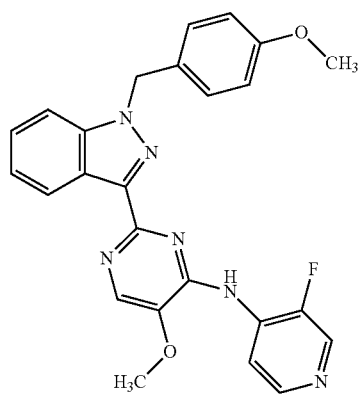 [SMILES: COc1ccc(Cn2nc(-c3ncc(OC)c(Nc4ccncc4F)n3)c3ccccc32)cc1] | N-(3-fluoropyridin-4-yl)-5-methoxy-2-[1-(4-methoxybenzyl)-1H-indazol-3-yl]pyrimidin-4-amine | $^1$H-NMR (300 MHz, DMSO-d6): δ [ppm] = 3.65 (s, 3H), 4.02 (s, 3H), 5.62 (br. s., 2H), 6.83 (d, 2H), 7.07-7.18 (m, 1H), 7.24 (br. s., 2H), 7.38 (t, 1H), 7.74 (d, 1H), 8.22 (d, 1H), 8.29-8.79 (m, 5H).<br>LC-MS:<br>retention time: 1.17 min<br>MS ES$^+$: 457.43 [M + H]$^+$<br>Method B |

| | | | |
|---|---|---|---|
| 34-4 SM = 1-4-1 | 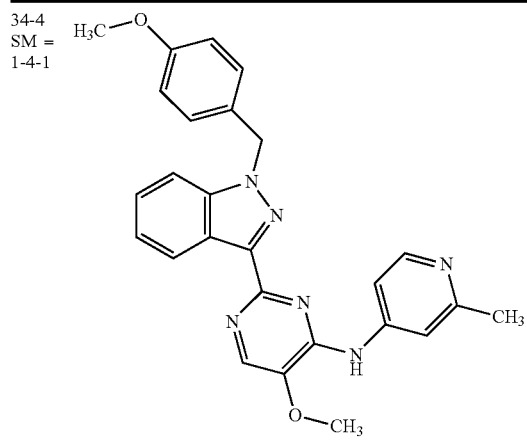 | 5-methoxy-2-[1-(4-methoxybenzyl)-1H-indazol-3-yl]-N-{2-methylpyridin-4-yl}pyrimidin-4-amine | ¹H-NMR (300 MHz, DMSO-d6): δ [ppm] = 2.41 (s, 3H), 3.66 (s, 3H), 4.01 (s, 3H), 5.65 (br. s., 2H), 6.85 (d, 2H), 7.20 (t, 1H), 7.31 (d, 2H), 7.40 (t, 1H), 7.72 (br. d, 1H), 7.79 (d, 1H), 8.23-8.27 (m, 2H), 8.32 (s, 1H) 8.44 (d, 1H), 9.30 (m, 1H). LC-MS (Method 2): retention time: 0.96 min MS ES⁺: 453.1 [M + H]⁺ |

Example 35-1

Preparation of N-(difluoromethyl)-2-[1-(4-ethoxy-2,6-difluorobenzyl)-1H-indazol-3-yl]-N-(pyridin-4-yl)pyrimidin-4-amine

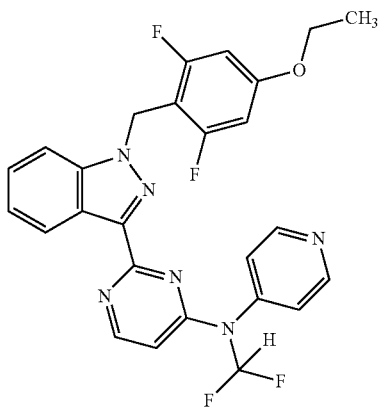 [SMILES: CCOc1cc(F)c(Cn2nc(-c3nccc(N(c4ccncc4)C(F)F)n3)c3ccccc32)c(F)c1]

119.176 mg of 2-[1-(4-ethoxy-2,6-difluorobenzyl)-1H-indazol-3-yl]-N-(pyridin-4-yl)pyrimidin-4-amine (5-1, 0.260 mmol, 1. eq.) were dissolved in 2 ml of dry N,N-dimethylformamide. 254.09 mg of cesium carbonate and 39.63 mg of sodium chloro(difluoro)acetate were added and stirred for two hours at 100° C. bath temperature under nitrogen atmosphere. Then the mixture was portioned between water and dichloromethane/isopropanol 4:1. The phases were separated and the aqueous layer (slightly brown) was extracted twice with dichloromethane/isopropanol 4:1. The combined organic layers were washed with brine, dried over a silicone filter and concentrated in vacuo. The residue was purified by flash chromatography to yield 9 mg (0.02 mmol, 6.13%) of the analytically pure target compound.

¹H-NMR (500 MHz, DMSO-d 6): δ [ppm]=1.27-1.31 (t, 3H), 4.04 (q, 2H), 5.69 (s, 2H), 6.70-6.82 (m, 5H), 7.24 (t, 1H), 7.42-7.68 (m, 1H), 7.47 (ddd, 1H), 7.79 (dd, 3H), 8.47 (d, 1H), 8.60 (d, 1H).

LC-MS:
retention time: 1.09 min
MS ES⁺: 509.1 [M+H]⁺

Method B

Example 36-1

Preparation of 2-[1-(4-ethoxy-2,6-difluorobenzyl)-1H-indazol-3-yl]-5-[2-(methylsulfinyl)ethoxy]-N-(pyridin-4-yl)pyrimidin-4-amine

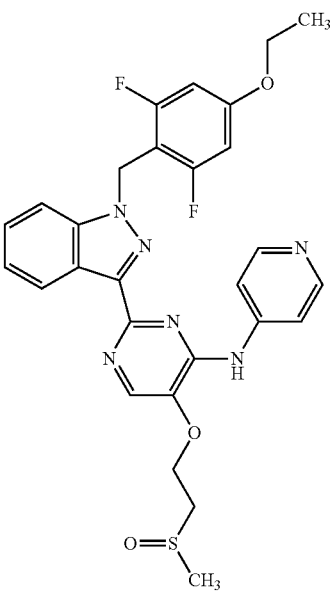 [SMILES: CCOc1cc(F)c(Cn2nc(-c3ncc(OCCS(C)=O)c(Nc4ccncc4)n3)c3ccccc32)c(F)c1]

To a solution of 1.24 g 2-[1-(4-ethoxy-2,6-difluorobenzyl)-1H-indazol-3-yl]-5-[2-(methylsulfanyl) ethoxy]-N-(pyridin-4-yl)pyrimidin-4-amine (4-16, 2.26 mmol, 1. eq.) in 2.15 ml of dry chloroform, was added slowly at 0° C. a solution of 557 mg 2-chlorobenzenecarboperoxoic acid (77%, 2.49 mmol, 1.1 eq.) in 2.15 ml chloroform. After 30 min dichloromethane and sodium thiosulfate-solution (10%) were added. The slurry was stirred for 5 min. After separating the solid (product) the aqueous layer was washed with dichloromethane twice. The organic layers were dried with sodium sulphate and concentrated in vacuo. The residue was purified by flash chromatography and combined the former isolated solid to yield 1.22 g (2.05 mmol, 91%) of the analytically pure target compound.

$^1$H-NMR (400 MHz, DMSO-d 6): δ [ppm]=1.29 (t, 3H), 2.72 (s, 3H), 3.18-3.28 (m, 1H), 3.34-3.47 (m, 1H), 4.04 (q, 2H), 4.58-4.78 (m, 2H), 5.69 (s, 2H), 6.73-6.87 (m, 2H), 7.21-7.34 (m, 1H), 7.43-7.56 (m, 1H), 7.80-7.92 (m, 1H), 8.08-8.17 (m, 2H), 8.39-8.52 (m, 4H), 9.40 (s, 1H)

LC-MS:

retention time: 0.98 min

MS ES$^+$: 564.0 [M+H]$^+$

Example 36-1 was separated into its enantiomers via chiral HPLC separation (Method:

Column: Chiralpak AD-H 5μ 150×4.6 Channel: UV_VIS_3

Solvent: A:Hexan C:EtOH Wavelength (nm): 280

Puffer: 0.1% DEA Flow (ml/min): 1,000

Gradient: Iso_70% A+30% C Run Time (min): 15.00

Solution: 1 mg/mL EtOH/MeOH 2:1 Vial Number: 6

Comment: 259C Injection Volume: 10.0)

| 36-2 SM = 36-1 | 2-[1-(4-ethoxy-2,6-difluorobenzyl)-1H-indazol-3-yl]-5-[2-(methylsulfinyl)ethoxy]-N-(pyridin-4-yl)pyrimidin-4-amine (Enantiomer 1) | $^1$H-NMR (400 MHz, DMSO-d 6): δ [ppm] = 1.29 (t, 3H), 2.72 (s, 3H), 3.18-3.28 (m, 1H), 3.34-3.47 (m, 1H), 4.04 (q, 2H), 4.58-4.78 (m, 2H), 5.69 (s, 2H), 6.73-6.87 (m, 2H), 7.21-7.34 (m, 1H), 7.43-7.56 (m, 1H), 7.80-7.92 (m, 1H), 8.08-8.17 (m, 2H), 8.39-8.52 (m, 4H), 9.40 (s, 1H). retention time: 10.08 min specific rotation: 18.5° +/− 0.08° |
| --- | --- | --- |
| 36-3 SM = 36-1 | 2-[1-(4-ethoxy-2,6-diflorobenzyl)-1H-indazol-3-yl]-5-[2-(methylsulfinyl)ethoxy]-N-(pyridin-4-yl)pyrimidin-4-amine (Enantiomer 2) | $^1$H-NMR (400 MHz, DMSO-d 6): δ [ppm] = 1.29 (t, 3H), 2.72 (s, 3H), 3.18-3.28 (m, 1H), 3.34-3.47 (m, 1H), 4.04 (q, 2H), 4.58-4.78 (m, 2H), 5.69 (s, 2H), 6.73-6.87 (m, 2H), 7.21-7.34 (m, 1H), 7.43-7.56 (m, 1H), 7.80-7.92 (m, 1H), 8.08-8.17 (m, 2H), 8.39-8.52 (m, 4H), 9.40 (s, 1H) retention time: 12.87 min specific rotation: −14.7° +/− 0.15° |

Example 37-1 Preparation of 2-[1-(4-ethoxy-2,6-difluorobenzyl)-1H-indazol-3-yl]-5-[2-(methylsulfonyl)ethoxy]-N-(pyridin-4-yl)pyrimidin-4-amine

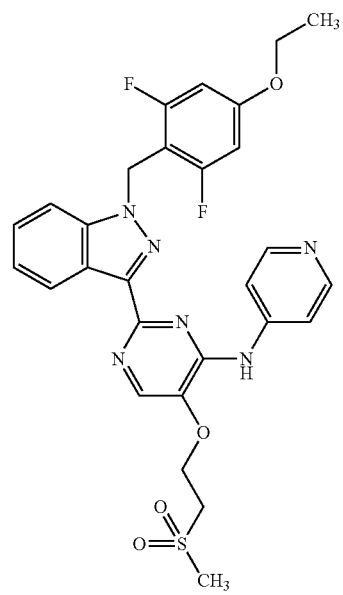 [SMILES: CCOc1cc(F)c(Cn2nc(-c3ncc(OCCS(C)(=O)=O)c(Nc4ccncc4)n3)c3ccccc32)c(F)c1]

100 mg of 2-[1-(4-ethoxy-2,6-difluorobenzyl)-1H-indazol-3-yl]-5-[2-(methylsulfinyl)ethoxy]-N-(pyridin-4-yl)pyrimidin-4-amine (36-1, 0.177 mmol, 1.0 eq.) were dissolved in 0.9 ml of anhydrous tetrahydrofuran. 0.09 ml of aqueous hydrogen peroxide (30%, 0.886 mmol, 5.0 eq.) and 37.0 mg Diethylazodicarboxylate were added. The reaction mixture was stirred at 50° C. for 2 h. A white precipitate was filtered off and purified by flash chromatography to yield 18.1 mg (0.03 mmol, 17.6%) of the analytically pure target compound.

$^1$H-NMR (300 MHz, DMSO-d 6): δ [ppm]=1.28 (t, 3H), 3.14 (s, 3H), 3.78 (t, 2H), 4.03 (q, 2H), 4.66 (t, 2H), 5.69 (s, 2H), 6.72-6.95 (m, 2H), 7.27 (t, 1H), 7.49 (t, 1H), 7.86 (d, 1H), 8.05-8.13 (m, 2H), 8.36-8.55 (m, 4H), 9.06 (s, 1H).

LC-MS (Method 1):

retention time: 1.03 min

MS ES$^+$: 581.2 [M+H]$^+$

Example 38-1

Preparation of 5-(2-aminoethoxy)-2-[1-(4-ethoxy-2,6-difluorobenzyl)-1H-indazol-3-yl]-N-(pyridin-4-yl)pyrimidin-4-amine

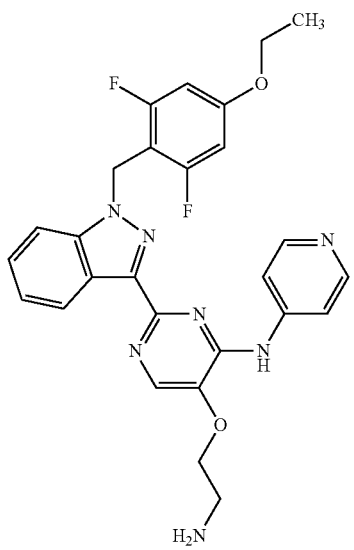 [SMILES: CCOc1cc(F)c(Cn2nc(-c3ncc(OCCN)c(Nc4ccncc4)n3)c3ccccc32)c(F)c1]

28.6 mg of tert-butyl [2-({2-[1-(4-ethoxy-2,6-difluorobenzyl)-1H-indazol-3-yl]-4-(pyridin-4-ylamino)pyrimidin-5-yl}oxy)ethyl]carbamate (4-23, 0.046 mmol, 1.0 eq.) were dissolved in 2 ml of dry dichloromethane. 0.071 ml of trifluoroacetic acid (0.926 mmol, 20.0 eq.) were added at 0° C. The reaction mixture was stirred over night at room temperature. Then a mixture 2 N sodium carbonate and dichloromethane/isopropanol 4:1 was added and the mixture was stirred for 30 min. The phases were separated and the aqueous layer (slightly brown) was extracted twice with dichloromethane/isopropanol 4:1. The combined organic layers were dried over a magnesium sulfate and concentrated in vacuo. The residue was purified by crystallization from ethylacetate to yield 6.8 mg (0.01 mmol, 27.0%) of the analytically pure target compound.

$^1$H-NMR (600 MHz, DMSO-d 6): δ [ppm]=1.29 (t, 3H), 2.98 (t, 2H), 4.05 (q, 2H), 4.15 (t, 2H), 5.68 (s, 2H), 6.75-6.82 (m, 2H), 7.23-7.29 (m, 1H), 7.47-7.50 (m, 1H), 7.85 (d, 1H), 8.13-8.17 (m, 2H), 8.31 (s, 1H), 8.35 (s, 1H), 8.42-8.45 (m, 2H), 8.46 (d, 1H).

LC-MS (Method 5):

retention time: 1.24 min

MS ES$^+$: 518.2 [M+H]$^+$

The following compounds were prepared according to the same procedure using the indicated starting materials (SM=starting material):

| | | | |
|---|---|---|---|
| 38-2<br>SM =<br>4-11 | 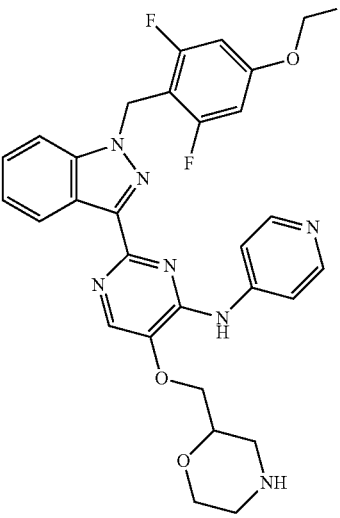 | 2-[1-(4-ethoxy-2,6-difluorobenzyl)-1H-indazol-3-yl]-5-(morpholin-2-ylmethoxy)-N-(pyridin-4-yl)pyrimidin-4-amine | $^1$H-NMR (400 MHz, DMSO-d$_6$): δ [ppm] = 1.28 (t, 3H), 2.51-2.57 (m, 1H), 2.64-2.71 (m, 2H), 2.94-3.02 (m, 1H), 3.45-3.56 (m, 1H), 3.74-3.81 (m, 1H), 3.83-3.92 (m, 1H), 4.02 (q, 2H), 4.12-4.27 (m, 2H), 5.67 (s, 2H), 6.73-6.84 (m, 2H), 7.20-7.30 (m, 1H), 7.43-7.53 (m, 1H), 7.80-7.87 (m, 1H), 8.10-8.17 (m, 2H), 8.38 (s, 1H), 8.39-8.47 (m, 3H), 9.14 (s, 1H).<br>LC-MS (Method 5):<br>retention time: 1.24 min<br>MS ES$^+$: 574.5 [M + H]$^+$ |

Example 39-1

Preparation of ethyl 4-({2-[1-(4-ethoxy-2,6-difluorobenzyl)-1H-indazol-3-yl]-5-methoxypyrimidin-4-yl}amino)pyridine-3-carboxylate

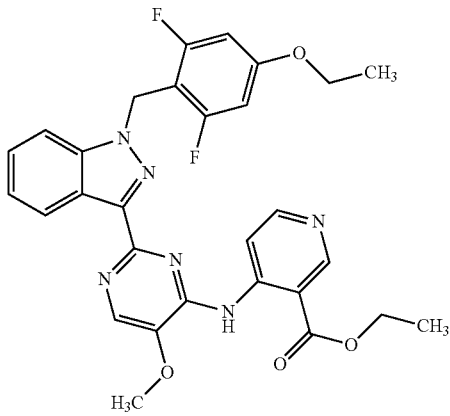 [SMILES: CCOC(=O)c1cnccc1Nc1nc(-c2nn(Cc3c(F)cc(OCC)cc3F)c3ccccc23)ncc1OC]

150 mg of 2-[1-(4-ethoxy-2,6-difluorobenzyl)-1H-indazol-3-yl]-5-methoxypyrimidin-4-amine (1-4-3, 0.365 mmol, 1.0 eq.), 89 mg of commercial ethyl 4-chloronicotinate (0.401 mmol, 1.1 eq.), 31.6 mg of (9,9-dimethyl-9H-xanthene-4,5-diyl)bis(diphenylphosphine) (0.055 mmol, 0.15 eq.), 356 mg of caesium carbonate (1.09 mmol, 3.0 eq.) and 8.2 mg of palladium diacetate (0.036 mmol, 0.1 eq.) were suspended in 4.7 mL of dry dioxane and stirred under nitrogen atmosphere at 105'C bath temperature for 3 h. Solids were filtered off, washed with dioxane and the filtrate was concentrated in vacuo. The residue was purified by flash chromatography yielding 77 mg from which only 15.7 mg were further purified by crystallization from THF to yield 3.1 mg (0.01 mmol, 1.44%) of analytically pure target compound.

$^1$H-NMR (300 MHz, DMSO-d 6): δ [ppm]=1.26 (t, 3H), 1.36 (t, 3H), 3.95-4.10 (m, 5H), 4.37 (q, 2H), 5.68 (s, 2H), 6.71-6.87 (m, 2H), 7.19-7.33 (m, 1H), 7.41-7.54 (m, 1H), 7.83 (d, 1H), 8.37-8.48 (m, 2H), 8.59 (d, 1H), 9.07 (s, 1H), 9.39 (d, 1H), 11.29 (s, 1H).

LC-MS:
retention time: 1.55 min
MS ES$^+$: 560.0 [M+H]$^+$

The following compounds were prepared according to the same procedure using the indicated starting materials (SM=starting material):

| | | | |
|---|---|---|---|
| 39-2<br>SM =<br>1-4-3 | 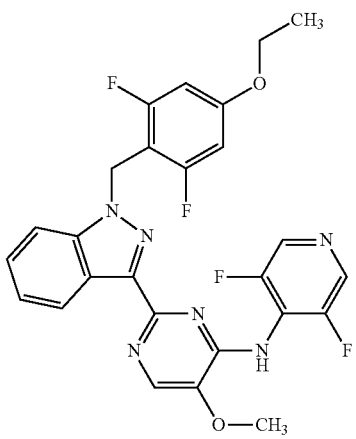 [SMILES: CCOc1cc(F)c(Cn2nc(-c3ncc(OC)c(Nc4c(F)cncc4F)n3)c3ccccc32)c(F)c1] | N-(3,5-difluoropyridin-4-yl)-2-[1-(4-ethoxy-2,6-difluorobenzyl)-1H-indazol-3-yl]-5-methoxypyrimidin-4-amine | $^1$H-NMR (400 MHz, DMSO-d$_6$): δ [ppm] = 1.26 (t, 3H), 3.90-4.12 (m, 5H), 5.58 (s, 2H), 6.62-6.79 (m, 2H), 6.94-7.04 (m, 1H), 7.25-7.40 (m, 1H), 7.65-7.74 (m, 1H), 7.76-7.85 (m, 1H), 8.24 (s, 1H), 8.59 (s, 2H), 9.36 (s, 1H).<br>LC-MS (Method 5):<br>retention time: 1.34 mln<br>MS ES$^+$: 525.2 [M + H]$^+$ |

Example 40-1

Preparation of 2-[1-(3-amino-2,6-dichlorobenzyl)-1H-indazol-3-yl]-5-methoxy-N-(pyridin-4-yl)pyrimidin-4-amine

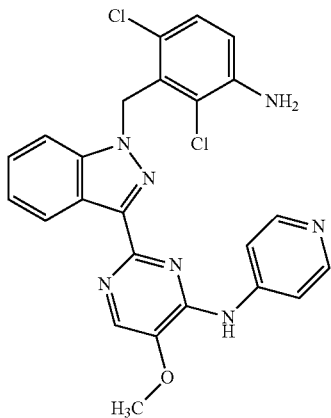 [SMILES: COc1cnc(-c2nn(Cc3c(Cl)ccc(N)c3Cl)c3ccccc23)nc1Nc1ccncc1]

52 mg of 2-[1-(2,6-dichloro-3-nitrobenzyl)-1H-indazol-3-yl]-5-methoxy-N-(pyridin-4-yl)pyrimidin-4-amine (2-44-1, 0.10 mmol, 1.0 eq.) were dissolved in 5.2 ml of dry methanol. 23.4 mg raney nickel (50%, 0.199 mmol, 2.0 eq.) and 0.045 ml hydrazine (35%, 0.498 mmol, 5.0 eq) were added. The reaction mixture was stirred at room temperature vigorously over night. The slurry was filtered over celite and washed with methanol twice. The filtrate was concentrated in vacuo and the residue was purified by flash chromatography to yield 19.2 mg (0.04 mmol, 38%) of the analytically pure target compound.

$^1$H-NMR (300 MHz, DMSO-d 6): δ [ppm]=4.00 (s, 3H), 5.62 (s, 2H), 5.78 (s, 2H), 6.82 (d, 1H), 7.22 (t, 2H), 7.46 (t, 1H), 7.86 (d, 1H), 8.14 (d, 2H), 8.32 (s, 1H), 8.38 (d, 2H), 8.47 (d, 1H), 9.34 (s, 1H).

LC-MS:
retention time: 0.97 min
MS ES$^+$: 492.1 [M+H]$^+$

Example 41-1

Preparation of N-[2,4-dichloro-3-({3-[5-methoxy-4-(pyridin-4-ylamino)pyrimidin-2-yl]-1H-indazol-1-yl}methyl)phenyl]acetamide

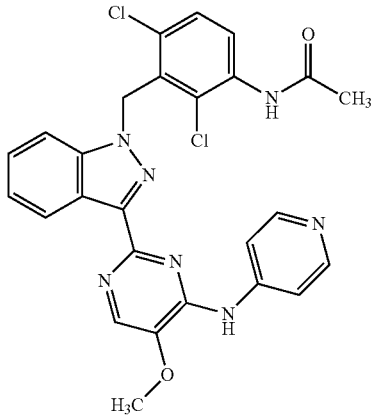 [SMILES: COc1cnc(-c2nn(Cc3c(Cl)ccc(NC(C)=O)c3Cl)c3ccccc23)nc1Nc1ccncc1]

50 mg of 2-[1-(3-amino-2,6-dichlorobenzyl)-1H-indazol-3-yl]-5-methoxy-N-(pyridin-4-yl)pyrimidin-4-amine (40-1, 0.102 mmol, 1.0 eq.) were dissolved in 0.6 ml of dry N,N-dimethylformamide. 0.014 ml N,N-diethylethanamine (0.102 mmol, 1.0 eq.) and 0.010 ml acetic anhydride (0.102 mmol, 1.0 eq.) were added at 0° C. and stirred for 3.5 h Then again 0.014 ml N,N-diethylethanamine (0.102 mmol, 1.0 eq.) and 0.010 ml acetic anhydride (0.102 mmol, 1.0 eq.) were added at 0° C. and stirred over night at room temperature. Saturated sodium hydrogen carbonate solution and ethyl acetate were added and the reaction mixture was stirred for 30 min. The organic layer was washed with ethyl acetate twice. The combined organic layers were dried over a silicone filter and concentrated in vacuum. The residue was purified by flash chromatography to yield 17.3 mg (0.03 mmol, 30%) of the analytically pure target compound.

$^1$H-NMR (400 MHz, DMSO-d 6): δ [ppm]=2.07 (s, 3H), 3.99 (s, 3H), 5.89 (s, 2H), 7.22-7.29 (m, 1H), 7.44-7.52 (m, 1H), 7.58 (d, 1H), 7.79 (d, 1H), 7.90 (d, 1H), 8.09-8.16 (m, 2H), 8.31 (s, 1H), 8.34-8.39 (m, 2H), 8.48 (d, 1H), 9.32 (s, 1H), 9.60 (s, 1H).

LC-MS (Method 1):
retention time: 0.97 min
MS ES$^+$: 534.1 [M+H]$^+$

Example 42-1

Preparation of 2-[1-(4-ethoxy-2,6-difluorobenzyl)-4-methyl-1H-indazol-3-yl]-5-methoxy-N-(pyridin-4-yl)pyrimidin-4-amine

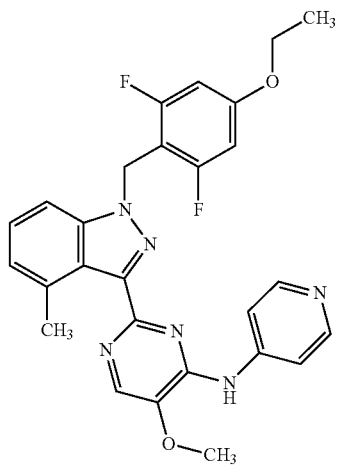 [SMILES: CCOc1cc(F)c(Cn2nc(-c3ncc(OC)c(Nc4ccncc4)n3)c3c(C)cccc32)c(F)c1]

100 mg of 2-[1-(4-ethoxy-2,6-difluorobenzyl)-4-methyl-1H-indazol-3-yl]-5-methoxypyrimidin-4-amine (1-4-6, 0.236 mmol, 1.0 eq.) and 94.2 mg 4-Fluoropyridin hydrochloride (0.705 mmol, 3.0 eq.) were dissolved in 1.1 ml of dry N,N-dimethylformamide. 113 mg sodium hydride (60%, 2.82 mmol, 12 eq.) were added. The reaction mixture was stirred at 90° C. for 2 h. Water and ethyl acetate were added and the aqueous layer was washed with ethyl acetate twice. The combined organic layers were dried over a silicone filter and concentrated in vacuum. The residue was purified by HPLC to yield 46 mg (0.09 mmol, 38%) of the analytically pure target compound.

$^1$H-NMR (300 MHz, DMSO-d 6): δ [ppm]=1.26 (t, 3H), 2.42 (s, 3H), 3.93-4.07 (m, 5H), 5.59 (s, 2H), 6.68-6.78 (m, 2H), 6.94 (d, 1H), 7.32 (t, 1H), 7.59 (d, 1H), 7.91-8.02 (m, 2H), 8.22-8.36 (m, 3H), 9.36 (s, 1H).

LC-MS (Method B):
retention time: 1.32 rain
MS ES+: 503.03 [M+H]+

Biological Investigations

The following assays can be used to illustrate the commercial utility of the compounds according to the present invention.

Examples were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values calculated utilizing data sets obtained from testing of one or more synthetic batch.

Biological Assay 1.0:
Bub1 Kinase Assay

Bub1-inhibitory activities of compounds described in the present invention were quantified using a time-resolved fluorescence energy transfer (TR-FRET) kinase assay which measures phosphorylation of the synthetic peptide Biotin-Ahx-VLLPKKSFAEPG (C-terminus in amide form), purchased from e.g. Biosyntan (Berlin, Germany) by the (recombinant) catalytic domain of human Bub1 (amino acids 704-1085), expressed in HI5 Insect cells with an N-terminal His6-tag and purified by affinity- (Ni-NTA) and size exclusion chromatography.

In a typical assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were tested in duplicate within the same microtiter plate. To this end, 100-fold concentrated compound solutions (in DMSO) were previously prepared by serial dilution (1:3.4) of 2 mM stocks in a clear low volume 384-well source microtiter plate (Greiner Bio-One, Frickenhausen, Germany), from which 50 nl of compounds were transferred into a black low volume test microtiter plate from the same supplier. Subsequently, 2 µl of Bub1 (the final concentration of Bub1 was adjusted depending on the activity of the enzyme lot in order to be within the linear dynamic range of the assay: typically ~200 µg/ml were used) in aqueous assay buffer [50 mM Tris/HCl pH 7.5, 10 mM magnesium chloride (MgCl2), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Trition X-100 (Sigma), 1× Complete EDTA-free protease inhibitor mixture (Roche)] were added to the compounds in the test plate and the mixture was incubated for 15 min at 229 to allow pre-equilibration of the putative enzyme-inhibitor complexes before the start of the kinase reaction, which was initiated by the addition of 3 µl 1.67-fold concentrated solution (in assay buffer) of adenosine-tri-phosphate (ATP, 10 µM final concentration) and peptide substrate (1 µM final concentration). The resulting mixture (5 µl final volume) was incubated at 22° C. during 60 min., and the reaction was stopped by the addition of 5 µl of an aqueous EDTA-solution (50 mM EDTA, in 100 mM HEPES pH 7.5 and 0.2% (w/v) bovine serum albumin) which also contained the TR-FRET detection reagents (0.2 µM streptavidin-XL665 [Cisbio Bioassays, Codolet, France] and 1 nM anti-phosho-Serine antibody [Merck Millipore, cat. #35-001] and 0.4 nM LANCE EU-W1024 labeled anti-mouse IgG antibody [Perkin-Elmer, product no. AD0077, alternatively a Terbium-cryptate-labeled anti-mouse IgG antibody from Cisbio Bioassays can be used]). The stopped reaction mixture was further incubated 1 h at 22° C. in order to allow the formation of complexes between peptides and detection reagents. Subsequently, the amount of product was evaluated by measurement of the resonance energy transfer from the Eu-chelate-antlbody complex recognizing the Phosphoserine residue to the streptavidin-XL665 bound to the biotin moiety of the peptide. To this end, the fluorescence emissions at 620 nm and 665 nm after excitation at 330-350 nm were measured in a TR-FRET plate reader, e.g. a Rubystar or Pherastar (both from BMG Labtechnologies, Offenburg, Germany) or a Viewlux (Perkin-Elmer) and the ratio of the emissions (665 nm/622 nm) was taken as indicator for the amount of phosphorylated substrate. The data were normalised using two sets of (typically 32-) control wells for high- (=enzyme reaction without Inhibitor=0%=Minimum inhibition) and low- (=all assay components without enzyme=100%=Maximum inhibition) Bub1 activity. IC50 values were calculated by fitting the normalized inhibition data to a 4-parameter logistic equation (Minimum, Maximum, IC50, Hill; Y=Max+(Min−Max)/(1+(X/IC50)Hill)) using a Bayer-proprietary analysis software.

Biological Assay 2.0:
Proliferation Assay:

Cultivated tumor cells (cells were ordered from ATCC, except HeLa-MaTu and HeLa-MaTu-ADR, which were ordered from EPO-GmbH, Berlin) were plated at a density of 1000 to 5000 cells/well, depending on the growth rate of the respective cell line, in a 96-well multititer plate in 200 µL of their respective growth medium supplemented 10% fetal calf serum. After 24 hours, the cells of one plate (zeropoint plate) were stained with crystal violet (see below), while the medium of the other plates was replaced by fresh culture medium (200 µl), to which the test substances were added in various concentrations (0 µM, as well as in the range of 0.001-10 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. Absorbtion was determined by photometry at a wavelength of 595 nm. The change of cell number, in percent, was calculated by normalization of the measured values to the aborbtion values of the zero-point plate (=0%) and the absorbtion of the untreated (0 µm) cells (=100%). The IC50 values were determined by means of a 4 parameter fit using the company's own software.

TAB. 1

Compounds had been evaluated in the following cell lines, which examplify the sub-inidications listed

| Tumor indication | Cell line |
|---|---|
| Cervical cancer | HeLa |
|  | HeLa-MaTu-ADR |
| Breast cancer | MDA-MB 453 |
|  | HCC-70 |
|  | MCF7 |
|  | MDA MB231 |
|  | MDA-MB-468 |
| Ovarian cancer | SKBR-3 |
|  | A2780 |
|  | COLO-704 |
|  | Caov-3 |
|  | ES-2 |
|  | SK-OV-3 |
|  | ORGOV-1 |
|  | OVCAR8 |
| Non-small cell lung cancer (NSCLC) | A549 |
|  | NCI-H460 |
|  | NCI-H1299 |
| Prostate cancer | DU145 |
| Colo cancer | Caco2 |
|  | HCT15 |
|  | HT29 |
| Pancreas cancer | MIAPaCa2 |
| Osteo sarcoma | U2OS |
| Acute myelogenous leucemia | KG1 |
|  | MOLM-13 |
|  | MV-4-11 |
| Burkitt lymphoma | RAMOS |
| Multiple myeloma | OPM-2 |
| Melanoma | B16F10 |

The following table gives the data regarding Bub1 kinase inhibition, and inhibition of HeLa cell proliferation, for the examples of the present invention for the biological assays 1 and 2:

| Example Nr. | Biological Assay 1: Bub1 kinase assay median IC50 [mol/l] | Biological Assay 2: Proliferation assay (HeLa cell line) median IC50 [mol/l] |
|---|---|---|
| 2-1-1 | 2.6e-009 | 3.8e-006 |
| 2-1-3 | 1.2e-007 | not tested |
| 2-10-1 | 6.7e-009 | ≥1.0e-005 |
| 2-10-2 | 1.2e-006 | not tested |
| 2-11-1 | 7.1e-009 | 2.9e-007 |
| 2-11-2 | 5.4e-007 | 3.4e-006 |
| 2-12-1 | 7.3-009 | 1.6e-006 |
| 2-13-1 | 8.0e-009 | 3.8e-006 |
| 2-14-1 | 8.3e-009 | 4.7e-006 |
| 2-14-2 | 7.3e-007 | not tested |
| 2-15-1 | 3.8e-008 | 4.7e-006 |
| 2-15-2 | 3.2e-006 | not tested |
| 2-16-1 | 8.4e-009 | 1.6e-006 |
| 2-17-1 | 8.8e-009 | ≥1.0e-005 |
| 2-17-2 | 8.9e-007 | not tested |
| 2-18-1 | 1.3e-008 | 9.3e-006 |
| 2-19-1 | 1.0e-008 | 3.4e-006 |
| 2-2-1 | 2.6e-009 | 3.4e-006 |
| 2-2-3 | 2.5e-008 | not tested |
| 2-20-1 | 1.1e-008 | 7.3e-006 |
| 2-21-1 | 1.2e-008 | ≥1.0e-005 |
| 2-21-2 | 2.0e-005 | not tested |
| 2-22-1 | 3.2e-006 | not tested |
| 2-23-1 | 1.3e-008 | 9.3e-006 |
| 2-24-1 | 1.4e-008 | 3.1e-006 |
| 2-25-1 | 1.5e-008 | 9.8e-006 |
| 2-26-1 | 1.6e-008 | 5.6e-007 |
| 2-26-2 | 8.4e-007 | 2.9e-006 |
| 2-27-1 | 2.0e-008 | ≥1.0e-005 |
| 2-28-1 | 2.2e-008 | 8.1e-006 |
| 2-29-1 | 2.3e-008 | 9.0e-006 |
| 2-3-1 | 4.4e-009 | 3.0e-006 |
| 2-3-3 | 3.6e-007 | 8.5e-006 |
| 2-30-1 | 2.3e-008 | 2.2e-006 |
| 2-31-1 | 2.8e-008 | ≥1.0e-005 |
| 2-32-1 | 2.9e-008 | 4.2e-006 |
| 2-33-1 | 3.8e-008 | ≥1.0e-005 |
| 2-33-2 | 1.1e-006 | not tested |
| 2-34-1 | 3.8e-008 | 1.6e-006 |
| 2-35-1 | 5.2e-008 | ≥1.0e-005 |
| 2-36-1 | 5.8e-008 | ≥1.0e-005 |
| 2-37-1 | 7.1e-008 | ≥1.0e-005 |
| 2-38-1 | 7.6e-008 | ≥1.0e-005 |
| 2-29-1 | 5.6e-009 | 3.6e-006 |
| 2-39-2 | 6.9e-006 | not tested |
| 2-4-1 | 4.5e-009 | 3.5e-006 |
| 2-4-2 | 3.5e-006 | not tested |
| 2-4-3 | 1.4e-008 | 3.9e-006 |
| 2-40-1 | 1.2e-007 | 5.6e-006 |
| 2-41-1 | 1.5e-007 | 7.9e-006 |
| 2-42-1 | 1.9e-007 | ≥1.0e-005 |
| 2-43-1 | 1.2e-006 | ≥1.0e-005 |
| 2-44-1 | 4.1E-8 | not tested |
| 2-45-1 | 1.1E-7 | not tested |
| 2-46-1 | 1.6e-008 | 1.4e-006 |
| 2-47-1 | 2.4E-6 | not tested |
| 2-48-1 | 5.5E-9 | ≥1.0e-005 |
| 2-49-1 | 1.5E-6 | not tested |
| 2-5-1 | 4.6e-009 | 2.1e-006 |
| 2-5-2 | 9.3e-006 | not tested |
| 2-5-3 | 2.1e-008 | ≥1.0e-005 |
| 2-50-1 | 1.1e-008 | ≥1.0e-005 |
| 2-51-1 | 1.0E-8 | 2.7E-6 |
| 2-52-1 | 1.1E-8 | 2.1E-6 |
| 2-53-1 | 8.3e-008 | 3.4e-006 |
| 2-6-1 | 4.7e-009 | 3.8e-006 |
| 2-6-3 | 5.9e-008 | ≥1.0e-005 |
| 2-7-1 | 4.8e-009 | ≥1.0e-005 |
| 2-7-2 | 2.1e-007 | not tested |
| 2-7-3 | 4.3e-007 | ≥1.0e-005 |
| 2-8-1 | 6.7e-009 | ≥1.0e-005 |
| 2-8-2 | 2.9e-007 | not tested |
| 2-8-3 | 5.7e-008 | 1.0e-005 |
| 2-9-1 | 6.7e-009 | ≥1.0e-005 |
| 2-9-2 | 2.4e-007 | not tested |
| 2-9-3 | 2.0e-005 | not tested |
| 3-1 | 4.7e-009 | ≥1.0e-005 |
| 3-2 | 9.8e-009 | ≥1.0e-005 |
| 3-3 | 1.5e-008 | ≥1.0e-005 |
| 3-4 | 4.8e-008 | ≥1.0e-005 |
| 4-1 | 2.4e-009 | 3.5e-006 |
| 4-10 | 9.0e-009 | 4.4e-006 |
| 4-11 | 2.4e-008 | not tested |
| 4-12 | 7.8e-009 | 9.0e-006 |
| 4-13 | 7.6e-009 | 8.0e-006 |
| 4-14 | 1.2e-008 | ≥1.0e-005 |
| 4-15 | 8.0e-009 | 3.9e-006 |
| 4-16 | 1.4e-008 | 4.4e-006 |
| 4-17 | 7.4E-9 | 4.8E-6 |
| 4-18 | 1.2E-8 | not tested |
| 4-19 | 1.0E-8 | 1.2E-6 |
| 4-2-1 | 3.3e-009 | 8.7e-006 |
| 4-2-2 | 4.3e-007 | not tested |
| 4-2-3 | 9.3E-9 | 4.9E-6 |
| 4-20 | 2.1E-7 | not tested |
| 4-21 | 7.8E-9 | 3.8E-6 |
| 4-22 | 5.8E-9 | 1.9E-6 |
| 4-23 | not tested | not tested |
| 4-3 | 7.5e-009 | 1.4e-005 |
| 4-4 | 1.4e-008 | 3.4e-006 |

| Example Nr. | Biological Assay 1: Bub1 kinase assay median IC50 [mol/l] | Biological Assay 2: Proliferation assay (HeLa cell line) median IC50 [mol/l] |
| --- | --- | --- |
| 4-5 | 1.8e-008 | ≥1.0e-005 |
| 4-5-2 | 3.3e-007 | not tested |
| 4-6 | 2.9e-008 | 3.6e-006 |
| 4-7 | 3.5e-008 | ≥1.0e-005 |
| 4-8 | 8.0e-009 | 1.3E-6 |
| 4-9 | 5.4E-9 | 1.7E-6 |
| 4-10 | 9.0E-9 | 4.4E-6 |
| 4-11 | 2.4E-8 | not tes6ted |
| 4-12 | 7.8E-9 | 9.0E-6 |
| 4-13 | 7.6E-8 | 8.0E-005 |
| 4-14 | 1.2E-8 | 1.0e-6 |
| 4-15 | 8.0E-9 | 3.9E-6 |
| 4-16 | 1.4E-8 | 4.4E-6 |
| 4-17 | 7.4E-9 | 4.8E-6 |
| 4-18 | 1.2E-8 | not tested |
| 4-19 | 1.0E-8 | 1.2E-6 |
| 4-20 | 2.1E-7 | not tested |
| 4-21 | 7.8E-9 | 3.8E-6 |
| 4-22 | 5.8E-9 | 1.9E-6 |
| 4-23 | 9.3E-9 | 4.9E-6 |
| 5-1 | 5.2e-009 | 1.4e-006 |
| 5-2 | 2.7e-008 | 7.1e-007 |
| 5-3 | 2.8e-008 | 7.4e-006 |
| 6-1 | 3.9e-009 | 3.1e-006 |
| 6-2 | 7.4e-009 | 1.4e-006 |
| 7-1 | 3.0e-009 | 4.4e-006 |
| 8-1 | 7.4e-009 | 3.2e-006 |
| 8-2 | 2.1e-008 | 5.5e-006 |
| 8-3 | 2.4e-007 | ≥1.0e-005 |
| 8-4 | 1.3E-8 | 5.0E-6 |
| 9-1 | 9.8e-009 | not tested |
| 9-2 | 2.1e-008 | ≥1.0e-005 |
| 9-3 | 2.3e-008 | 7.0e-006 |
| 10-1 | 1.2e-008 | 2.0e-006 |
| 10-2 | 4.2e-007 | 1.7e-006 |
| 10-3 | 3.6e-007 | 9.6e-006 |
| 11-1 | 1.8e-008 | 8.1e-006 |
| 11-2 | 1.0e-008 | ≥1.0e-005 |
| 12-1 | 1.1e-008 | ≥1.0e-005 |
| 12-2 | 4.6e-009 | ≥1.0e-005 |
| 12-3 | 4.8e-009 | ≥1.0e-005 |
| 13-1 | 3.3e-009 | 1.5e-006 |
| 13-2 | 7.2e-009 | 9.6e-006 |
| 13-3 | 1.7e-008 | ≥1.0e-005 |
| 13-4 | 4.7e-009 | 8.0e-006 |
| 13-5 | 6.5e-009 | ≥1.0e-005 |
| 13-6 | 8.6e-009 | ≥1.0e-005 |
| 14-1 | 3.3e-006 | ≥1.0e-005 |
| 15-1 | 5.2e-009 | 1.4e-006 |
| 15-2 | 5.5e-009 | ≥1.0e-005 |
| 15-3 | 5.7e-009 | 1.7e-006 |
| 15-4 | 7.3e-009 | ≥1.0e-005 |
| 15-5 | 1.2e-008 | 9.9e-006 |
| 15-6 | 4.6e-009 | ≥1.0e-005 |
| 16-1 | 1.7e-007 | 2.8e-006 |
| 16-2 | 2.3e-008 | 3.5e-006 |
| 16-3 | 2.1e-007 | 4.1e-006 |
| 16-4 | 2.0e-008 | 2.7e-006 |
| 17-1 | 1.7e-007 | ≥1.0e-005 |
| 17-2 | 2.4e-006 | ≥1.0e-005 |
| 18-1 | 1.6e-008 | 1.4e-006 |
| 18-2 | 2.8e-006 | 3.5e-006 |
| 19-1 | 2.0e-005 | not tested |
| 19-2 | 6.3E-9 | ≥1.0E-5 |
| 20-1 | 2.0e-007 | 1.9e-007 |
| 20-2 | 4.0e-008 | 3.3e-006 |
| 20-3 | 1.2e-006 | 4.1e-006 |
| 20-4 | 7.5e-007 | ≥1.0e-005 |
| 20-5 | 8.8e-006 | 5.9e-006 |
| 20-6 | 6.7e-006 | not tested |
| 21-1 | 2.8e-008 | 3.8e-006 |
| 22-1 | 7.7e-007 | not tested |
| 23-1 | 1.4e-006 | ≥1.0e-005 |
| 24-1 | 6.2e-008 | ≥1.0e-005 |
| 24-2 | 2.0e-005 | not tested |
| 24-3 | 1.3e-008 | 9.3e-006 |
| 24-4 | 4.28e-006 | not tested |
| 24-5 | 1.1E-8 | not tested |
| 24-6 | 9.4E-7 | not tested |
| 24-7 | 1.2E-6 | 1.0e-005 |
| 24-8 | 2.6E-8 | 1.0e-005 |
| 24-9 | not tested | not tested |
| 25-1 | 1.3e-008 | ≥1.0e-005 |
| 25-2 | 5.4e-009 | ≥1.0e-005 |
| 25-3 | 8.8E-9 | 4.4E-5 |
| 25-4 | 5.03E-9 | 1.0e-005 |
| 26-1 | 1.7e-008 | 9.2e-006 |
| 26-2 | 2.4e-006 | not tested |
| 27-1 | 5.5e-008 | 3.9e-006 |
| 28-1 | 3.7e-006 | not tested |
| 29-1 | 1.1e-008 | ≥1.0e-005 |
| 29-2 | 8.9e-009 | ≥1.0e-005 |
| 30-1 | 1.7e-008 | ≥1.0e-005 |
| 30-2 | 2.0e-008 | ≥1.0e-005 |
| 30-3 | 8.4e-009 | ≥1.0e-005 |
| 31-1 | 4.7e-006 | not tested |
| 32-1 | 1.2e-007 | ≥1.0e-005 |
| 33-1 | 1.1e-008 | ≥1.0e-005 |
| 34-1 | 2.3e-007 | ≥1.0e-005 |
| 34-2 | 6.2E-6 | ≥1.0e-005 |
| 34-3 | 2.8e-008 | 8.7e-006 |
| 34-4 | 1.2E-7 | not tested |
| 35-1 | 1.3e-006 | not tested |
| 36-1 | 4.91E-9 | 3.3E-6 |
| 36-2 | 6.2E-9 | 4.4E-7 |
| 36-3 | 6.3E-9 | 4.3E-7 |
| 37-1 | 5.7E-9 | 4.2E-6 |
| 38-1 | 3.4E-9 | 1.4E-6 |
| 38-2 | 3.8E-9 | 1.2E-6 |
| 39-1 | under evaluation | under evaluation |
| 39-2 | 6.7E-7 | ≥1.0e-005 |
| 40-1 | 3.9E-8 | not tested |
| 41-1 | 1.9E-8 | 6.0E-6 |
| 42-1 | 6.7E-9 | 3.6E-6 |

Inhibition of proliferation of HeLa-MaTu-ADR, NCI-H460, DU145, Caco-2 and B16F10 cells by compounds according to the present invention, determined as described under Biological Assays 2.0. All IC$_{50}$ (inhibitory concentration at 50% of maximal effect) values are indicated in [mol/L].

| Example Nr. | Biological Assay 2: Proliferation assay (HeLa-MaTu-ADR cell line) median IC50 [mol/l] | Biological Assay 2: Proliferation assay (MCF7 cell line) median IC50 [mol/l] | Biological Assay 2: Proliferation assay (H460 cell line) median IC50 [mol/l] | Biological Assay 2: Proliferation assay (DU145 cell line) median IC50 [mol/l] | Biological Assay 2: Proliferation assay (Caco2 cell line) median IC50 [mol/l] | Biological Assay 2: Proliferation assay (B16F10 cell line) median IC50 [mol/l] |
|---|---|---|---|---|---|---|
| 2-4-1 | 1.3E−06 | not tested | 4.2E−06 | 3.3E−06 | 1.4E−06 | 1.2E−06 |
| 2-5-1 | 1.2E−06 | 3.1E−06 | 1.4E−06 | 1.7E−06 | 1.2E−06 | 1.1E−06 |
| 2-9-1 | 8.1E−06 | not tested | 1.0E−05 | 1.0E−05 | 1.0E−05 | 9.5E−06 |
| 2-11-1 | 3.0E−06 | not tested | 3.0E−06 | 3.0E−06 | 3.0E−06 | 2.9E−06 |
| 2-12-1 | 1.3E−06 | not tested | 1.5E−06 | 1.6E−06 | 1.4E−06 | 1.4E−06 |
| 2-16-1 | 1.2E−06 | 2.0E−06 | 2.9E−06 | 2.0E−06 | 2.6E−06 | 9.9E−07 |
| 2-24-1 | 1.3E−06 | not tested | 2.0E−06 | 1.3E−06 | 1.5E−06 | 1.4E−06 |
| 2-25-1 | 1.0E−05 | not tested | 1.0E−05 | 1.0E−05 | 1.0E−05 | 1.0E−05 |
| 2-26-1 | 3.9E−07 | not tested | 1.0E−06 | 5.3E−07 | 3.8E−07 | 4.2E−07 |
| 2-32-1 | 2.3E−06 | not tested | 8.5E−06 | 5.3E−06 | 2.4E−06 | 1.3E−06 |
| 2-34-1 | 1.2E−06 | not tested | 6.6E−06 | 2.6E−06 | 3.4E−06 | 1.2E−06 |
| 2-46-1 | 3.8E−07 | not tested | 8.8E−07 | 8.5E−07 | 9.0E−07 | 7.1E−07 |
| 2-11-2 | 1.0E−05 | not tested | 2.3E−06 | 3.6E−06 | 8.0E−06 | 2.1E−06 |
| 2-4-3 | 1.0E−07 | not tested | 9.0E−06 | 2.5E−06 | 1.9E−06 | 1.5E−06 |
| 4-2-1 | 5.8E−06 | not tested | 6.5E−06 | 1.0E−05 | 9.9E−06 | 3.7E−06 |
| 4-4 | 1.2E−06 | not tested | 3.5E−06 | 4.5E−06 | 9.0E−07 | 5.0E−07 |
| 4-8 | 3.6E−07 | not tested | 1.1E−06 | 1.2E−06 | 7.6E−07 | 5.7E−07 |
| 4-9 | 8.6E−07 | not tested | 1.3E−06 | 1.3E−06 | 7.8E−07 | 5.3E−07 |
| 4-19 | 1.0E−05 | not tested | 2.2E−06 | 2.3E−06 | 1.0E−05 | 5.3E−07 |
| 4-22 | 1.0E−05 | not tested | 2.1E−06 | 3.6E−06 | 9.5E−06 | 1.2E−06 |
| 5-2 | 3.0E−06 | not tested | 3.0E−06 | 3.0E−06 | 3.0E−06 | 3.0E−06 |
| 6-2 | 1.6E−06 | not tested | 1.7E−06 | 1.4E−06 | 1.2E−06 | 1.1E−06 |
| 10-2 | 5.9E−07 | not tested | 1.5E−06 | 1.4E−06 | 1.1E−06 | 9.0E−07 |
| 12-1 | 1.0E−05 | not tested | 1.0E−05 | 1.0E−05 | 1.0E−05 | 1.0E−05 |
| 13-1 | 1.3E−06 | not tested | 1.3E−06 | 1.6E−06 | 1.2E−06 | 7.9E−07 |
| 15-1 | 1.2E−06 | not tested | 2.2E−06 | 1.2E−06 | 1.2E−06 | 7.6E−07 |
| 20-1 | 3.0E−06 | not tested | 3.0E−06 | 3.0E−06 | 3.0E−06 | 2.4E−06 |
| 38-2 | 1.1E−06 | not tested | 1.1E−06 | 1.3E−06 | 6.0E−07 | 6.0E−07 |
| 41-1 | 1.0E−05 | not tested | 1.0E−05 | 1.0E−05 | 3.3E−06 | 1.8E−06 |

The invention claimed is:

1. A compound which is selected from the group consisting of:

5-methoxy-2-{1-[3-(5-methyl-1,2,4-oxadiazol-3-yl)benzyl]-1H-indazol-3-yl}-N-(pyridin-4-yl)pyrimidin-4-amine;

5-methoxy-2-{1-[4-(pentafluoro-$\lambda^6$-sulfanyl)benzyl]-1H-indazol-3-yl}-N-(pyridin-4-yl)pyrimidin-4-amine;

2-({3-[5-methoxy-4-(pyridin-4-ylamino)pyrimidin-2-yl]-1H-indazol-1-yl}methyl)benzonitrile;

5-methoxy-N-(pyridin-4-yl)-2-(1-{3-[(trifluoromethyl)sulfanyl]benzyl}-1H-indazol-3-yl)pyrimidin-4-amine;

5-methoxy-2-{1-[4-(1H-pyrazol-1-yl)benzyl]-1H-indazol-3-yl}-N-(pyridin-4-yl)pyrimidin-4-amine;

5-methoxy-N-(pyridin-4-yl)-2-(1-{4-[(trifluoromethyl)sulfanyl]benzyl}-1H-indazol-3-yl)pyrimidin-4-amine;

5-methoxy-2-[1-(4-propylbenzyl)-1H-indazol-3-yl]-N-(pyridin-4-yl)pyrimidin-4-amine;

7-({3-[5-methoxy-4-(pyridin-4-ylamino)pyrimidin-2-yl]-1H-indazol-1-yl}methyl)-3,4-dihydroquinolin-2(1H)-one;

7-({3-[5-methoxy-4-(pyridin-4-ylamino)pyrimidin-2-yl]-1H-indazol-1-yl}methyl)-4-methyl-2H-chromen-2-one;

ethyl [3-({3-[5-methoxy-4-(pyridin-4-ylamino)pyrimidin-2-yl]-1H-indazol-1-yl}methyl)phenyl]acetate;

2-[1-(4-fluorobenzyl)-1H-indazol-3-yl]-5-methoxy-N-(pyridin-4-yl)pyrimidin-4-amine;

N-cyclopropyl-4-({3-[5-methoxy-4-(pyridin-4-ylamino)pyrimidin-2-yl]-1H-indazol-1-yl}methyl)benzenesulfonamide;

6-({3-[5-methoxy-4-(pyridin-4-ylamino)pyrimidin-2-yl]-1H-indazol-1-yl}methyl)-1-benzofuran-2(3H)-one;

ethyl 2-[3-({3-[5-methoxy-4-(pyridin-4-ylamino)pyrimidin-2-yl]-1H-indazol-1-yl}methyl)phenyl]-2-methylpropanoate;

4-({3-[5-methoxy-4-(pyridin-4-ylamino)pyrimidin-2-yl]-1H-indazol-1-yl}methyl)benzonitrile;

5-methoxy-2-{1-[4-(morpholin-4-ylsulfonyl)benzyl]-1H-indazol-3-yl}-N-(pyridin-4-yl)pyrimidin-4-amine;

3-({3-[5-methoxy-4-(pyridin-4-ylamino)pyrimidin-2-yl]-1H-indazol-1-yl}methyl)benzonitrile;

5-methoxy-N-(pyridin-4-yl)-2-{1-[3-(1H-pyrrol-1-yl)benzyl]-1H-indazol-3-yl}pyrimidin-4-amine;

2-[1-(4-fluorobenzyl)-1H-indazol-3-yl]-4-(pyridin-4-ylamino)pyrimidin-5-ol;

5-[2-(dimethylamino)ethoxy]-2-[1-(4-fluorobenzyl)-1H-indazol-3-yl]-N-(pyridin-4-yl)pyrimidin-4-amine;

2-[3-({3-[5-methoxy-4-(pyridin-4-ylamino)pyrimidin-2-yl]-1H-indazol-1-yl}methyl)phenyl]ethanol;

2-[3-({3-[5-methoxy-4-(pyridin-4-ylamino)pyrimidin-2-yl]-1H-indazol-1-yl}methyl)phenyl]-2-methylpropan-1-ol;

1-[3-({3-[5-methoxy-4-(pyridin-4-ylamino)pyrimidin-2-yl]-1H-indazol-1-yl}methyl)phenyl]-2-methylpropan-2-ol;

4-({5-methoxy-2-[1-(4-propylbenzyl)-1H-indazol-3-yl]pyrimidin-4-yl}amino)nicotinonitrile; and 4-({5-methoxy-2-[1-(4-propylbenzyl)-1H-indazol-3-yl]pyrimidin-4-yl}amino)pyridine-3-carboxamide, or an N-oxide, a salt, a tautomer or a stereoisomer thereof, or a salt of said N-oxide, tautomer or stereoisomer.

2. A method for treating a cervical-, breast-, non-small cell lung-, prostate-, colon- or melanoma tumor in a mammal in need thereof, comprising administering a therapeutically effective amount of the compound of claim 1, or an N-oxide, a pharmaceutically acceptable salt, a tautomer or a stereoisomer thereof, or a pharmaceutically acceptable salt of said N-oxide, tautomer or stereoisomer, to the mammal.

3. A pharmaceutical composition comprising at least one compound according to claim 1, or an N-oxide, a pharmaceutically acceptable salt, a tautomer or a stereoisomer thereof, or a pharmaceutically acceptable salt of said N-oxide, tautomer or stereoisomer, together with at least one pharmaceutically acceptable auxiliary.

4. A method for treating a cervical-, breast-, non-small cell lung-, prostate-, colon- or melanoma tumor in a mammal in need thereof comprising administering the composition according to claim 3 to the mammal.

5. A combination comprising one or more first active ingredients selected from a compound according to claim 1, or an N-oxide, a pharmaceutically acceptable salt, a tautomer or a stereoisomer thereof, or a pharmaceutically acceptable salt of said N-oxide, tautomer or stereoisomer, and one or more second active ingredients selected from chemotherapeutic anti-cancer agents and target-specific anti-cancer agents.

6. The compound of claim 1 or a pharmaceutically acceptable salt thereof.

* * * * *